(12) United States Patent
Rosselli et al.

(10) Patent No.: US 11,770,974 B2
(45) Date of Patent: Sep. 26, 2023

(54) P ACTIVE MATERIALS FOR ORGANIC PHOTOELECTRIC CONVERSION LAYERS IN ORGANIC PHOTODIODES

(71) Applicant: Sony Corporation, Tokyo (JP)

(72) Inventors: Silvia Rosselli, Stuttgart (DE); Nikolaus Knorr, Stuttgart (DE); Anthony Roberts, Stuttgart (DE); Tzenka Miteva, Stuttgart (DE); Gabriele Nelles, Stuttgart (DE); Vitor Deichmann, Stuttgart (DE); David Danner, Stuttgart (DE); William E. Ford, Stuttgart (DE); Dennis Chercka, Stuttgart (DE); Vladimir Yakutkin, Stuttgart (DE); Lars Peter Scheller, Stuttgart (DE)

(73) Assignee: Sony Corporation, Tokyo (JP)

( * ) Notice: Subject to any disclaimer, the term of this patent is extended or adjusted under 35 U.S.C. 154(b) by 387 days.

(21) Appl. No.: 16/756,745

(22) PCT Filed: Oct. 22, 2018

(86) PCT No.: PCT/EP2018/078864
§ 371 (c)(1),
(2) Date: Apr. 16, 2020

(87) PCT Pub. No.: WO2019/081416
PCT Pub. Date: May 2, 2019

(65) Prior Publication Data
US 2021/0193935 A1    Jun. 24, 2021

(30) Foreign Application Priority Data
Oct. 23, 2017    (EP) ..................................... 17197786

(51) Int. Cl.
*H10K 85/60* (2023.01)
*C07D 495/04* (2006.01)
(Continued)

(52) U.S. Cl.
CPC ....... *H10K 85/6576* (2023.02); *C07D 495/04* (2013.01); *H10K 85/615* (2023.02);
(Continued)

(58) Field of Classification Search
CPC ............ H01L 51/0074; H01L 51/0052; H01L 51/4253; H01L 27/307; H01L 27/286; C07D 495/04
(Continued)

(56) References Cited

U.S. PATENT DOCUMENTS

2015/0284504 A1    10/2015 Cheng et al.
2018/0057492 A1    3/2018 Rosselli et al.
(Continued)

FOREIGN PATENT DOCUMENTS

CN    103664995 A    3/2014
CN    102007131    *    6/2015
(Continued)

OTHER PUBLICATIONS

Yu Han et al:"Benzothienobenzothiophene-Based ,Conjugated Oligomers as Semiconductors for Stable Organic Thin-Film Transistors",Applied Materials & Interfaces,vol. 6, No. 7, Apr. 9, 2014 (Apr. 9, 2014),pp. 5255-5262, XP055830976.
(Continued)

*Primary Examiner* — Sheng-Bai Zhu
(74) *Attorney, Agent, or Firm* — Oblon, McClelland, Maier & Neustadt, L.L.P.

(57) ABSTRACT

The present disclosure relates to transparent P materials and their use in absorption layer(s), photoelectric conversion
(Continued)

layer(s) and/or an organic image sensor and methods for their synthesis.

27 Claims, 38 Drawing Sheets

(51) Int. Cl.
  *H10K 19/20* (2023.01)
  *H10K 30/30* (2023.01)
  *H10K 39/32* (2023.01)

(52) U.S. Cl.
  CPC ............. *H10K 19/20* (2023.02); *H10K 30/30* (2023.02); *H10K 39/32* (2023.02)

(58) Field of Classification Search
  USPC ....................................................... 136/263
  See application file for complete search history.

(56) References Cited

U.S. PATENT DOCUMENTS

| | | |
|---|---|---|
| 2018/0114926 A1 | 4/2018 | Ujiie et al. |
| 2019/0081251 A1 | 3/2019 | Obana |

FOREIGN PATENT DOCUMENTS

| | | |
|---|---|---|
| JP | 2009267134 A | 11/2009 |
| JP | 2010275192 A | 12/2010 |
| WO | WO 2006/077888 A1 | 7/2006 |
| WO | WO 2010/058692 A1 | 5/2010 |
| WO | WO-2015163349 A1 | 10/2015 |
| WO | WO 2016/156535 A1 | 10/2016 |
| WO | WO 2016/156546 A1 | 10/2016 |
| WO | WO 2016156535 | * 10/2016 |
| WO | WO2016/185858 A1 | 11/2016 |
| WO | WO 2016/185858 A1 | 11/2016 |
| WO | WO-2016186186 A1 | 11/2016 |
| WO | 2017-79317 A | 4/2017 |
| WO | WO 2017/159025 A1 | 9/2017 |
| WO | WO-2017159684 A1 | 9/2017 |

OTHER PUBLICATIONS

U.S. Appl. No. 15/560,857, filed Sep. 22, 2017, U.S. Pat. No. 2018/0123050 A1, Silvia Rosselli et al.

International Search Report dated Mar. 29, 2019 in PCT/EP2018/078864 filed on Oct. 22, 2018.

Capodilupo, A. L. et al., "[1]Benzothieno[3,2-b]benzothiophene-Based Organic Dyes for Dye-Sensitized Solar Cells," The Journal of Organic Chemistry, vol. 81, 2016, pp. 3235-3245, XP055546300.

Ljubic, D. et al., "Effect of Polymer Binders on UV-Responsive Organic Thin-Film Phototransistors with Benzothienobenzothiophene Semiconductor," ACS Applied Materials & Interfaces, vol. 8, 2016, pp. 3744-3754, XP055546308.

Sato, R. et al., "Charge-Transfer Complexes of Benzothienobenzothiophene with Tetracyanoquinodimethane and the n-Channel Organic Field-Effect Transistors," The Journal of Physical Chemistry C, vol. 121, 2017, pp. 6561-6568, XP055546575.

Timothy E. Barder; et al; "Catalysts for Suzuki-Miyaura Coupling Processes: Scope and Studies of the Effect of Ligand Structure", J.AM.CHEM.SOC,2005, vol. 127, pp. 4685-4696.

The Chemical Society of Japan, 5th Series of Experiment Chemistry, 18 Synthesis of organic compounds VI—Organic synthesis using metal-, Maruzen Publishing Co., Ltd., 2004, pp. 338-340.

The Chemical Society of Japan, New Series of Experiment Chemistry, 14 Synthesis and reaction of organic compounds I, Maruzen Publishing Co., Ltd., 1977, pp. 341-343.

* cited by examiner

Figure 6

| Top electrode | N-layer (n-buffer), 10 nm | p-material: absorber: C60 e.g. P:N1:N2 | p-layer (p-buffer), 10 nm | Bottom electrode on substrate |

P ACTIVE MATERIALS FOR ORGANIC PHOTOELECTRIC CONVERSION LAYERS IN ORGANIC PHOTODIODES

CROSS REFERENCE TO RELATED APPLICATIONS

The present application claims priority to European Patent Application 17197786.1 filed by the European Patent Office on Oct. 23, 2017, the entire contents of which is incorporated herein by reference.

BACKGROUND

The field of the DISCLOSURE lies in active materials for organic image sensors.

The present disclosure relates to transparent P materials and their use in absorption layer(s), photoelectric conversion layer(s) and/or an organic image sensor and methods for their synthesis.

The present disclosure also relates to photoelectric conversion layer(s) including an active material according to the present disclosure, to a device, including active material(s) according to the present disclosure or photoelectric conversion layer(s) according to the present disclosure.

Moreover, the present disclosure relates to an organic image sensor including photoelectric conversion layer(s) according to the present disclosure.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Image sensors, which are semiconductor devices for converting an optical image into an electric signal, include a light-sensing unit for sensing light and a logic circuit unit for processing the sensed light into an electrical signal to store data.

In the state of the art, the light-sensing unit includes a color filter and a photoelectric conversion film, a semiconductor p-n junction, such as silicon. The color filter separates light according to colors, but reduces the spatial resolution and light collection and utilization efficiency.

In order to overcome this problem geometries are reported where photoelectric conversion units capable of detecting light of different wavelengths are stacked in a longitudinal direction. In particular such photoelectrical conversion unit is an organic photoelectric conversion layer based on p-n junction or bulk heterojunction. The photoelectric conversion efficiency of such a unit depends strongly on the type of materials used in the layer. With the organic materials available so far, low conversion efficiencies and high dark currents are reported.

In another solution, an organic layer is used that is capable to absorb in the IR region but not in the visible reagion, that could be combined with a complementary metal oxide semiconductor (CMOS) based imager part for the visible range or with an organic based imager part that could absorb in the visible range. In both cases white light is collected and filter have to be used to get the BGR pixel resolution. In this case, as well as in the case of color filter, light is separated according to colors but the spatial resolution and light collection and utilization efficiency is reduced.

SUMMARY

The present disclosure provides a transparent P material, which has the quality when comprised in a P:N heterojunction or P:N bilayer or multilayer junction, particularly a P:N1:N2 or a P1:P2:N heterojunction or multilayer junction, to dissociate efficiently the excitons created in colored N, or in a mixture of colored N materials (N1:N2), or in another colored P or in a mixture of colored P and N materials (P2:N) via a process of HOMO dissociation, and/or has the quality to accept hole from the colored N or the mixture of colored N materials, from another colored P material or from a mixture of colored N and another P material.

It might also have the quality to transport the holes.
Wherein
transparent refers to:
an extinction coefficient of less than about 60,000 $M^{-1}$ $cm^{-1}$ in the visible wavelength range in the region of about 450 to about 700 nm and to an extinction coefficient of less than about 100,000 $M^{-1}$ $cm^{-1}$ in the visible wavelength range in the region of about 400 to about 450 nm, or
an absorption coefficient (in single material film) of less than 70,000 $cm^{-1}$ for wavelengths longer than 450 nm, or
an absorption coeffiecient (in single material film) of less than 40,000 $cm^{-1}$ for wavelengths longer than 500 nm, and
colored refers to an absorption coefficient of more than about 60,000 $cm^{-1}$ in the visible wavelength range in the region from about 400 nm to about 700 nm (with maxima anywhere in this region or absorbing everywhere in this region).

The present disclosure provides a transparent P material, wherein the material
is an organic based compound forming high quality homogenous films when using deposition methods (such as vacuum deposition or spincoating)
has an extinction coefficient of less than about 60,000 $M^{-1}$ $cm^{-1}$ in the visible wavelength range in the region of about 450 to about 700 nm and an extinction coefficient of less than about 100,000 $M^{-1}$ $cm^{-1}$ in the visible wavelength range in the region of about 400 to about 450 nm,
and
is an organic based compound forming high quality homogenous films when using deposition methods (such as vacuum deposition or spincoating),
has an absorption coefficient (in single material film) of less than 70,000 $cm^{-1}$ for wavelengths longer than 450 nm, or
an absorption coeffiecient (in single material film) of less than 40,000 $cm^{-1}$ for wavelengths longer than 500 nm.

The present disclosure provides the use of a transparent P material according to the present disclosure in an absorption layer and/or in a photoelectric conversion layer and/or in an organic and/or hybrid module for optoelectronic application.

The present disclosure provides a photoelectric conversion layer including a transparent P material according to the present disclosure. The present disclosure provides an absorption layer including a transparent P material according to the present disclosure.

The present disclosure provides a device including transparent P material(s) according to the present disclosure or a photoelectric conversion layer(s) according to the present disclosure.

The present disclosure provides an organic image sensor, including an organic photoelectric conversion unit including photoelectric conversion layer(s) according to the present disclosure.

The present disclosure provides a hybrid Silicon-organic image sensor, including an organic photoelectric conversion unit including photoelectric conversion layer(s) according to the present disclosure.

The present disclosure provides a method for synthesis of transparent P materials, in particular thiophene-based, selenophene-based materials, and dimers thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 6 shows an example for a three component photoelectric conversion layer.

FIG. 8A shows the synthetic route for the preparation of a thiophene-based P material, called BTBT14, according to Example 2.

FIG. 9 B shows the MALDI-TOF mass spectrum of BTBT2 (see i), plain line: sublimed BTBT2; dotted lines, simulated mass spectrum of BTBT2), TG (see ii)) and DSC (see iii)) of sublimed BTBT2 and the UV-Vis absorption and PL spectra of BTBT2 (see iv)).

FIG. 10 B shows the MALDI-TOF mass spectrum of BTBT9 (see i), plain line: sublimed BTBT9; dotted lines, simulated mass spectrum of BTBT9), TG (see ii)) and DSC (see iii)) of sublimed BTBT9 and the UV-Vis absorption and PL spectra of BTBT9 (see iv)).

FIG. 11 B shows the MALDI-TOF mass spectrum of TT1 (see i), plain line: sublimed TT1; dotted lines, simulated mass spectrum of TT1), TG (see ii)) and DSC (see iii)) of sublimed TT1 and the UV-Vis absorption and PL spectra of TT1 (see iv)).

DETAILED DESCRIPTION OF THE EMBODIMENTS

Figure 1:
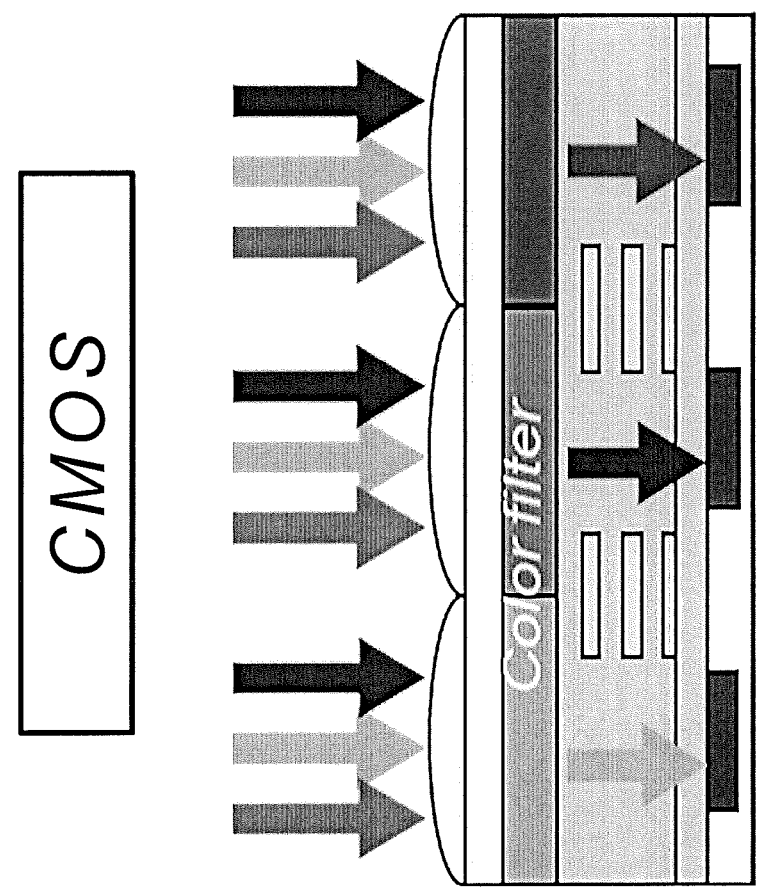
FIG. 1 shows a CMOS image sensor.

As discussed above, the present disclosure provides a transparent P material.

The transparent P material according to the present disclosure has the quality when comprised in a P:N heterojunction or P:N bilayer or multilayer junction, particularly a P:N1:N2 or a P1:P2:N heterojunction or multilayer junction, to dissociate efficiently the excitons created in colored N, or in a mixture of colored N materials (N1:N2), or in another colored P or in a mixture of colored P and N materials (P2:N) via a process of HOMO dissociation. It might also have the quality to further transport the holes.

According to the present disclosure, the transparent P material donates electron into the HOMO of the excited colored material (the P material(s) or the N material(s) absorbing photons), which is equivalent to accepting a hole.

According to the present disclosure "transparent" refers to an extinction coefficient of less than about 60,000 $M^{-1}$ $cm^{-1}$ in the visible wavelength range in the region of about 450 to about 700 nm and to an extinction coefficient of less than about 100,000 $M^{-1}cm^{-1}$ in the visible wavelength range in the region of about 400 to about 450 nm, or to an absorption coefficient (in single material film) of less than 70,000 $cm^{-1}$ for wavelengths longer than 450 nm, or to an absorption coefficient (in single material film) of less than 40,000 $cm^{-1}$ for wavelengths longer than 500 nm, and "colored" refers to an absorption coefficient of more than about 60,000 $cm^{-1}$ in the visible wavelength range in the region from about 400 nm to about 700 nm (with maxima anywhere in this region or absorbing everywhere in this region).

In one embodiment, the transparent P material of the present disclosure
is an organic based compound forming high quality homogenous films when using deposition methods (such as vacuum deposition or spincoating),
has an extinction coefficient of less than about 60,000 $M^{-1}$ $cm^{-1}$ in the visible wavelength range in the region of about 450 to about 700 nm and an extinction coefficient of less than about 100,000 $M^{-1}$ $cm^{-1}$ in the visible wavelength range in the region of about 400 to about 450 nm.

The transparent P material has an absorption coefficient (in single material film) of less than 70,000 $cm^{-1}$ for wavelengths longer than 450 nm, or an absorption coeffiecient (in single material film) of less than 40,000 $cm^{-1}$ for wavelengths longer than 500 nm.

In one embodiment, the transparent P material of the present disclosure is selected from the group of
thiophene-based materials,
selenophene-based material, and
dimers thereof.

In one embodiment, the transparent P material of the present disclosure is a thiophene- or selenophene-based material represented by the general formula IX

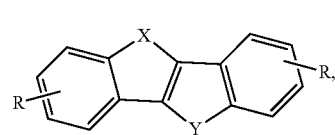

IX wherein,
X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl, and
R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

In a preferred embodiment of the thiophene- or selenophene-based material represented by the general formula IX, X and Y are the same or different and are, at each occurrence, independently selected from S and Se.

In a preferred embodiment of the thiophene- or selenophene-based material represented by the general formula IX, R is selected from

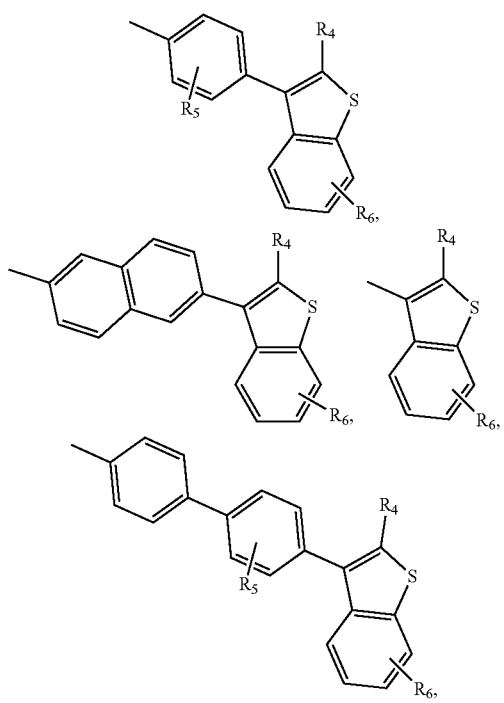

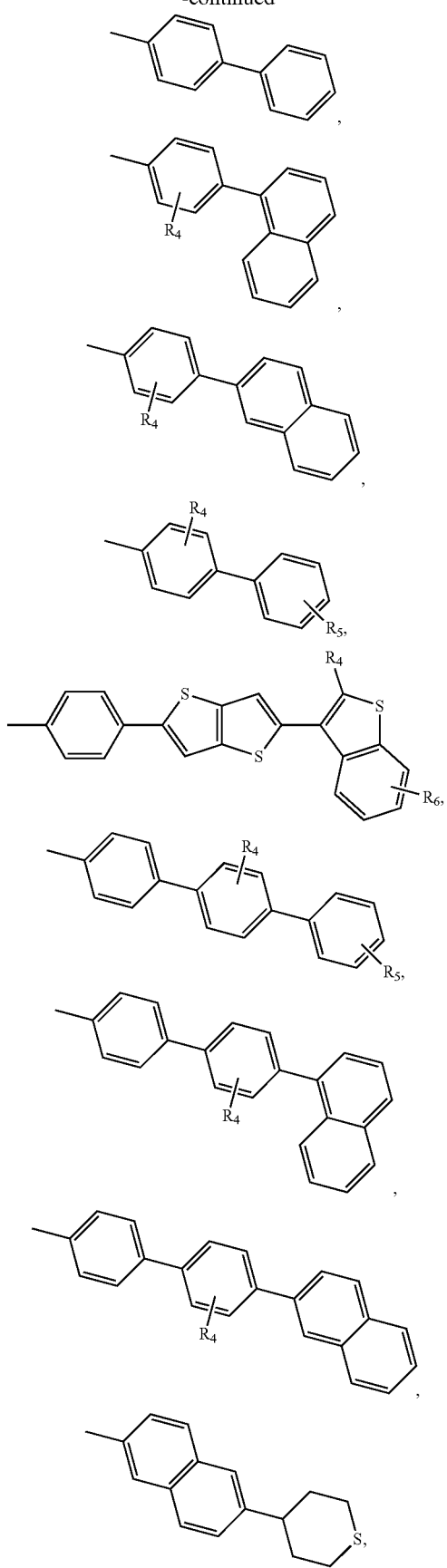
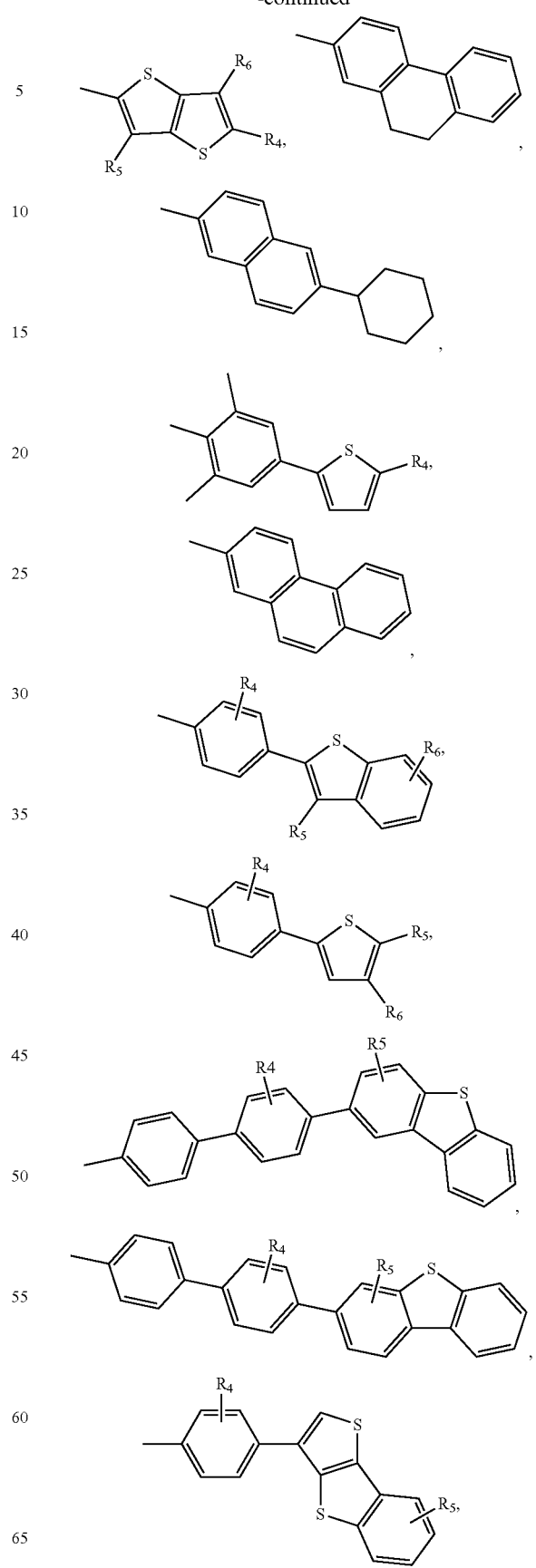

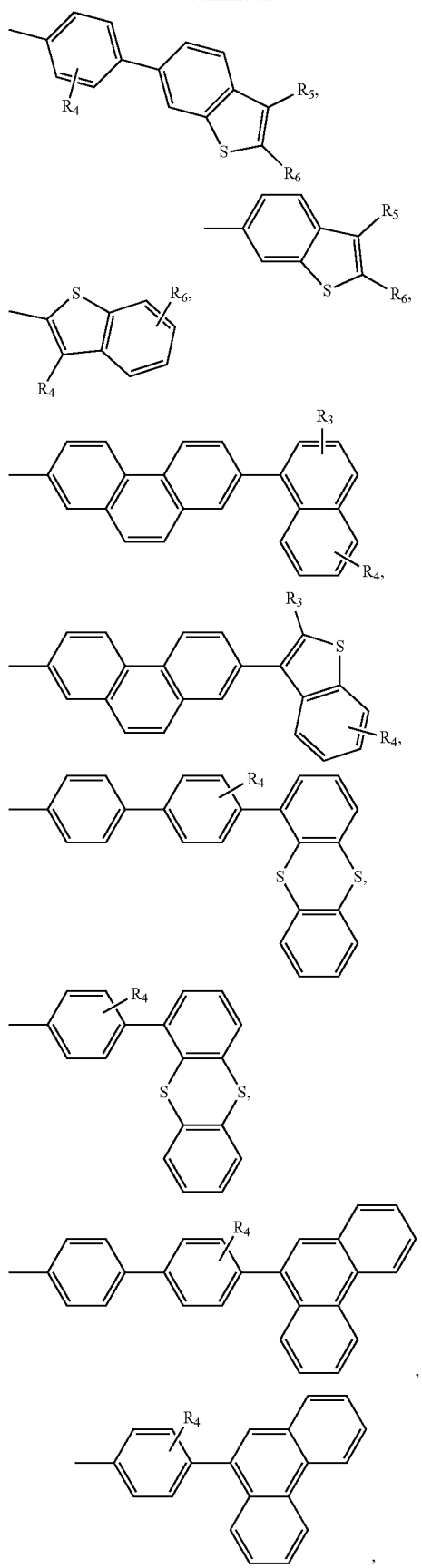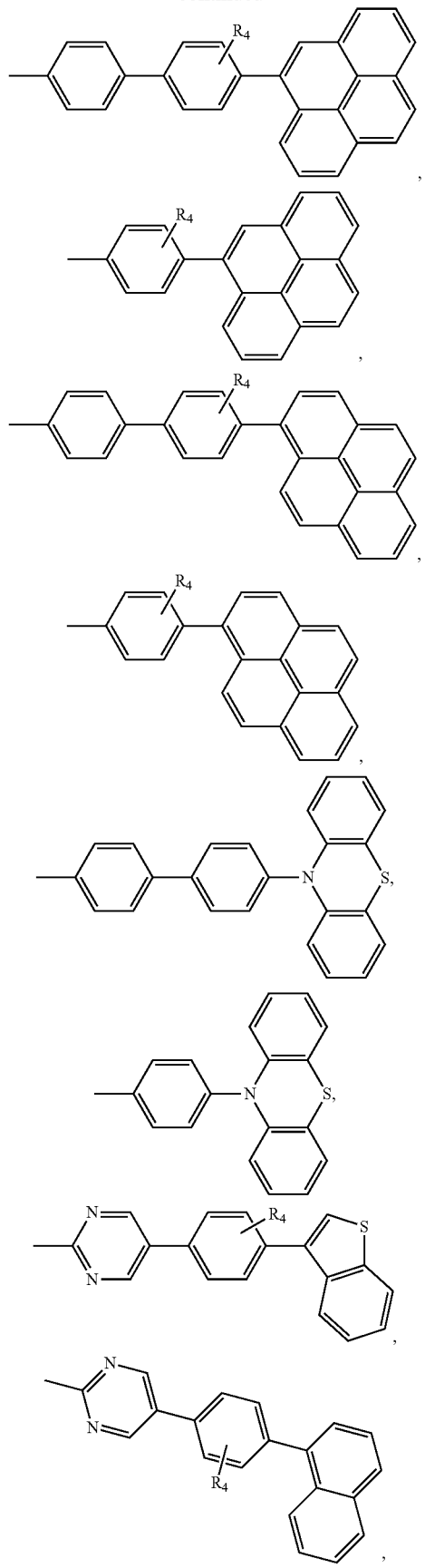

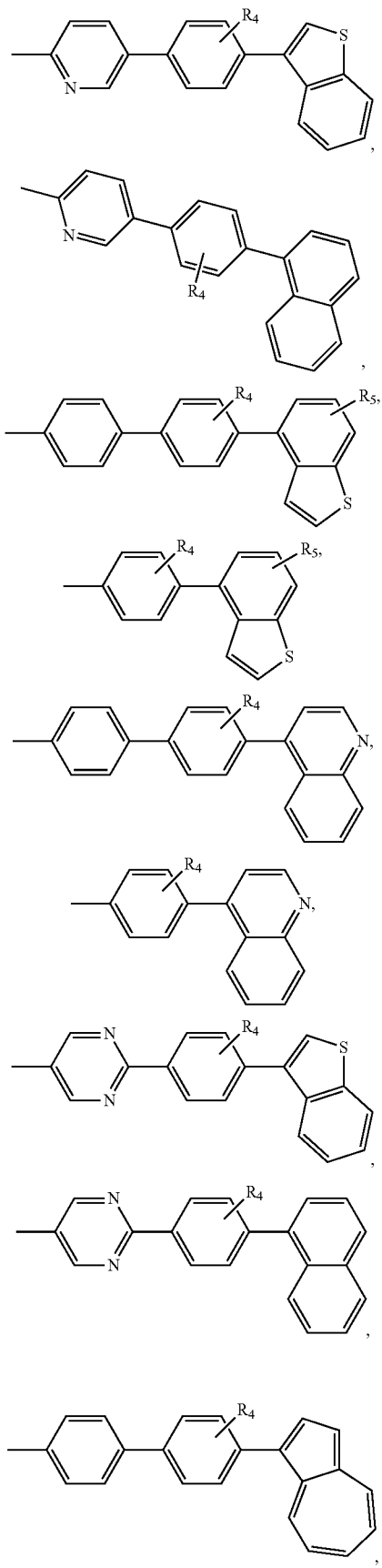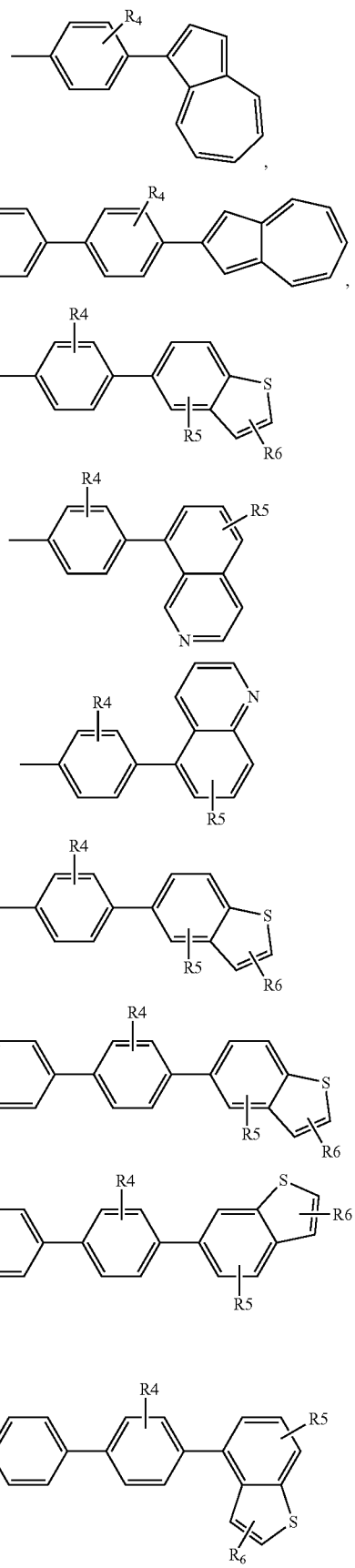

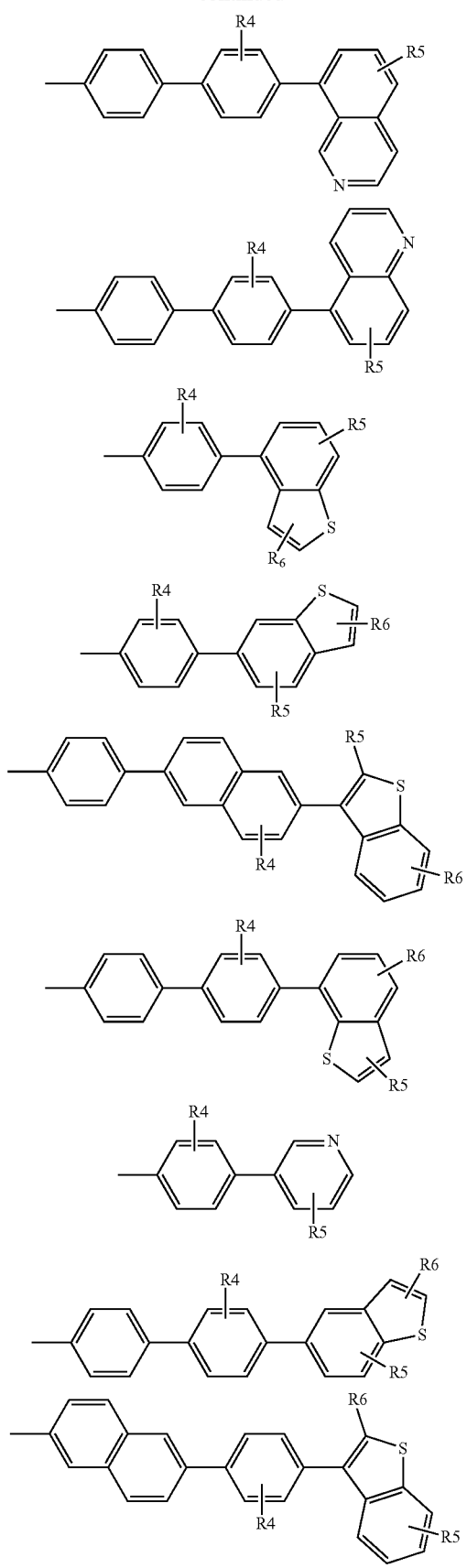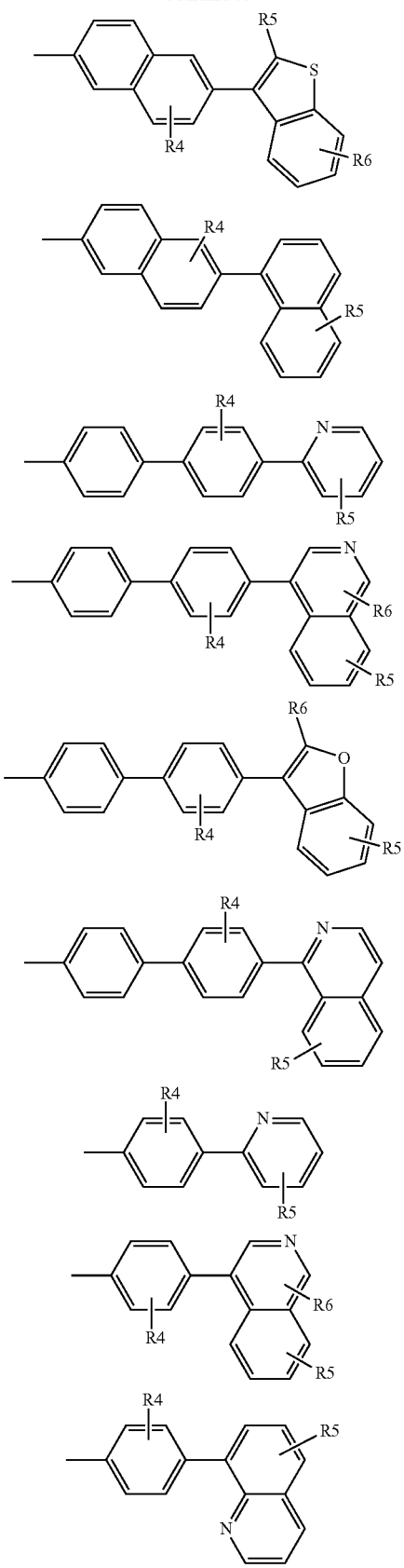

-continued
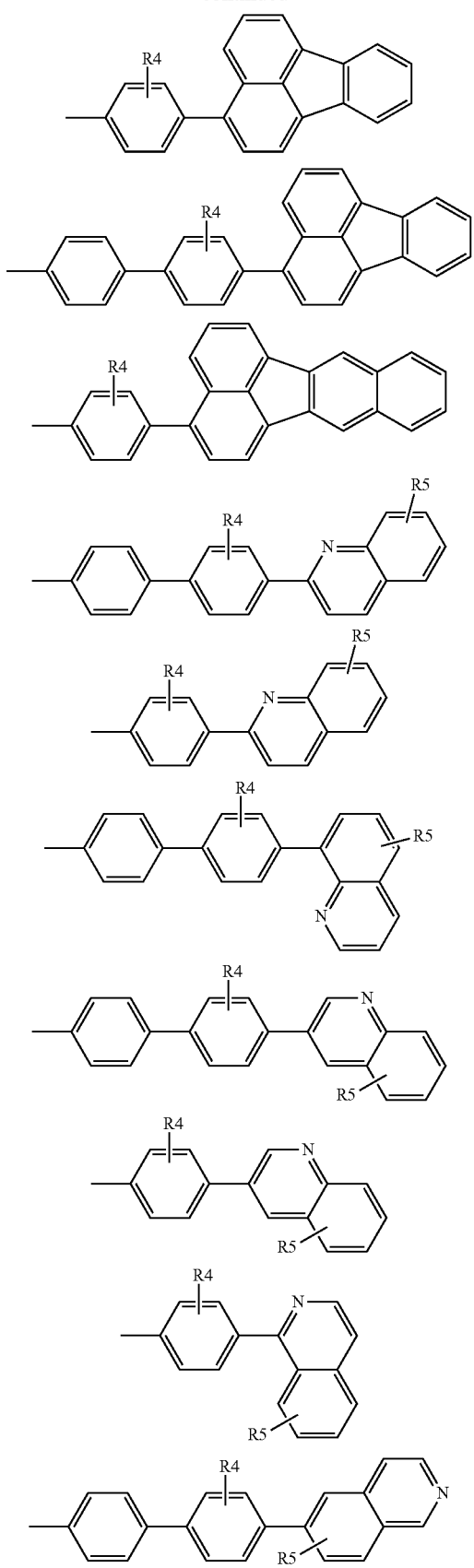
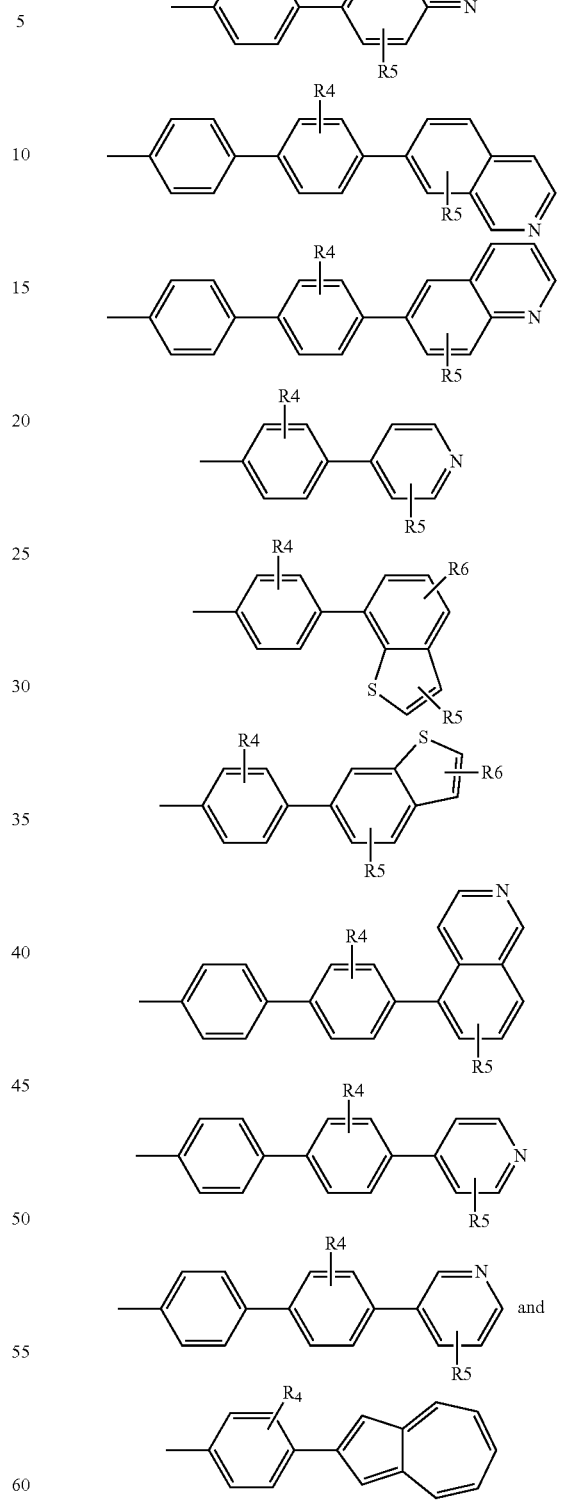
wherein $R_4$, $R_5$, $R_6$ are the same or different and are, at each occurrence, independently selected from H, F, $CH_3$, $CF_3$, aryl and alkyl.
In a preferred embodiment of the thiophene- or selenophene-based material represented by the general formula IX, X and Y are the same or different and are, at each occurrence, independently selected from S and Se, and
R is selected from
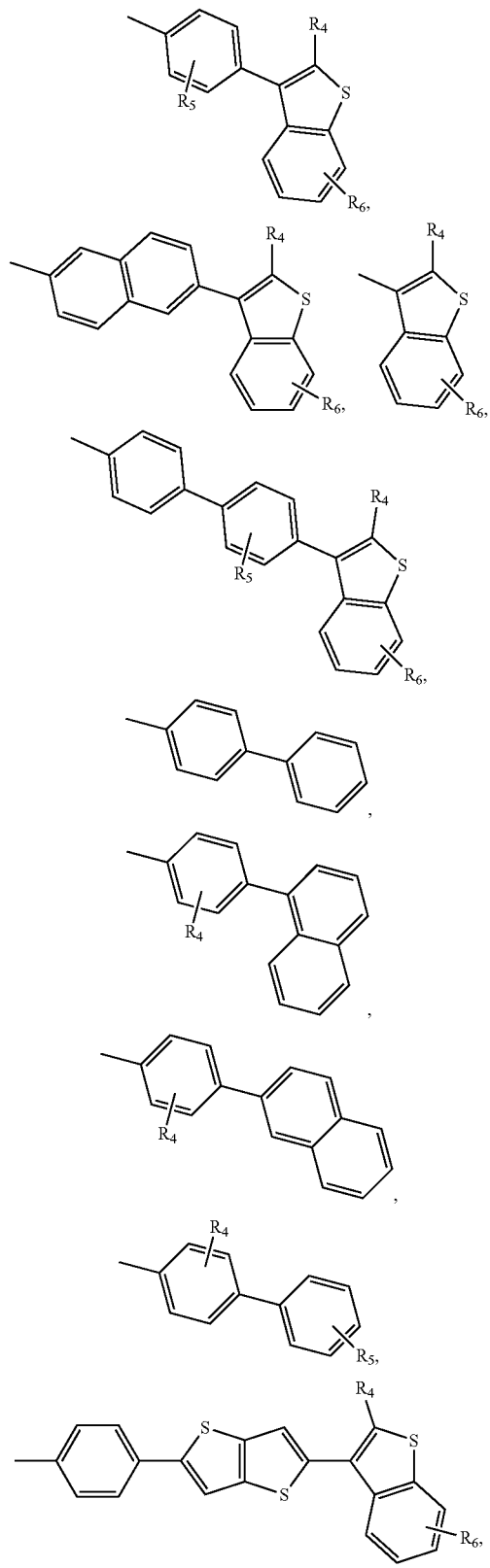
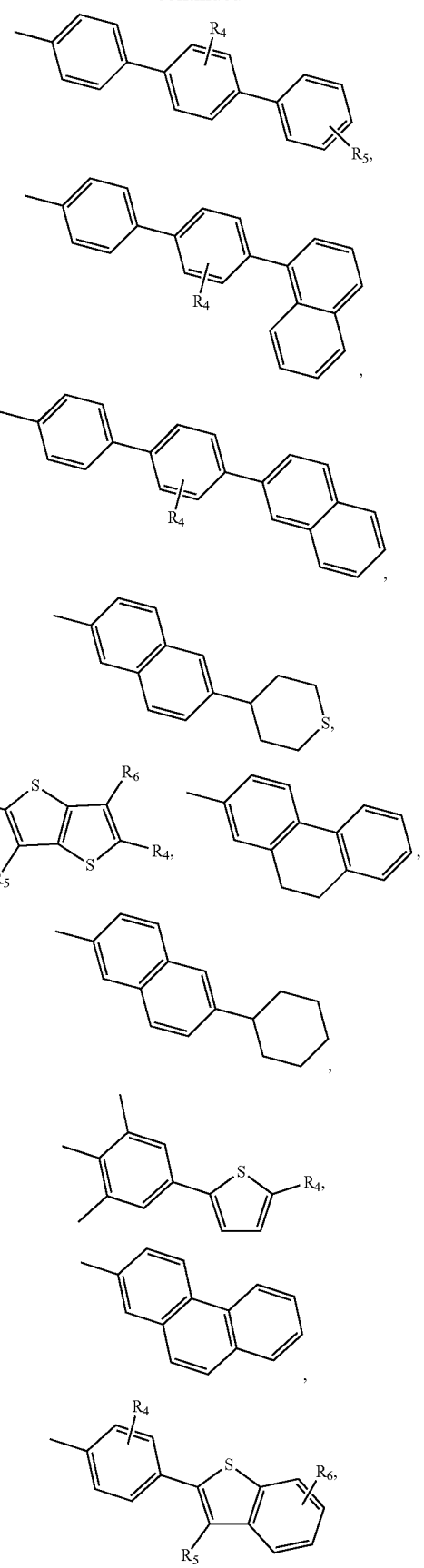

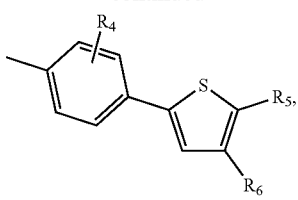
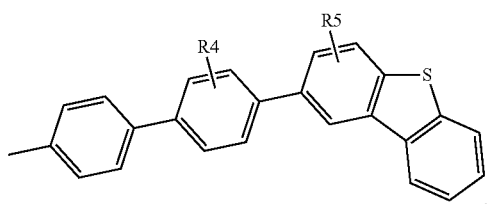
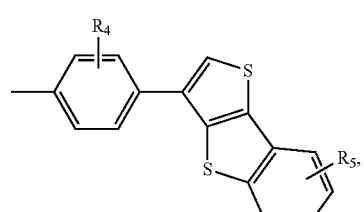
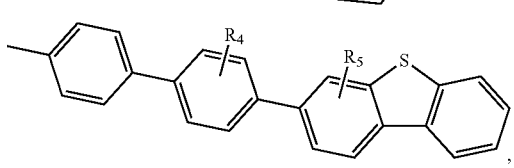
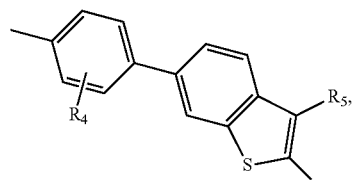
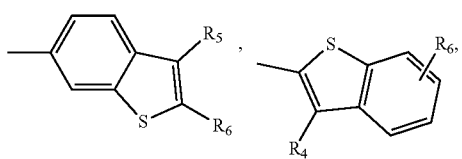
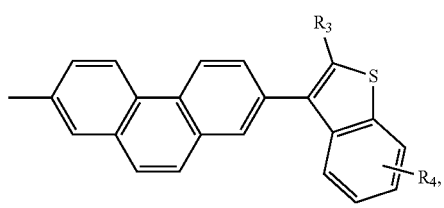
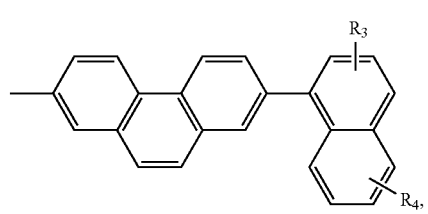
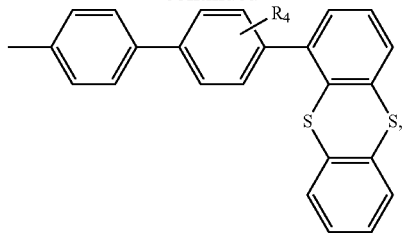
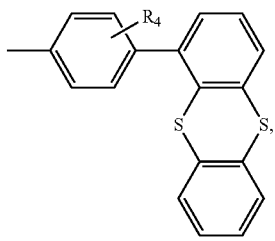
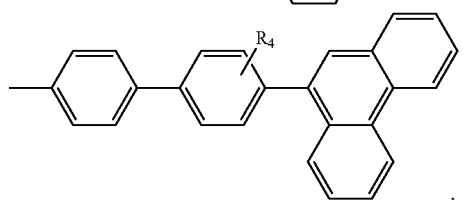
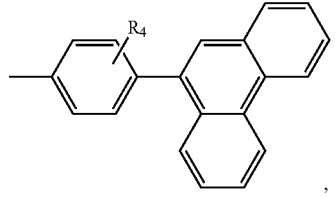
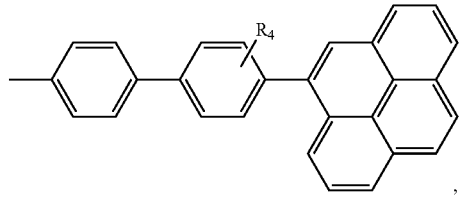
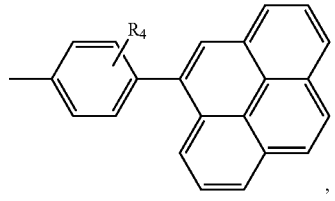
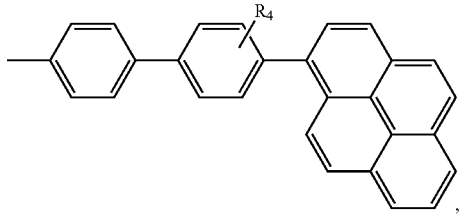
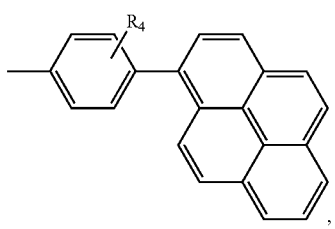

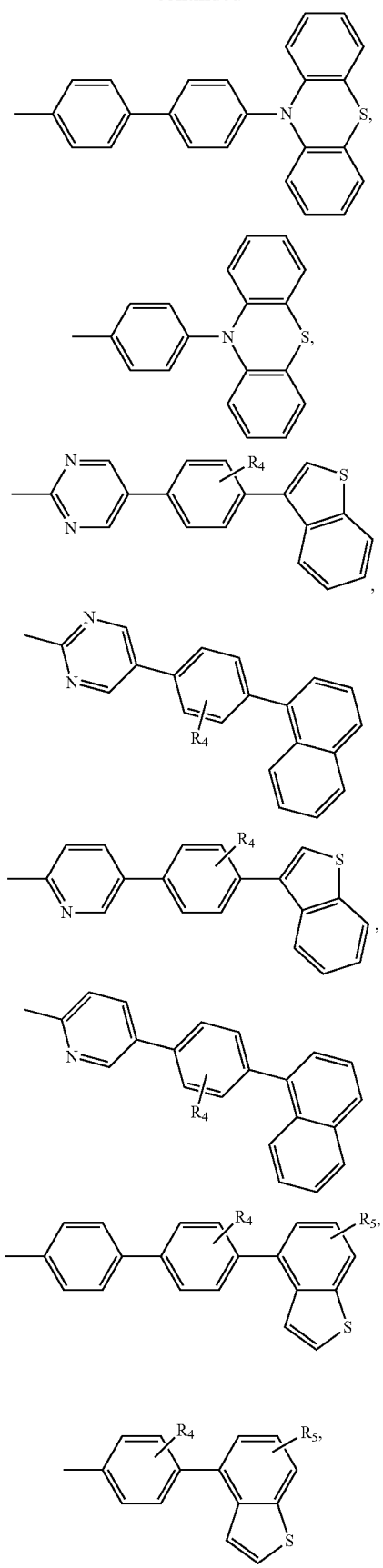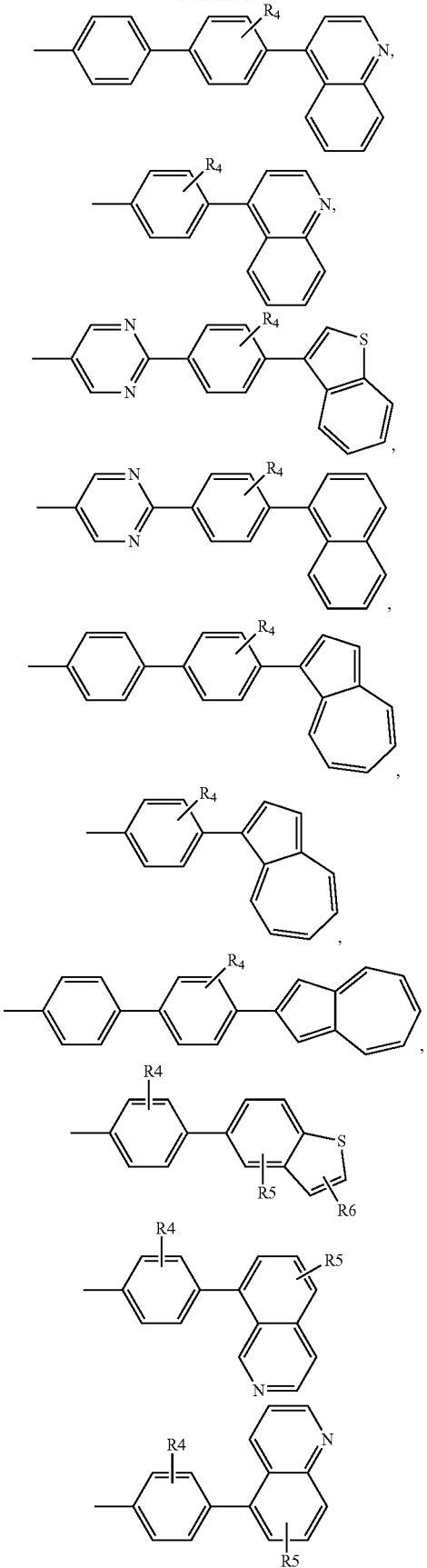

-continued
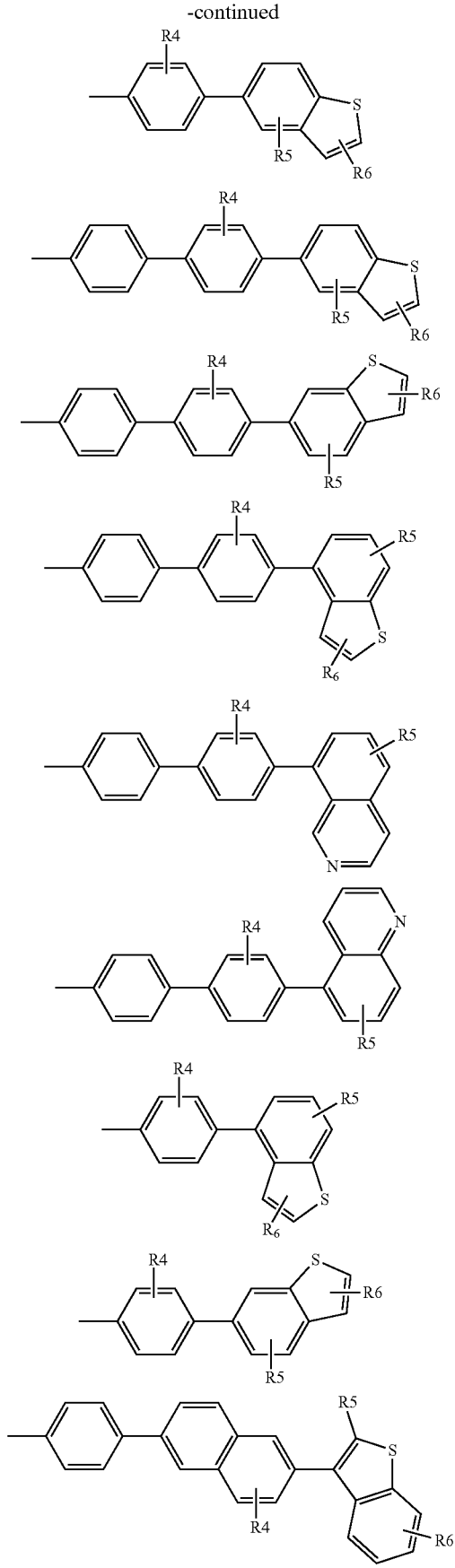
-continued
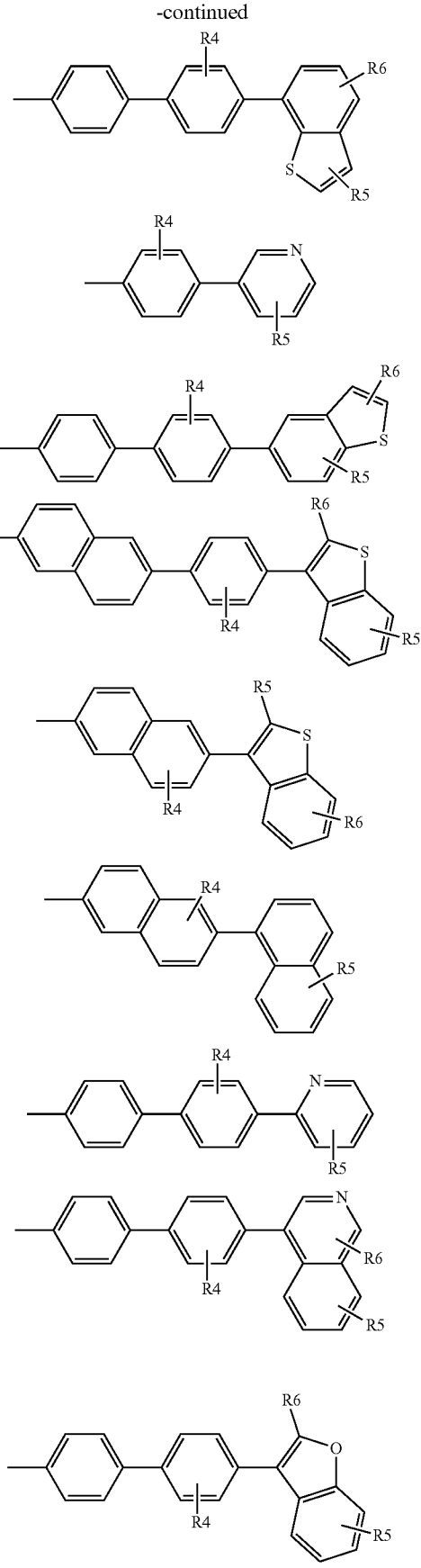

-continued
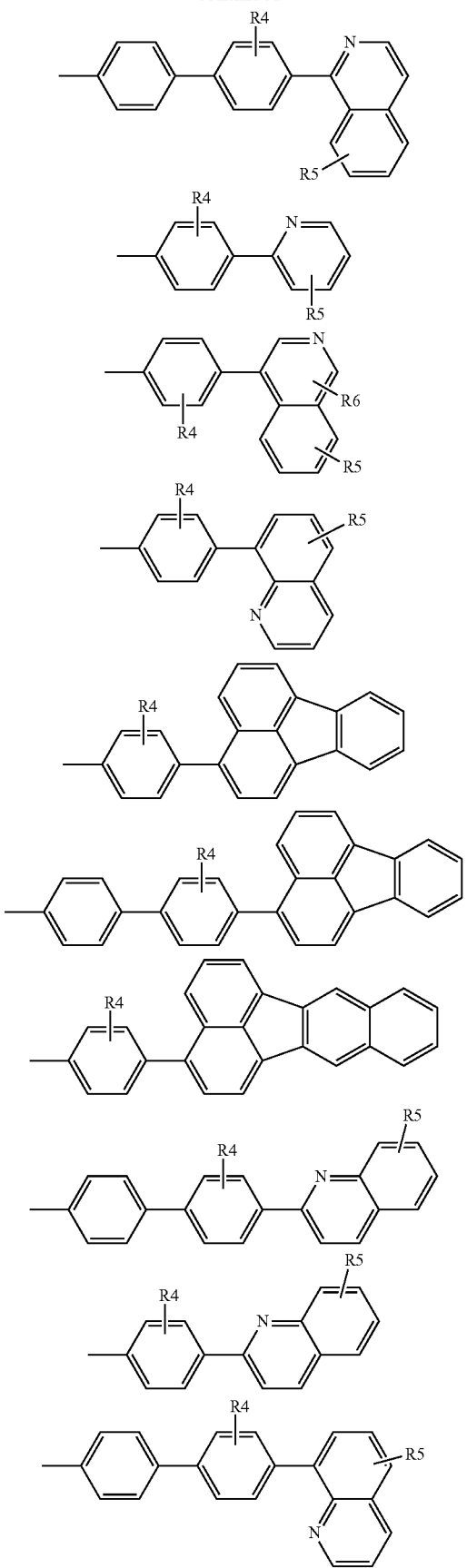
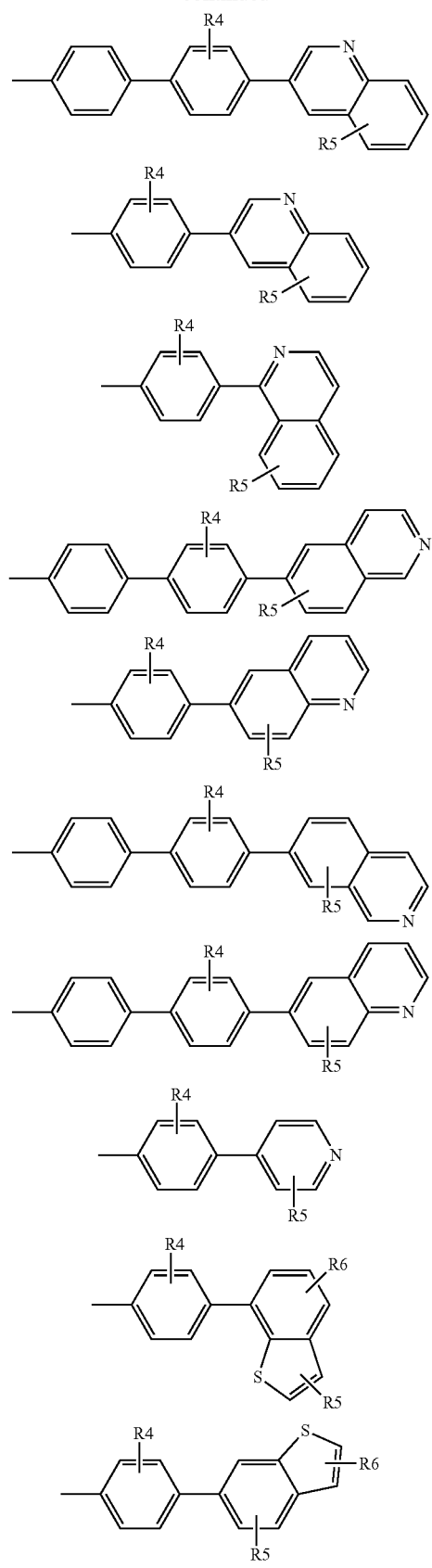

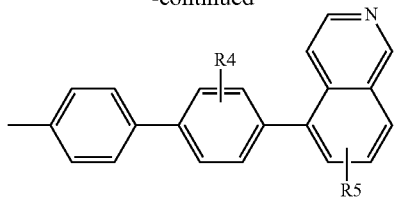
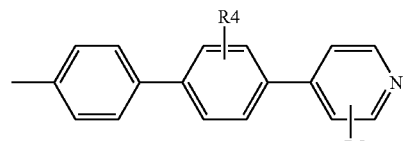
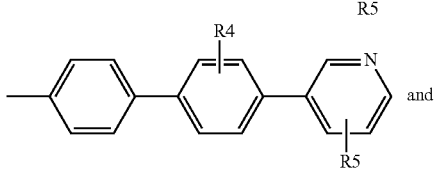
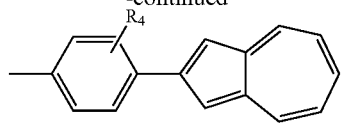
wherein $R_4$, $R_5$, $R_6$ are the same or different and are, at each occurrence, independently selected from H, F, $CH_3$, $CF_3$, aryl and alkyl.
In a more preferred embodiment of the thiophene- or selenophene-based material represented by the general formula IX, the material is selected from the group consisting of
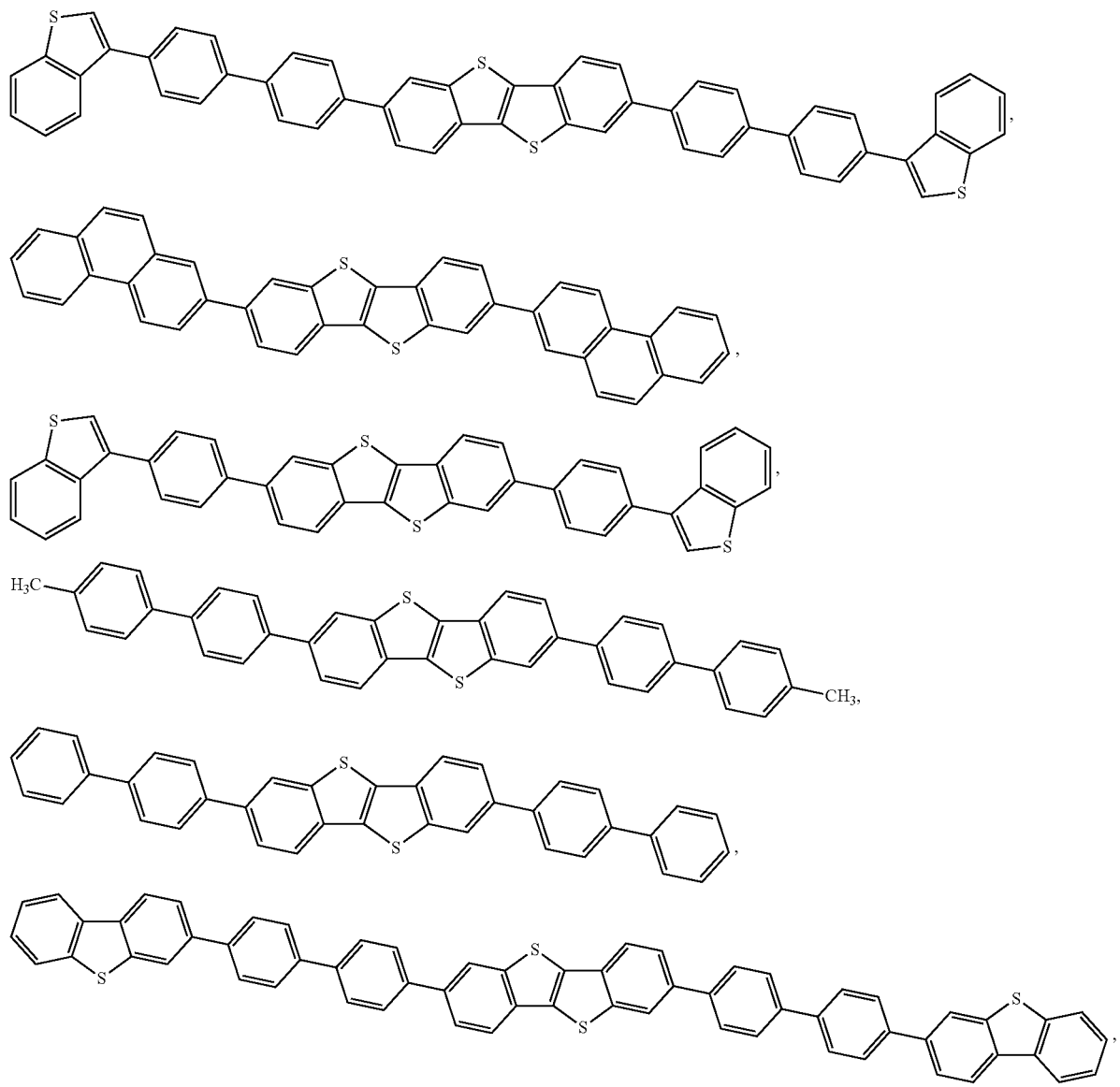

-continued
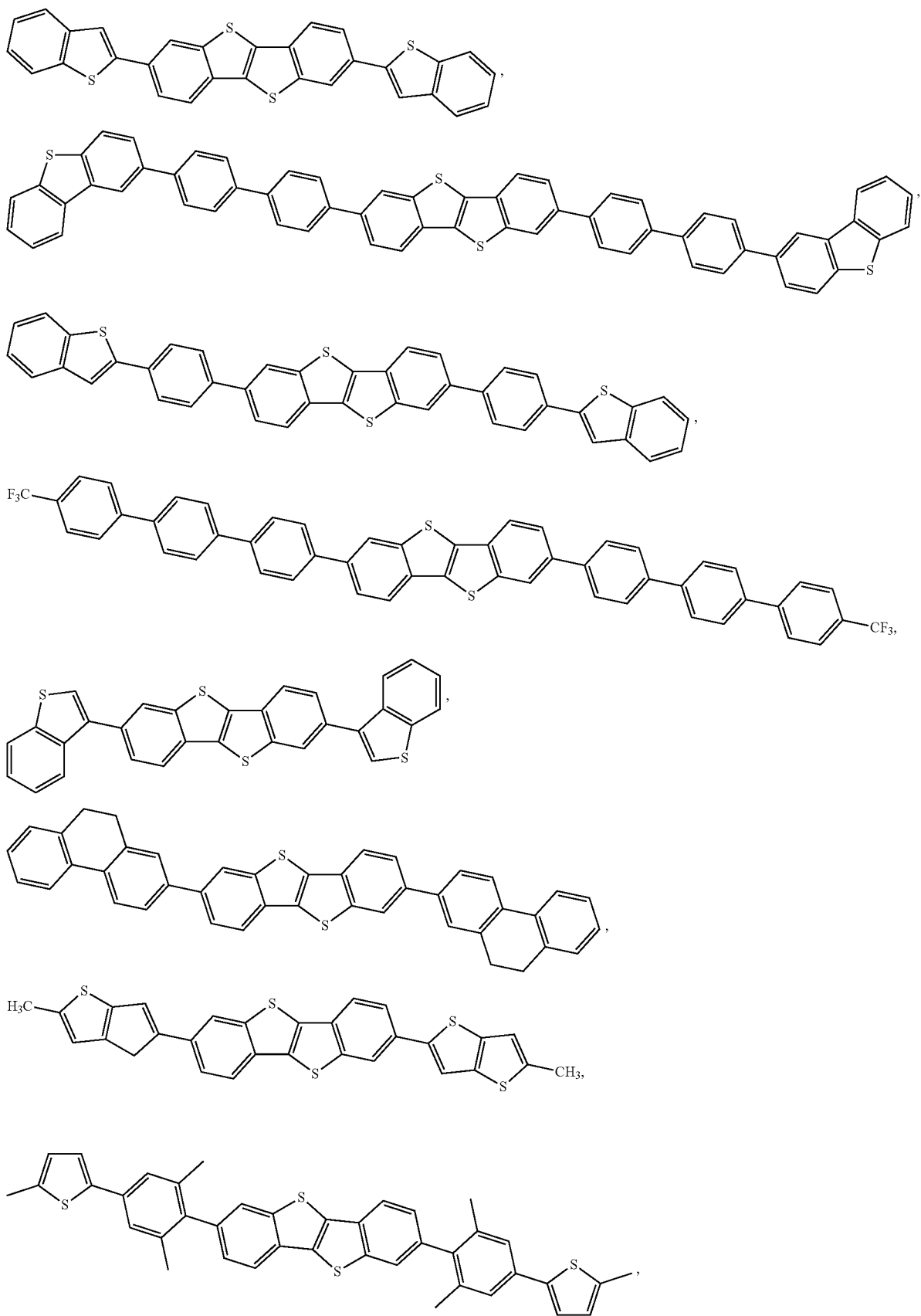

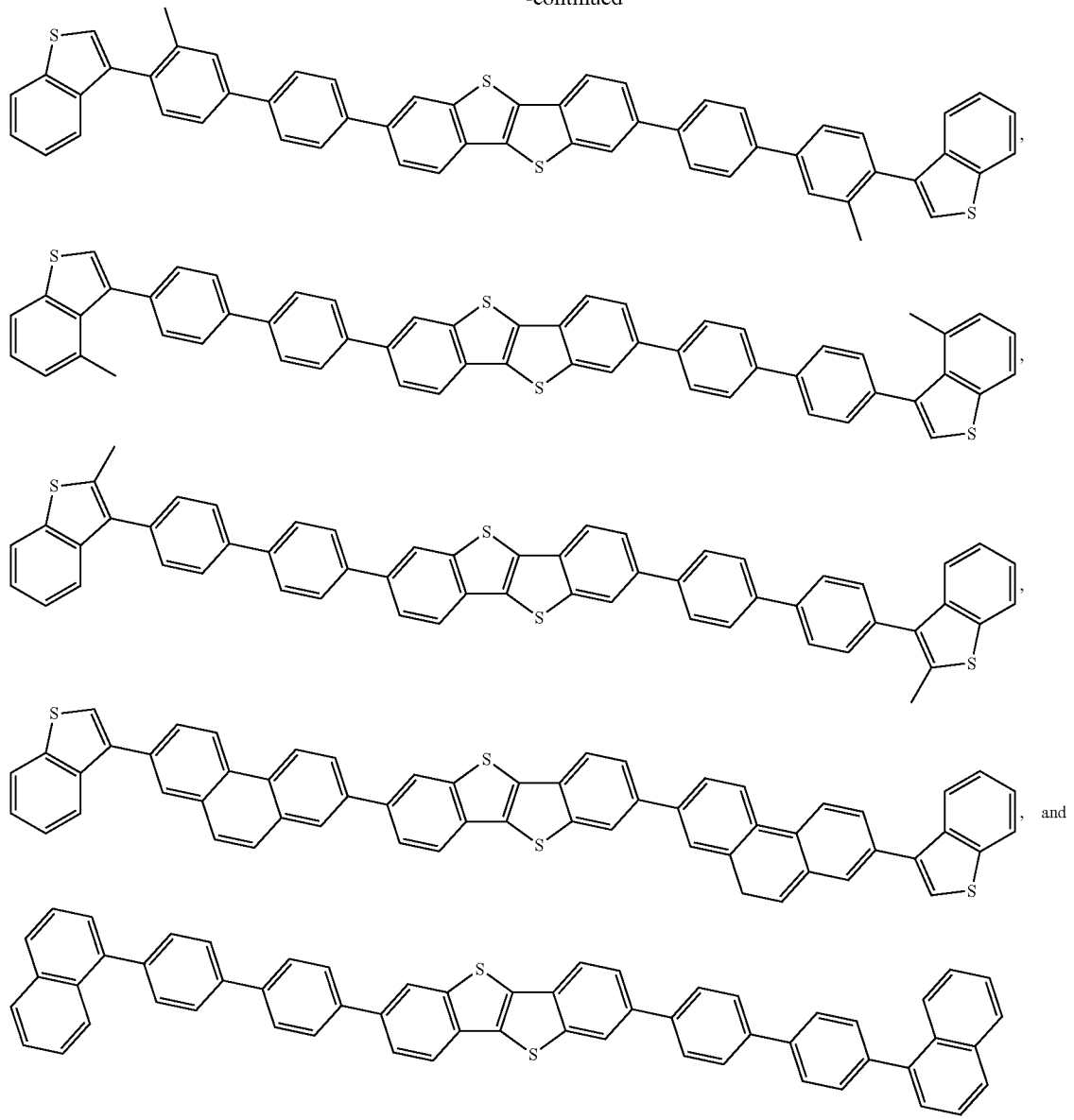

In one embodiment, the transparent P material of the present disclosure is a thiophene- or selenophene-based material represented by the general formula Xa

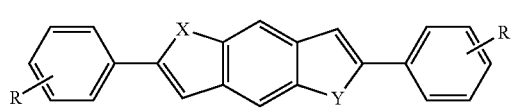

wherein,
X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl; and R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

In a preferred embodiment of the thiophene- or selenophene-based material represented by the general formula Xa,
X and Y are the same or different and are, at each occurrence, independently selected from S and Se.

In a preferred embodiment of the thiophene- or selenophene-based material represented by the general formula Xa, R is selected from
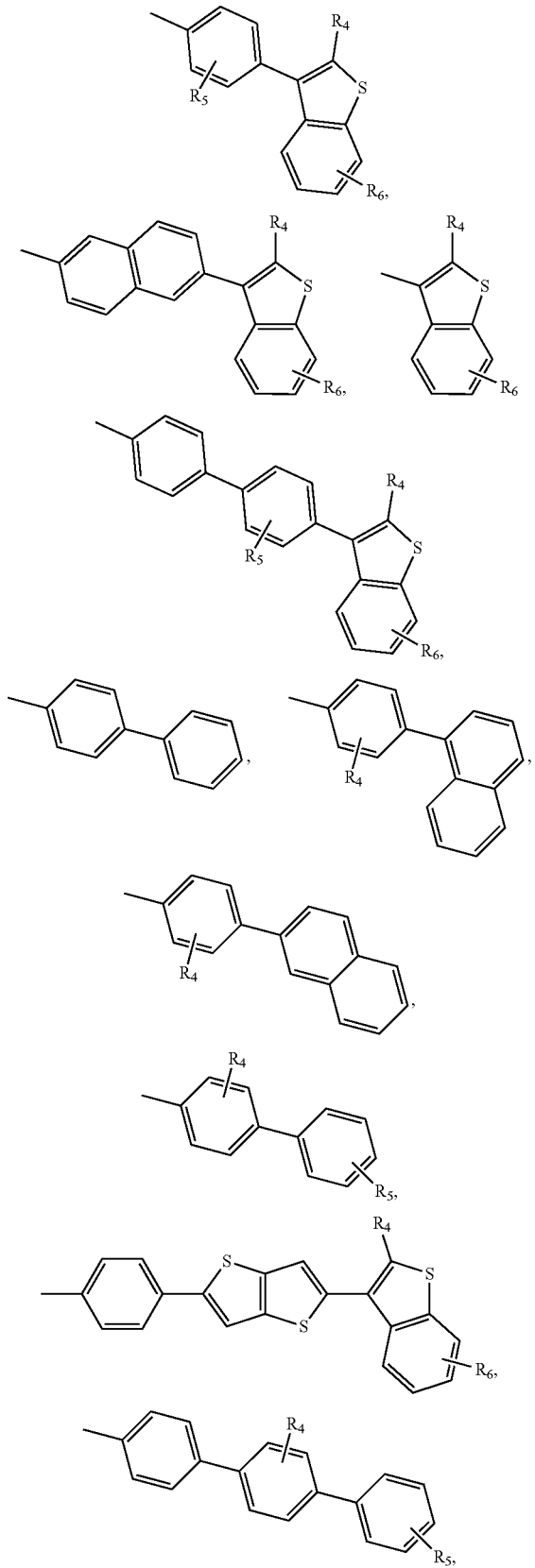
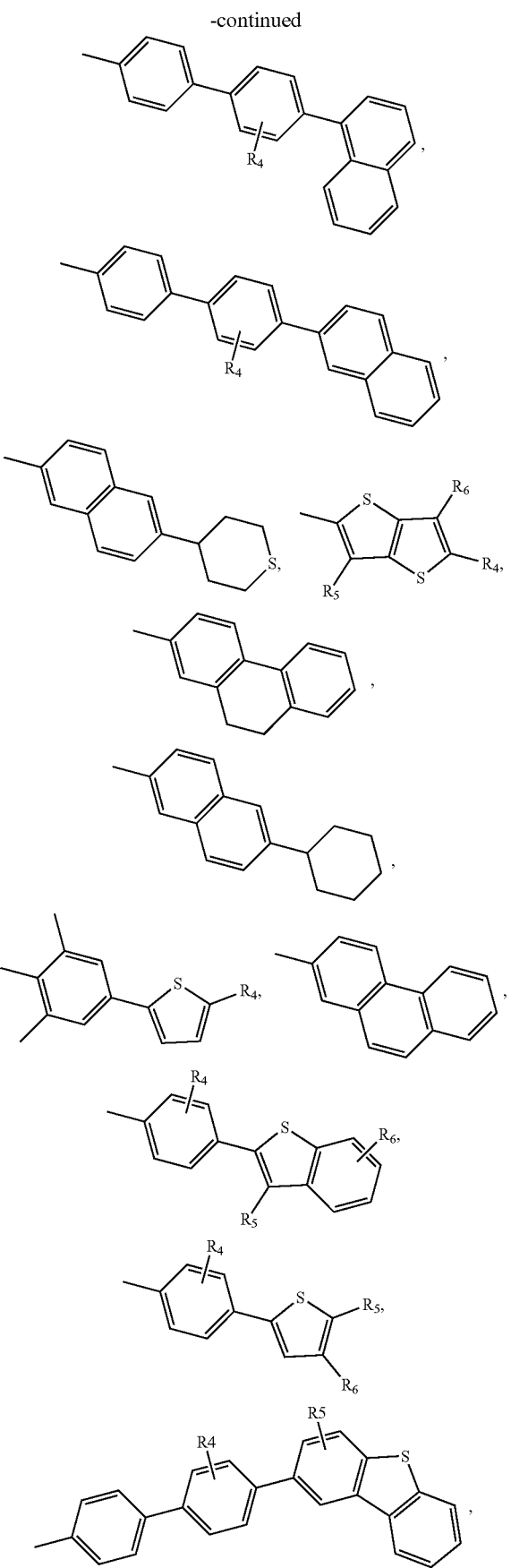

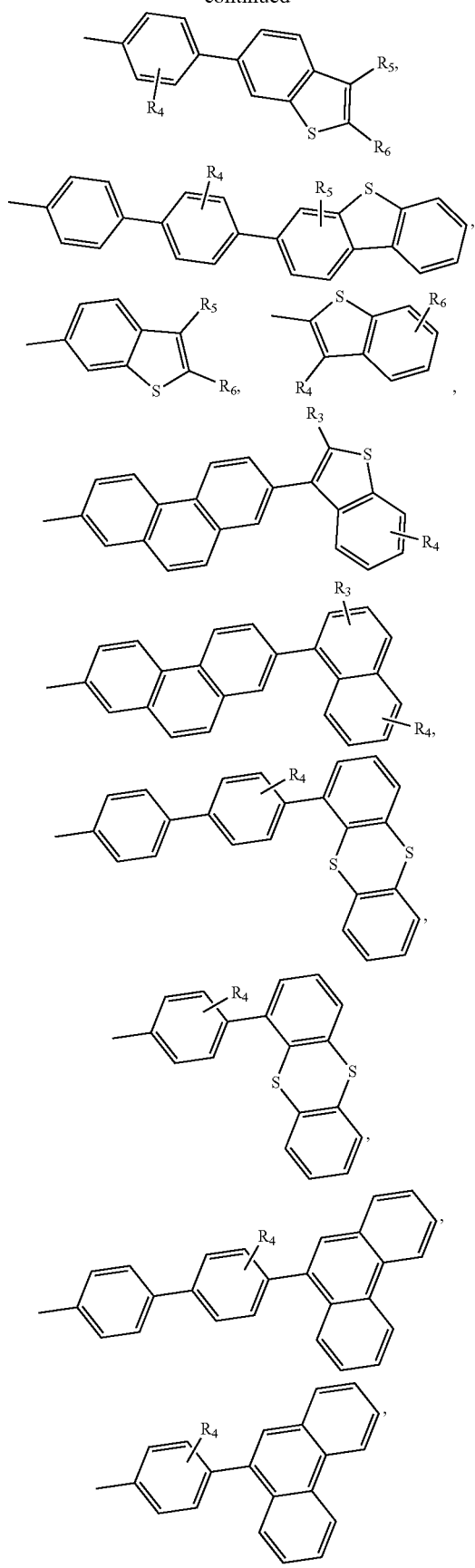
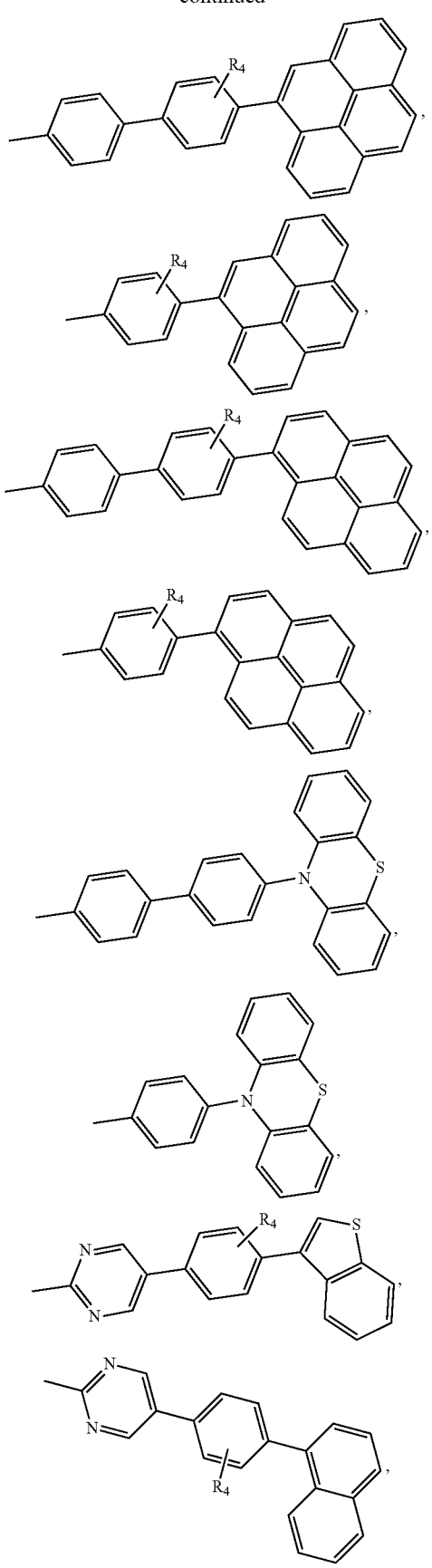

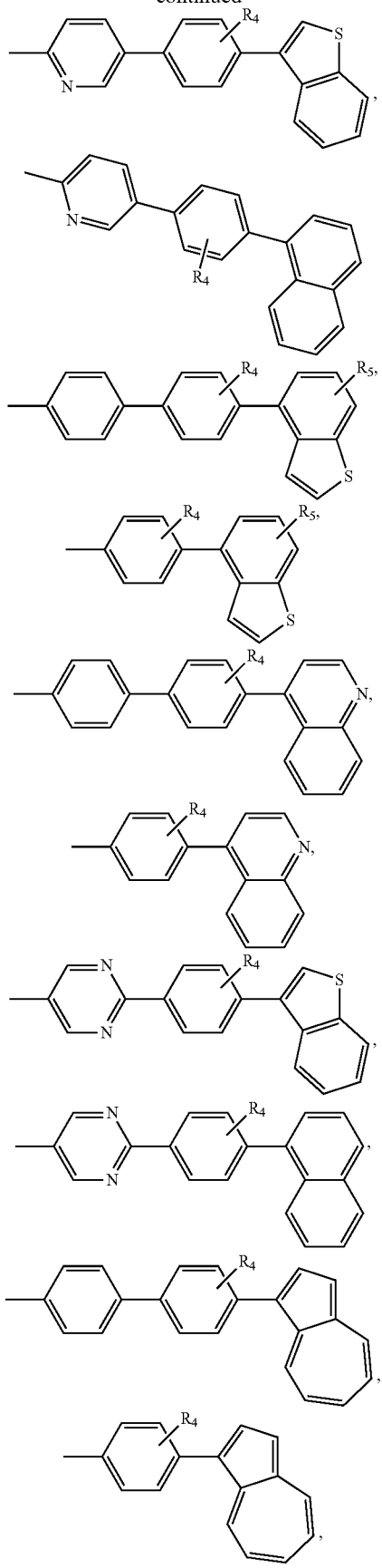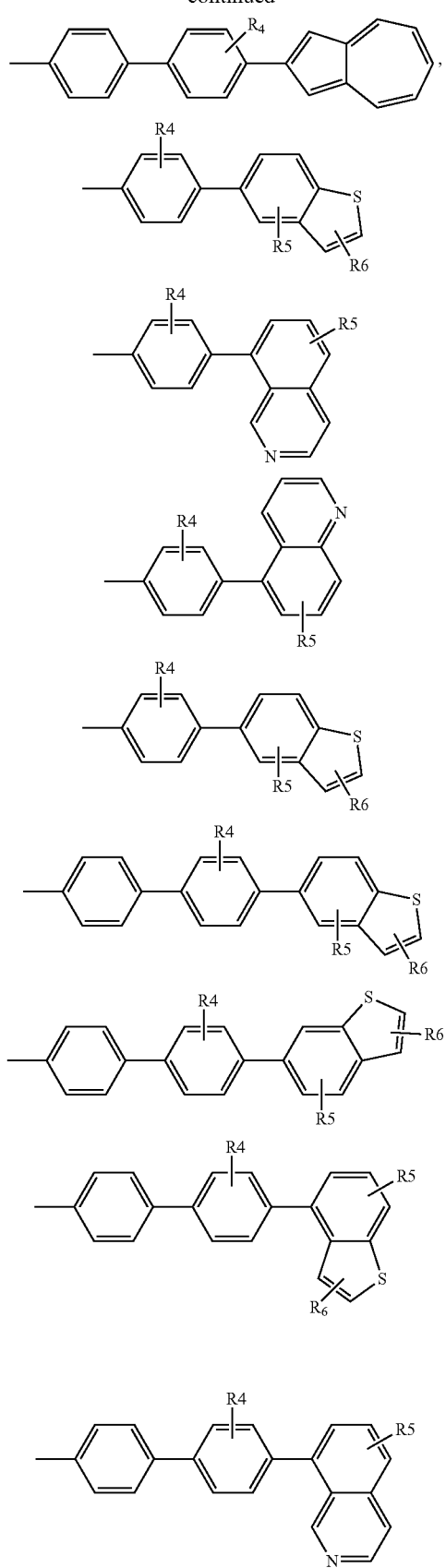

-continued
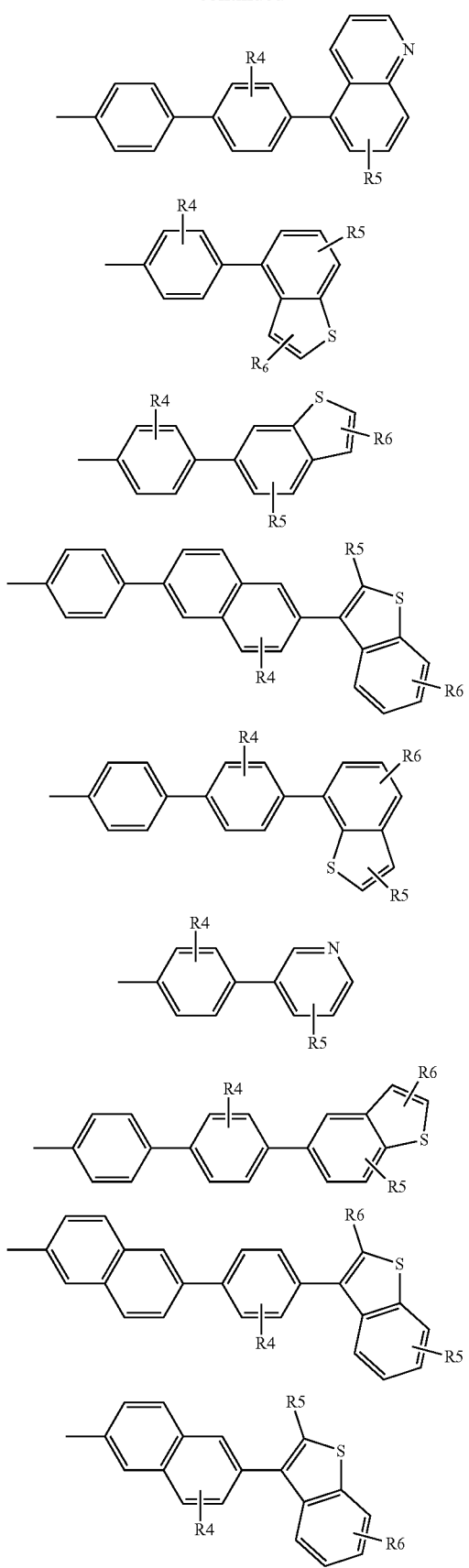
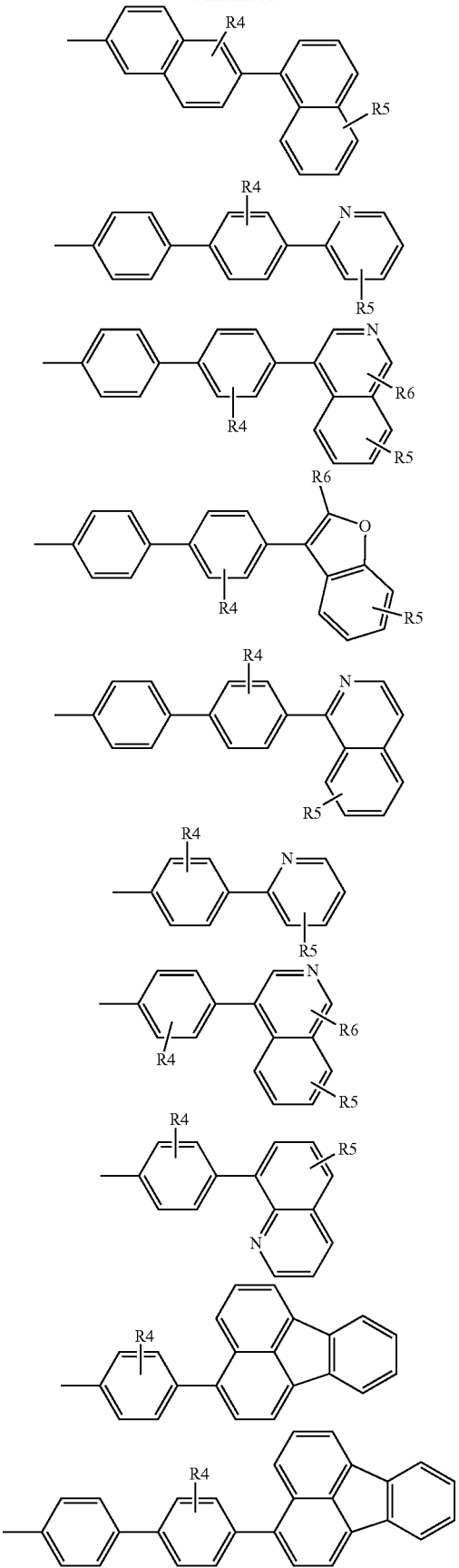

-continued
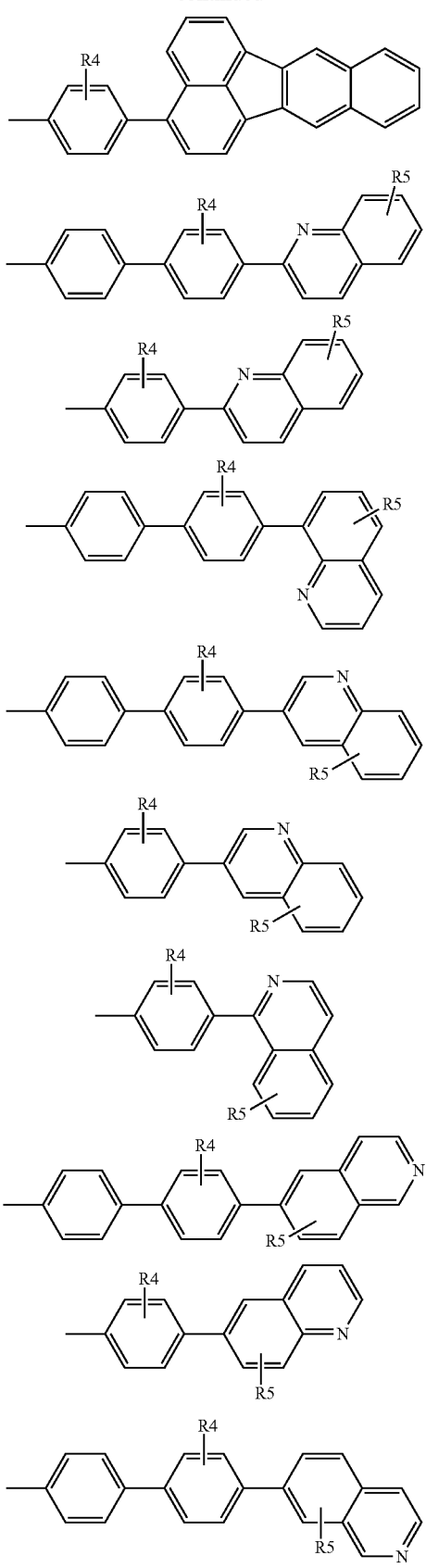
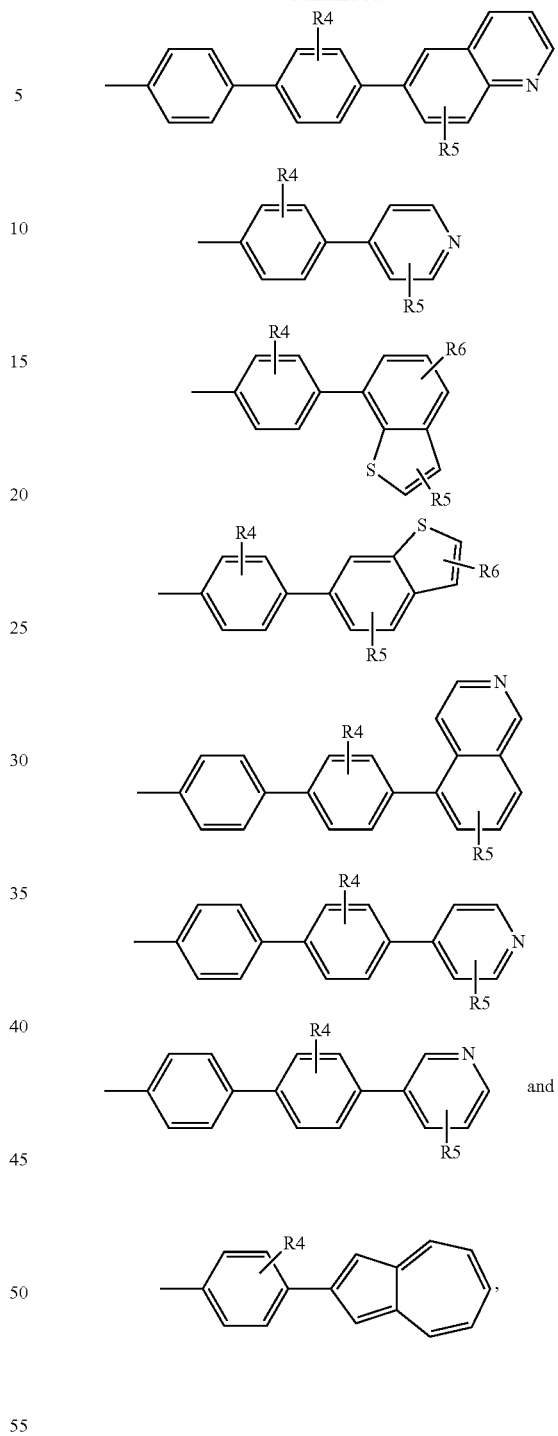
wherein $R_4$, $R_5$, $R_6$ are the same or different and are, at each occurrence, independently selected from H, F, $CH_3$, $CF_3$, aryl and alkyl.
In a preferred embodiment of the thiophene- or selenophene-based material represented by the general formula Xa,
X and Y are the same or different and are, at each occurrence, independently selected from S and Se; and R is selected from
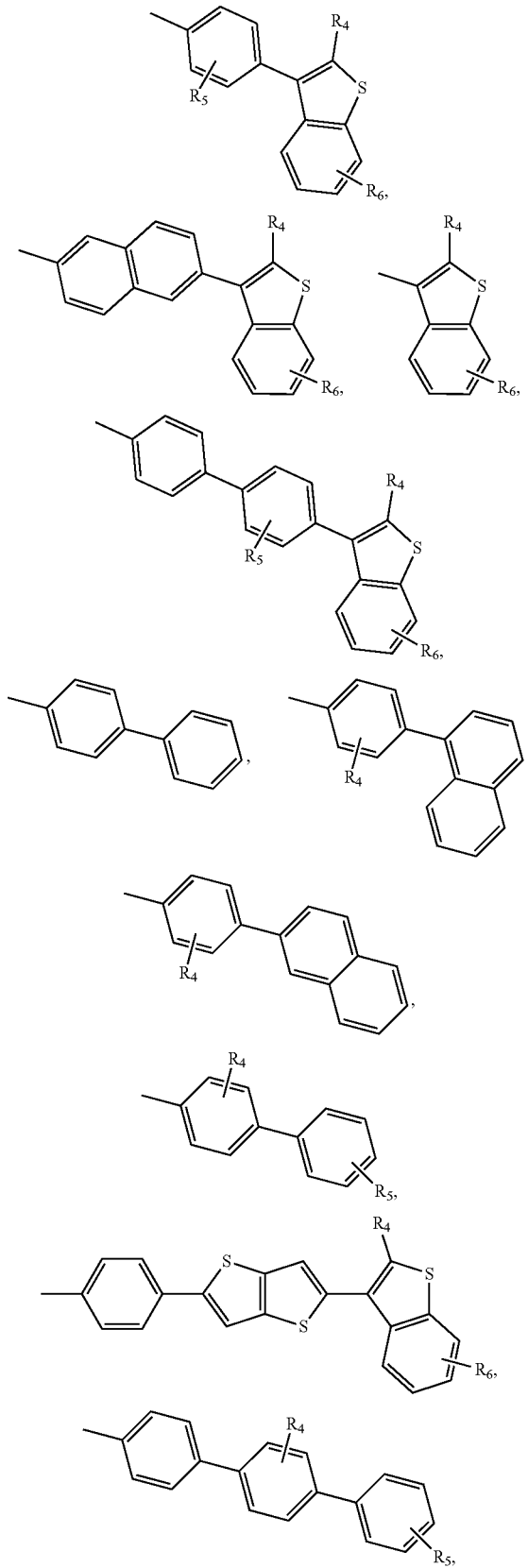
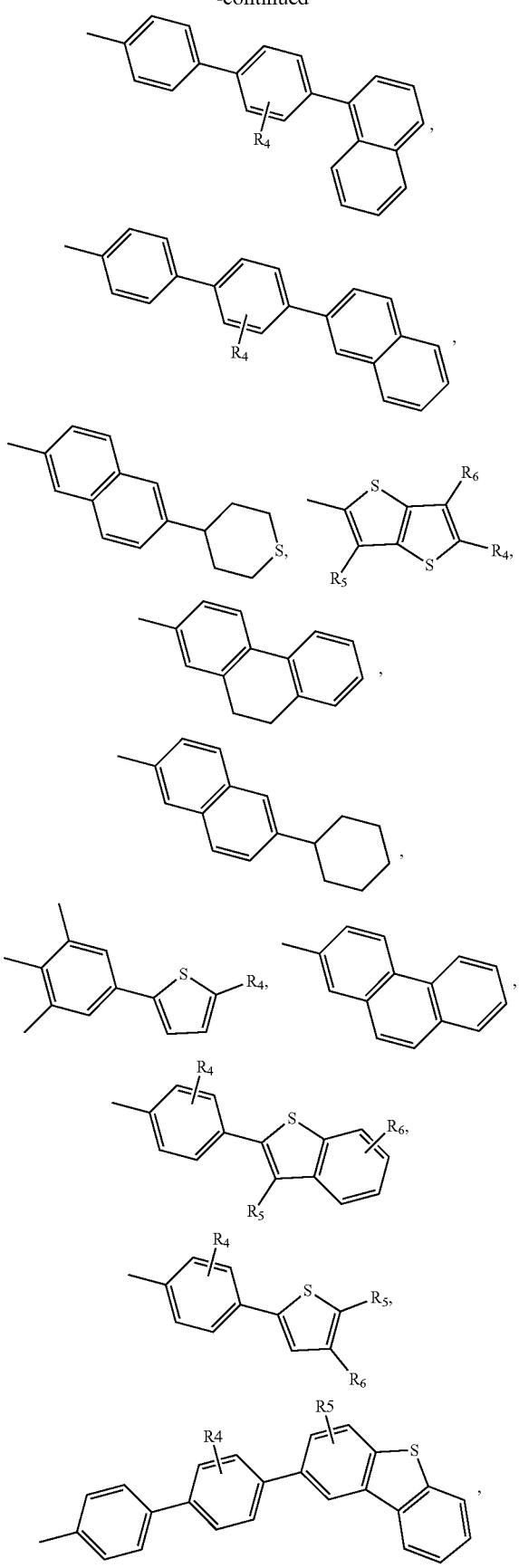

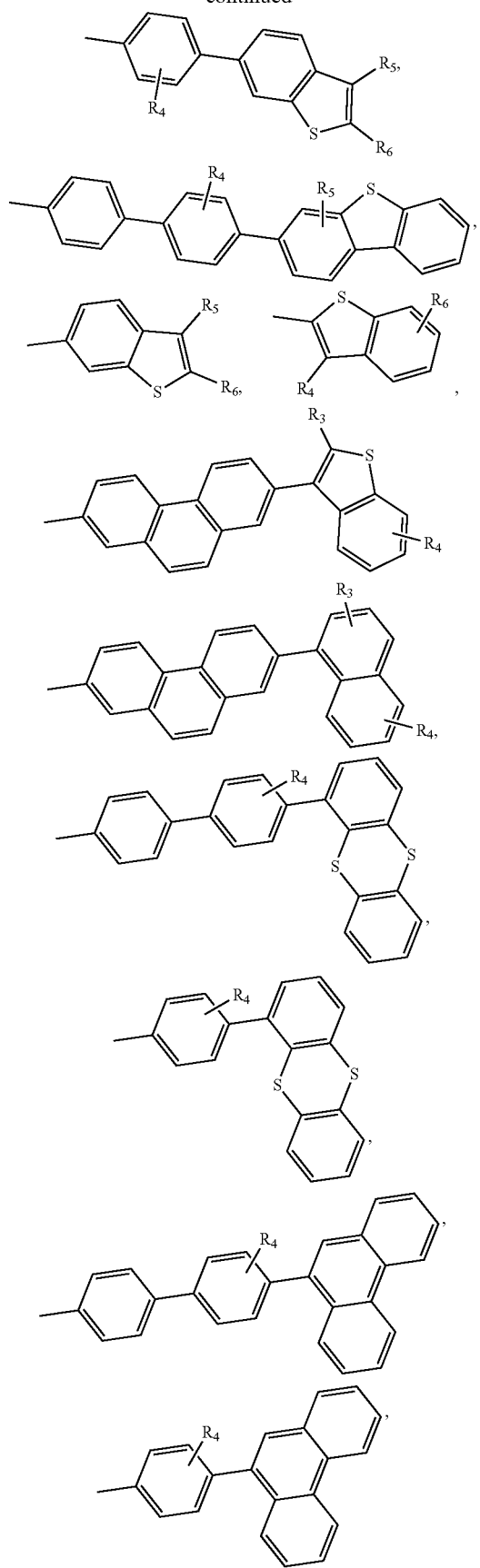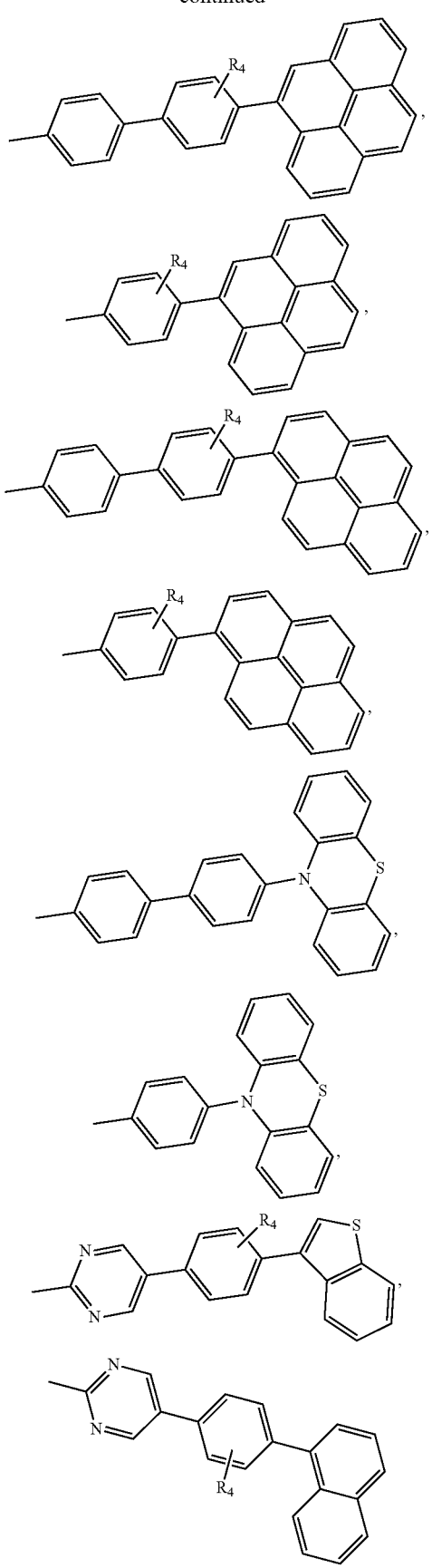

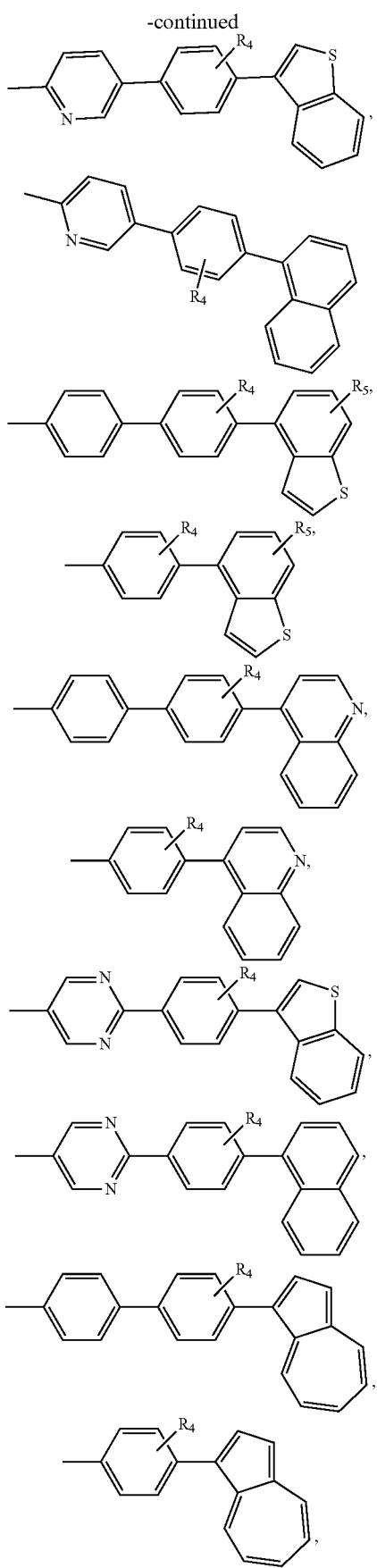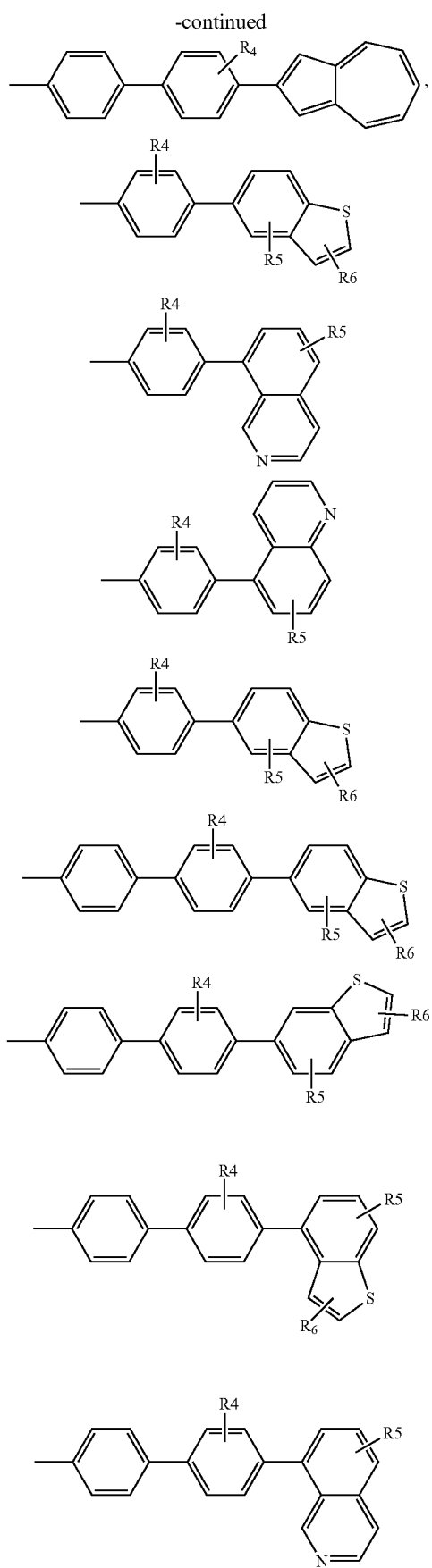

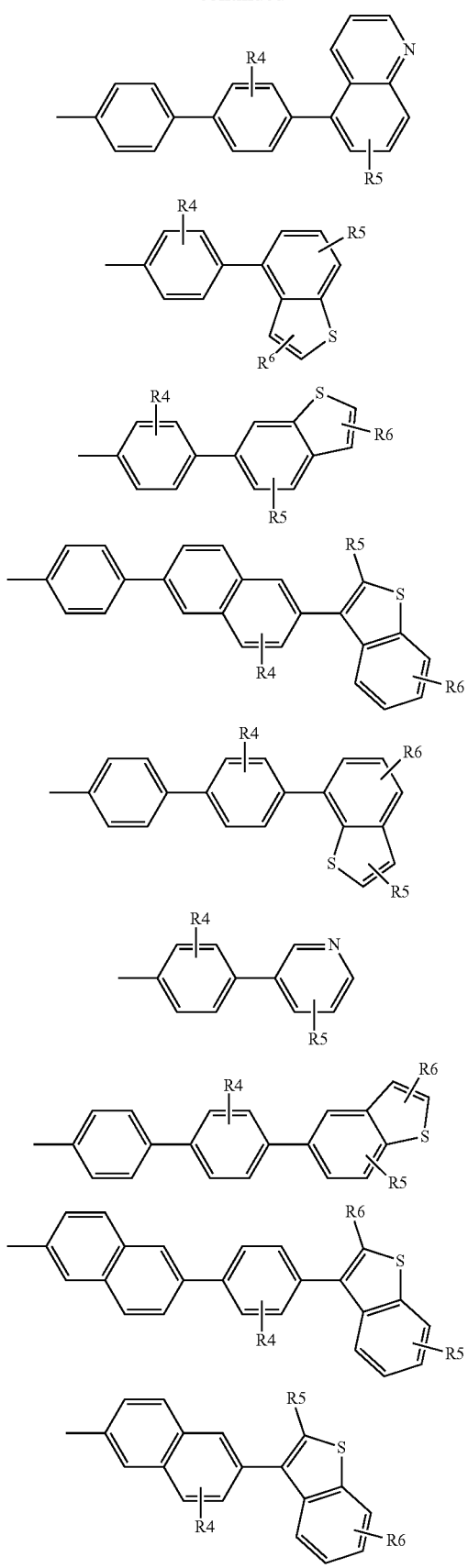
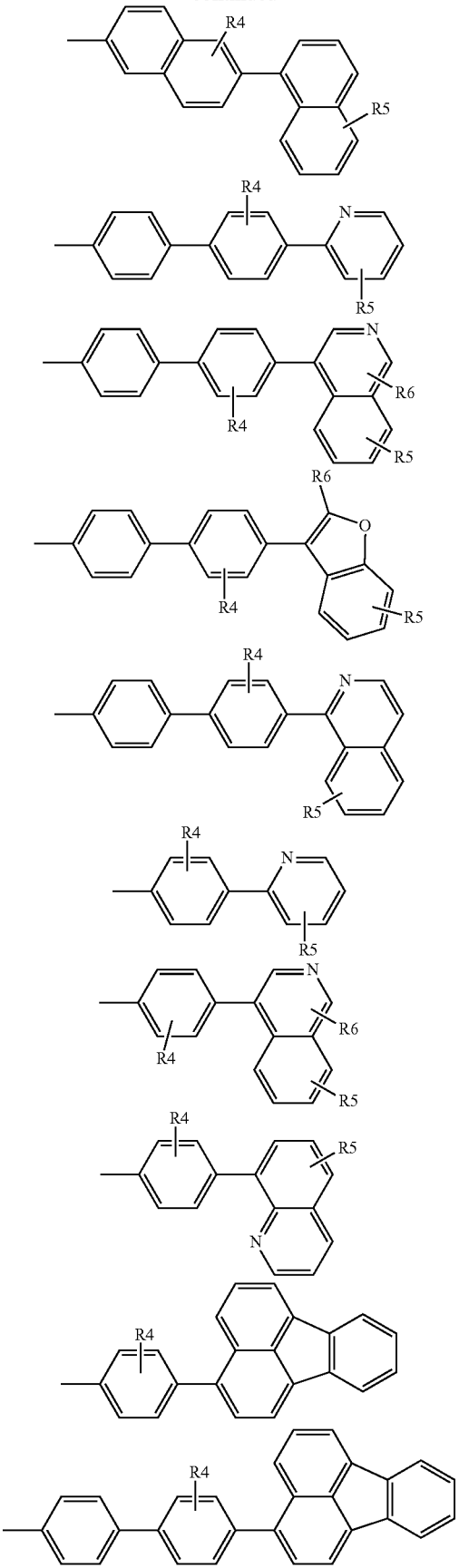

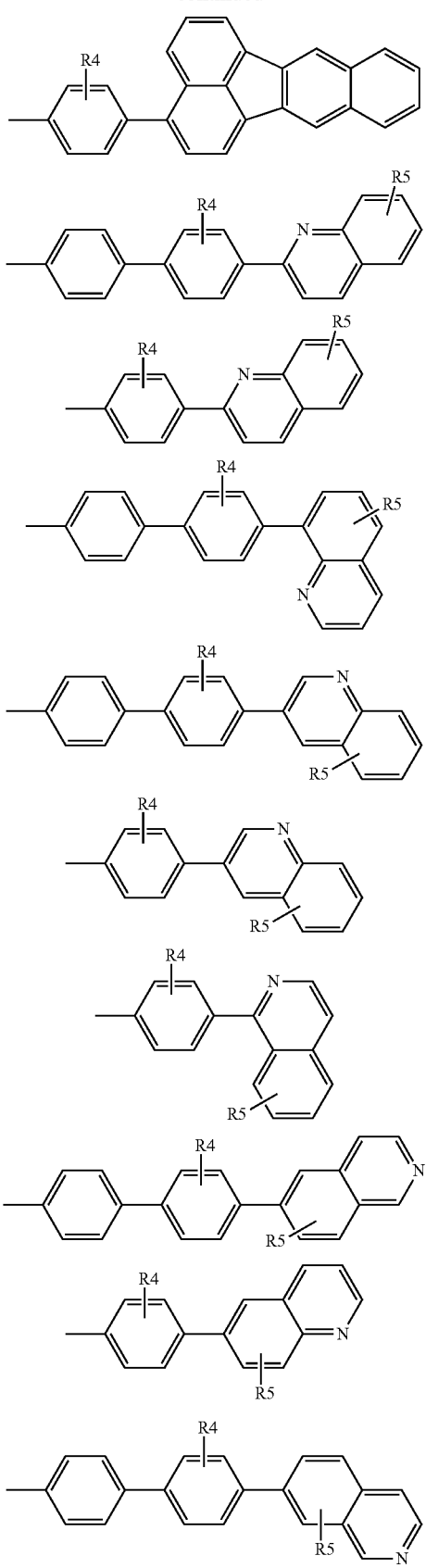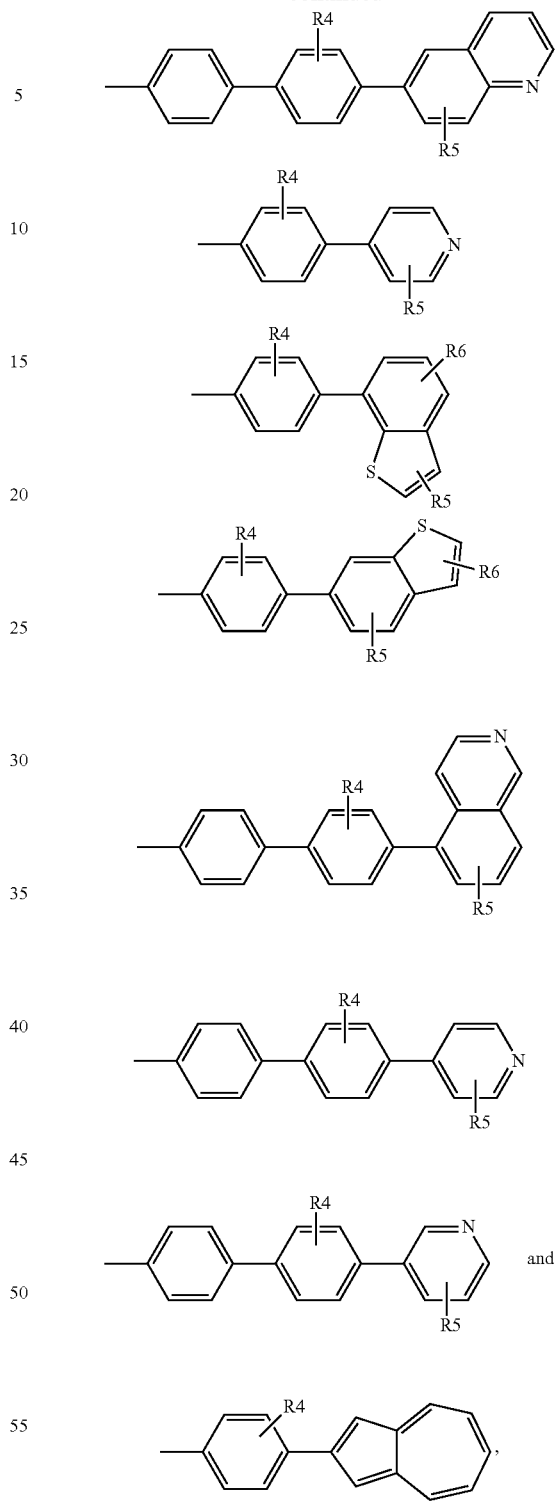
wherein $R_4$, $R_5$, $R_6$ are the same or different and are, at each occurrence, independently selected from H, F, $CH_3$, $CF_3$, aryl and alkyl.
In a more preferred embodiment of the thiophene- or selenophene-based material represented by the general formula Xa, the material is selected from the group consisting of

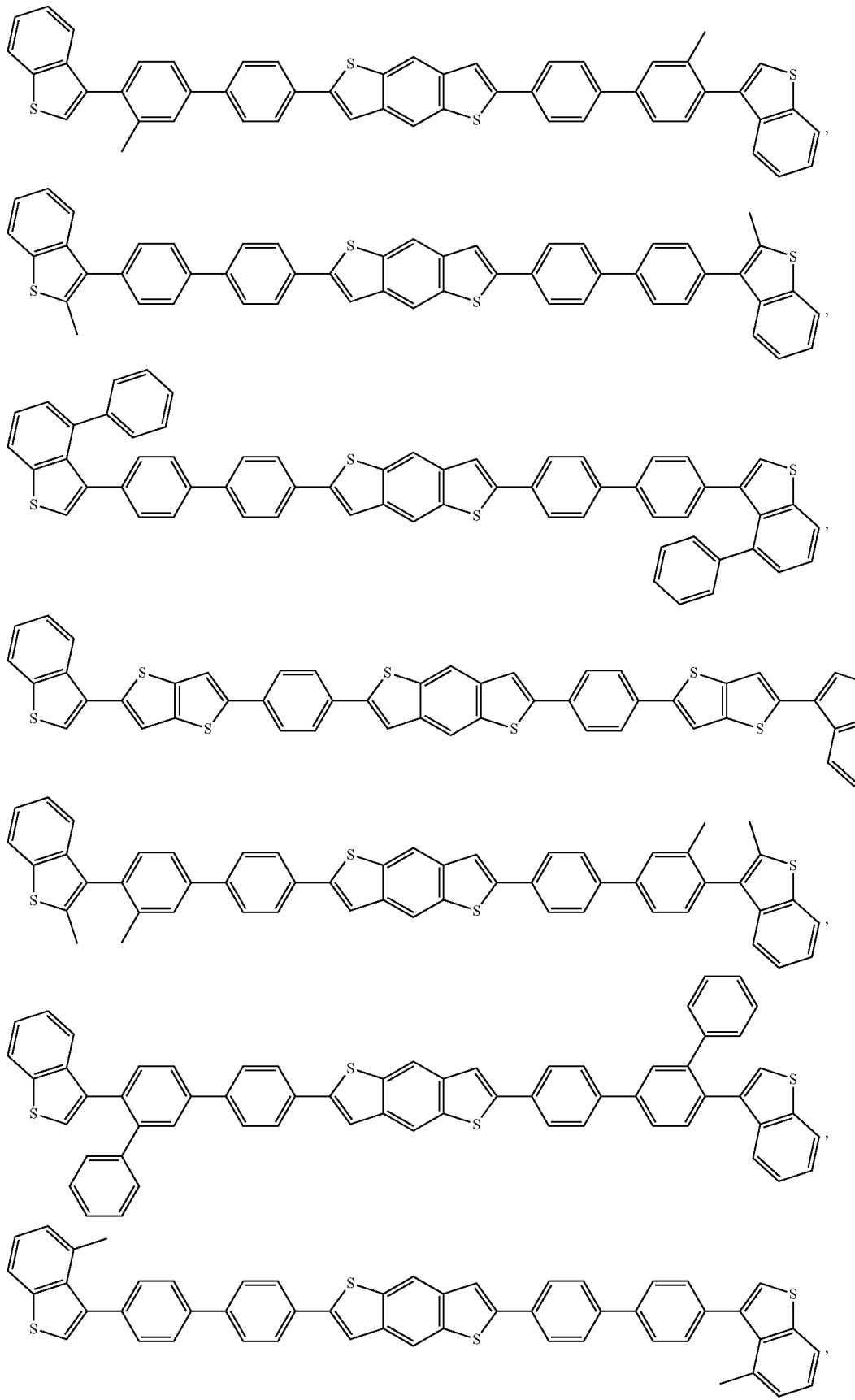

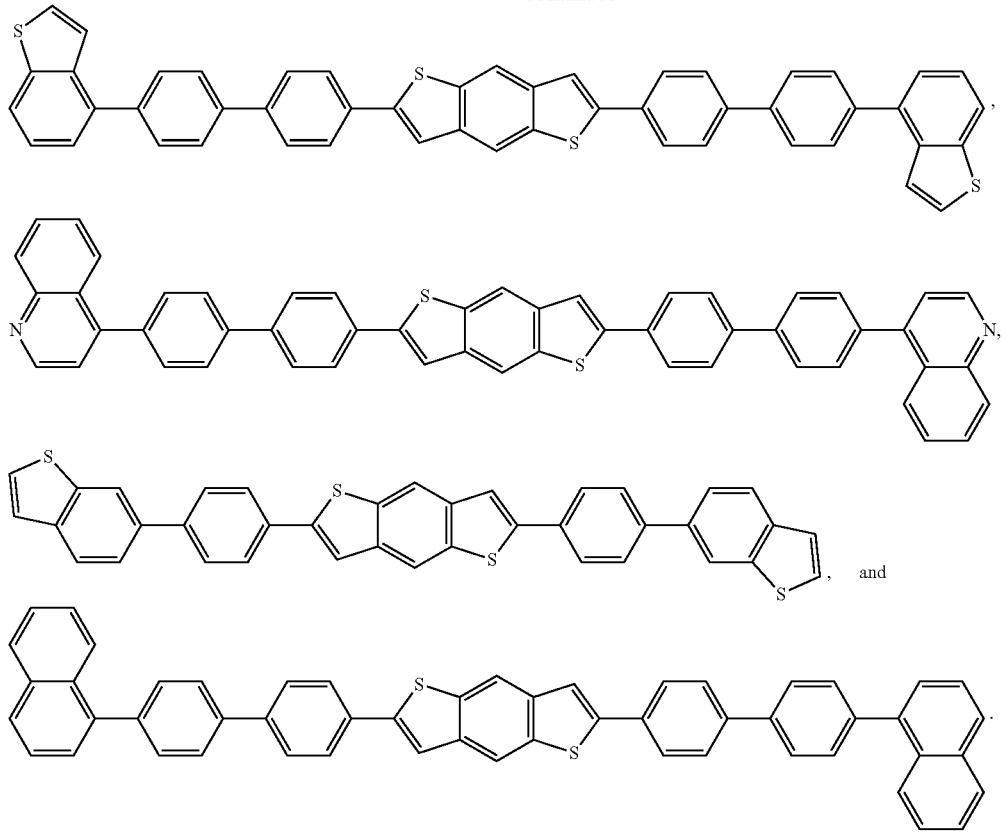

In one embodiment, the transparent P material of the present disclosure is a thiophene- or selenophene-based material represented by the general formula Xb

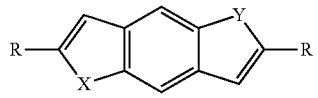

wherein,

X and Y are the same or different and are independently, at each occurrence, selected from $CR_2$, S, O, Se, N—R and Si—$R_2$, wherein $R_2$ is selected from H, $CH_3$, $CF_3$, phenyl, alkyl and aryl; and R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

In a preferred embodiment of thiophene- or selenophene-based material represented by the general formula Xb, X and Y are the same or different and are, at each occurrence, independently selected from S and Se.

In a preferred embodiment of thiophene- or selenophene-based material represented by the general formula Xb, R is selected from

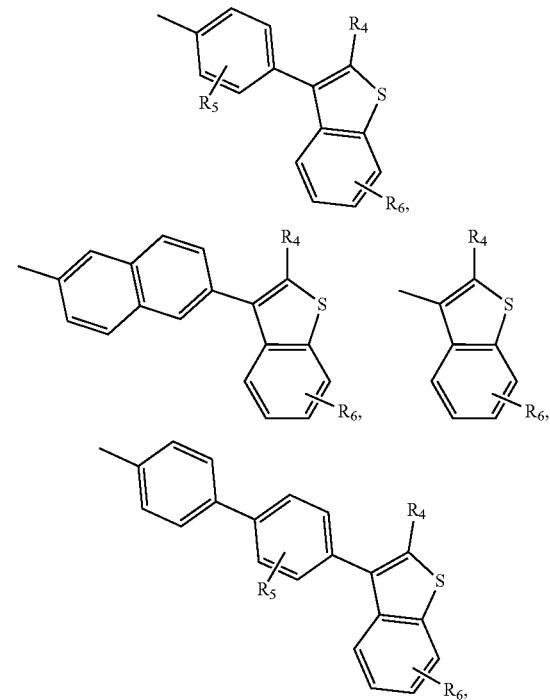

-continued
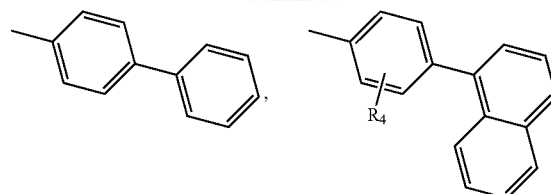
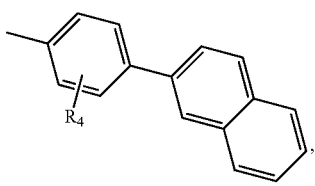
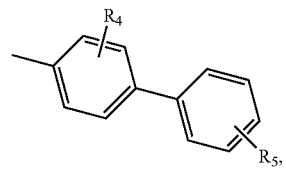
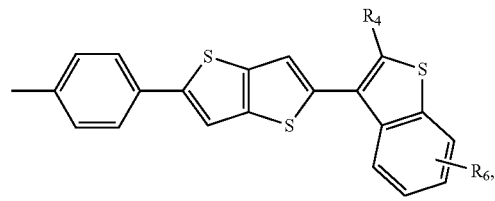
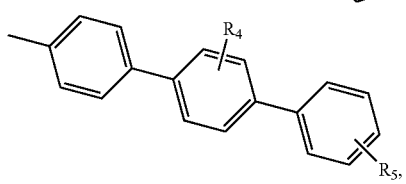
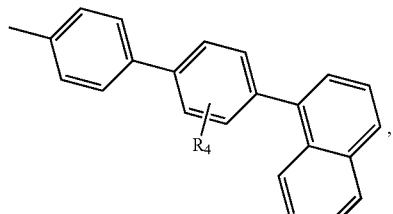
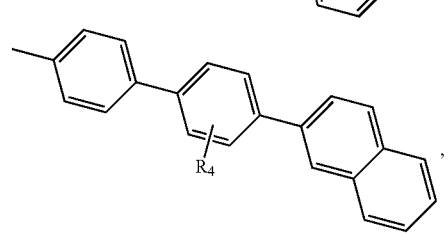
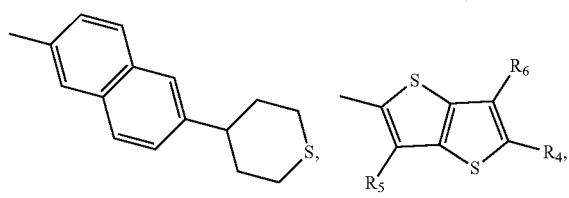
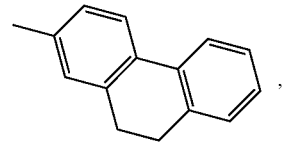
-continued
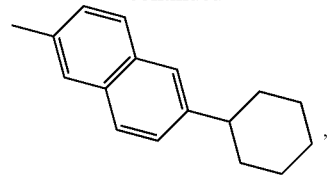
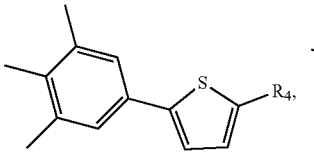
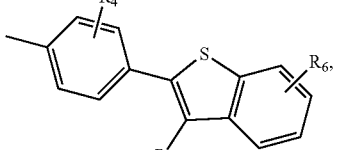
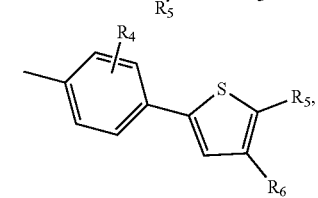
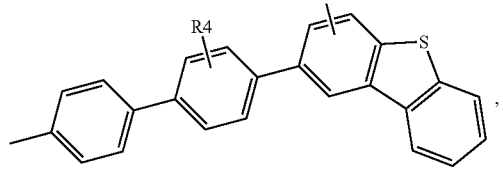
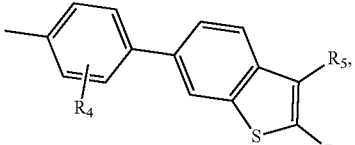
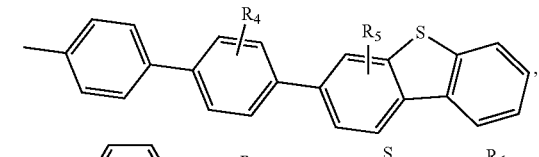
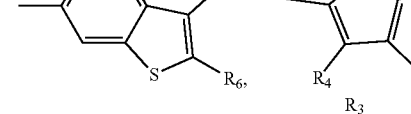
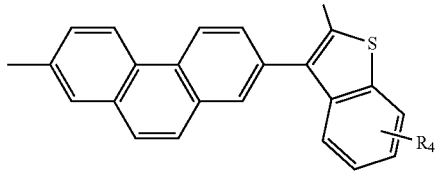
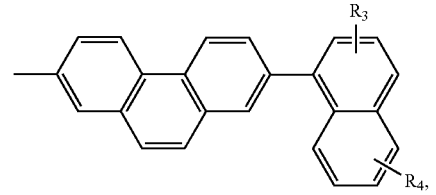

59
-continued
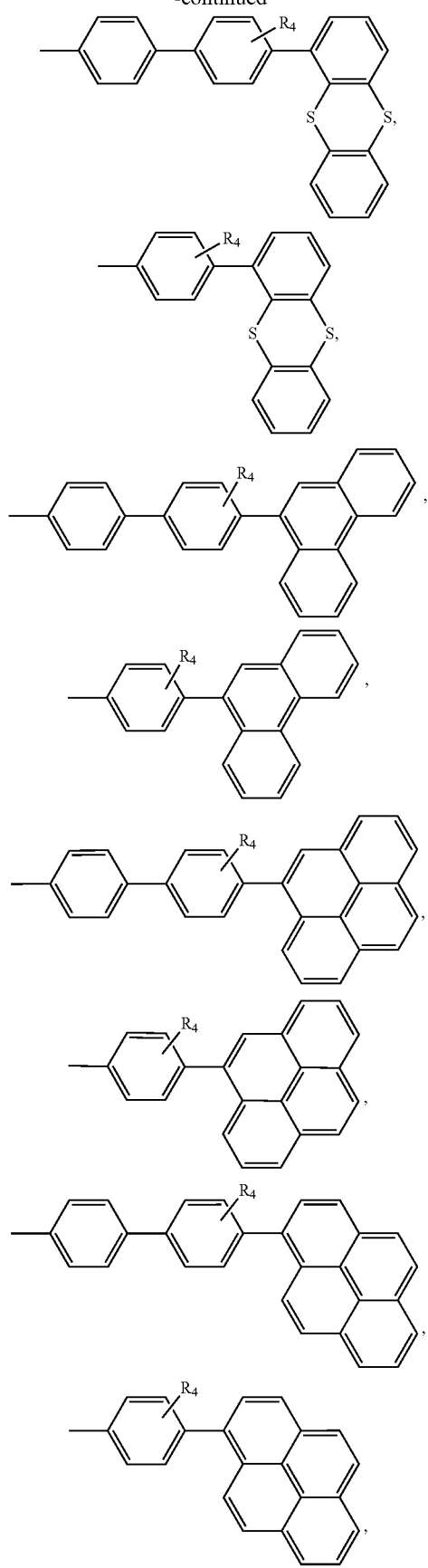
60
-continued
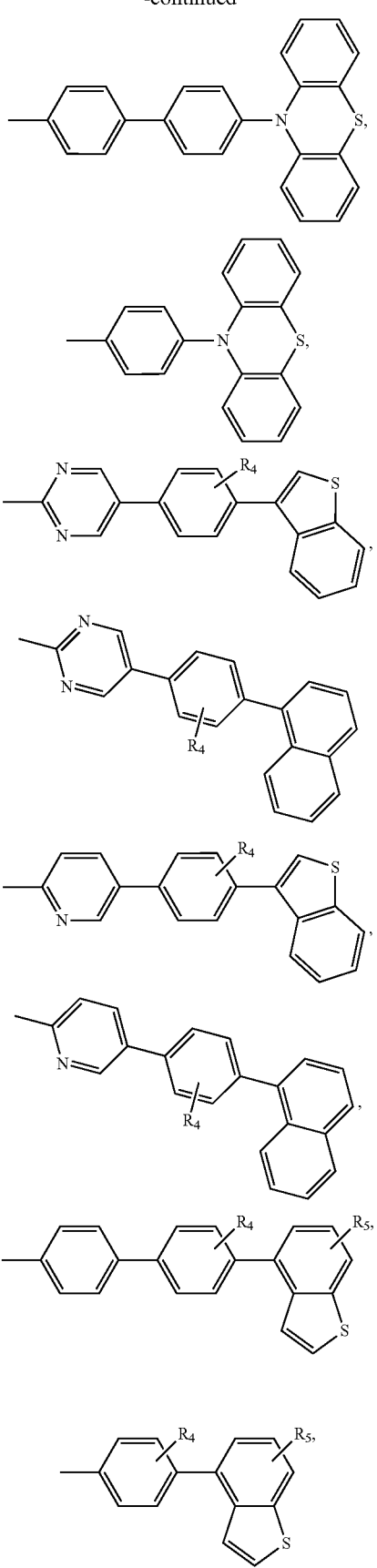

-continued
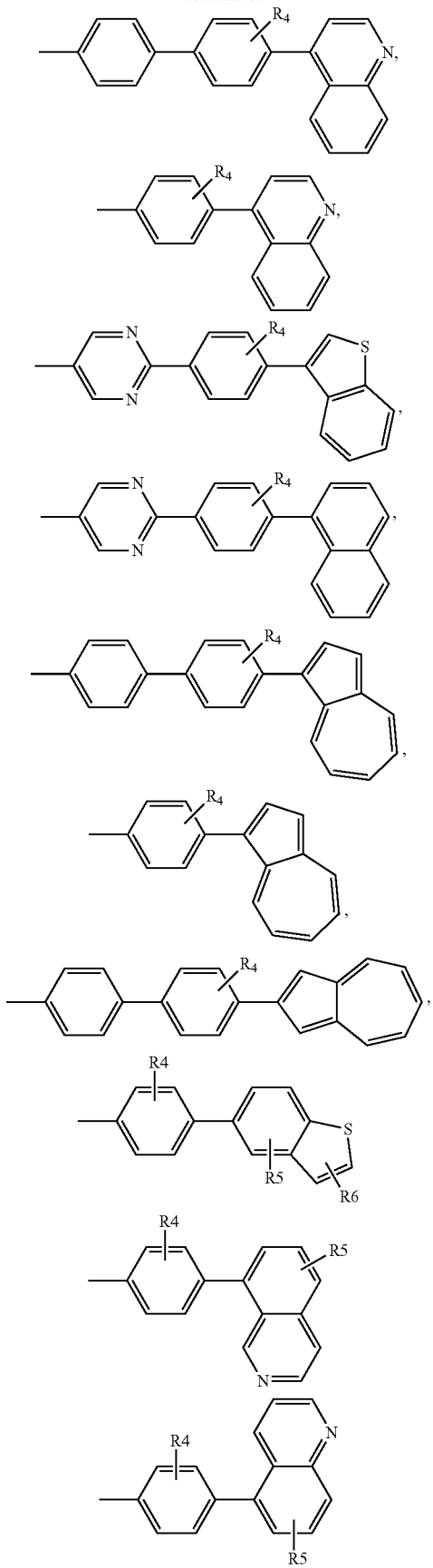
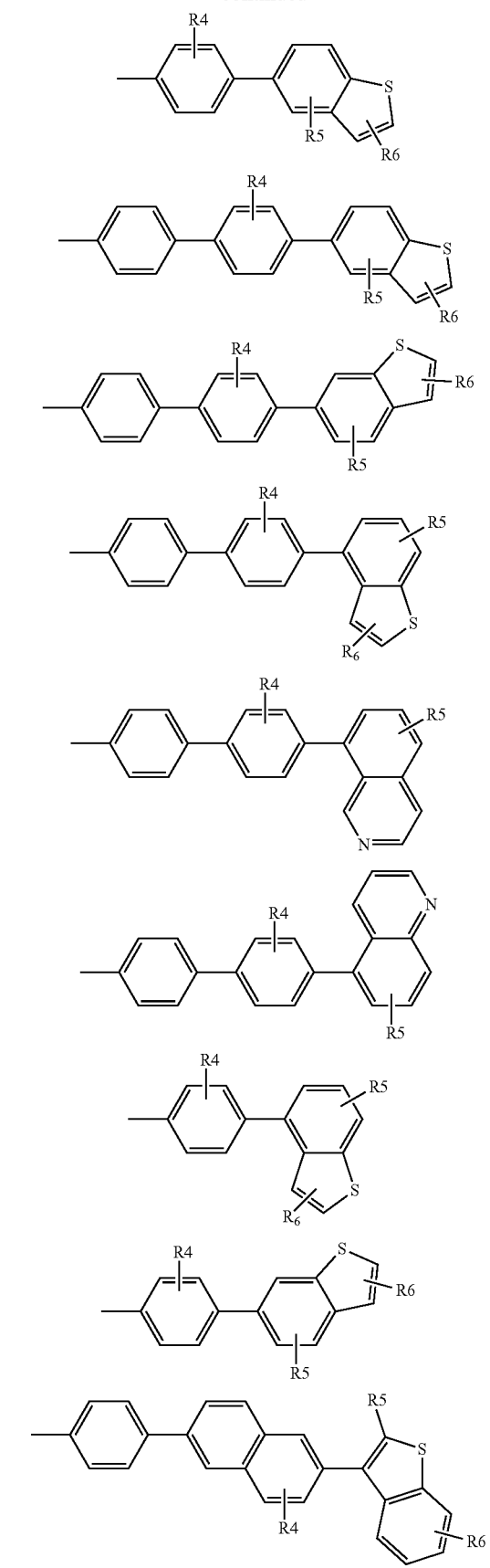

-continued
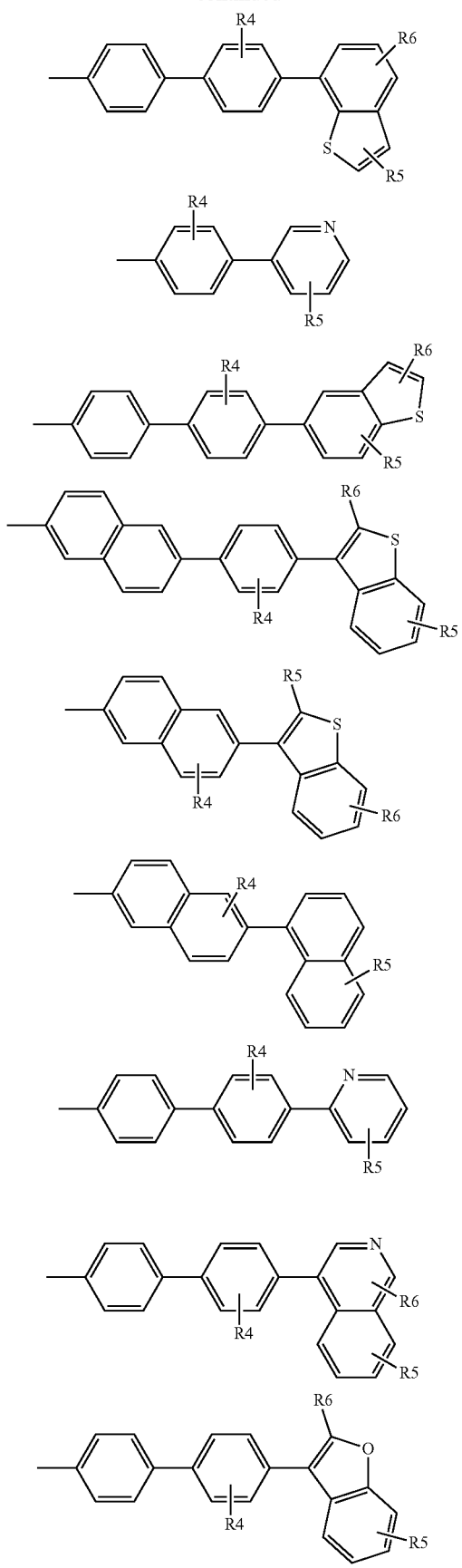
-continued
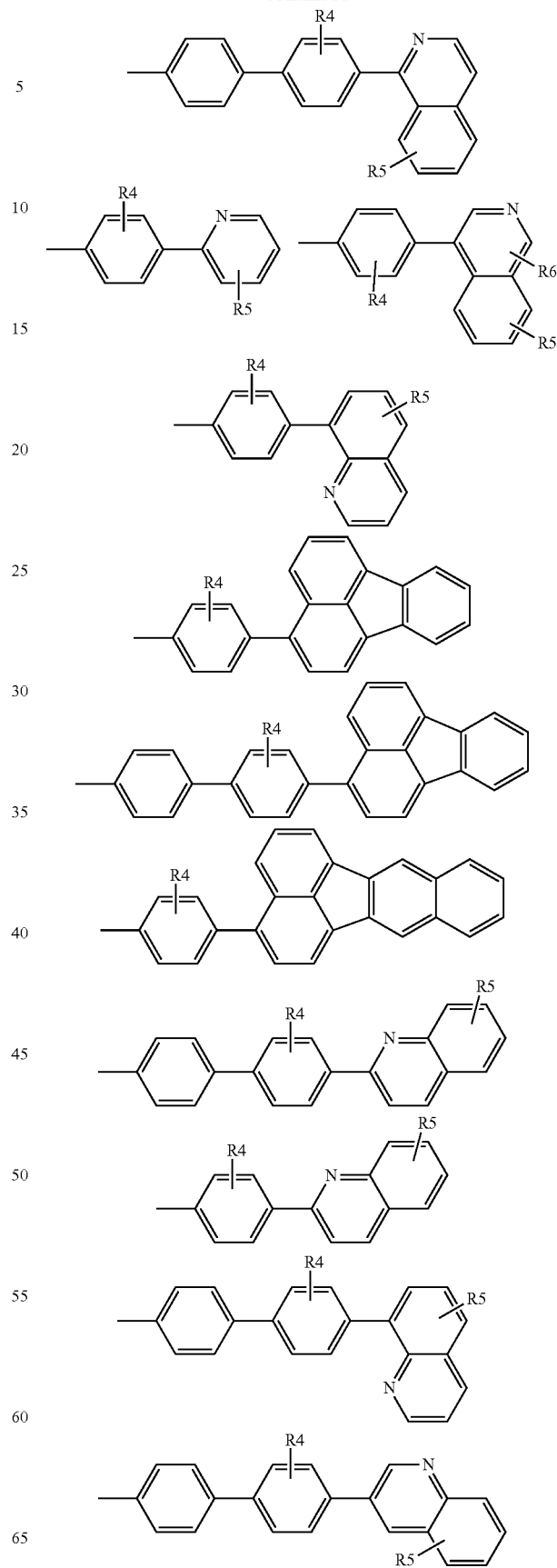

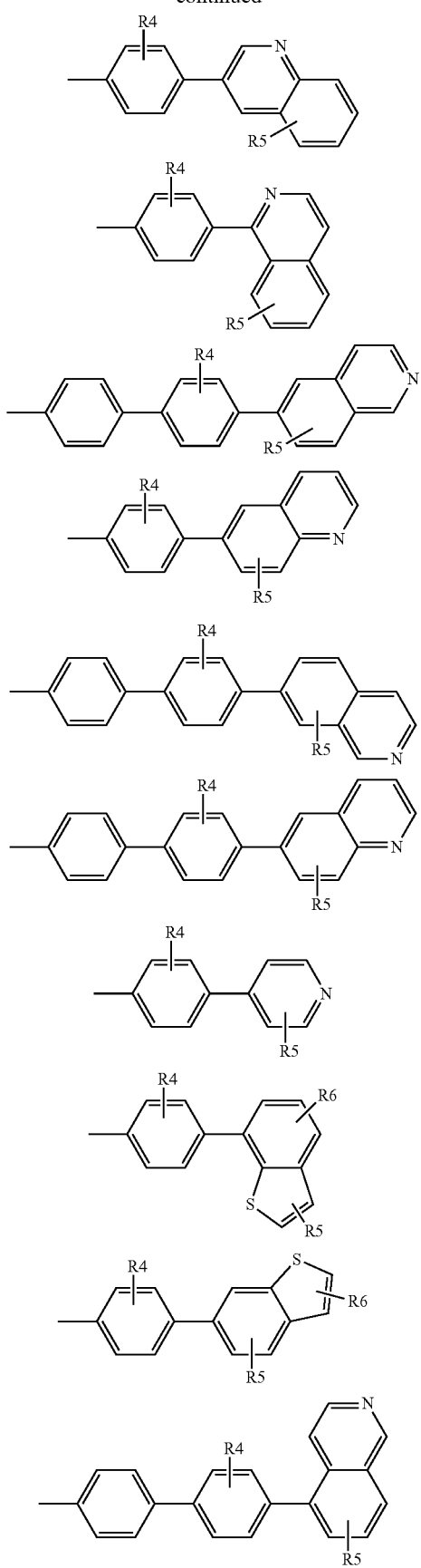
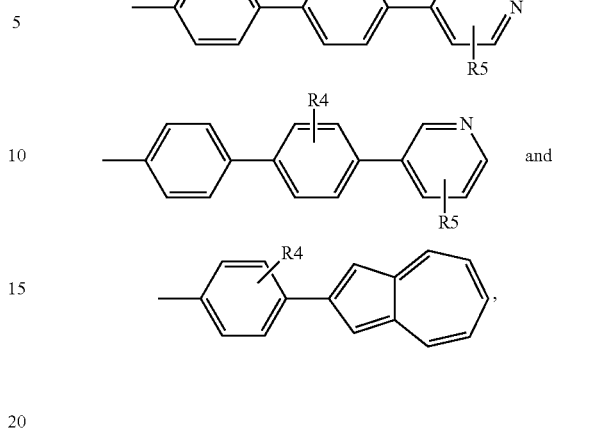
wherein $R_4$, $R_5$, $R_6$ are the same or different and are, at each occurrence, independently selected from H, F, $CH_3$, $CF_3$, aryl and alkyl.
In a preferred embodiment of thiophene- or selenophene-based material represented by the general formula Xb,
X and Y are the same or different and are, at each occurrence, independently selected from S and Se; and
R is selected from
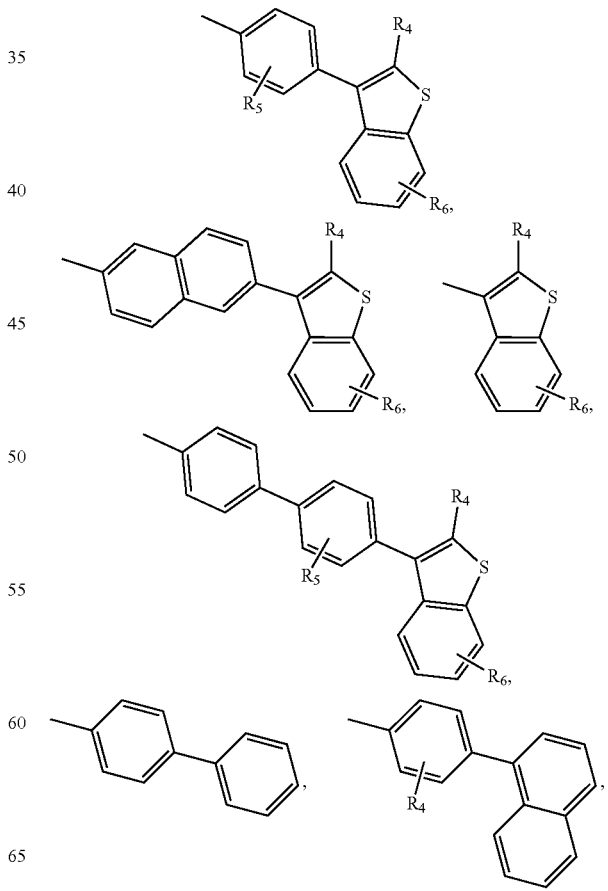

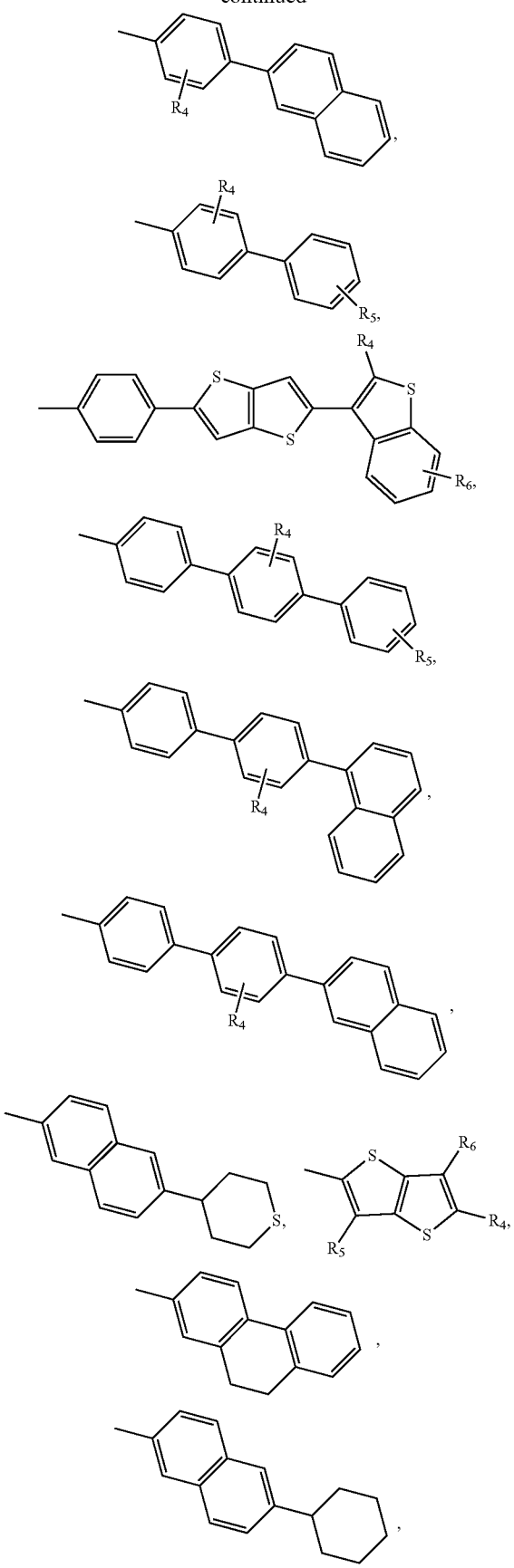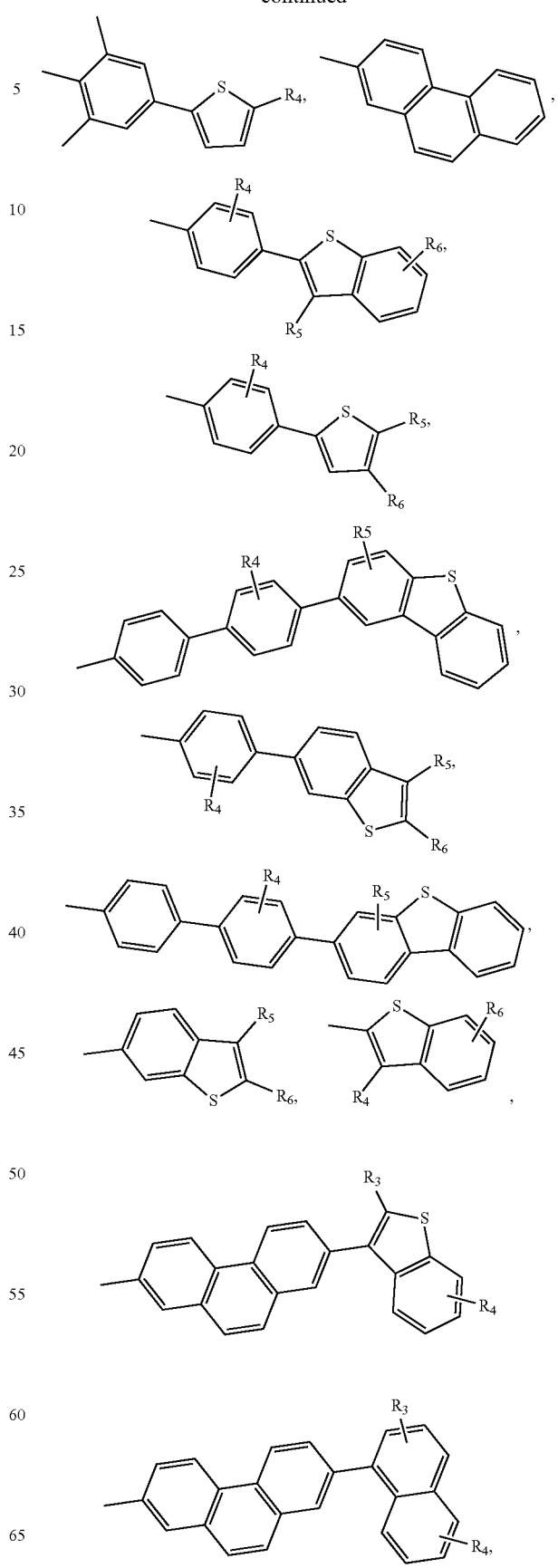

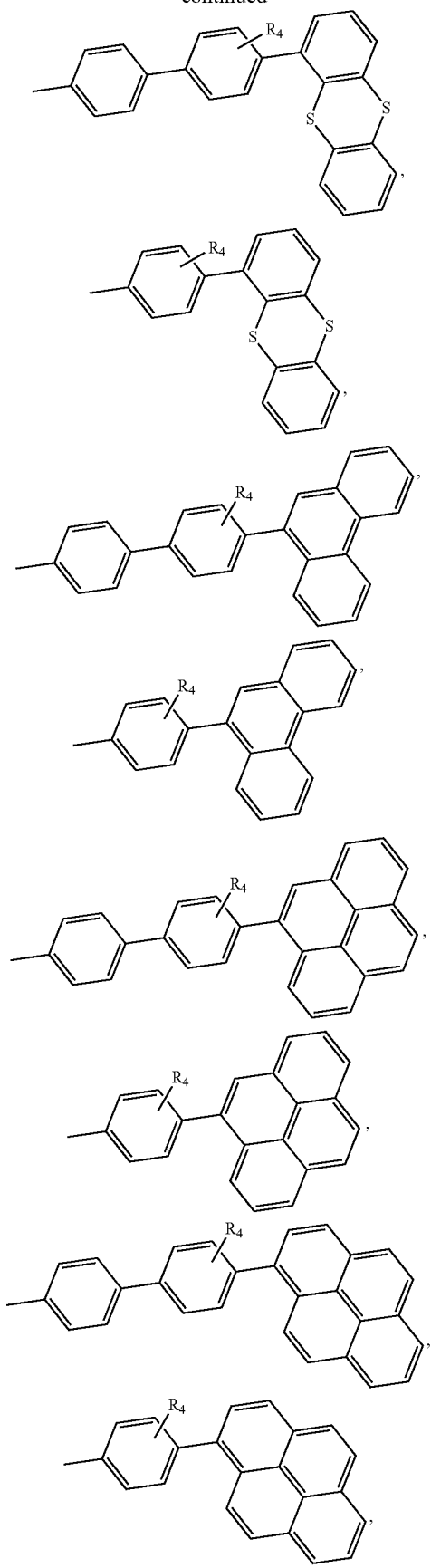
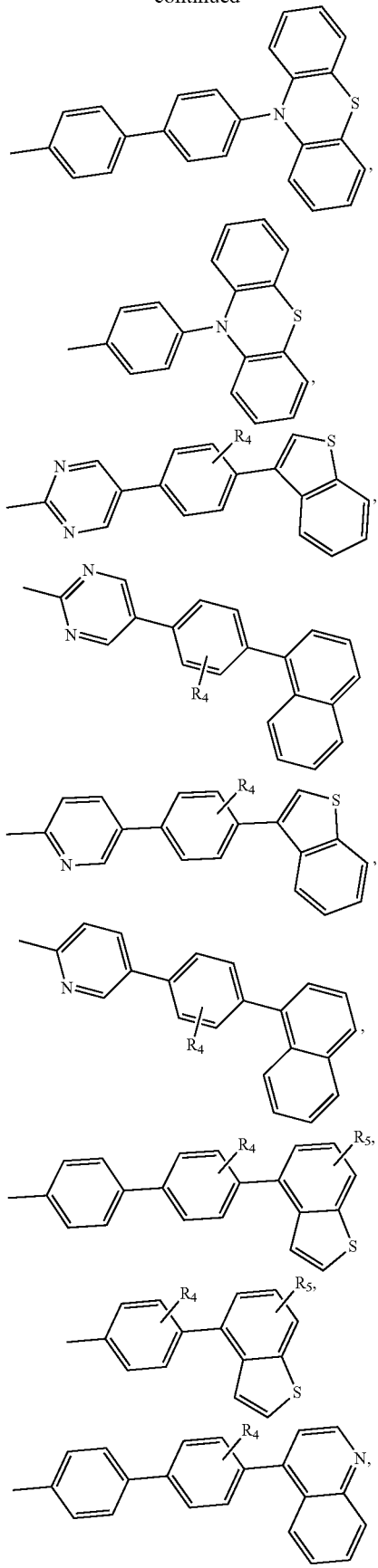

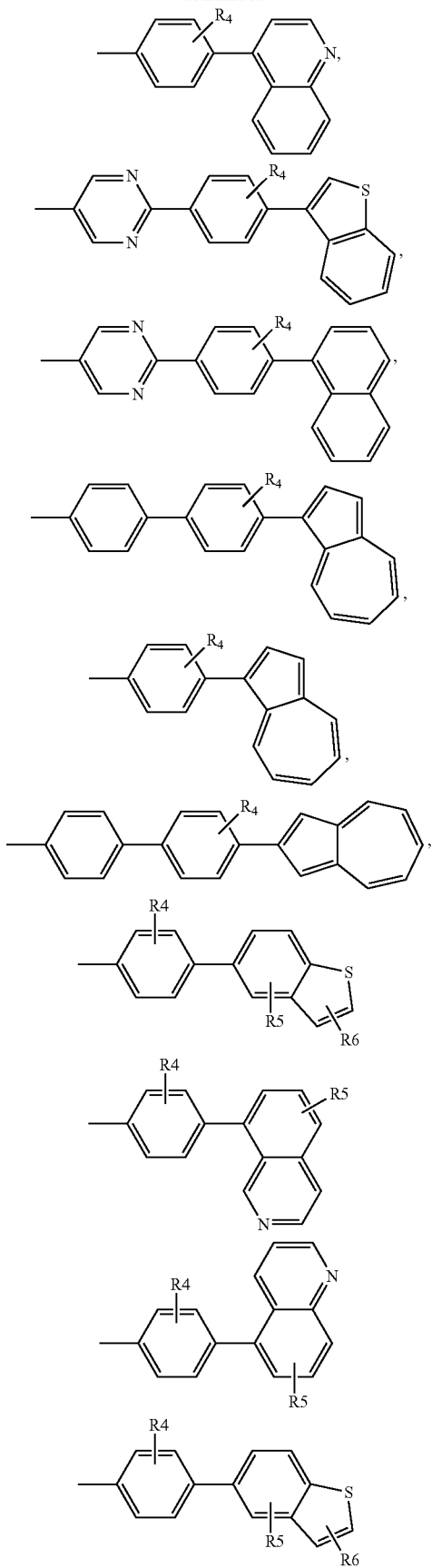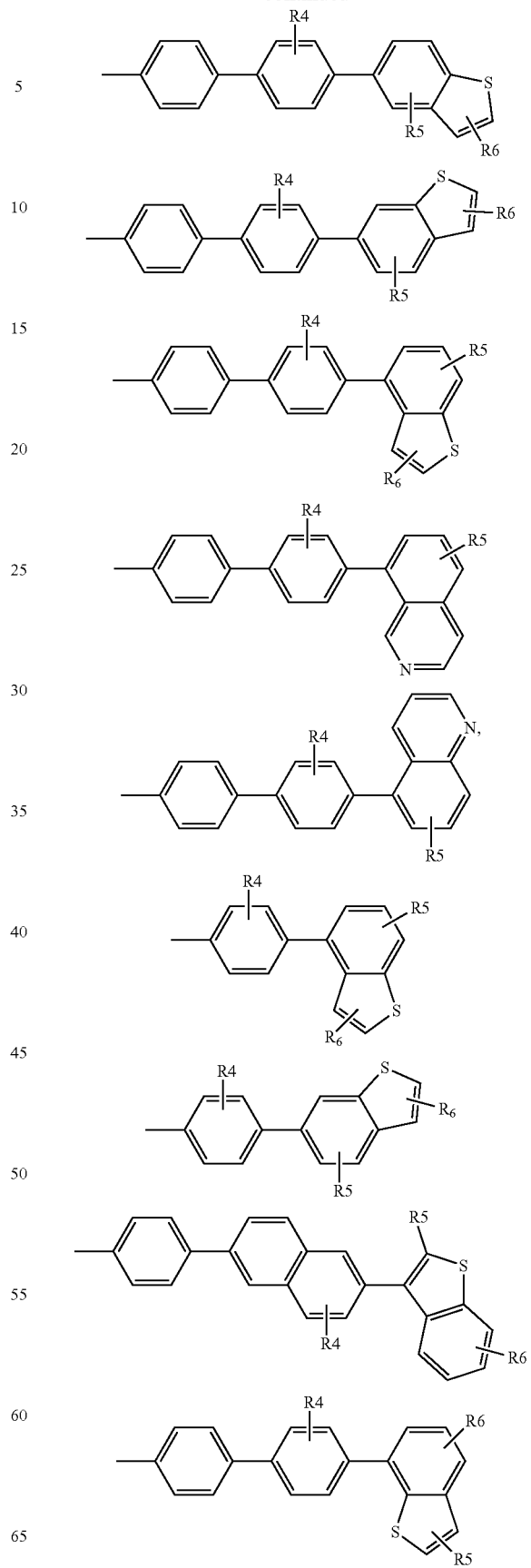

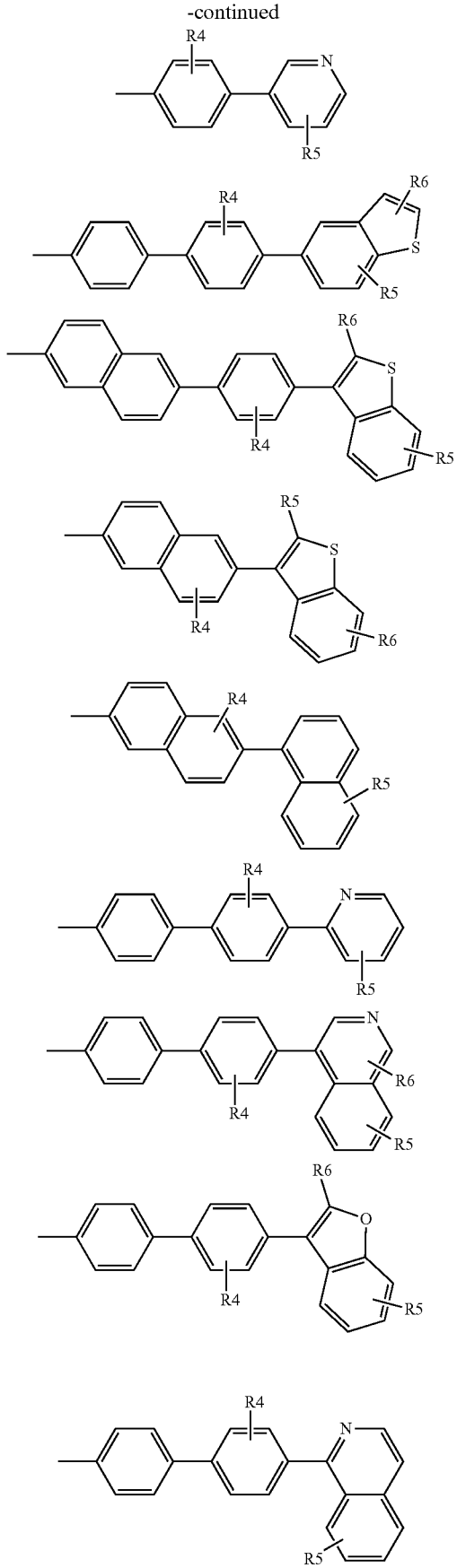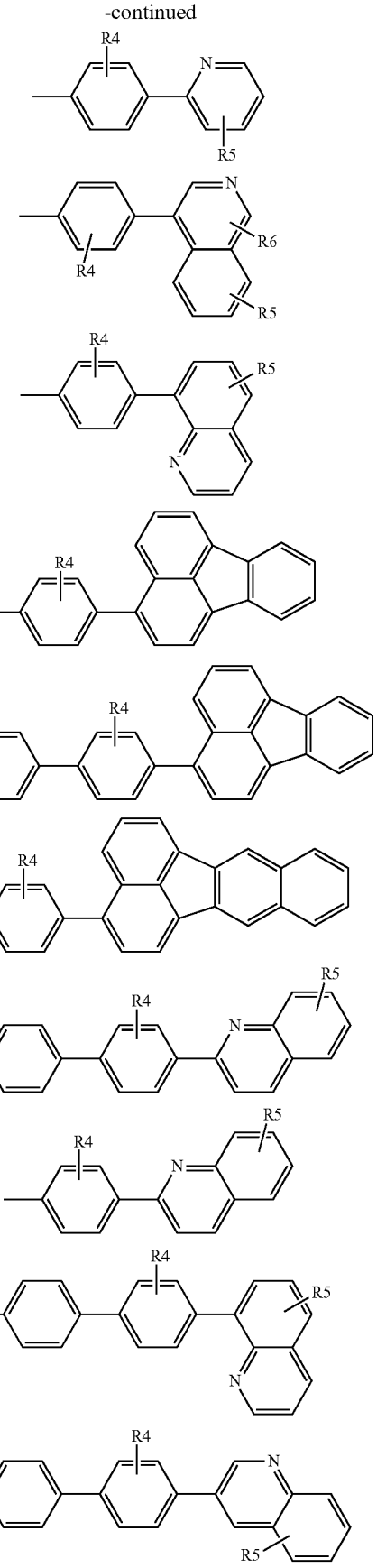

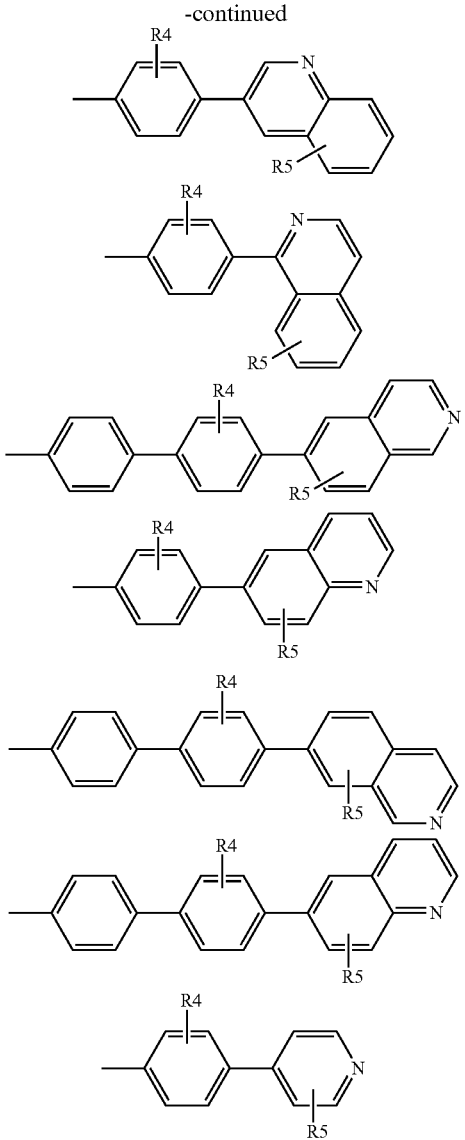
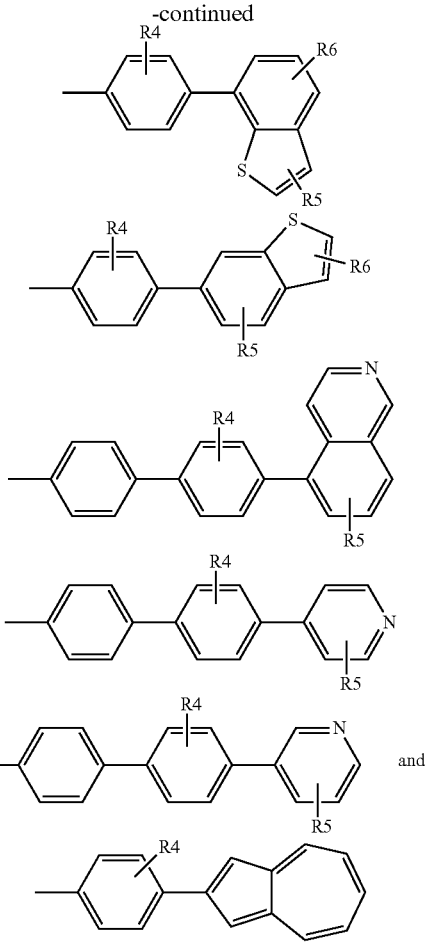
wherein $R_4$, $R_5$, $R_6$ are the same or different and are, at each occurrence, independently selected from H, F, $CH_3$, $CF_3$, aryl and alkyl.
In a more preferred embodiment of the thiophene- or selenophene-based material represented by the general formula Xb, the material is selected from the group consisting of
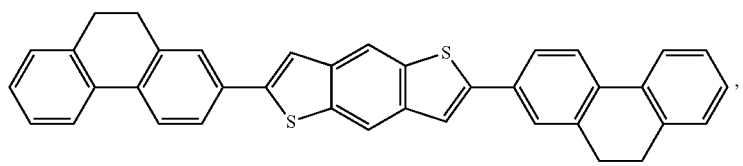
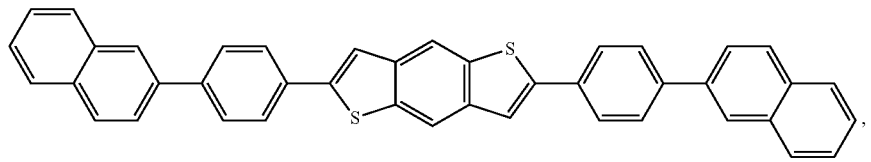
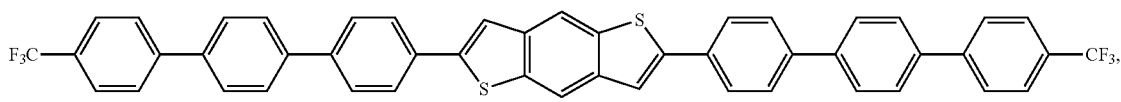

-continued
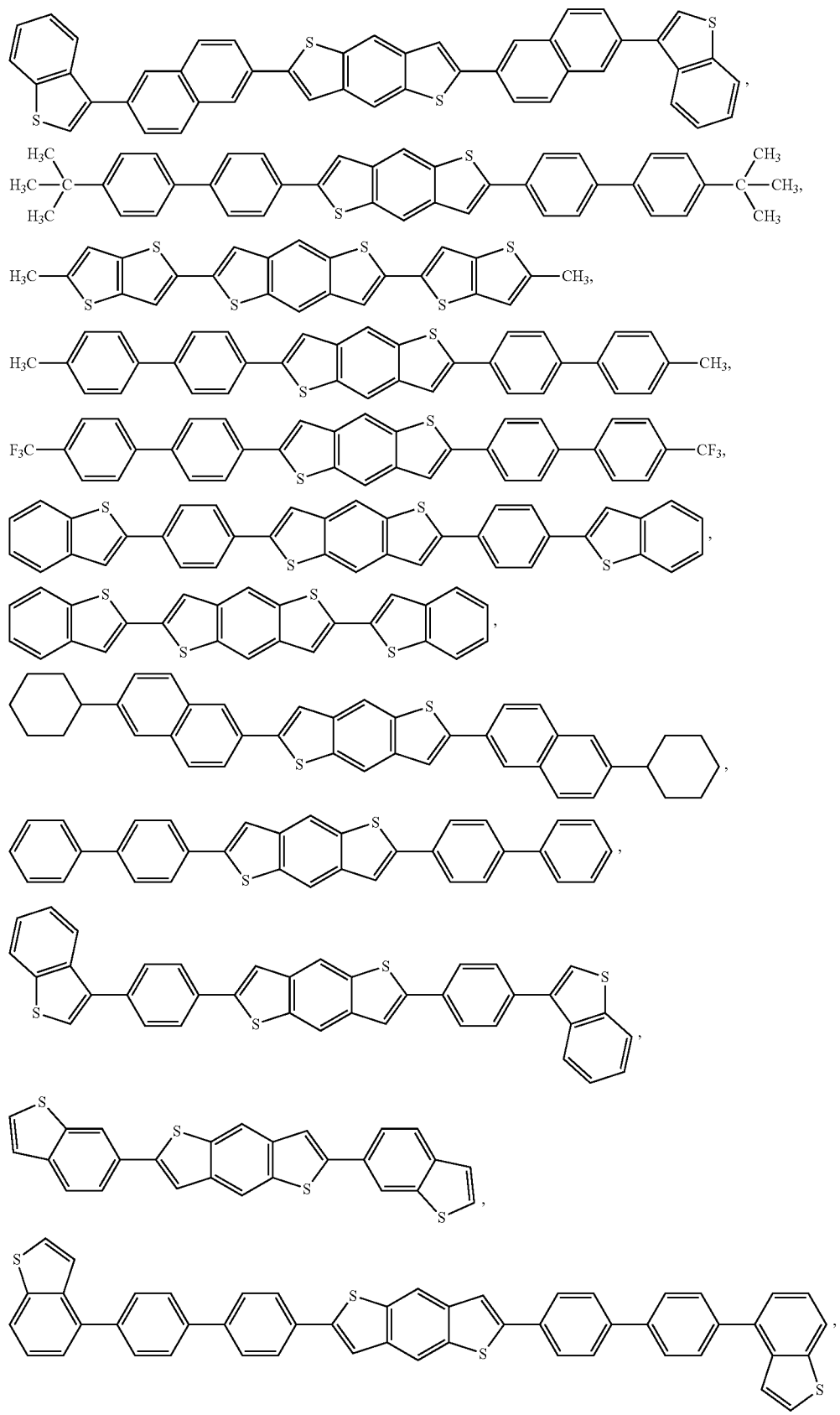

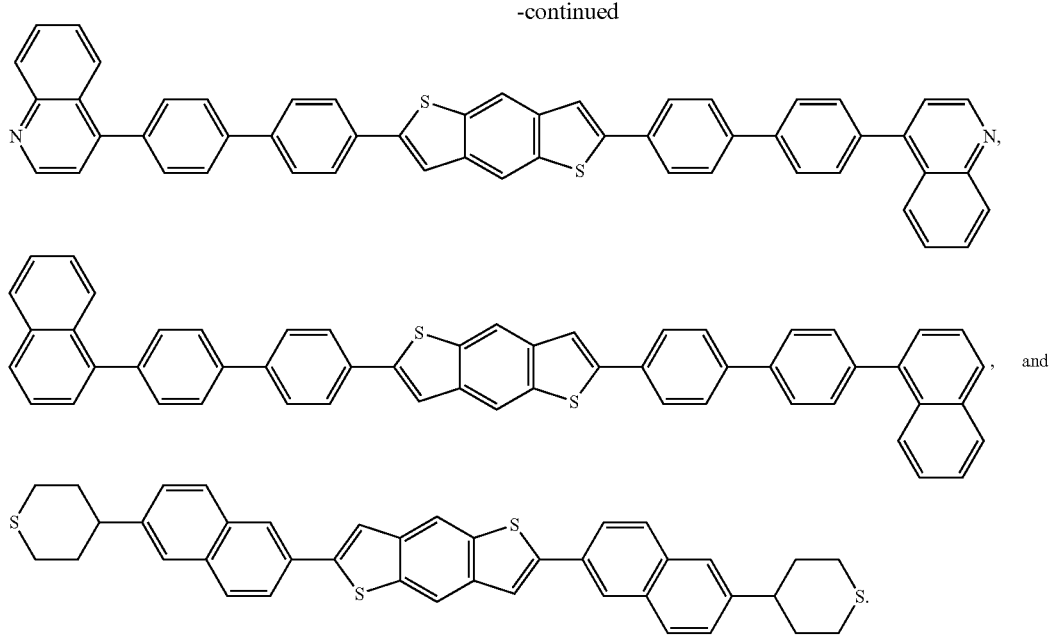

In one embodiment, the transparent P material of the present disclosure is a thiophene- or selenophene-based material represented by the general formula XXXIa and XXXIb XXXIa XXXIb wherein,
X and Y are the same or different and are, at each occurrence, independently selected from CR₂, S, O, Se, N—R and Si—R₂, wherein R₂ is selected from H, CH₃, CF₃, phenyl, alkyl and aryl; and
R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

In a preferred embodiment of the thiophene- or selenophene-based material represented by the general formula XXXIa and XXXIb,
X and Y are the same or different and are, at each occurrence, independently selected from S and Se.

In a preferred embodiment of the thiophene- or selenophene-based material represented by the general formula XXXIa and XXXIb, R is selected from

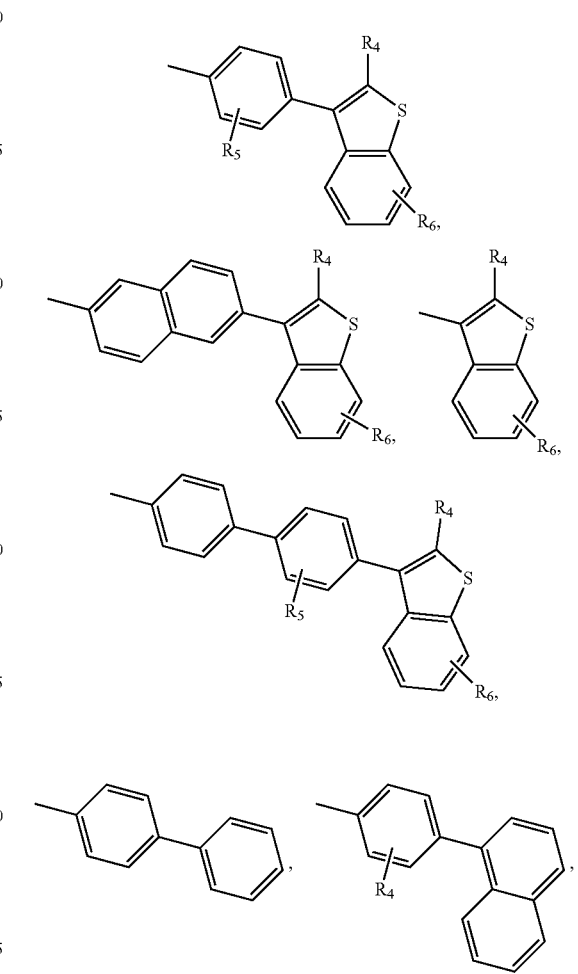

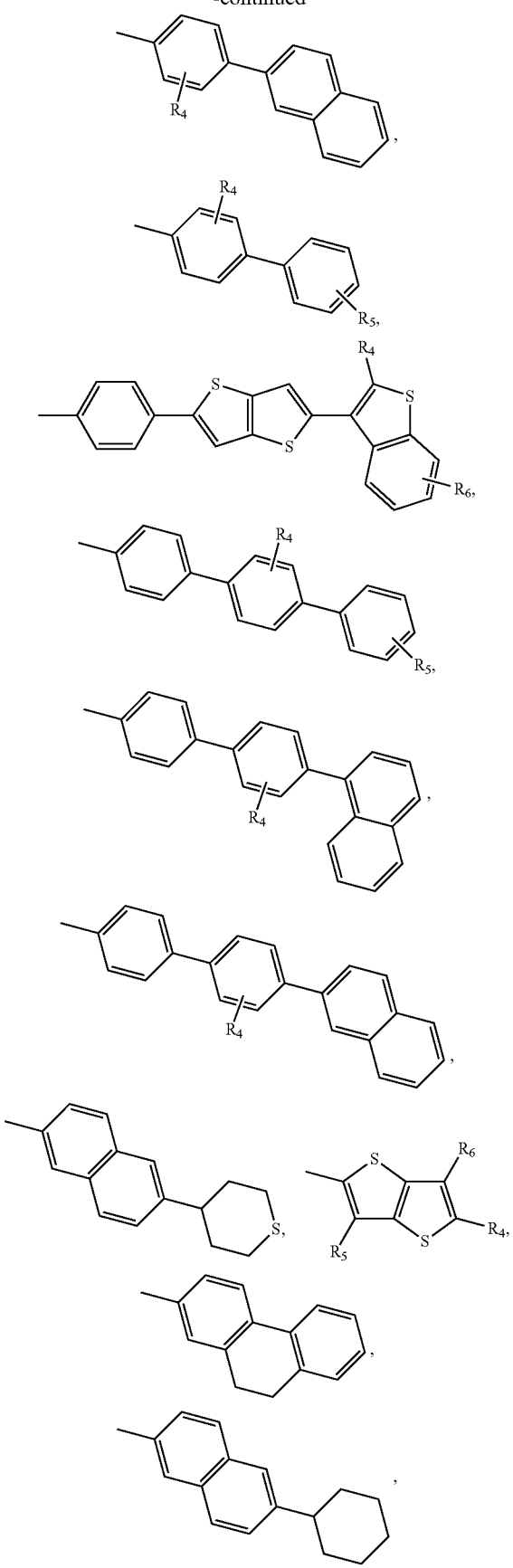
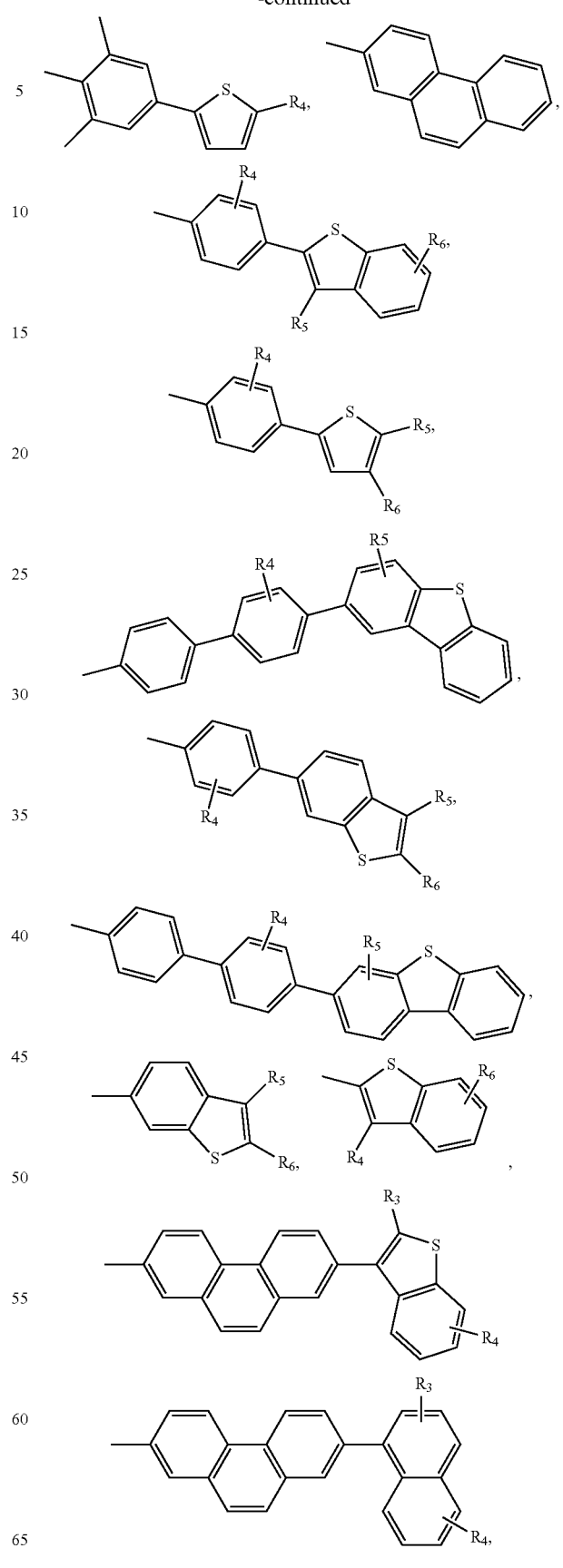

-continued
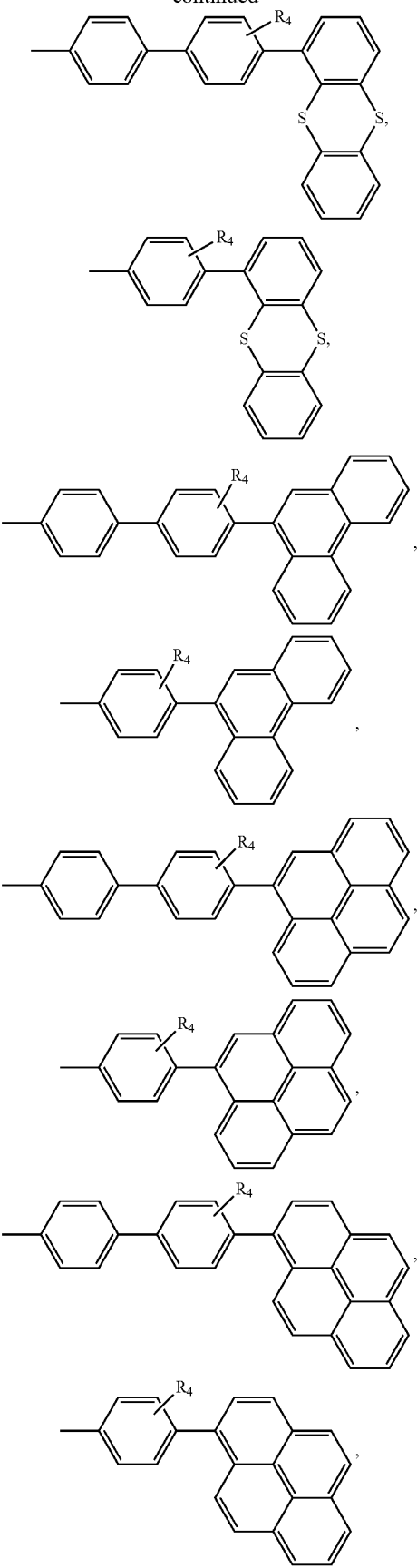
-continued
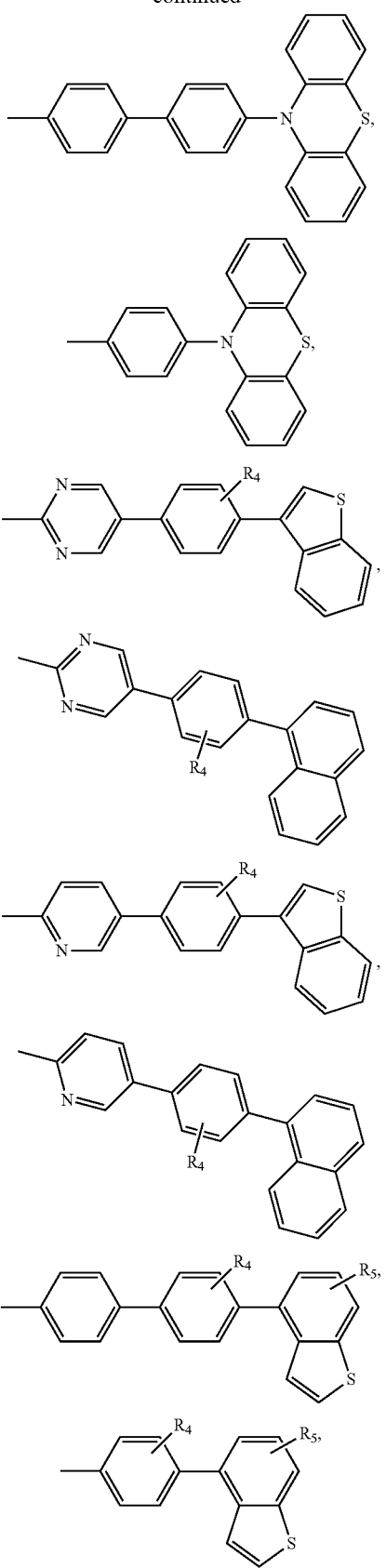

-continued
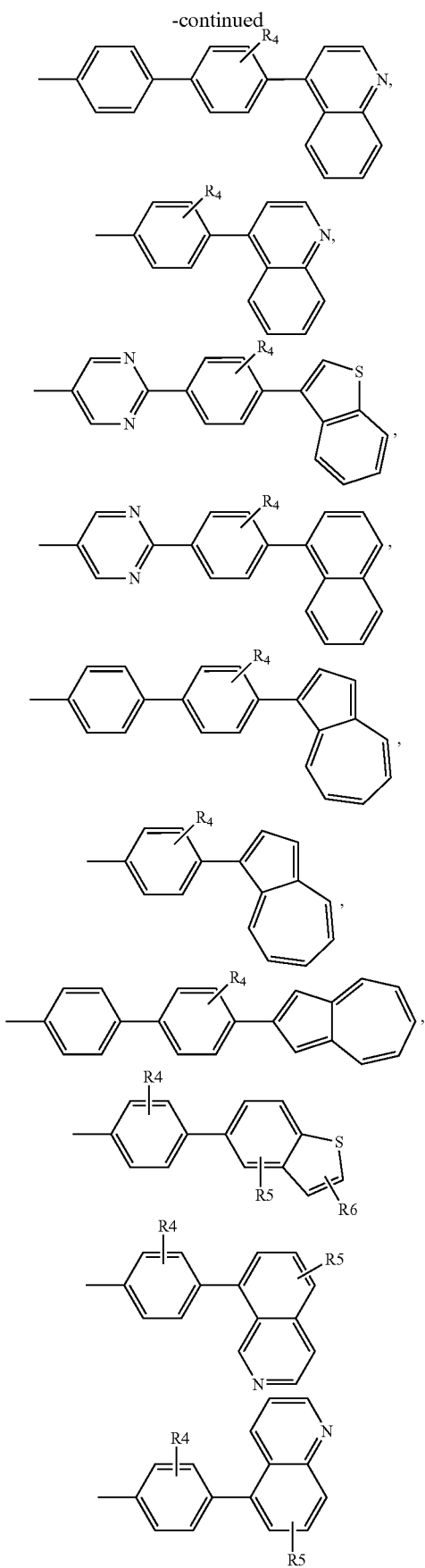
-continued
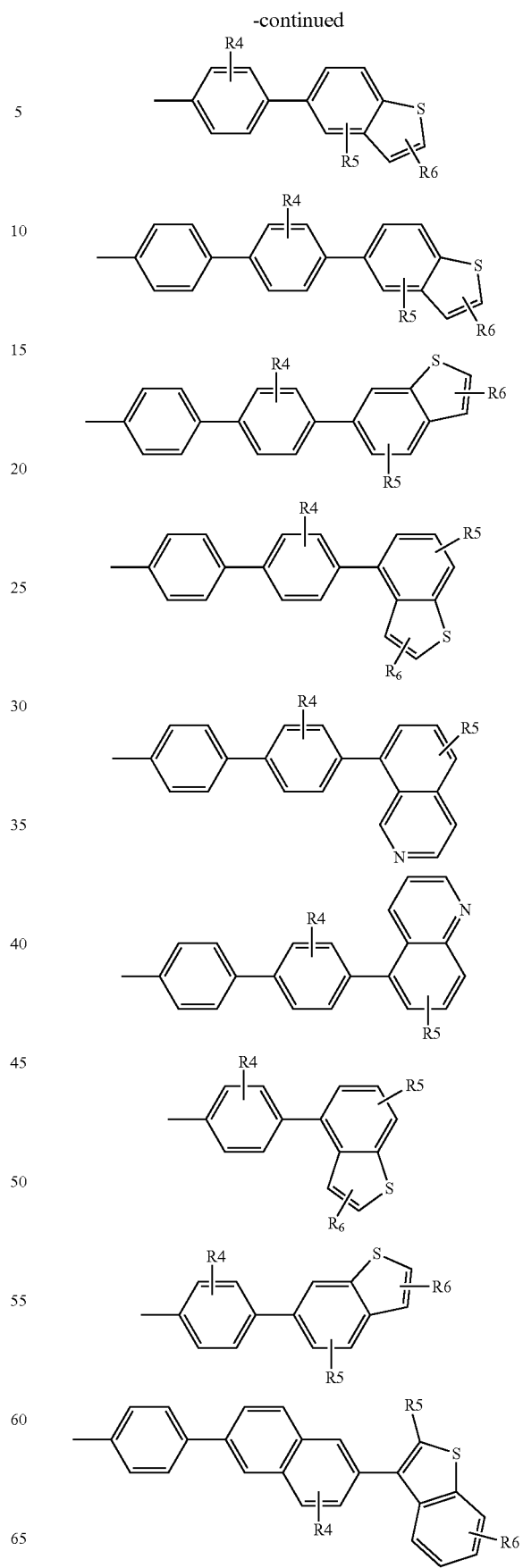

-continued
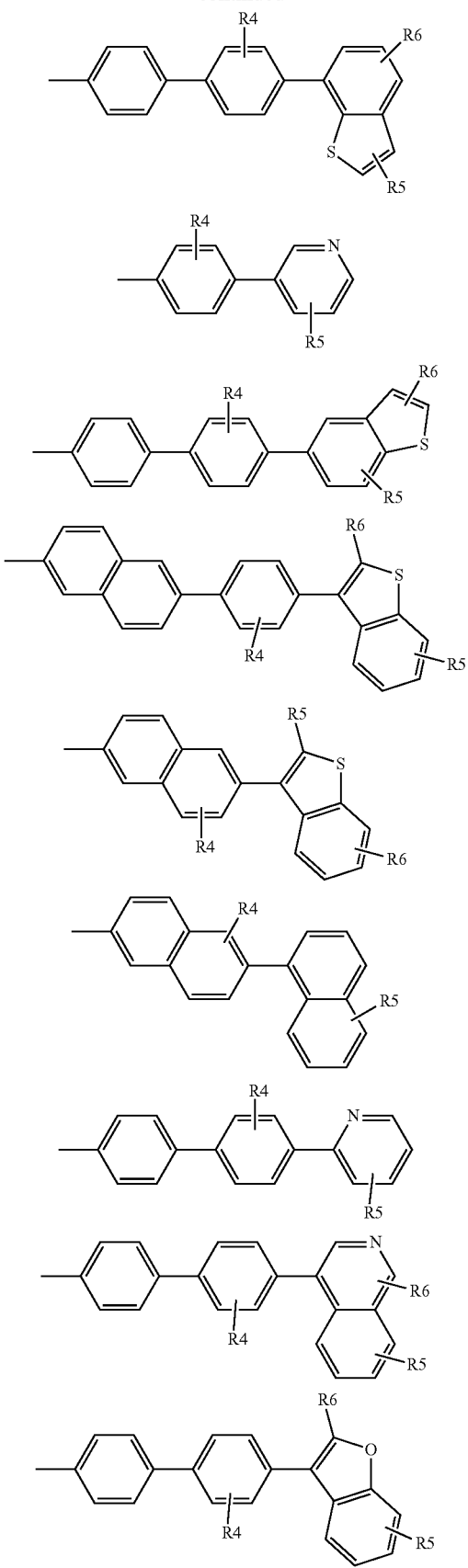
-continued
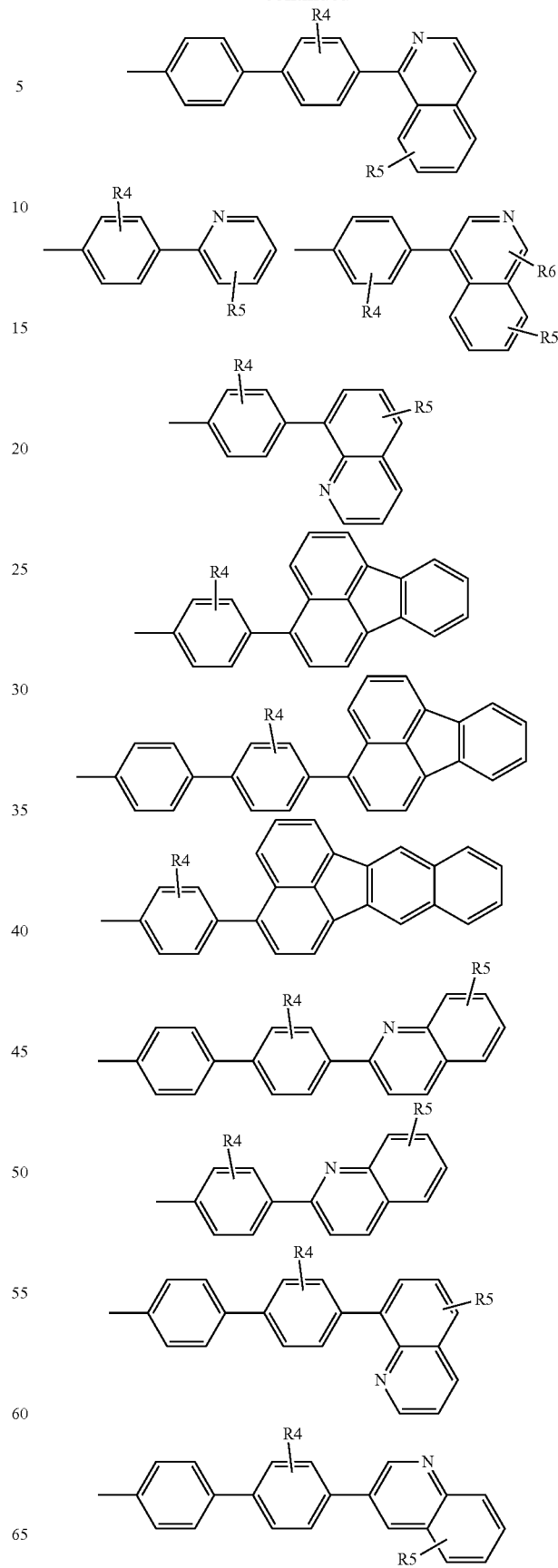

-continued

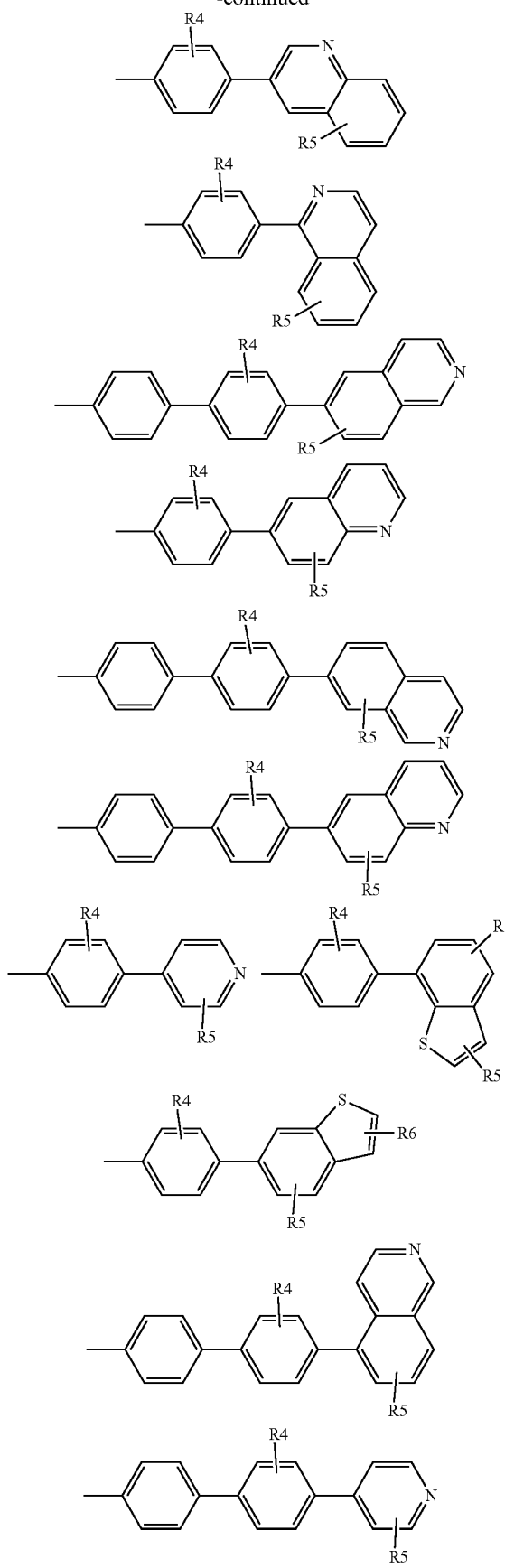

-continued

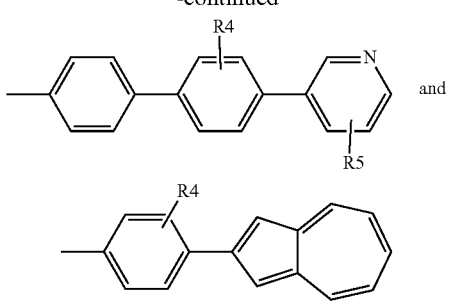

wherein $R_4$, $R_5$, $R_6$ are the same or different and are, at each occurrence, independently selected from H, F, $CH_3$, $CF_3$, aryl and alkyl.

In a preferred embodiment of the thiophene- or selenophene-based material represented by the general formula XXXIa and XXXIb, X and Y are the same or different and are, at each occurrence, independently selected from S and Se; and R is selected from

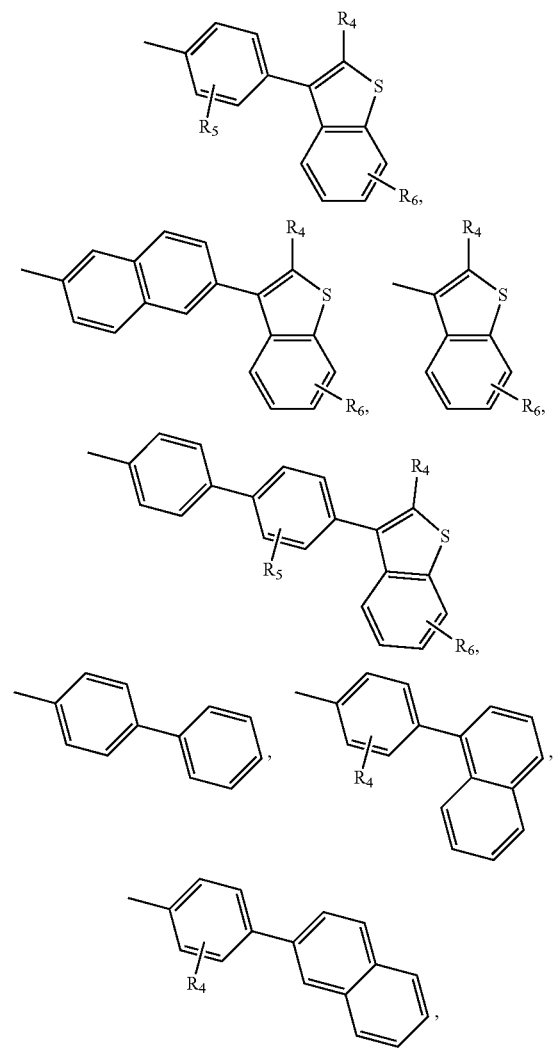

-continued
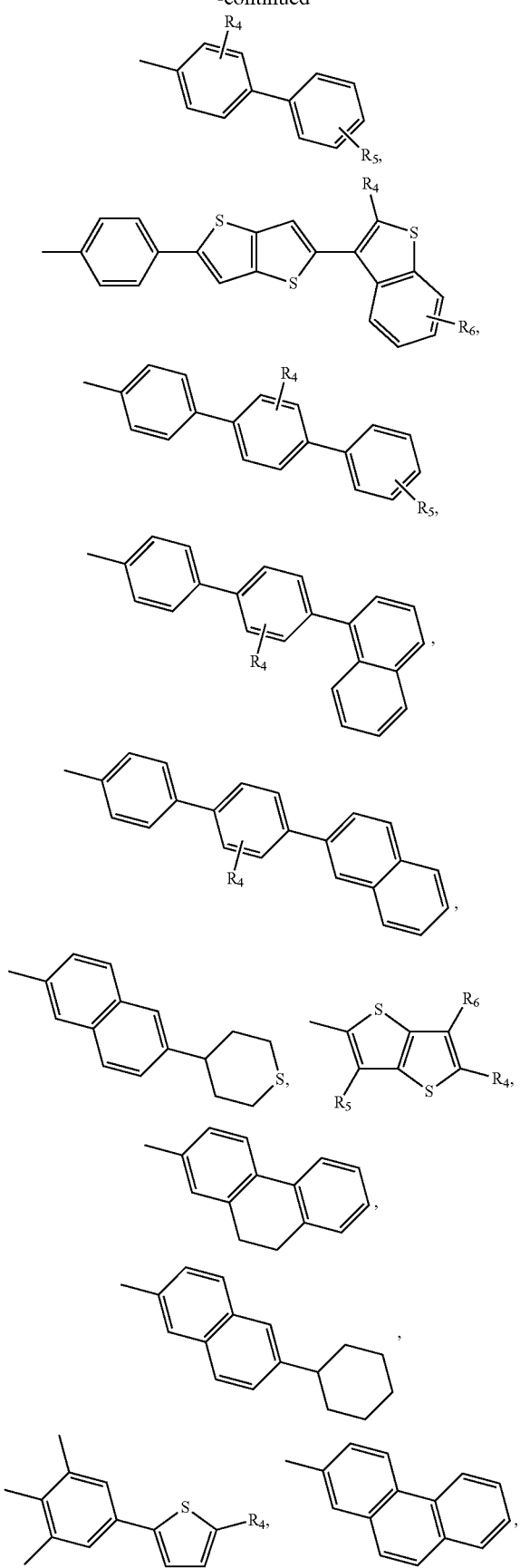
-continued
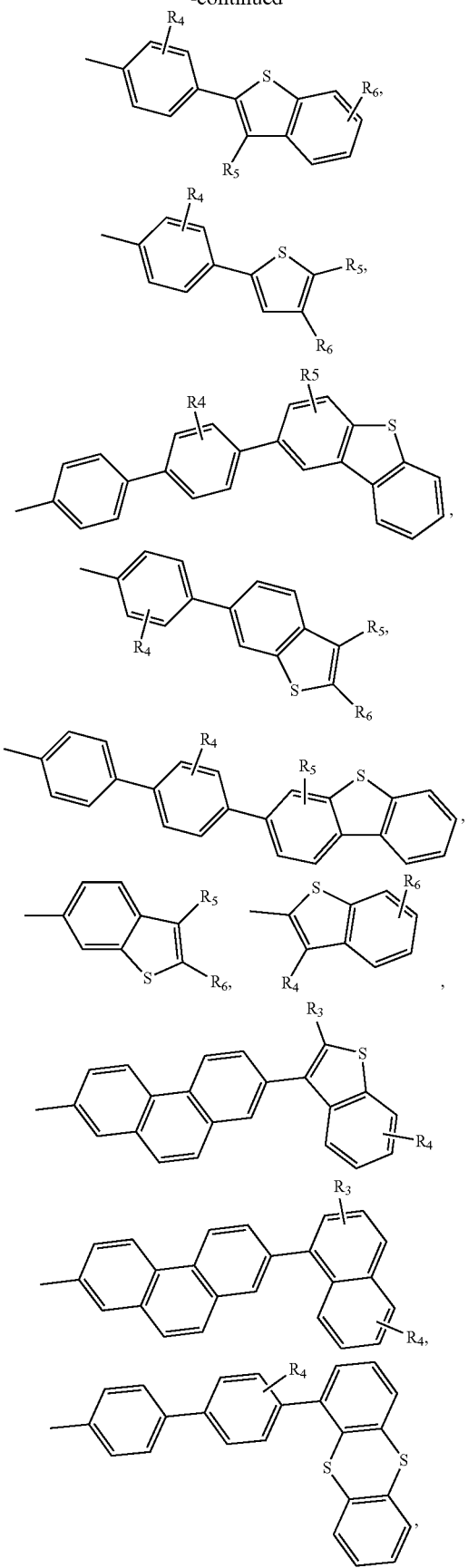

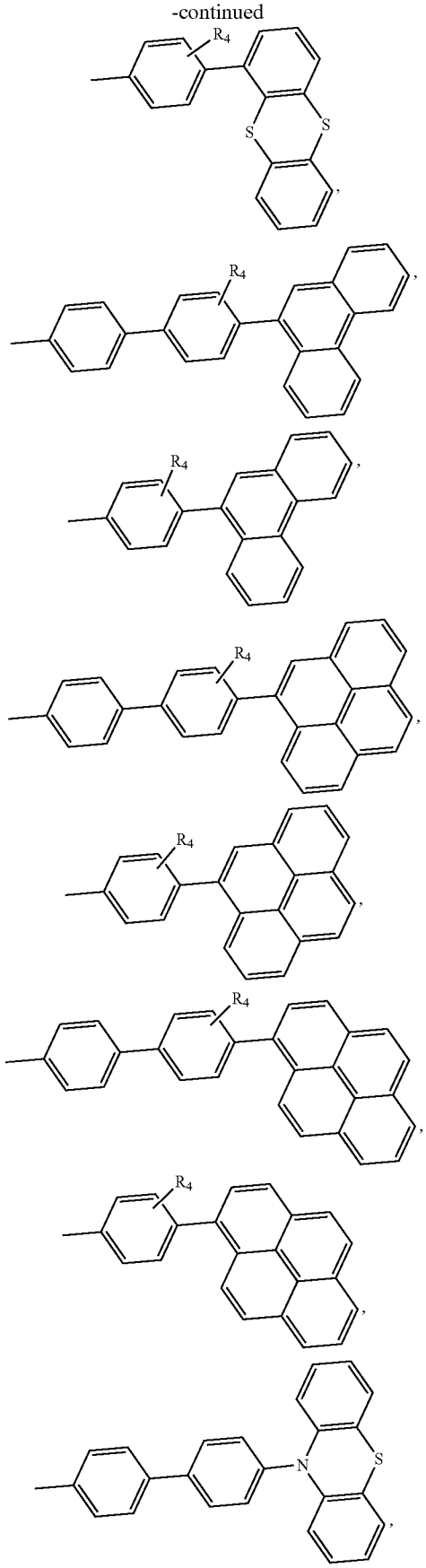
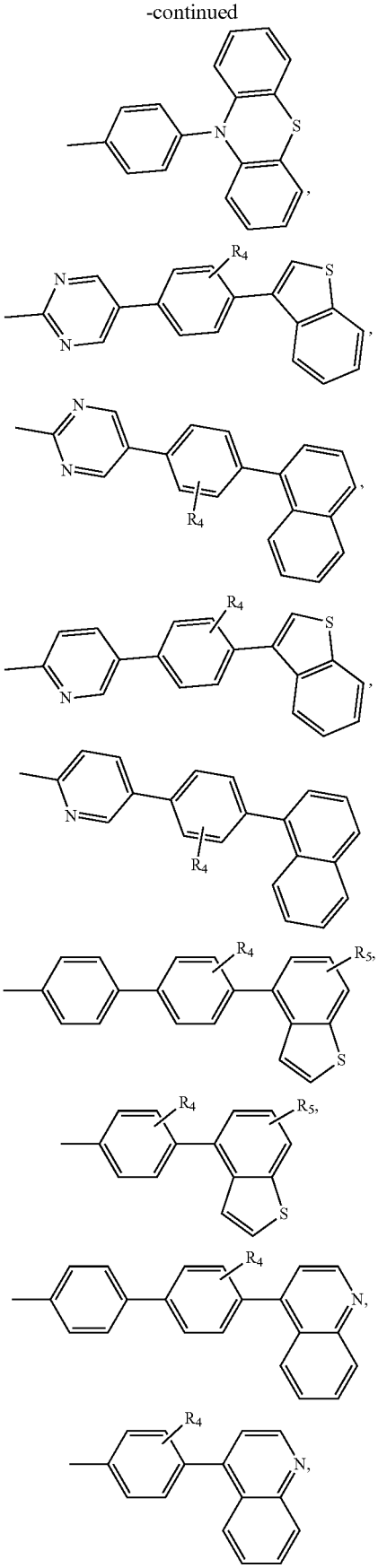

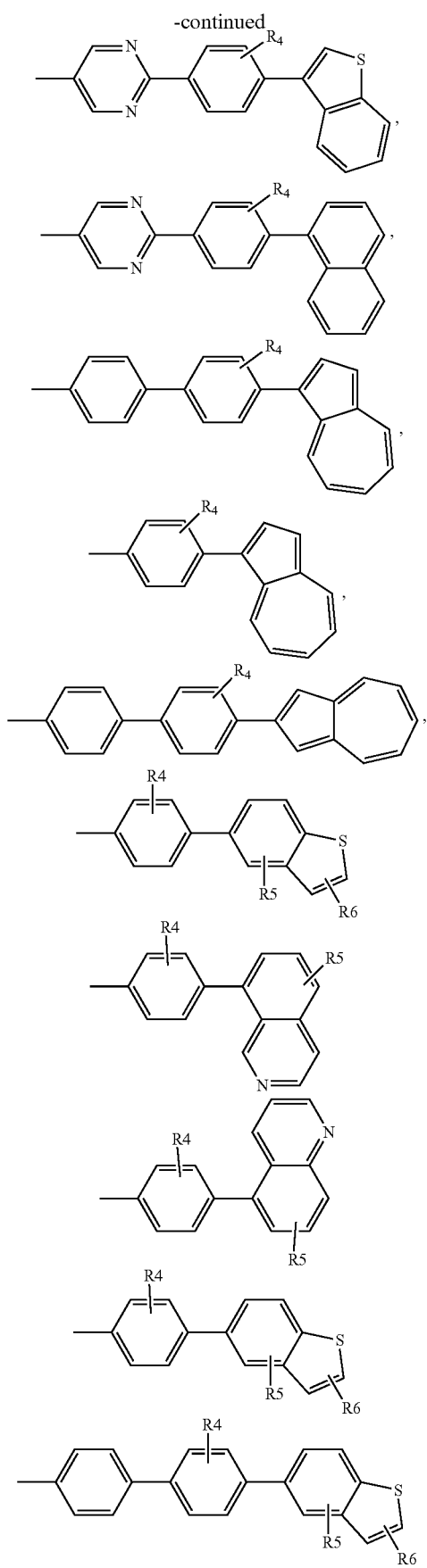
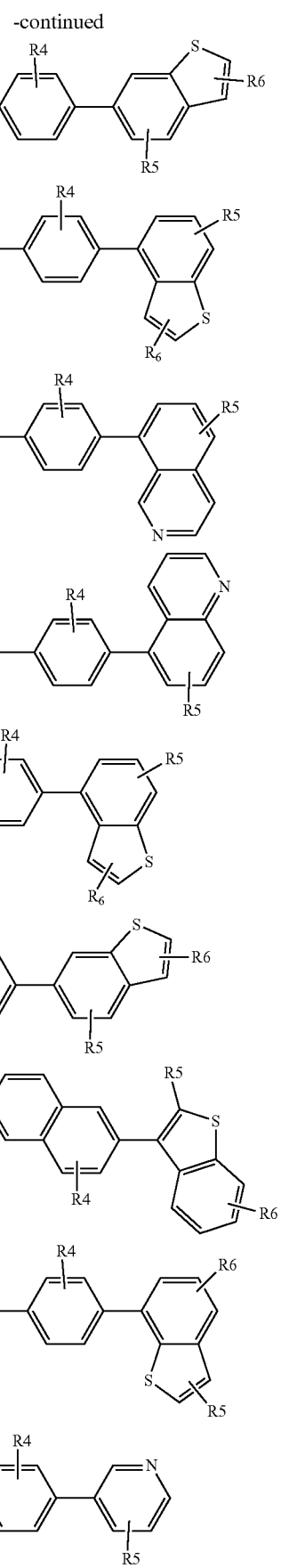

97
-continued
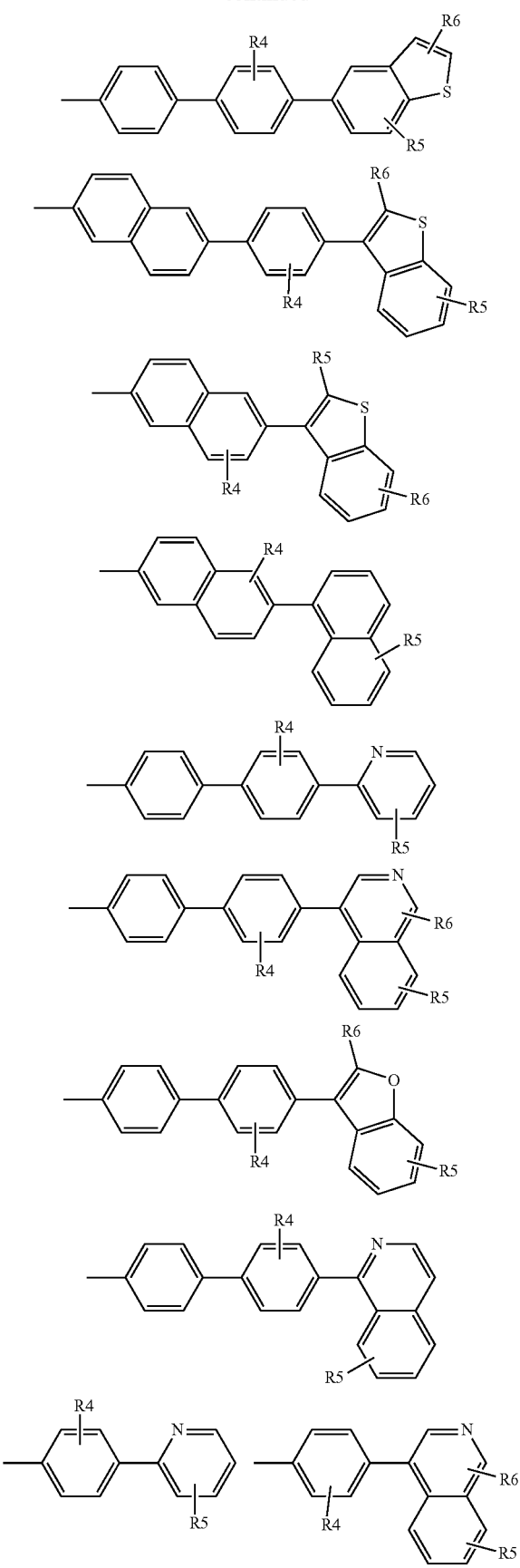
98
-continued
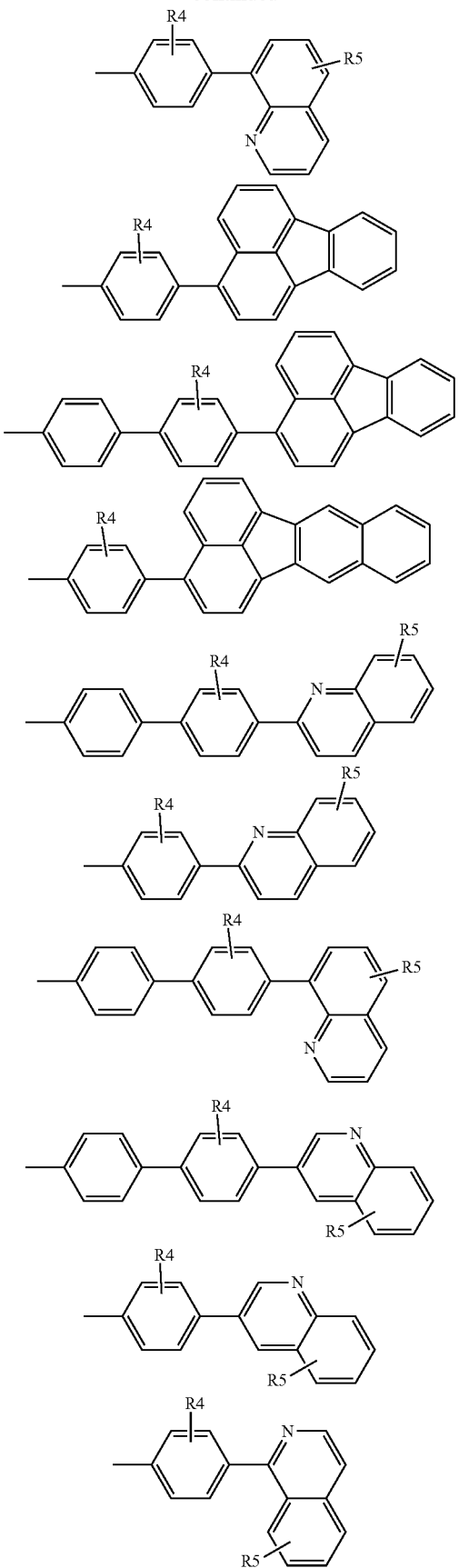

99
-continued
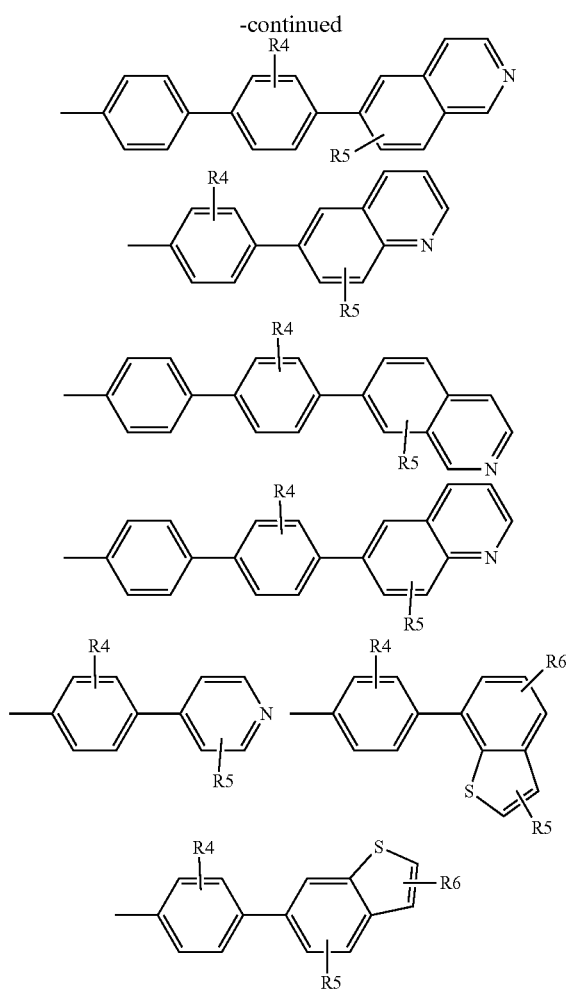
100
-continued
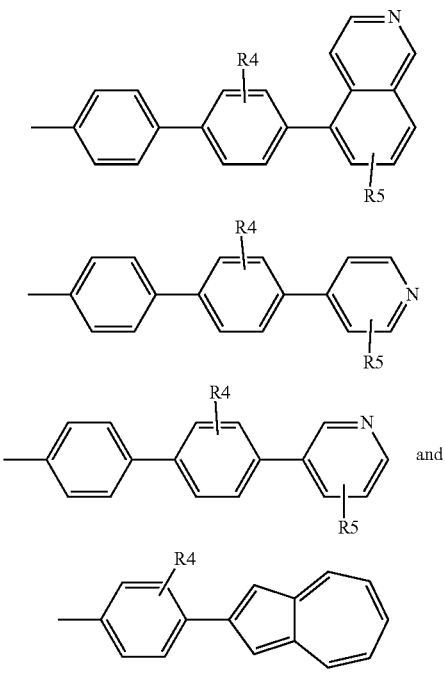
wherein $R_4$, $R_5$, $R_6$ are the same or different and are, at each occurrence, independently selected from H, F, $CH_3$, $CF_3$, aryl and alkyl.
In a more preferred embodiment of the thiophene- or selenophene-based material represented by the general formula XXXIa and XXXIb, the material is selected from the group consisting of
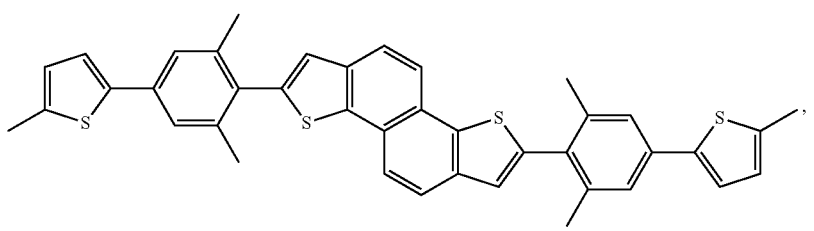
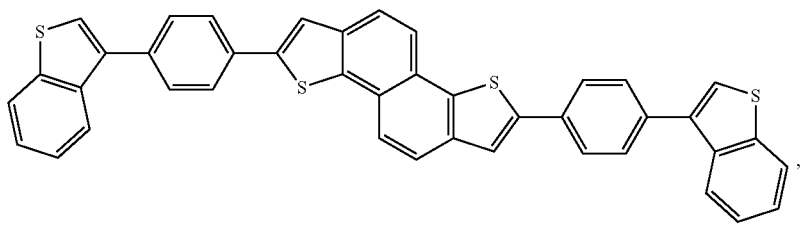
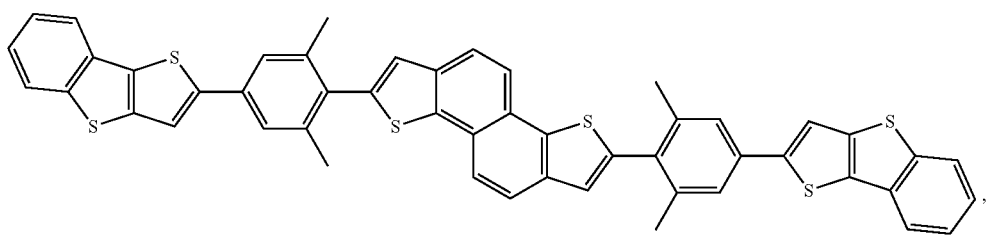

-continued
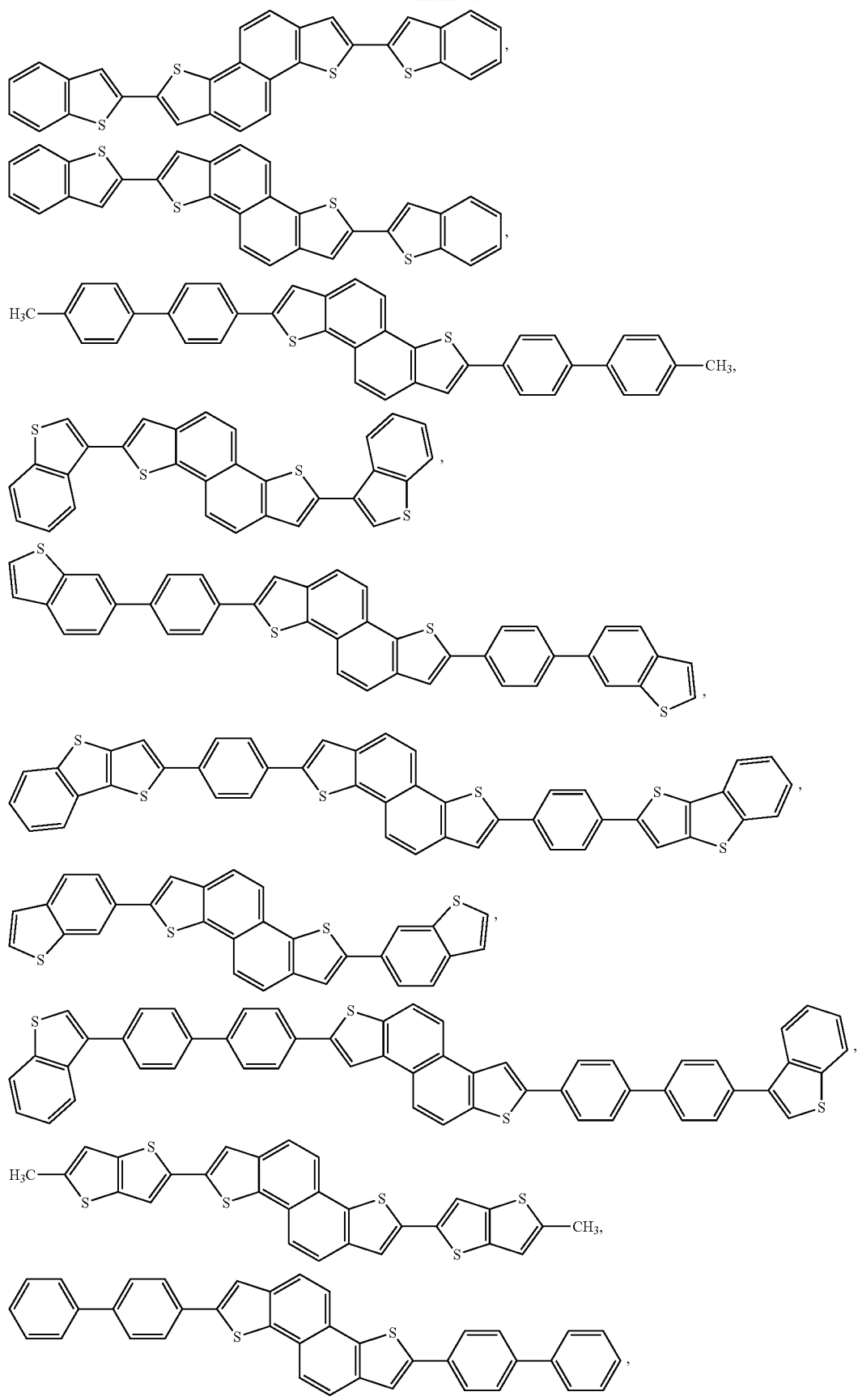

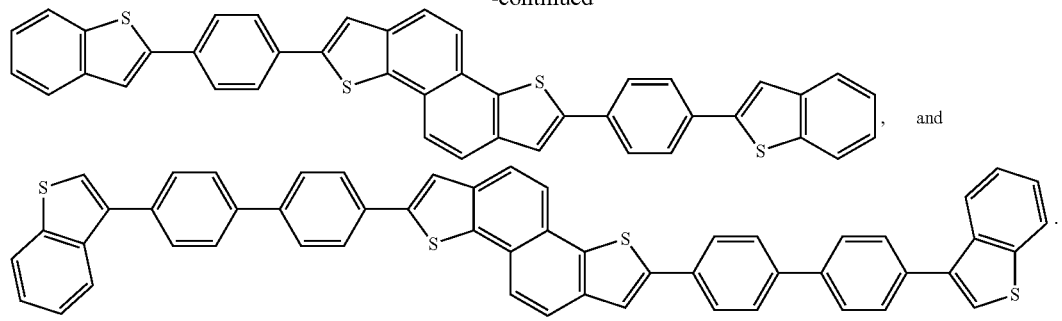
In one embodiment, the transparent P material of the present disclosure is a thiophene- or selenophene-based material represented by the general formula XXXIX,
T-B-T                                    XXXIX,
wherein,
T is selected from a structure with one of the general formulas IX, Xa, Xb, XI, XIIa, XIIb, XXII to XXXVIII:
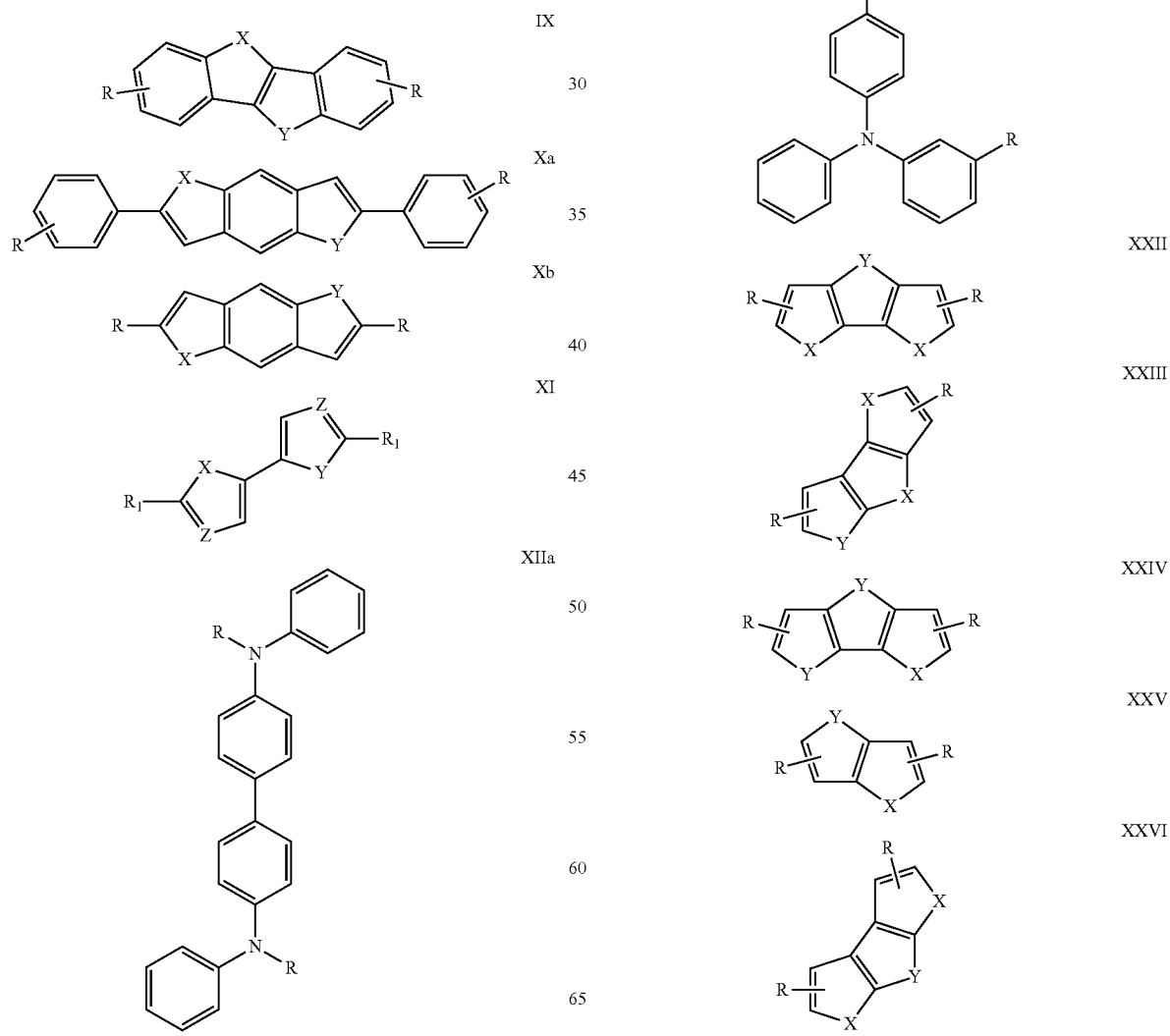

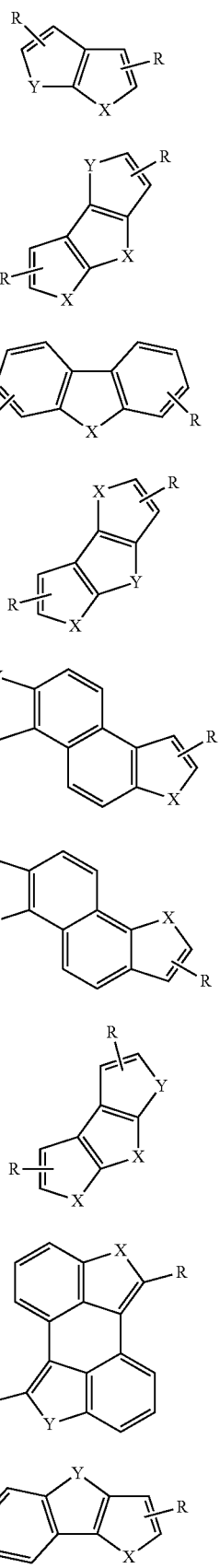
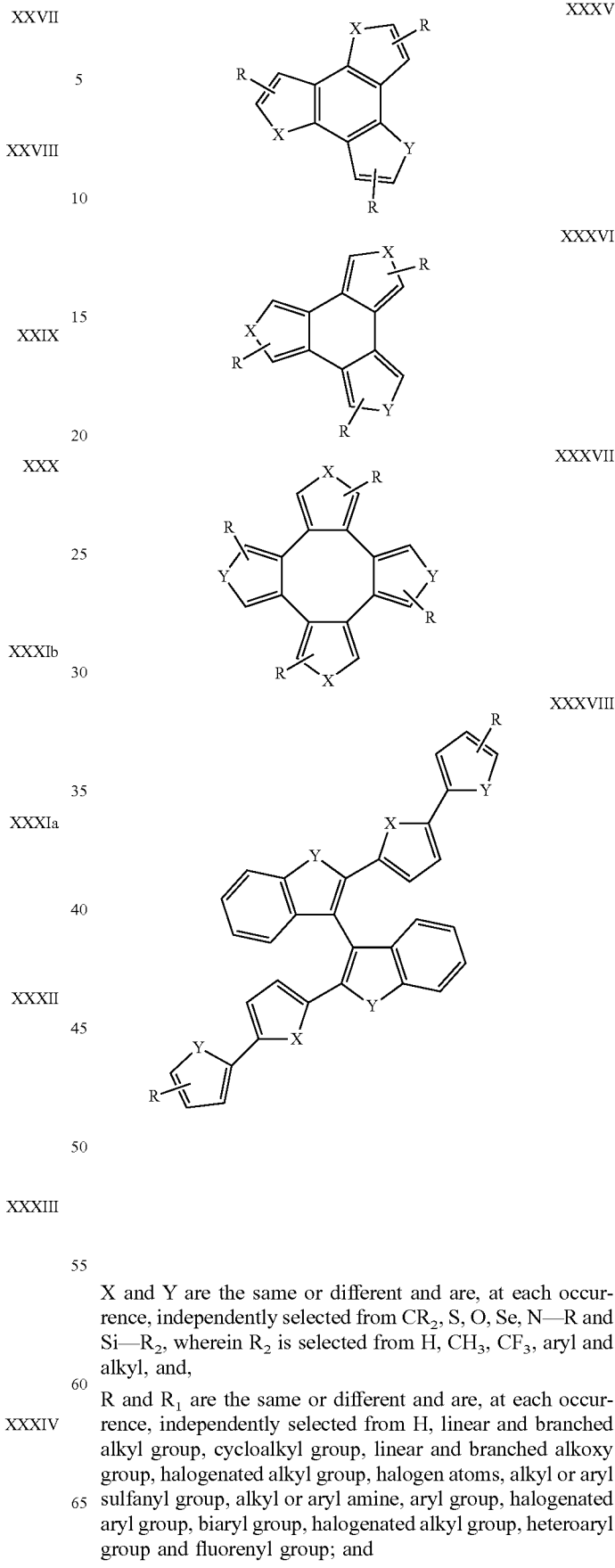

X and Y are the same or different and are, at each occurrence, independently selected from $CR_2$, S, O, Se, N—R and Si—$R_2$, wherein $R_2$ is selected from H, $CH_3$, $CF_3$, aryl and alkyl, and, R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group; and B is selected from none,
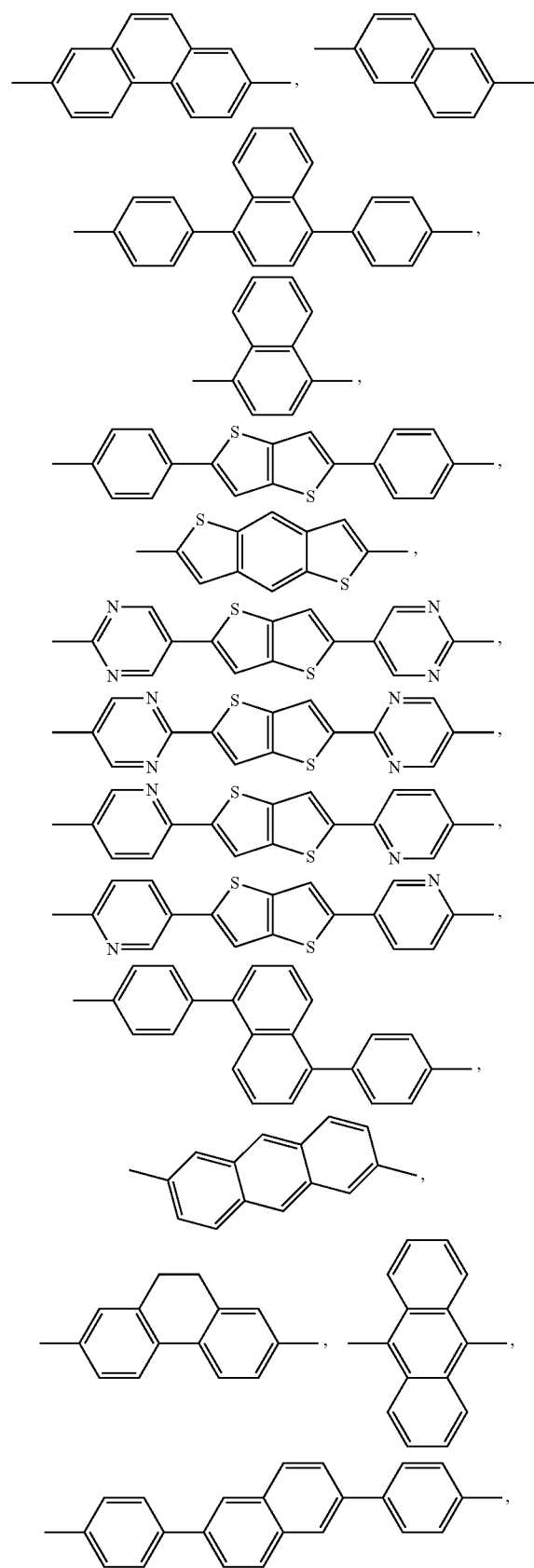
-continued
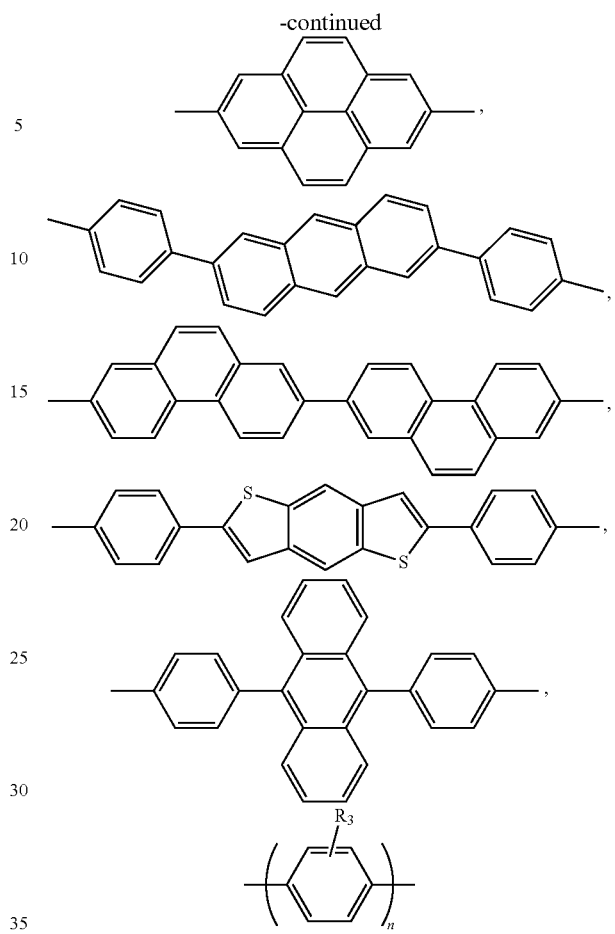
with R₃ selected from
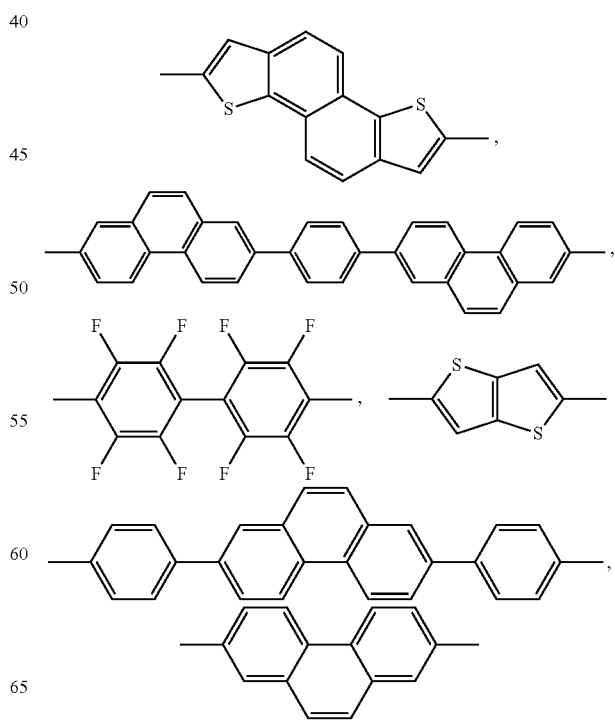

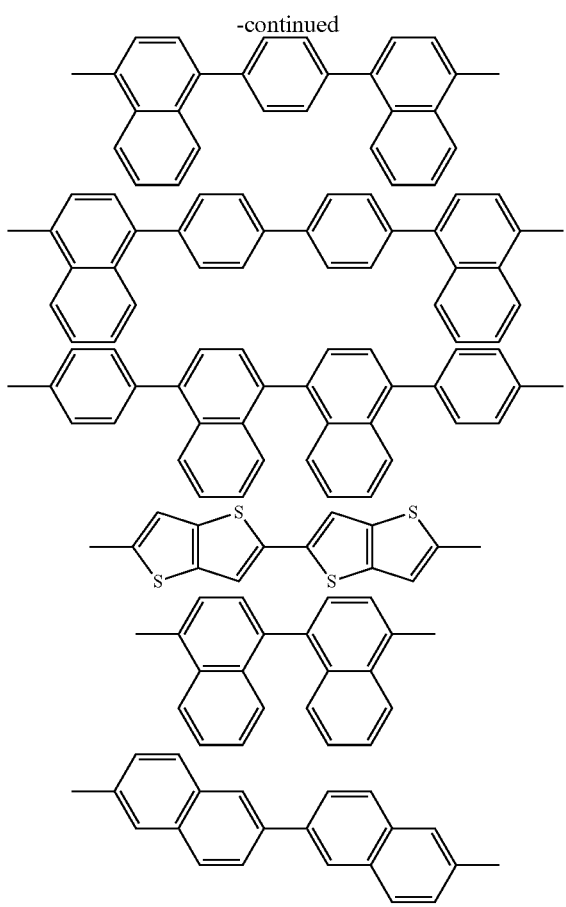
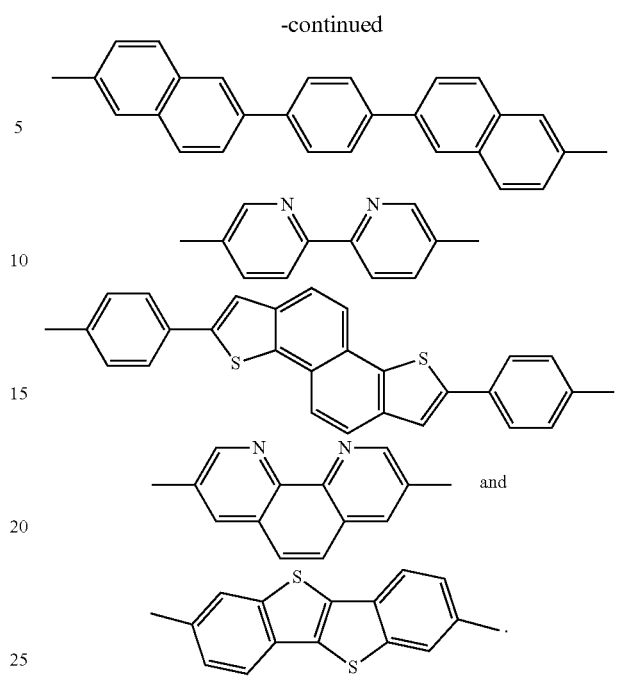
H, alkyl group, aryl group or halogen and n being 0 to 6,
In a more preferred embodiment of the thiophene- or selenophene-based material represented by the general formula XXXIX, the material is selected from the group consisting of
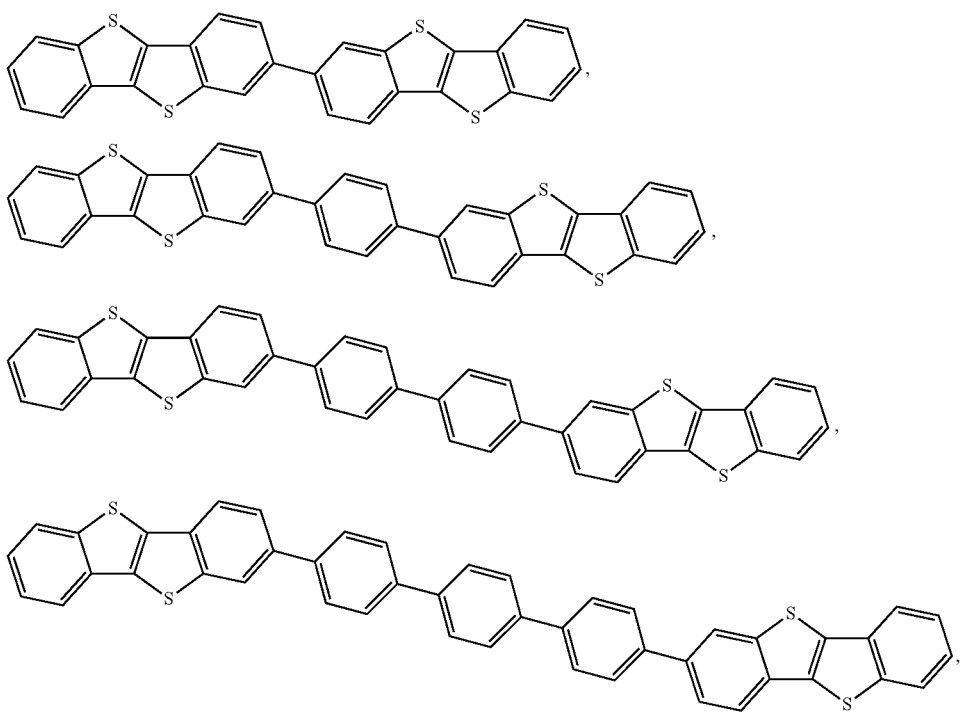

-continued
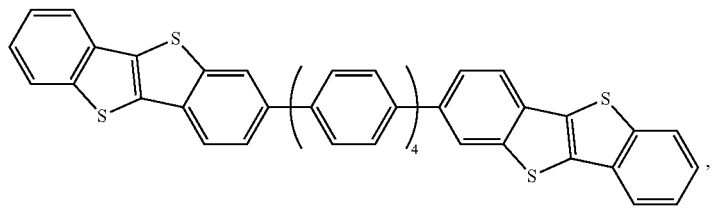
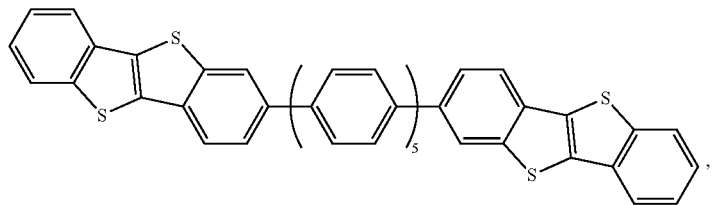
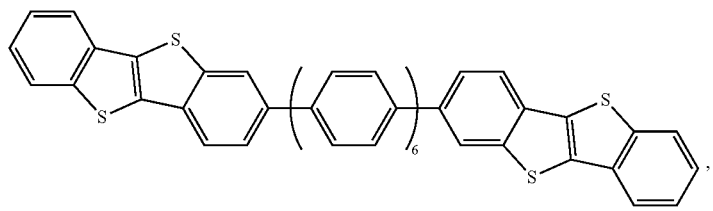
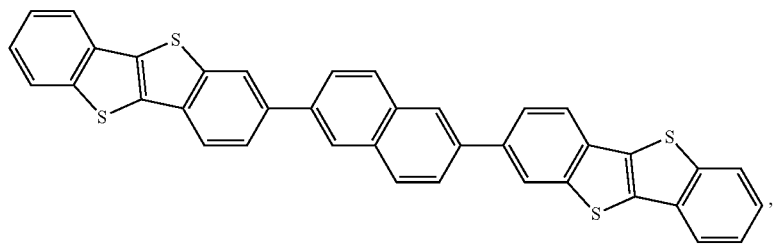
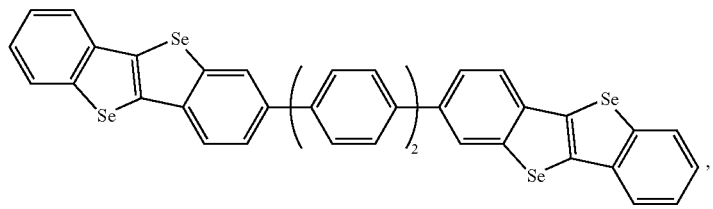
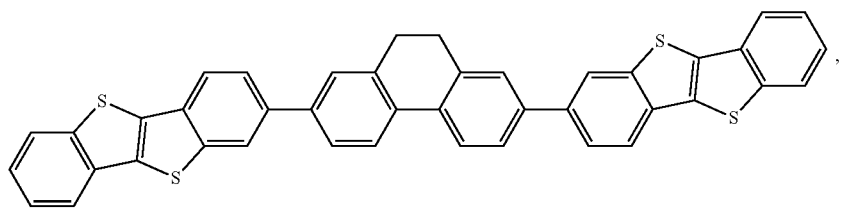
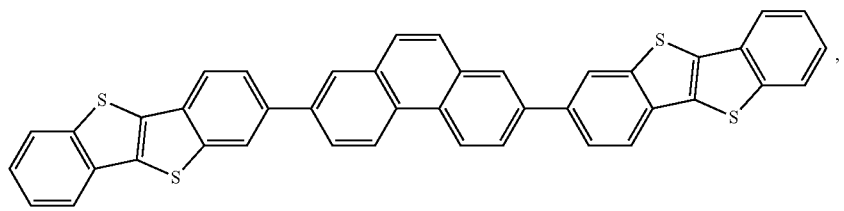
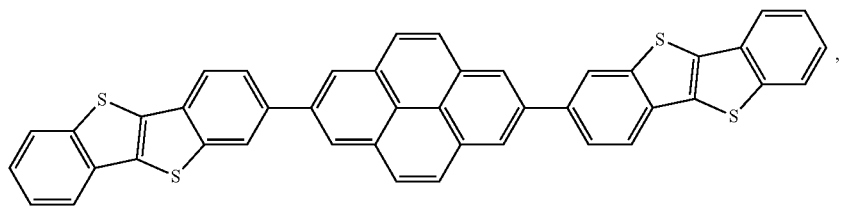

-continued
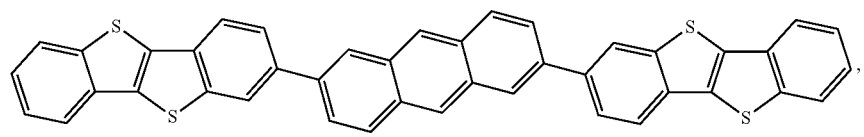,
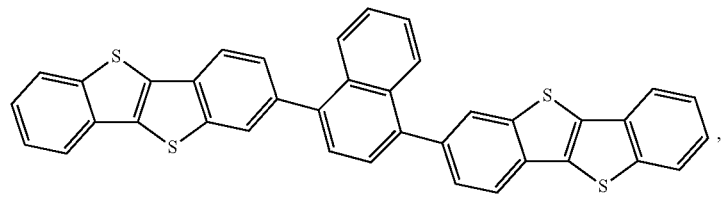,
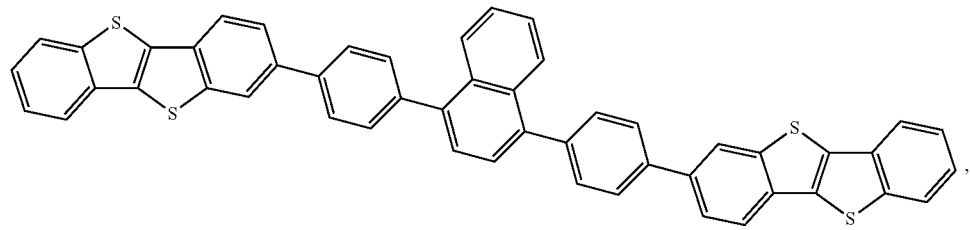,
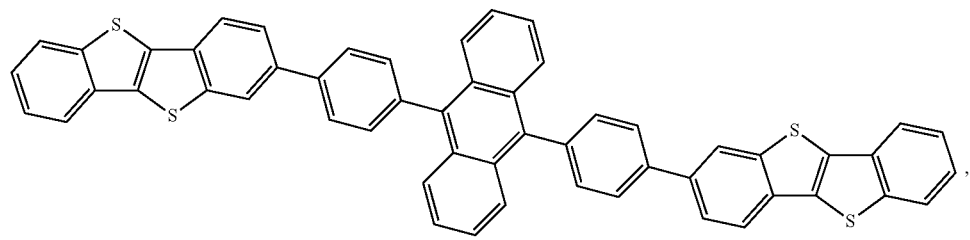,
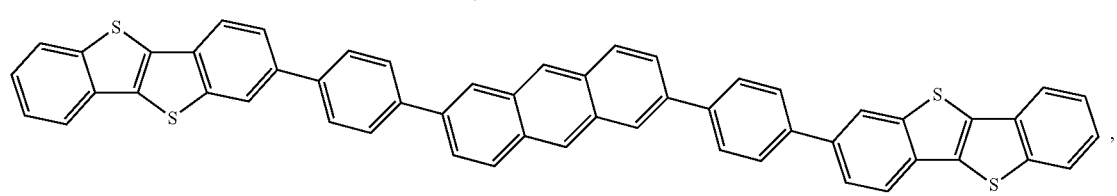,
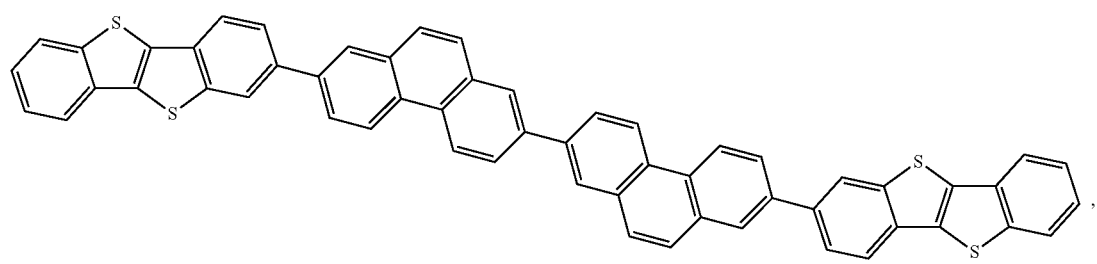,
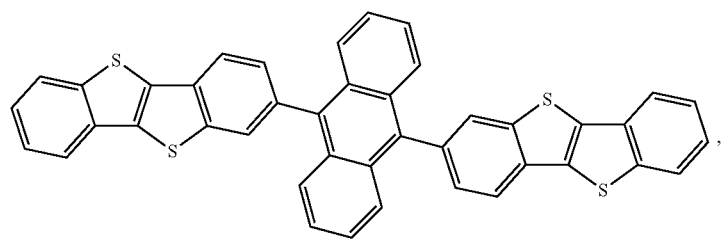,
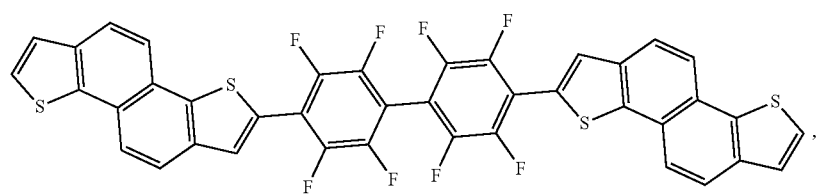, -continued
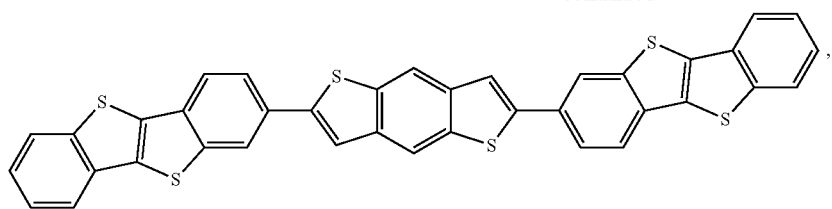
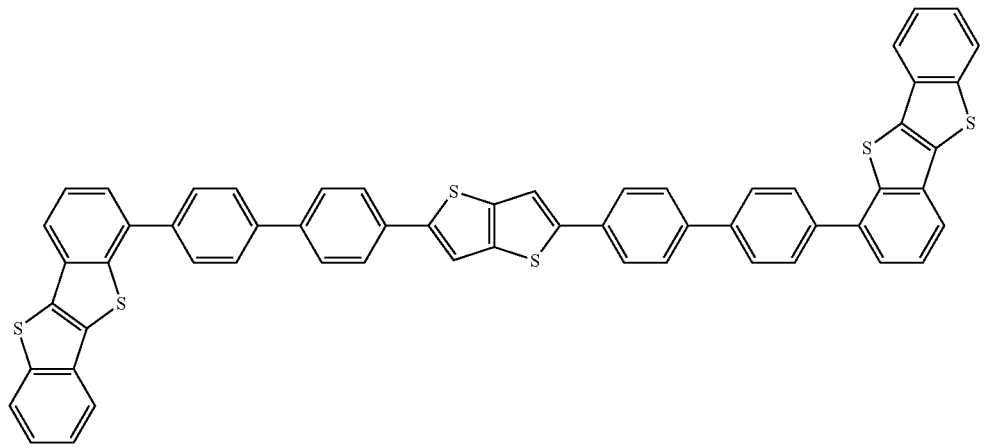
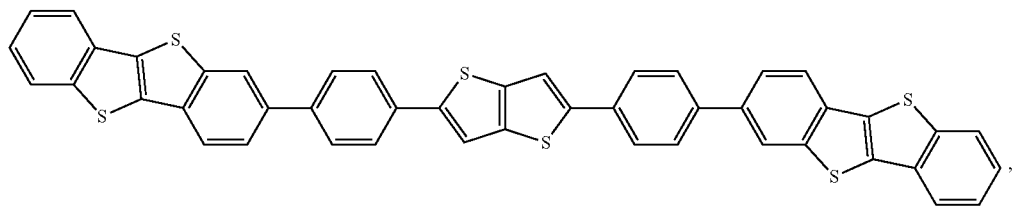
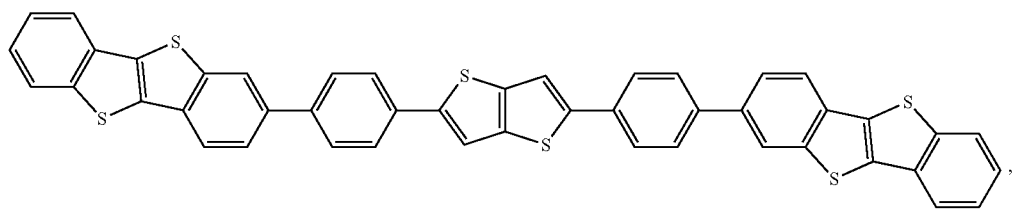
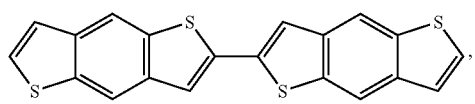
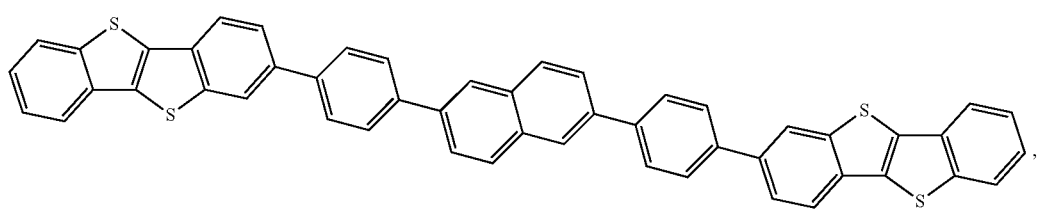
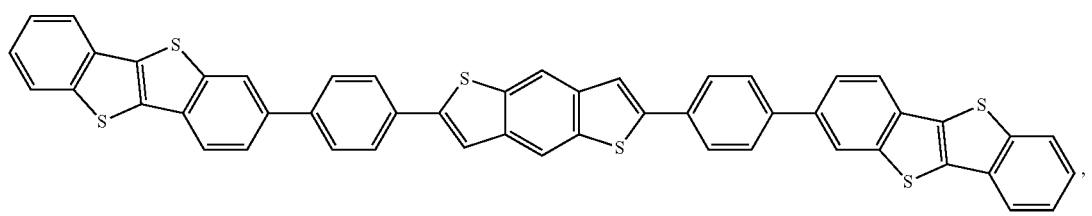

-continued
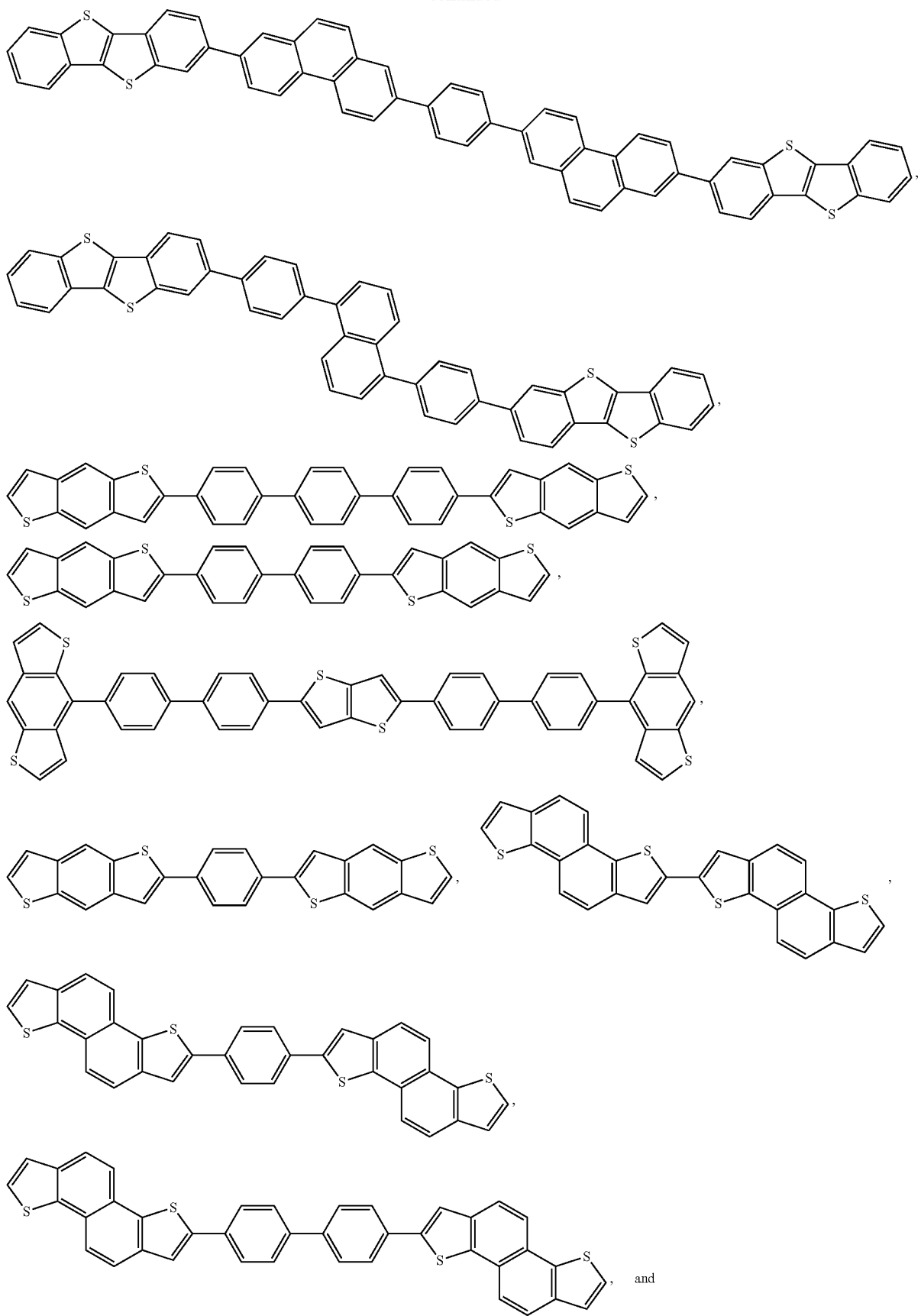

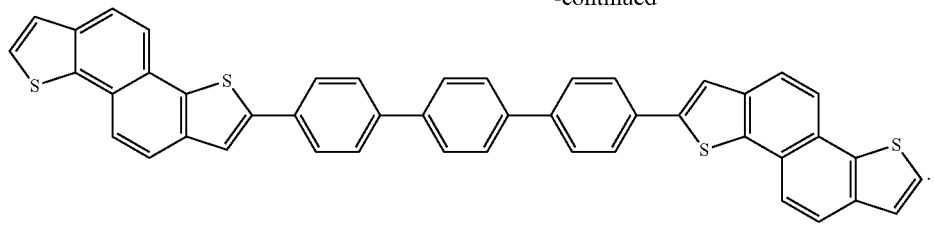
In one embodiment, the transparent P material of the present disclosure is a thiophene- or selenophene-based material represented by the general formula XL
T-H     XL,
T is selected from a structure with one of the general formulas IX, Xa, Xb, XI, XIIa, XXII to XXXVIII:
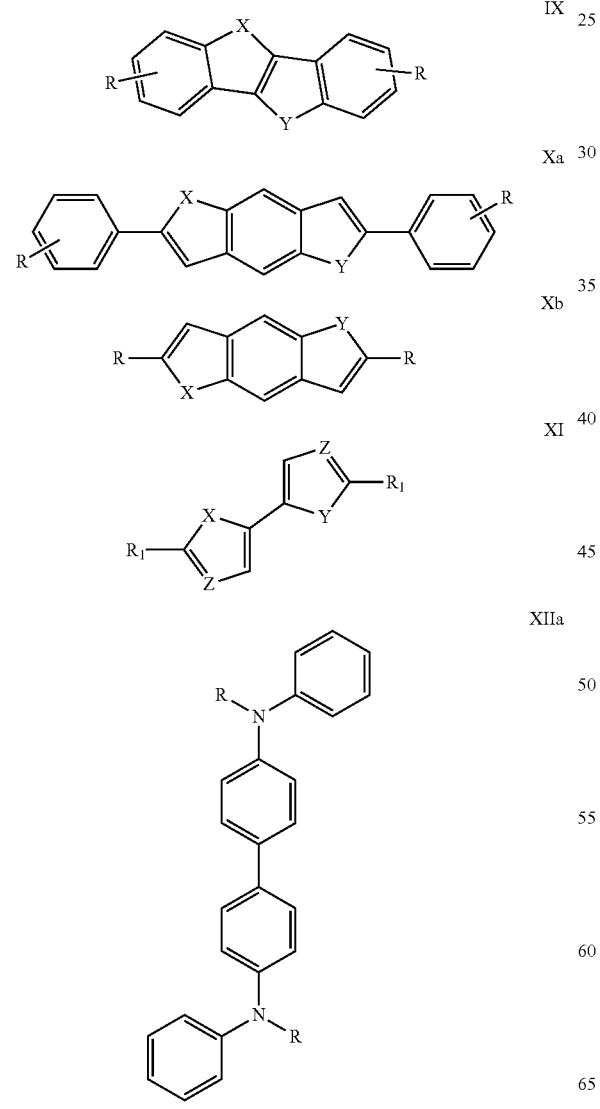
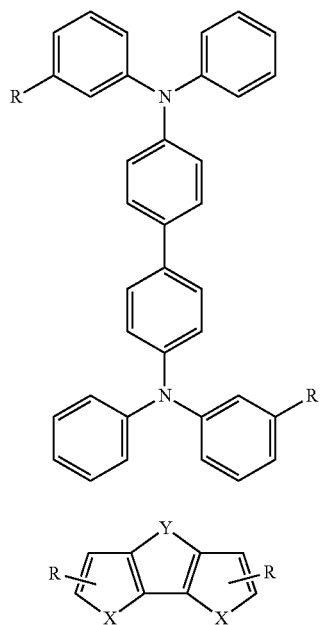
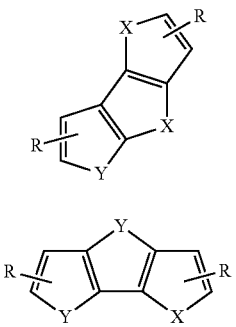
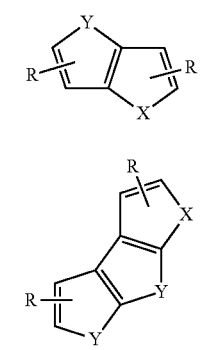

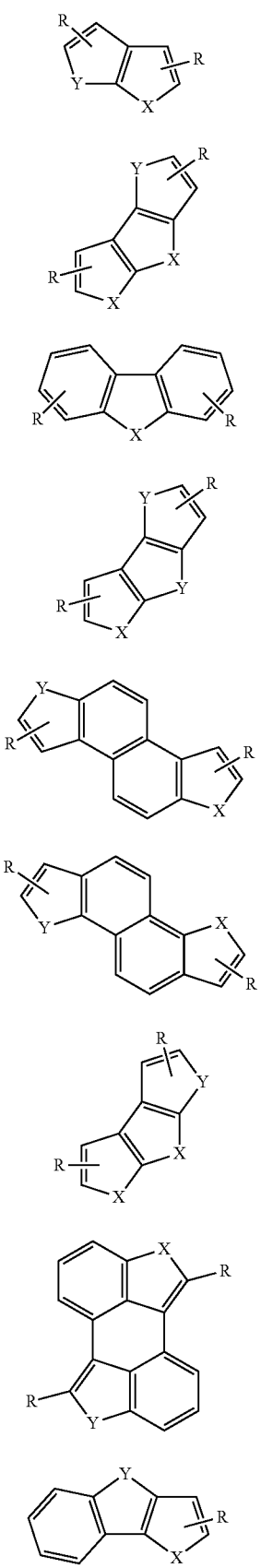
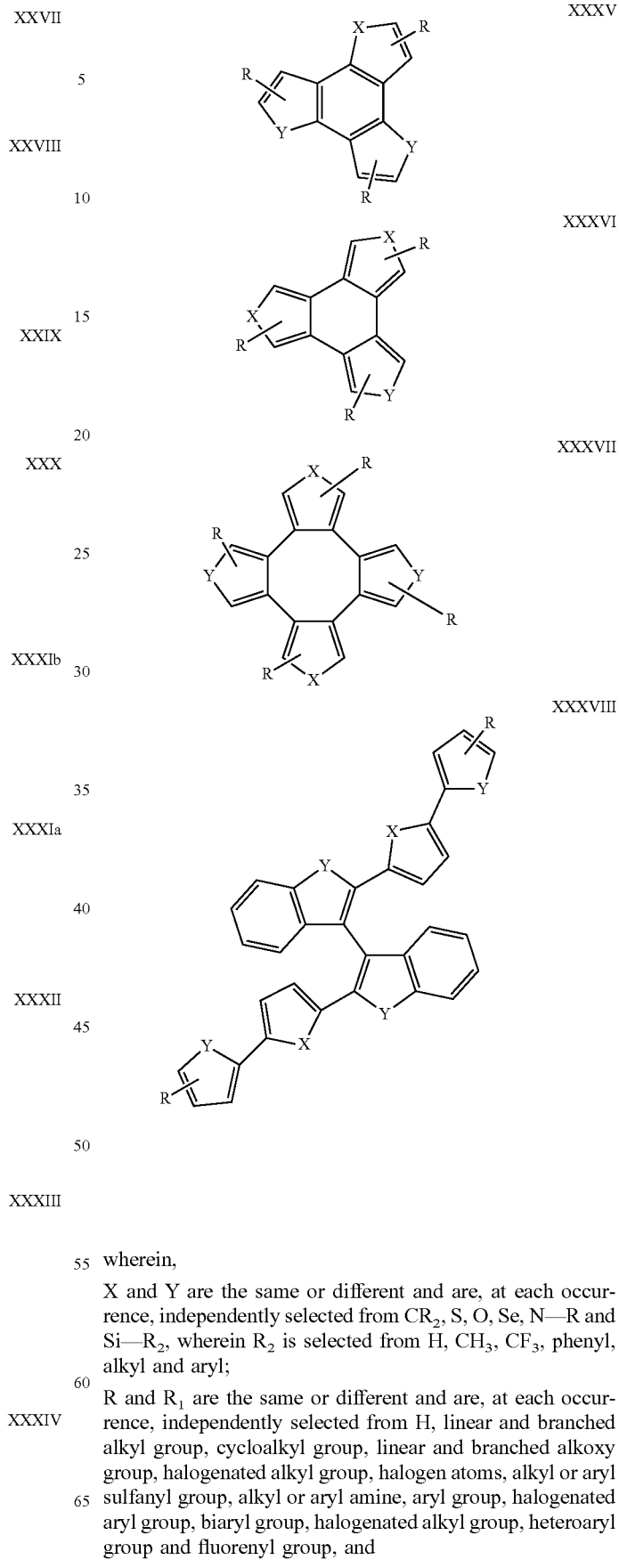

wherein,

X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl;

R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group, and 123
H is selected from any one of
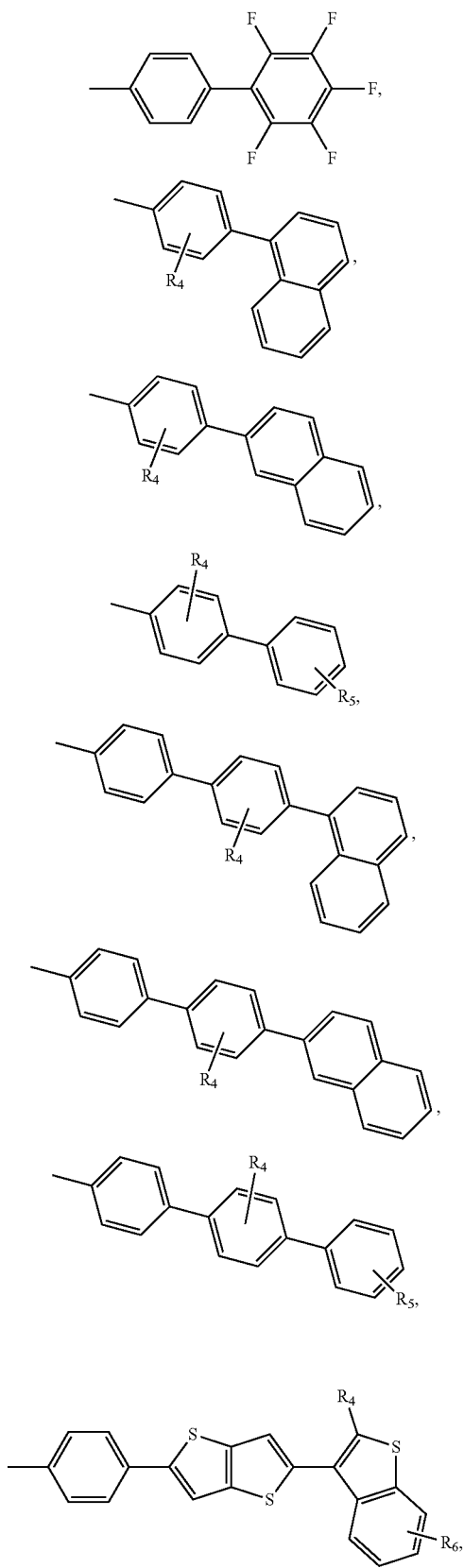
124
-continued
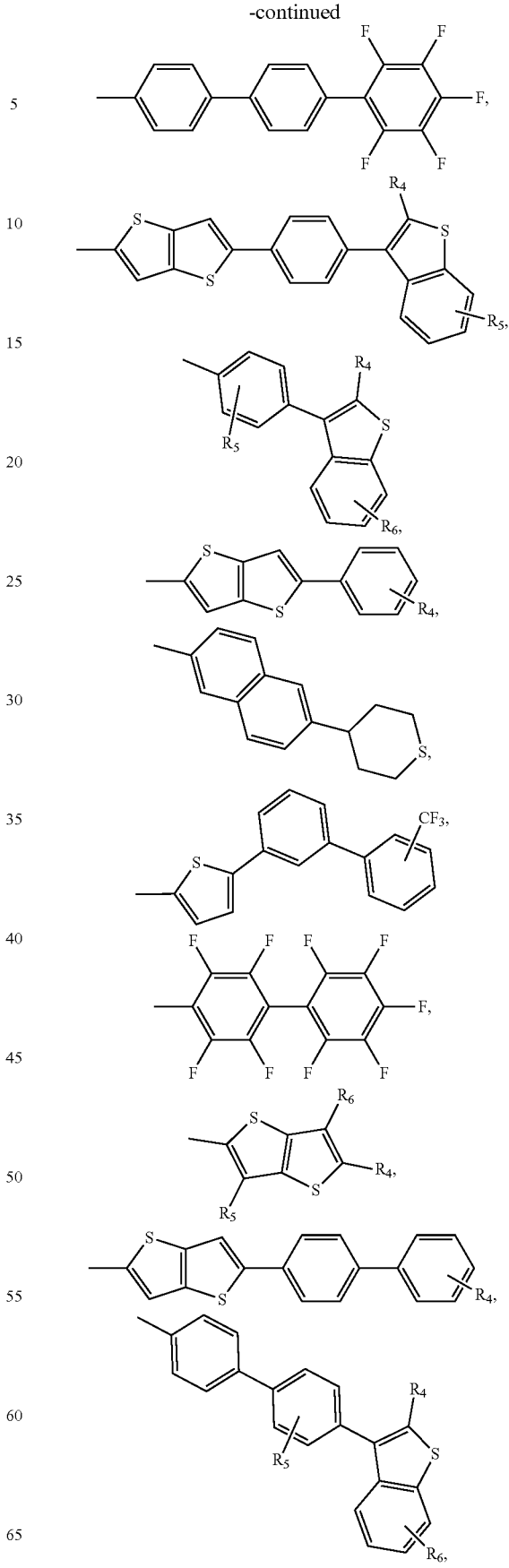

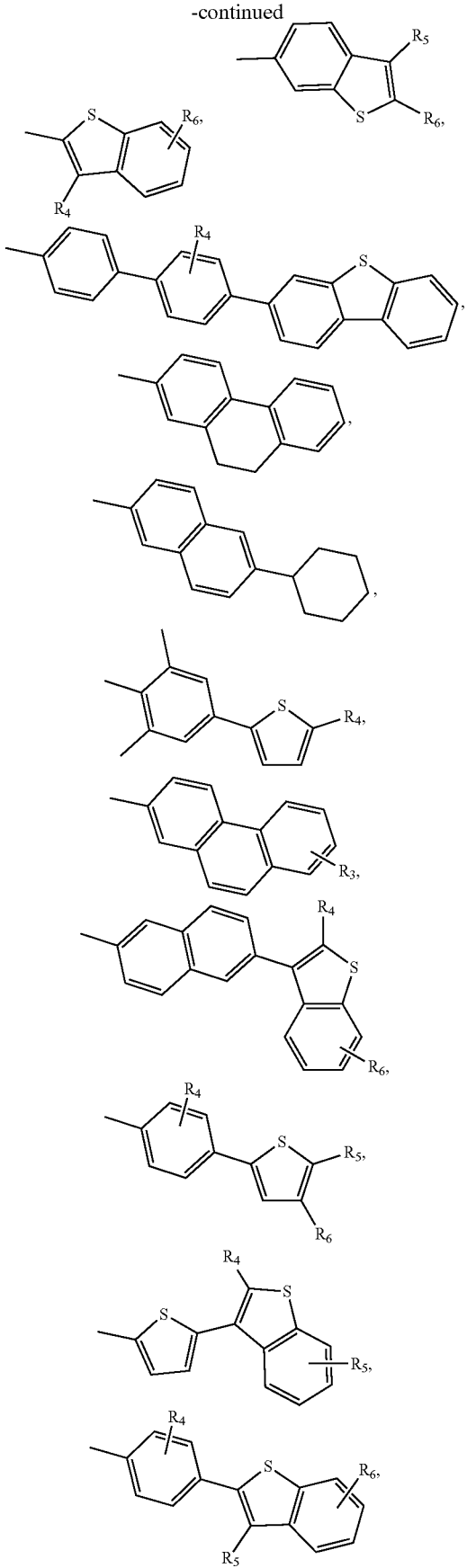
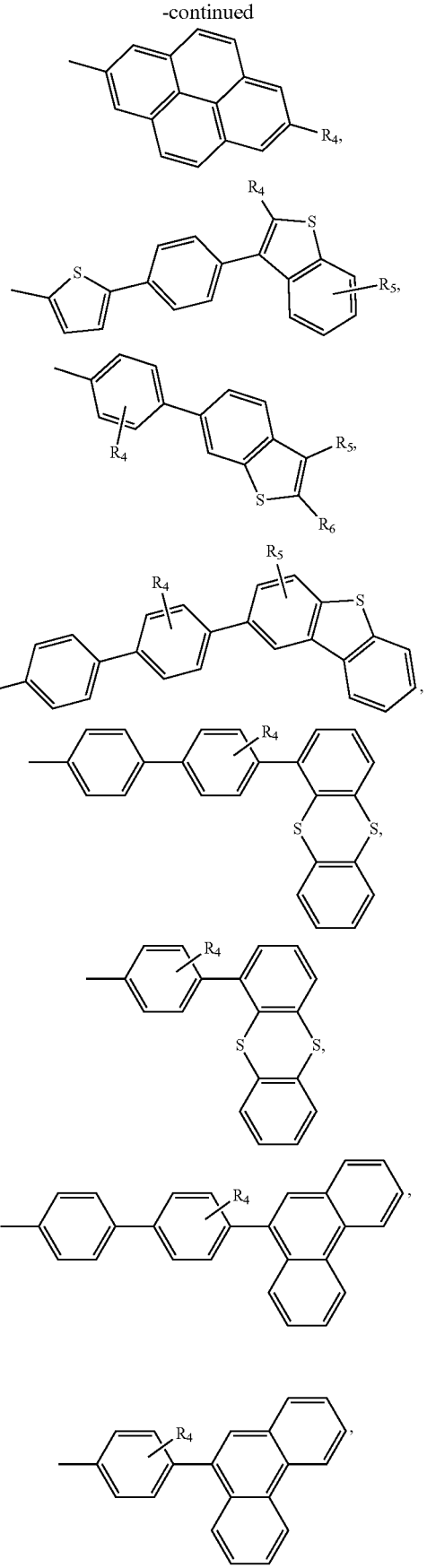

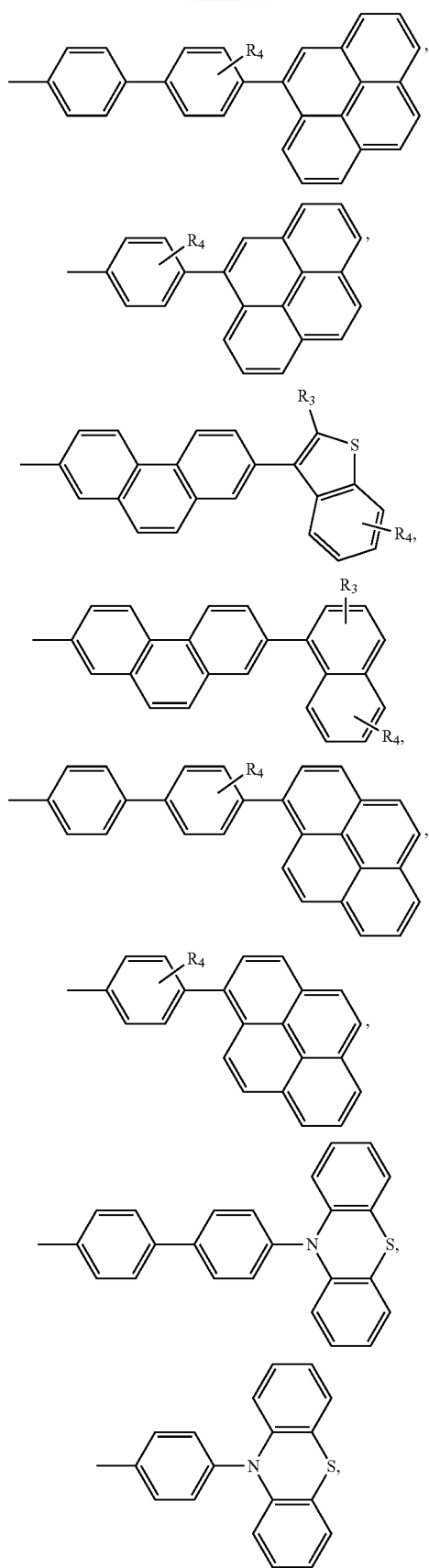
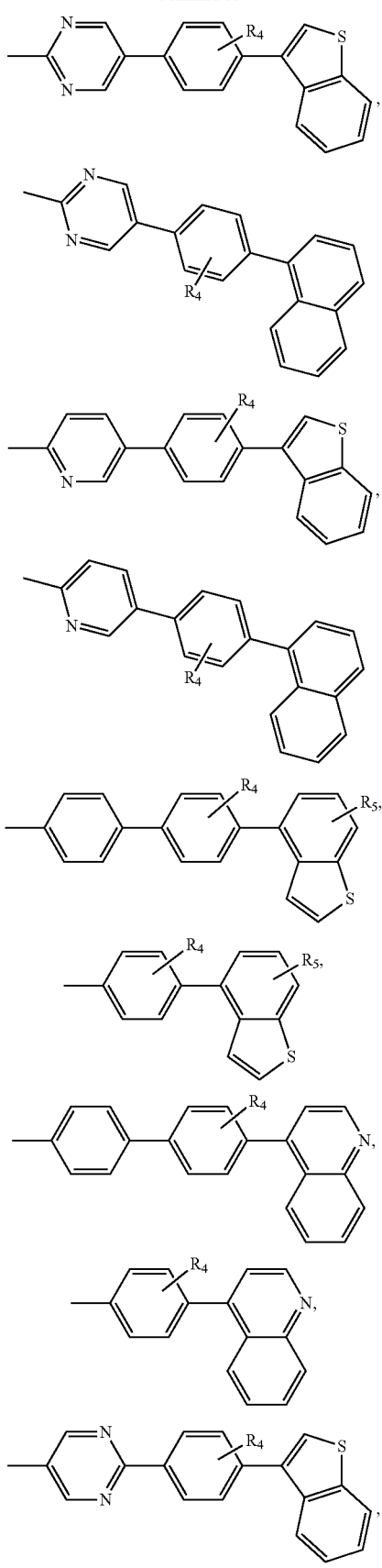

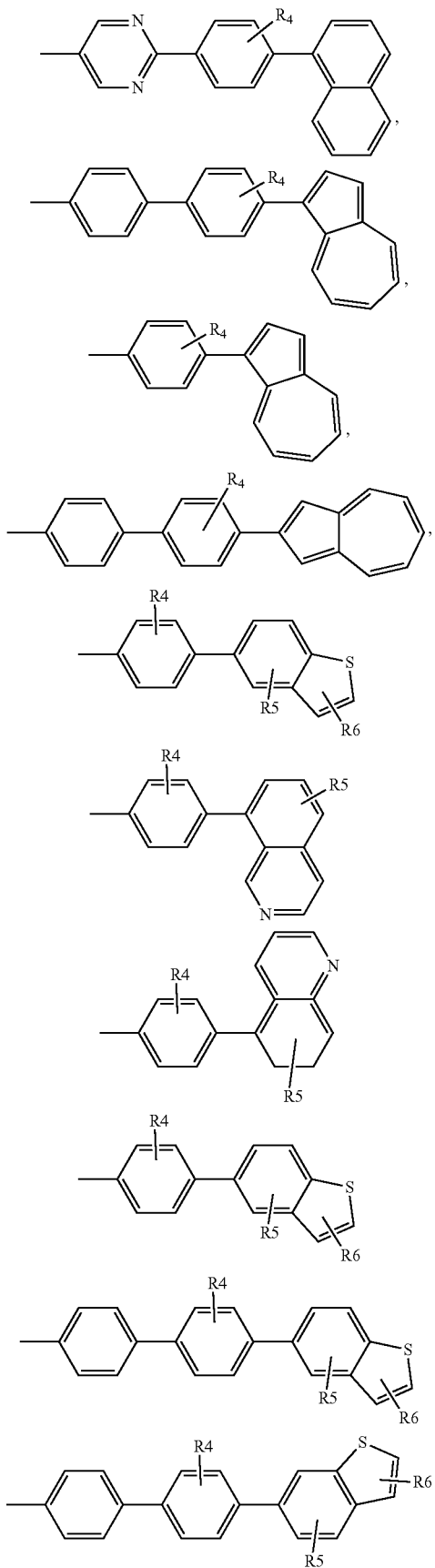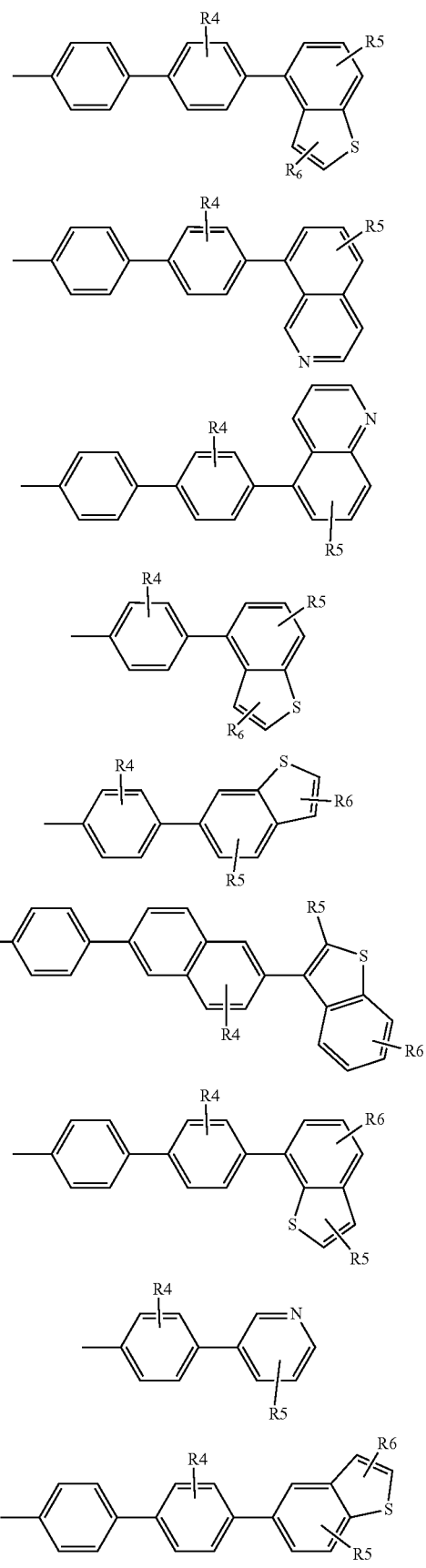

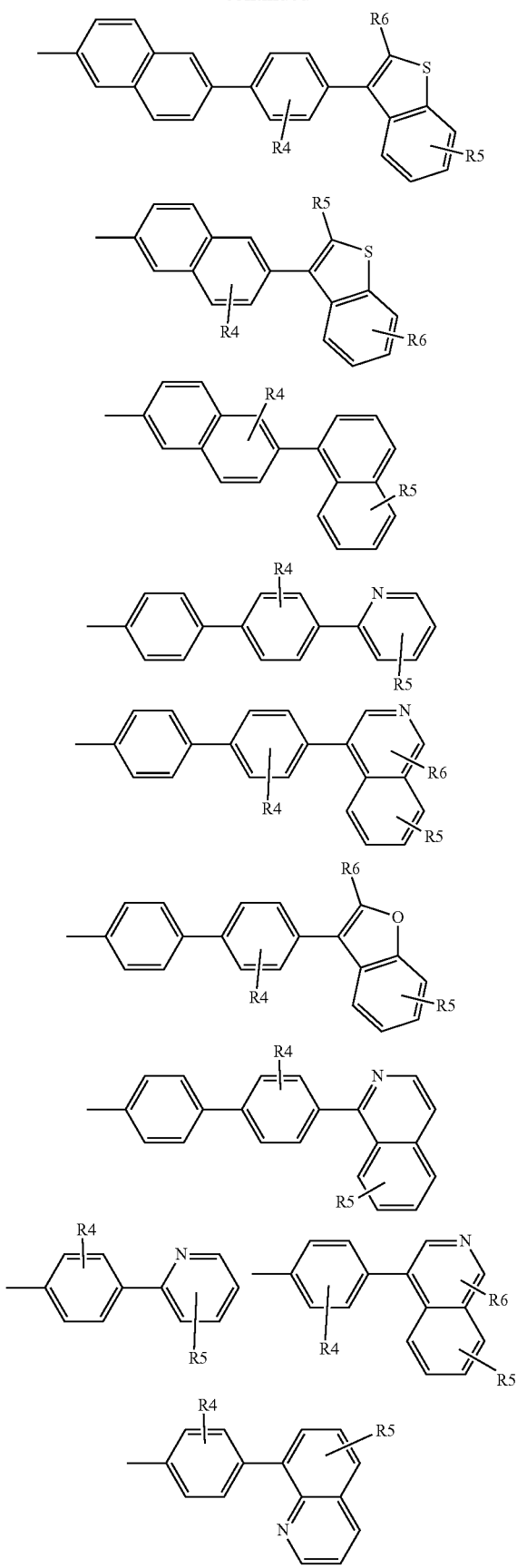
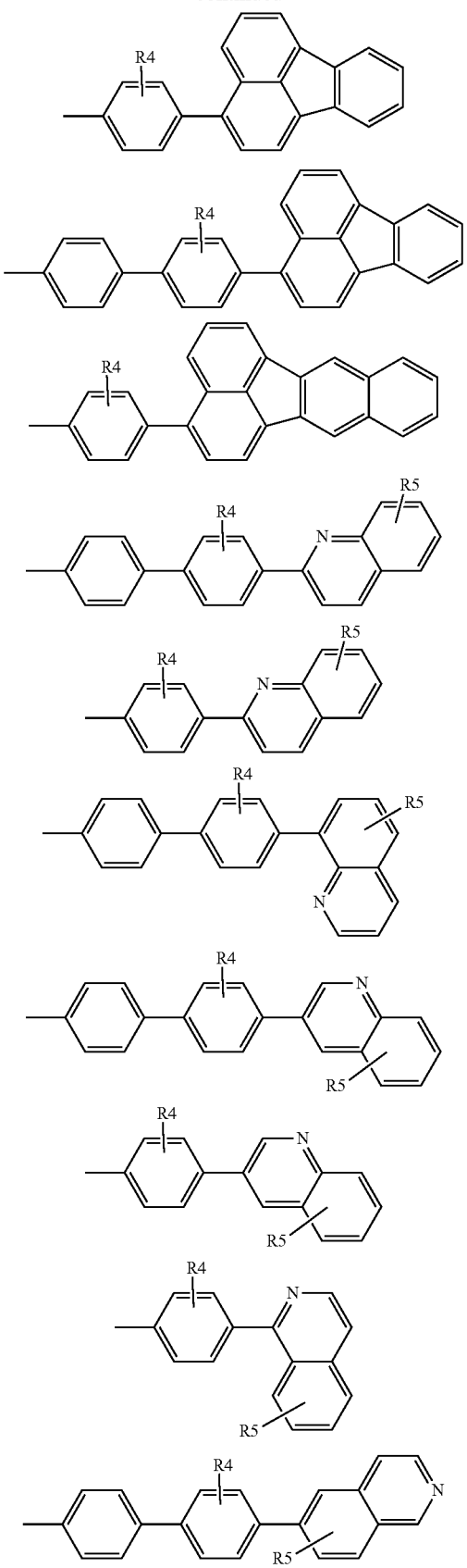

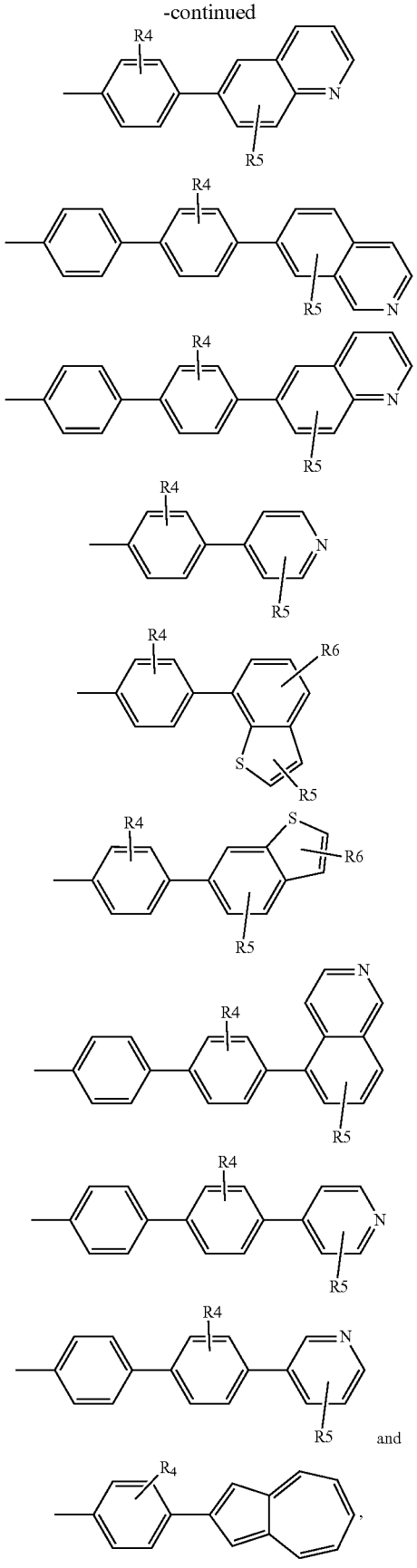
wherein $R_4$, $R_5$, $R_6$ are the same or different and are, at each occurrence, independently selected from H, F, $CH_3$, alkyl group and aryl group.
In a more preferred embodiment of the thiophene- or selenophene-based material represented by the general formula XL, the material is selected from the group consisting of
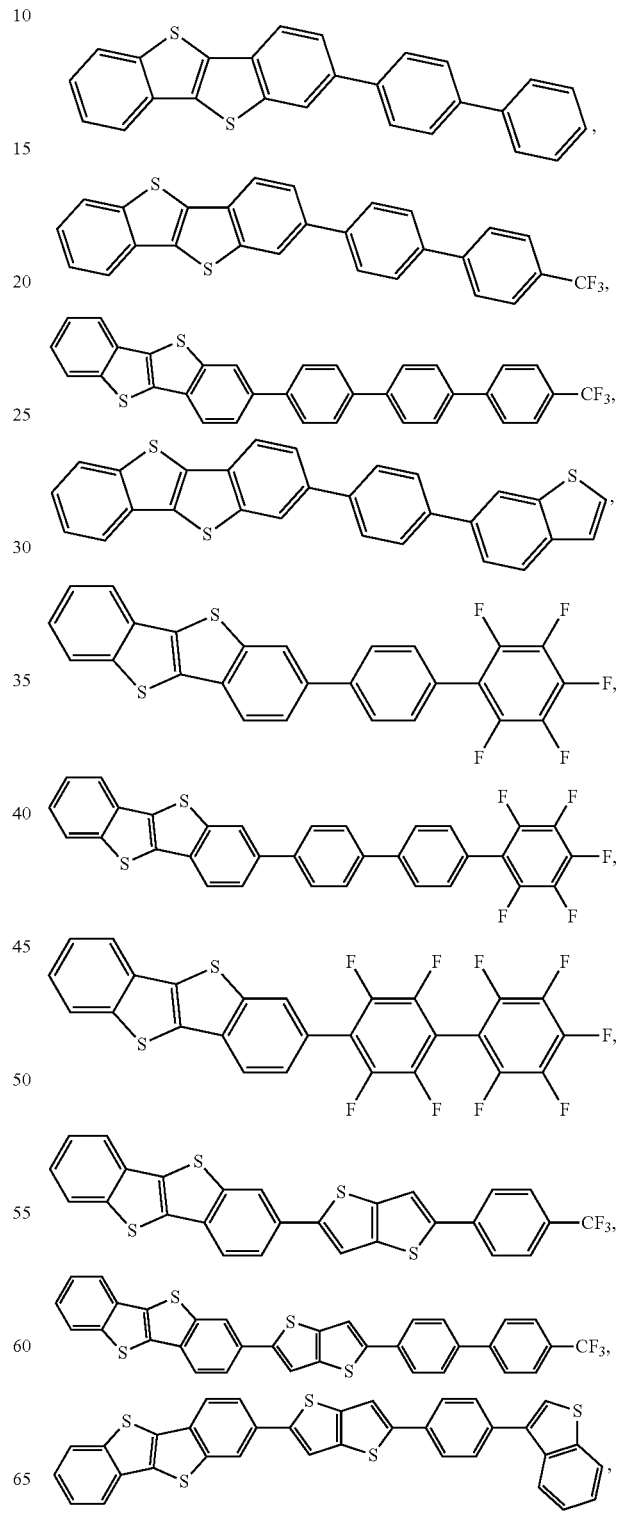

-continued
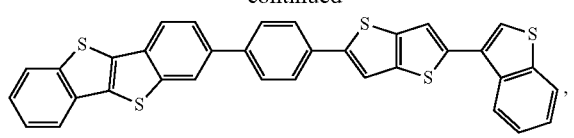
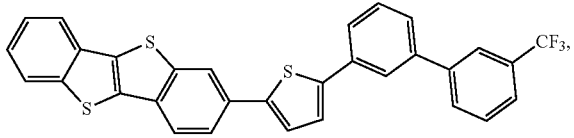
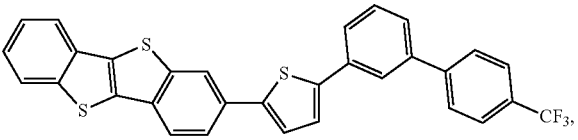
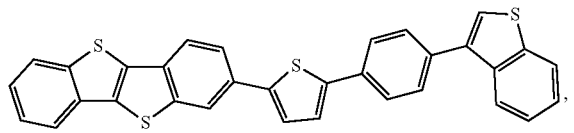
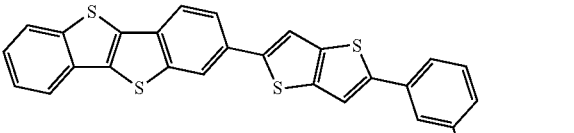
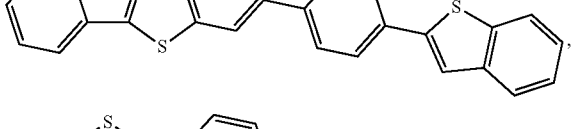
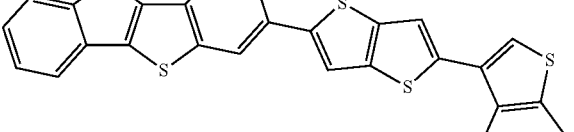
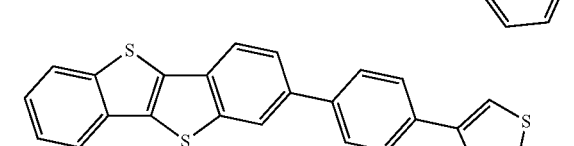
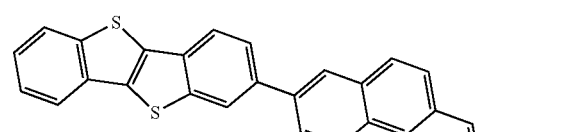
-continued
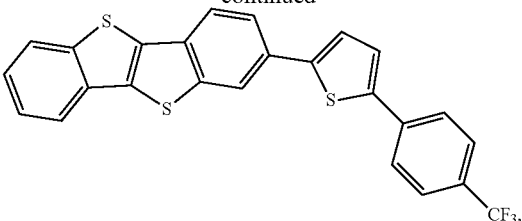
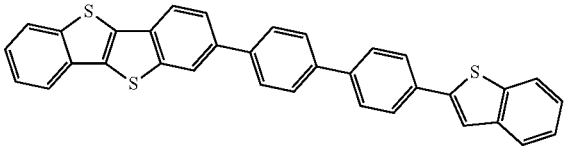
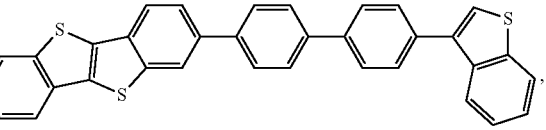
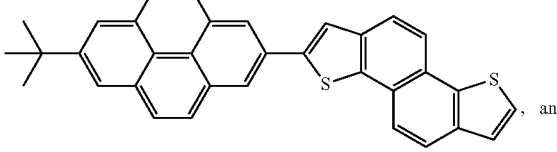
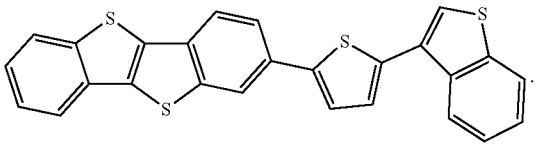
, and
In one embodiment the transparent P material of the present disclosure is a thiophene- or selenophene-based material represented by the general formula XLI,
H-T-B-T-H        XLI,
wherein,
T is none or selected from a structure with one of the general formulas IX, Xa, Xb, XI, XIIa, XIIb, XXII to XXXVIII:
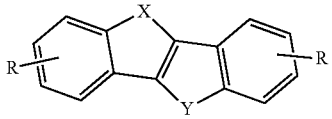    IX
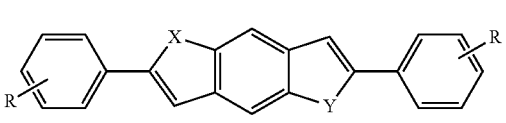    Xa
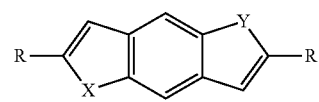    Xb
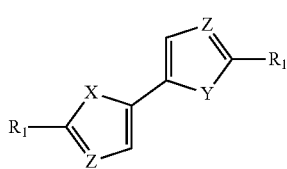    XI

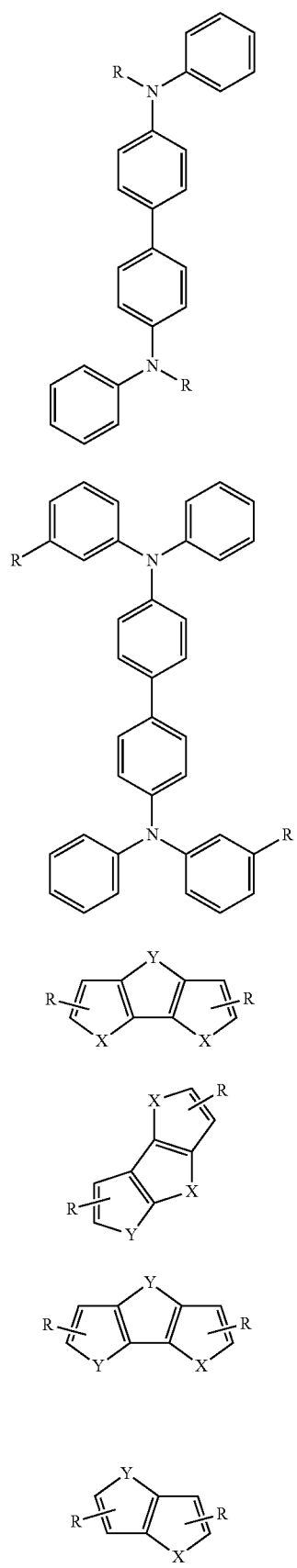
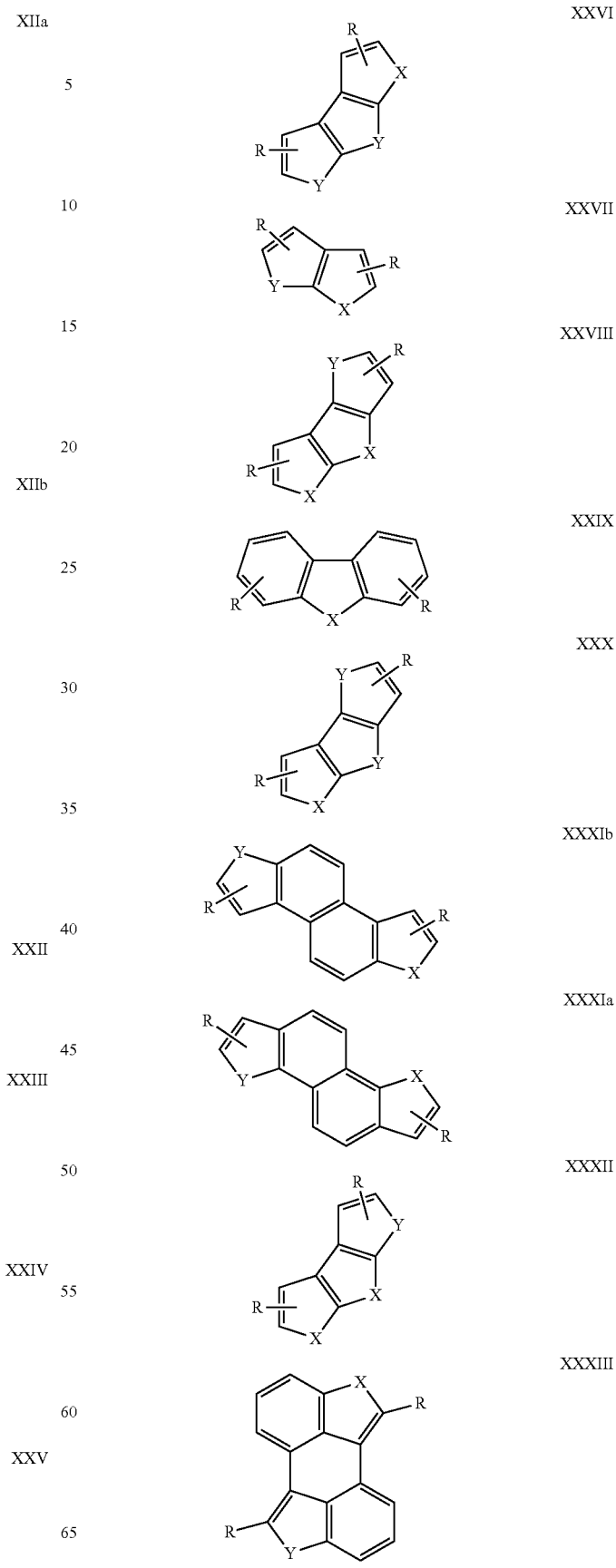

-continued

XXXIV

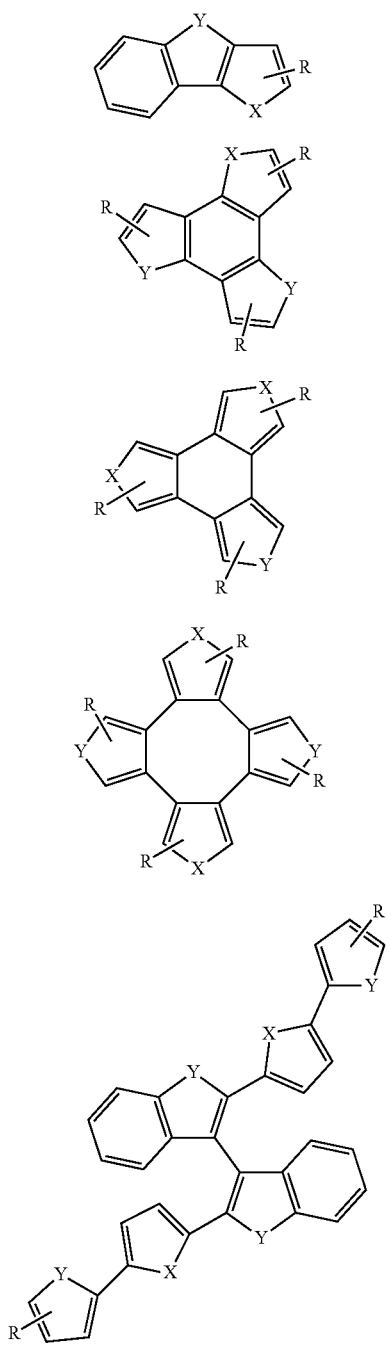

XXXV

XXXVI

XXXVII

XXXVIII wherein,

X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl; and R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group;

B is selected from
none

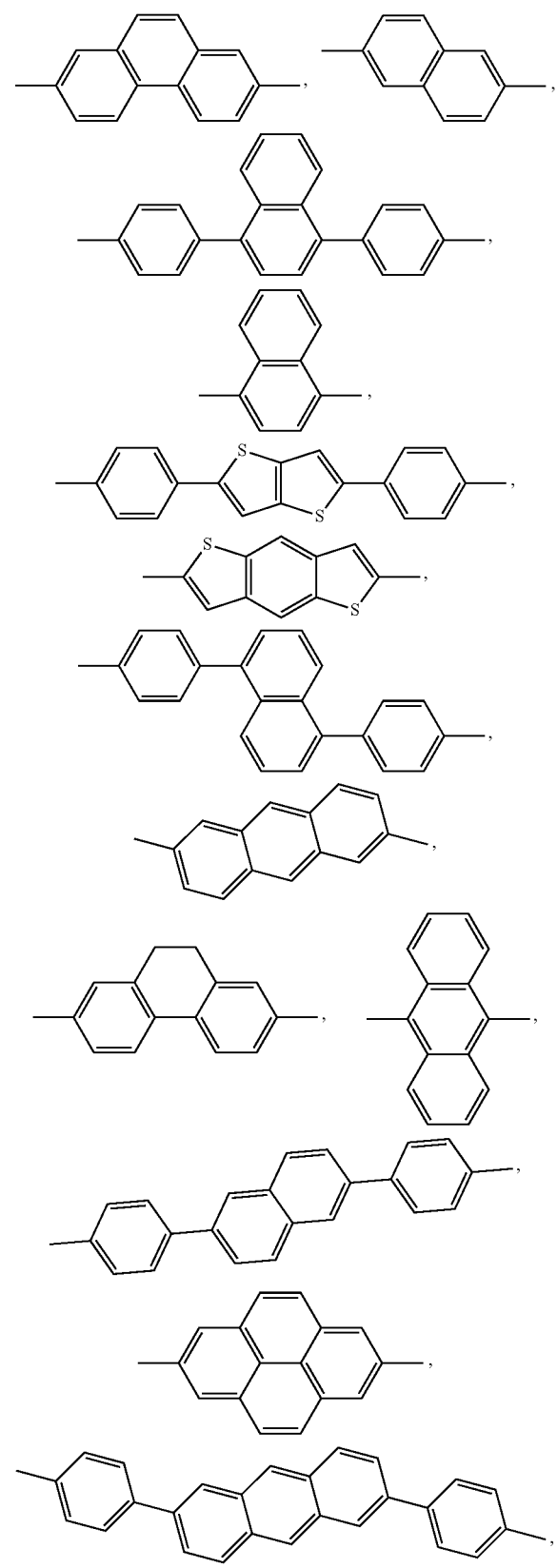

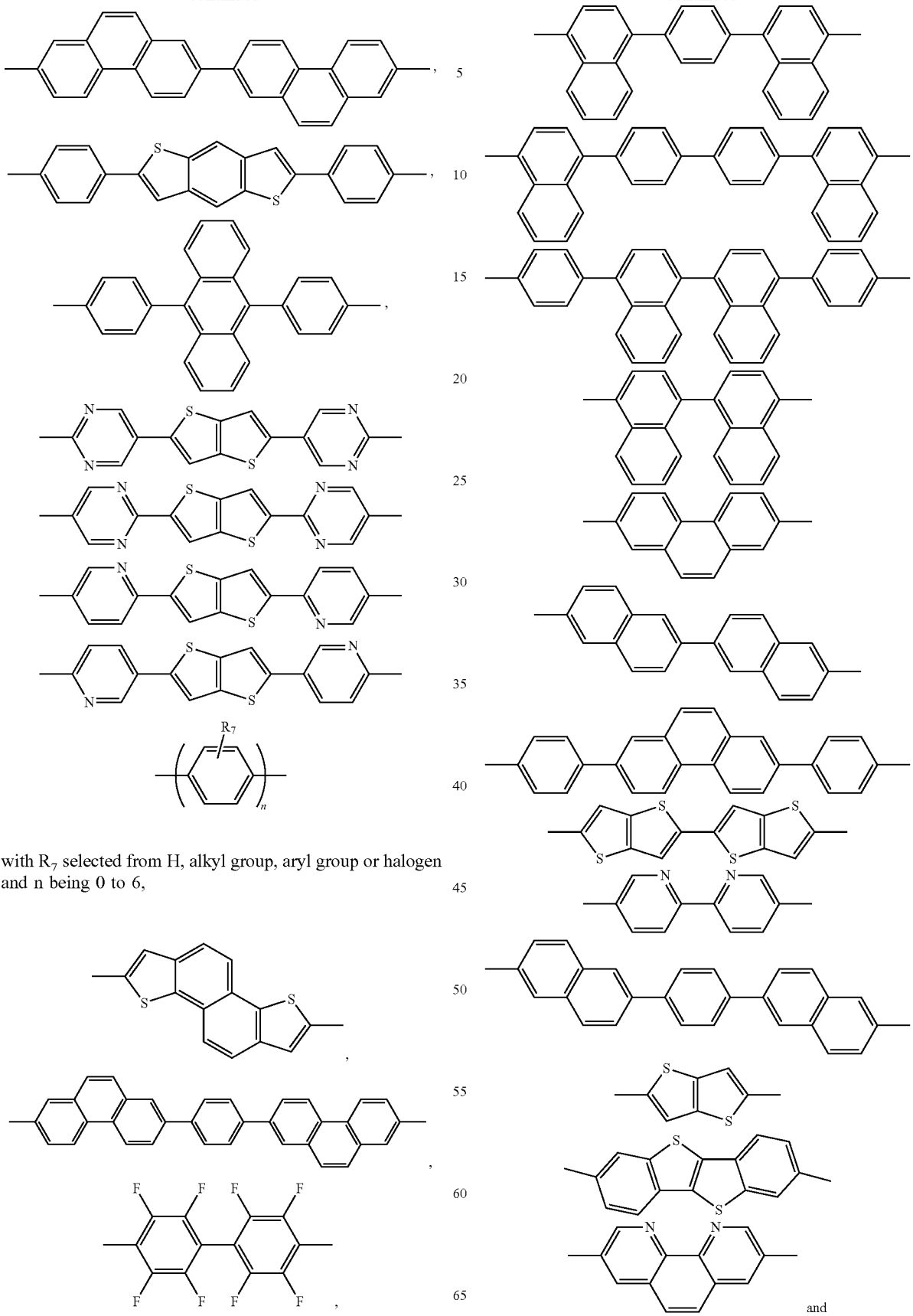
with R_7 selected from H, alkyl group, aryl group or halogen and n being 0 to 6,

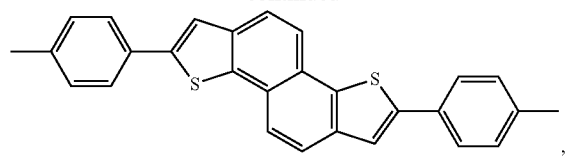
H is selected from
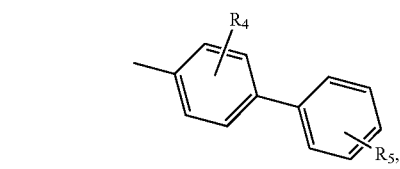
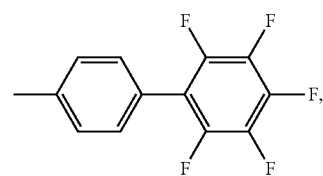
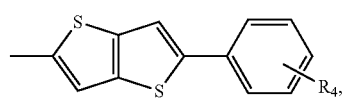
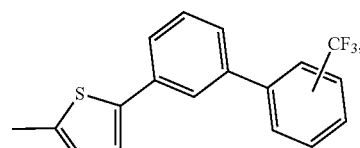
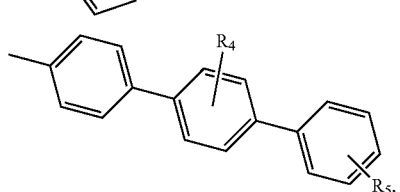
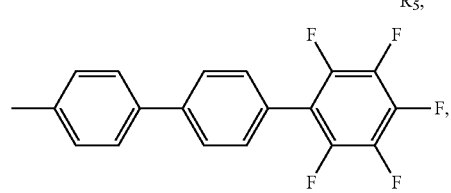
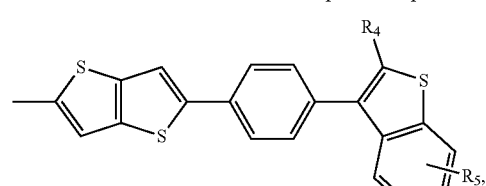
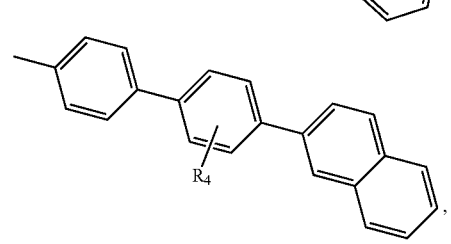
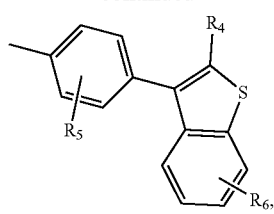
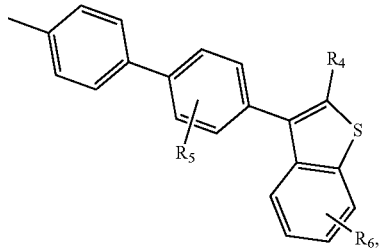
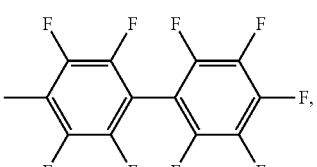
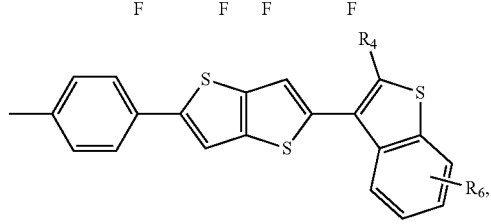
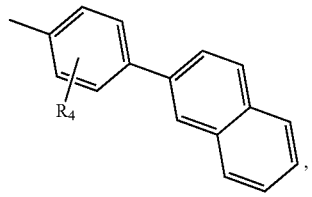
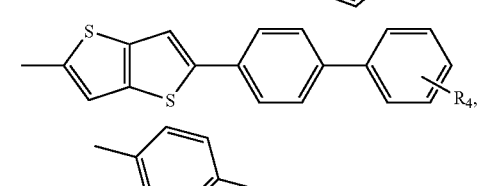
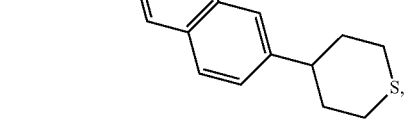
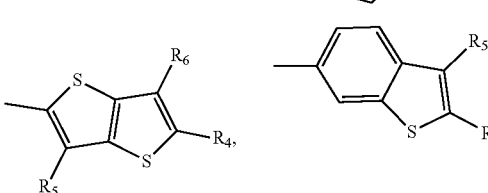
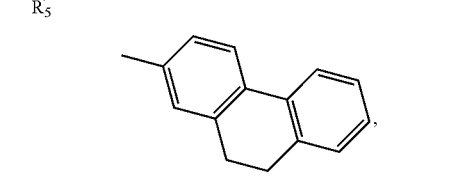

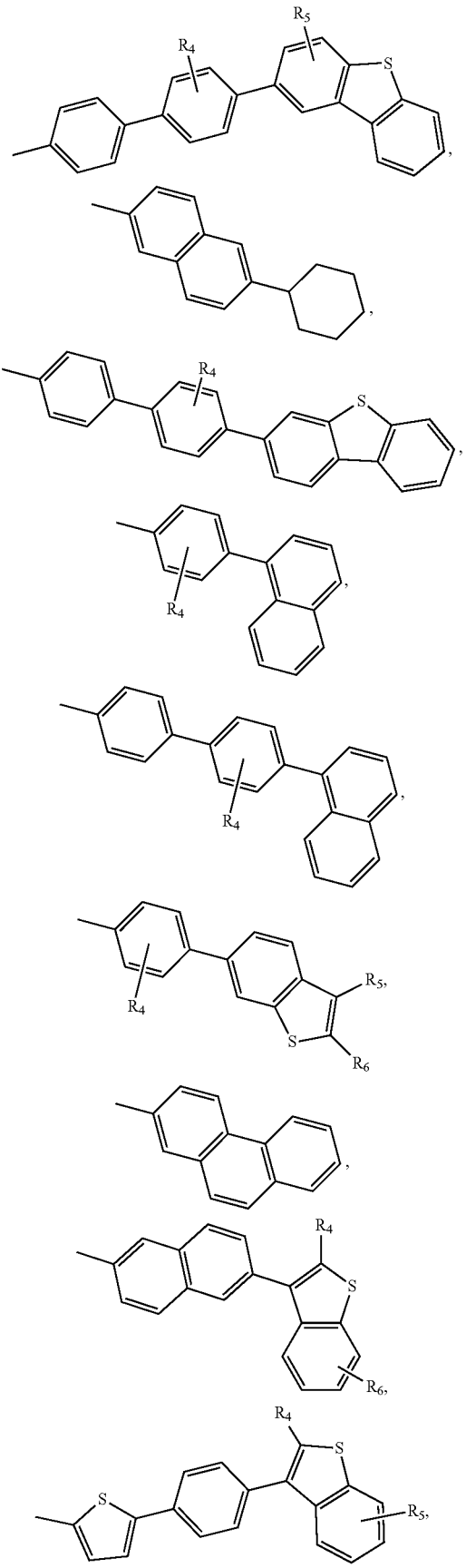
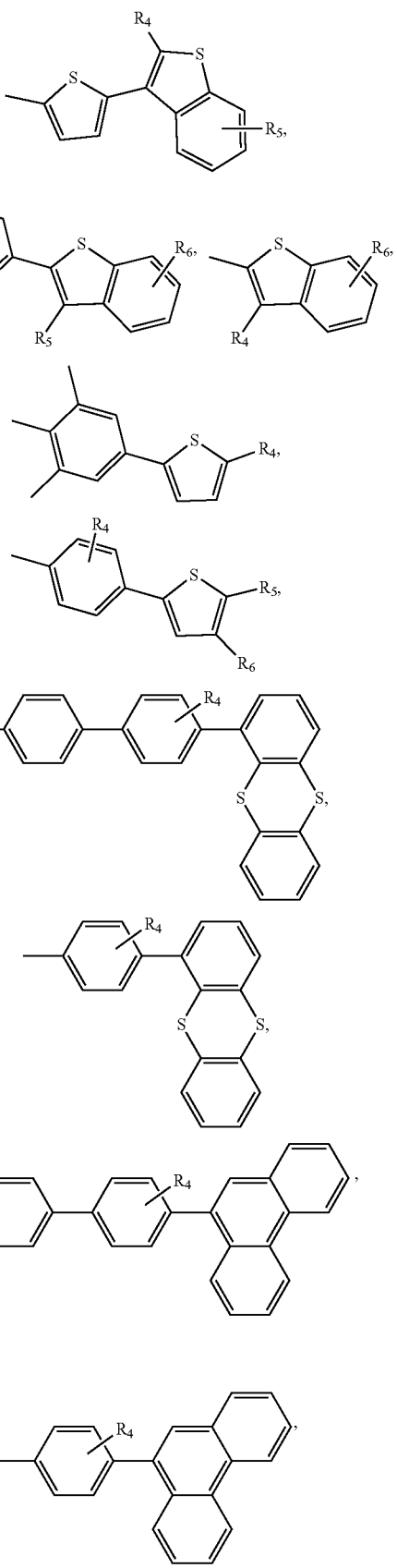

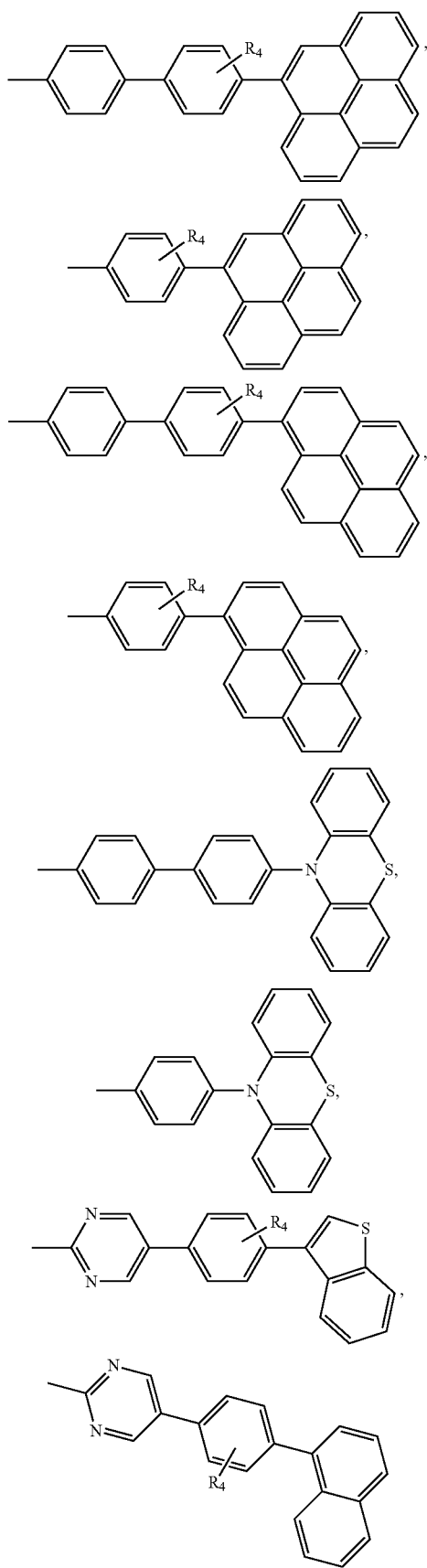
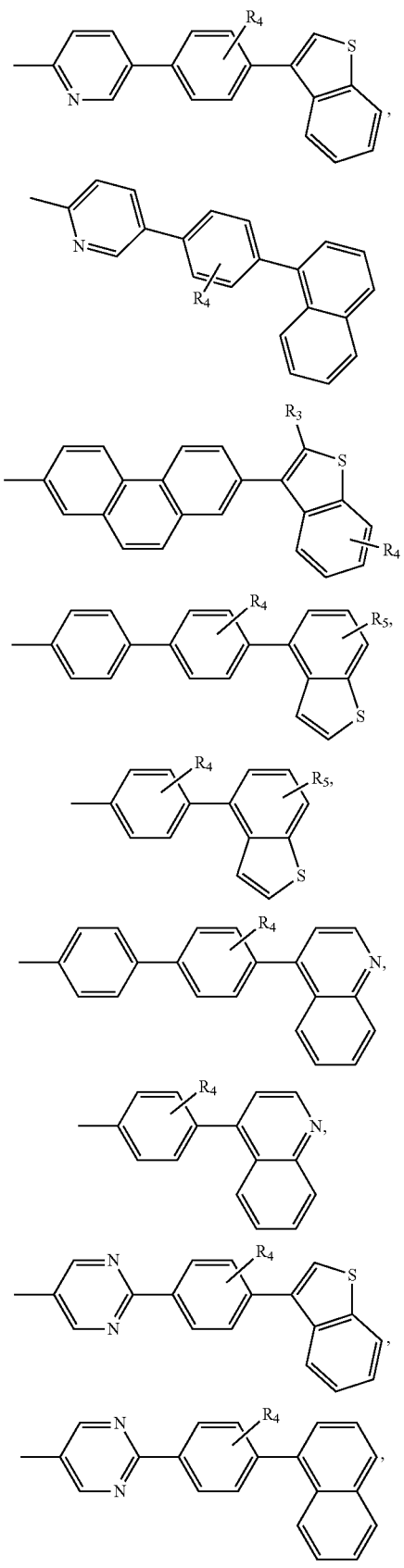

-continued
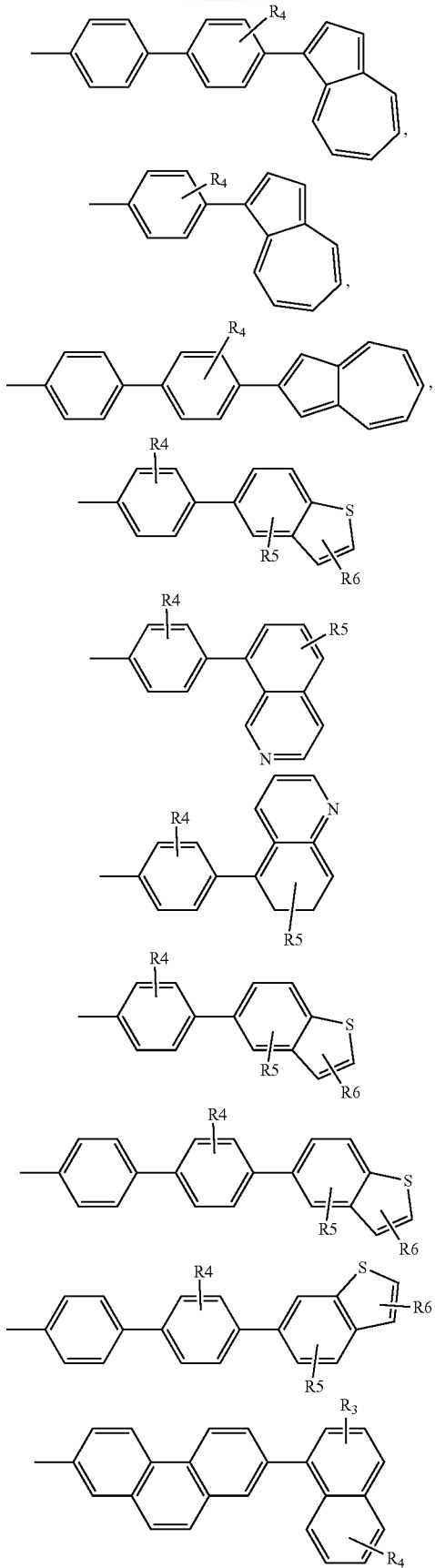
-continued
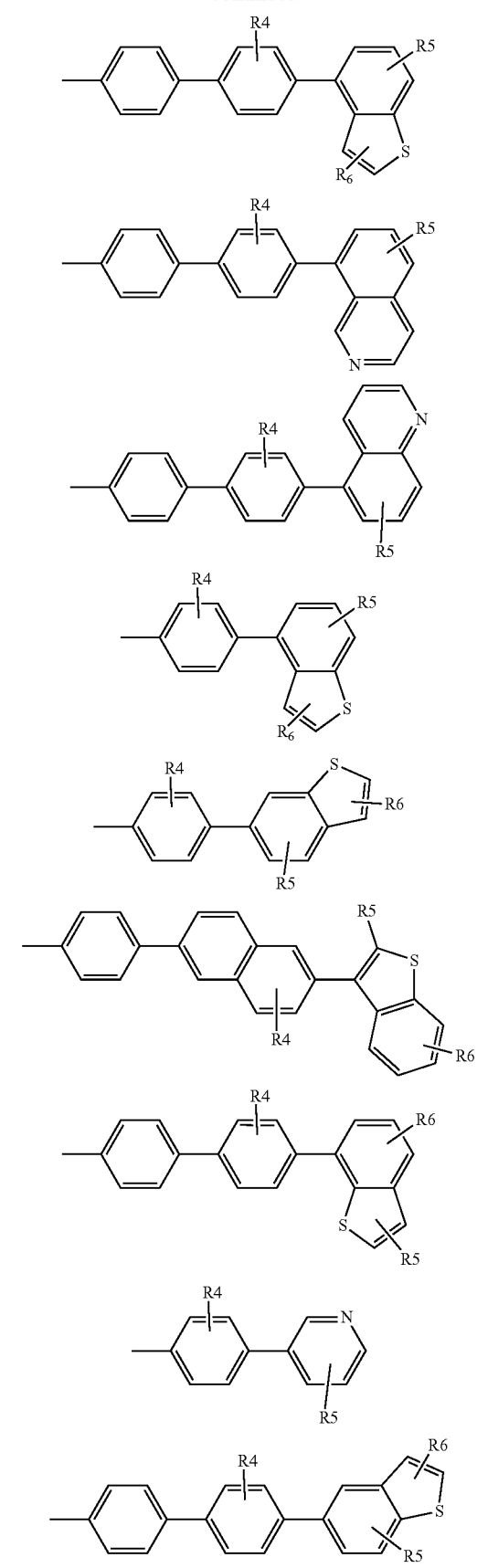

151
-continued
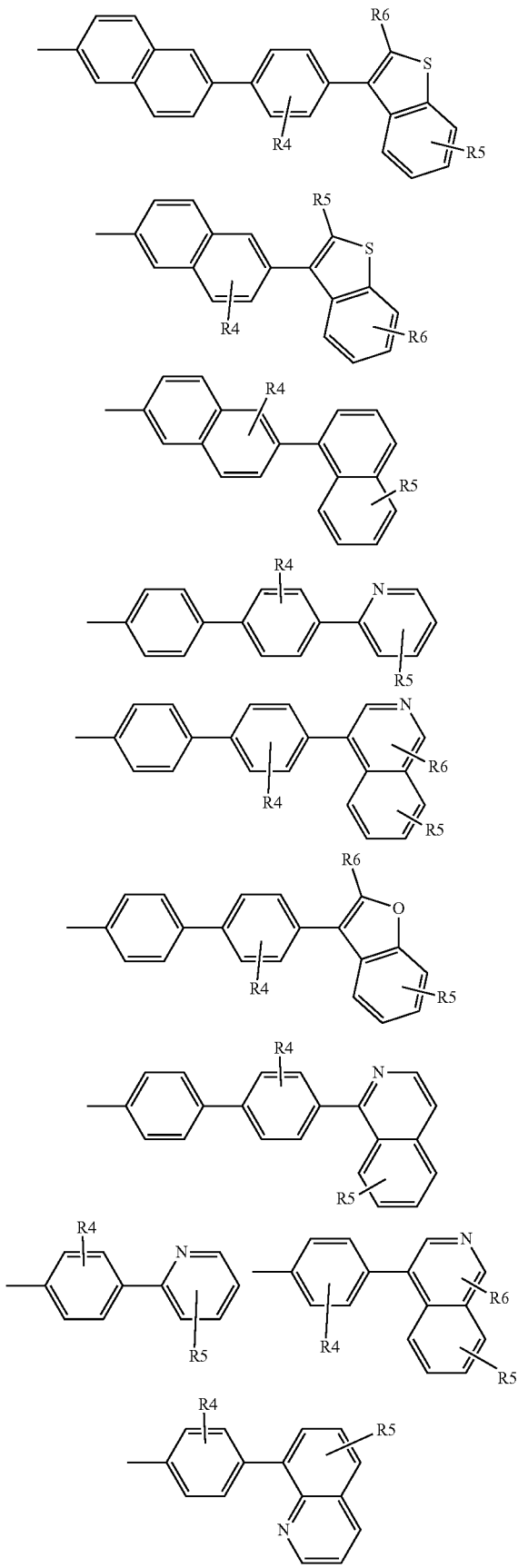
152
-continued
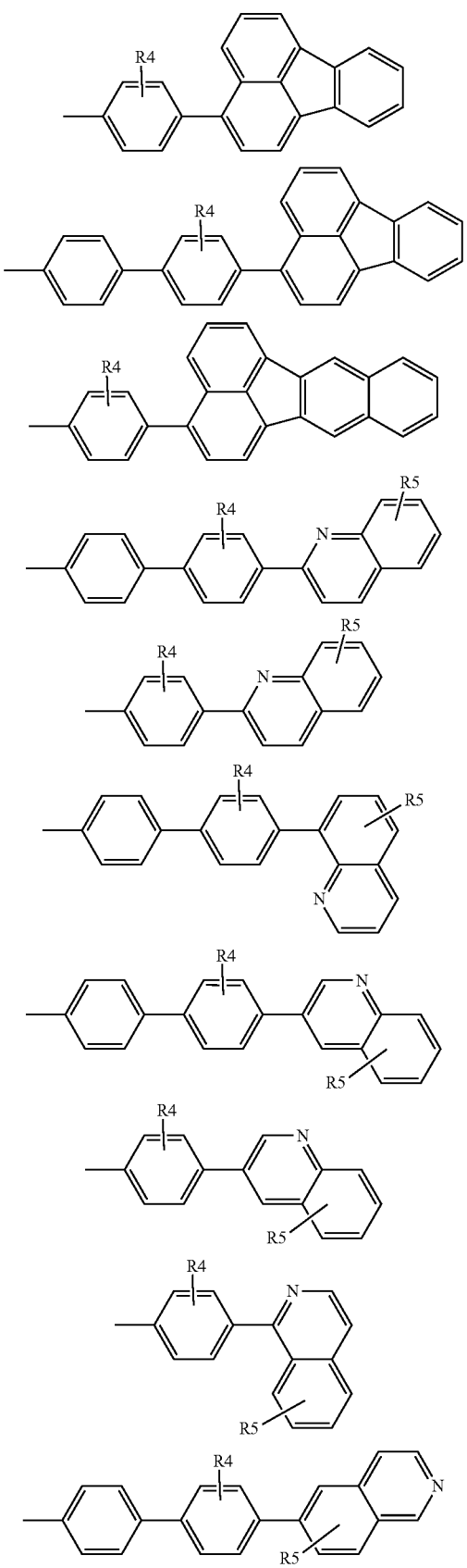

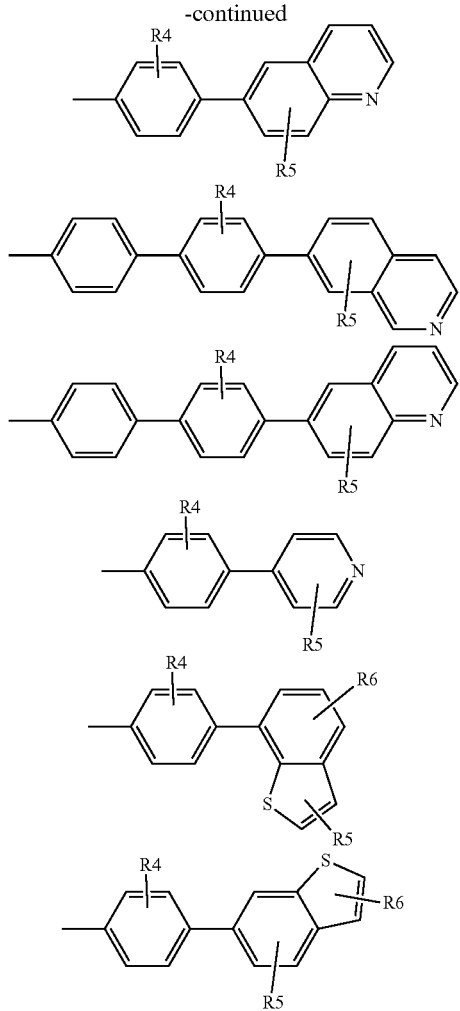
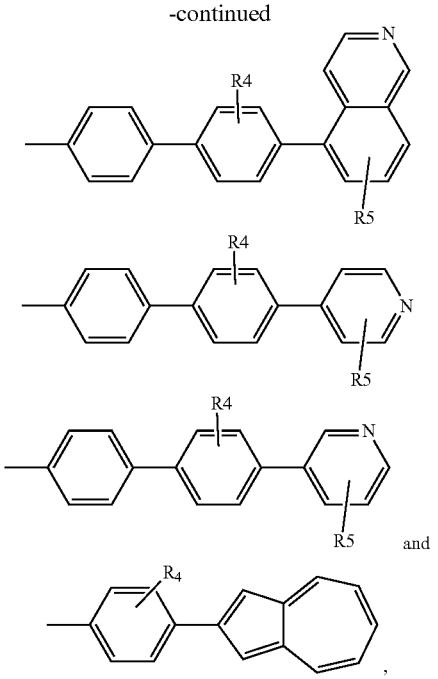
wherein $R_4$, $R_5$, $R_6$ are the same or different and are, at each occurrence, independently selected from H, F, $CH_3$, alkyl and aryl.
In a more preferred embodiment of the thiophene- or selenophene-based material represented by the general formula XLI, the material is selected from the group consisting of
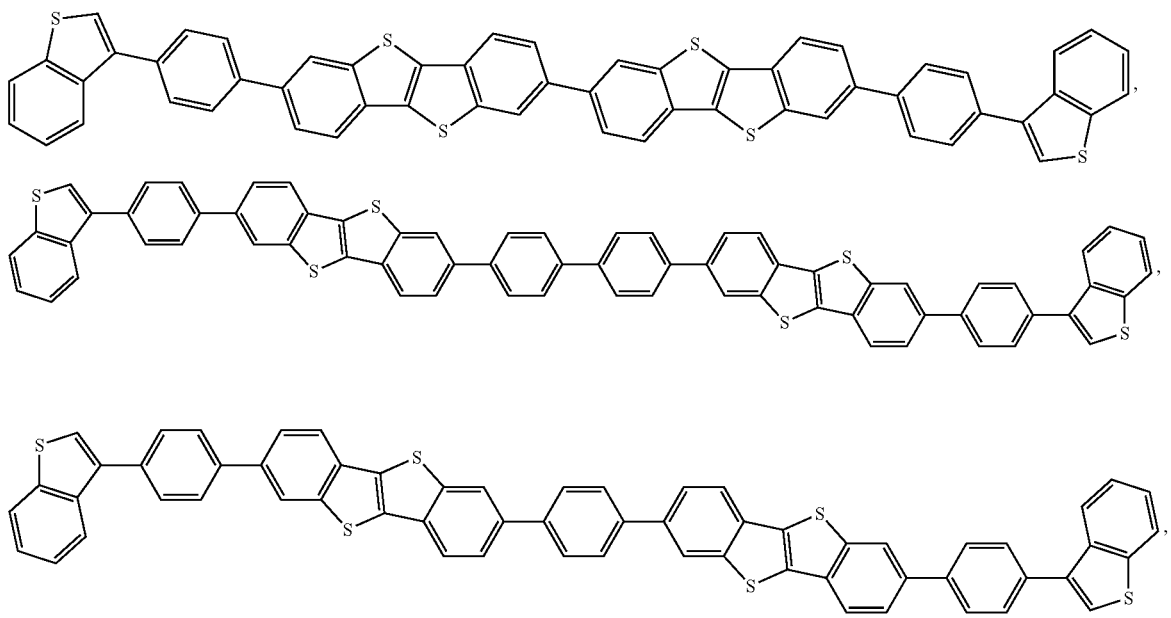

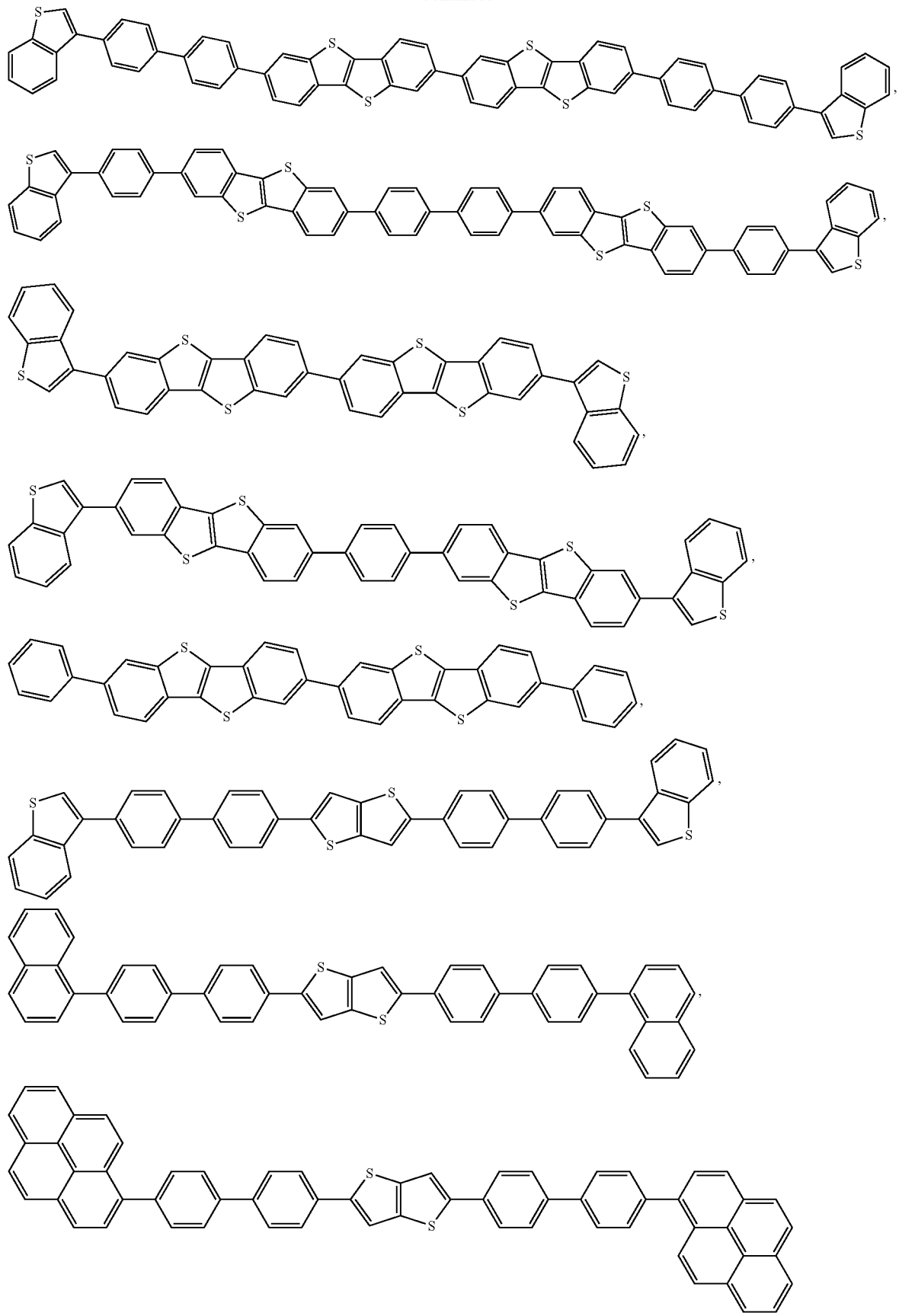

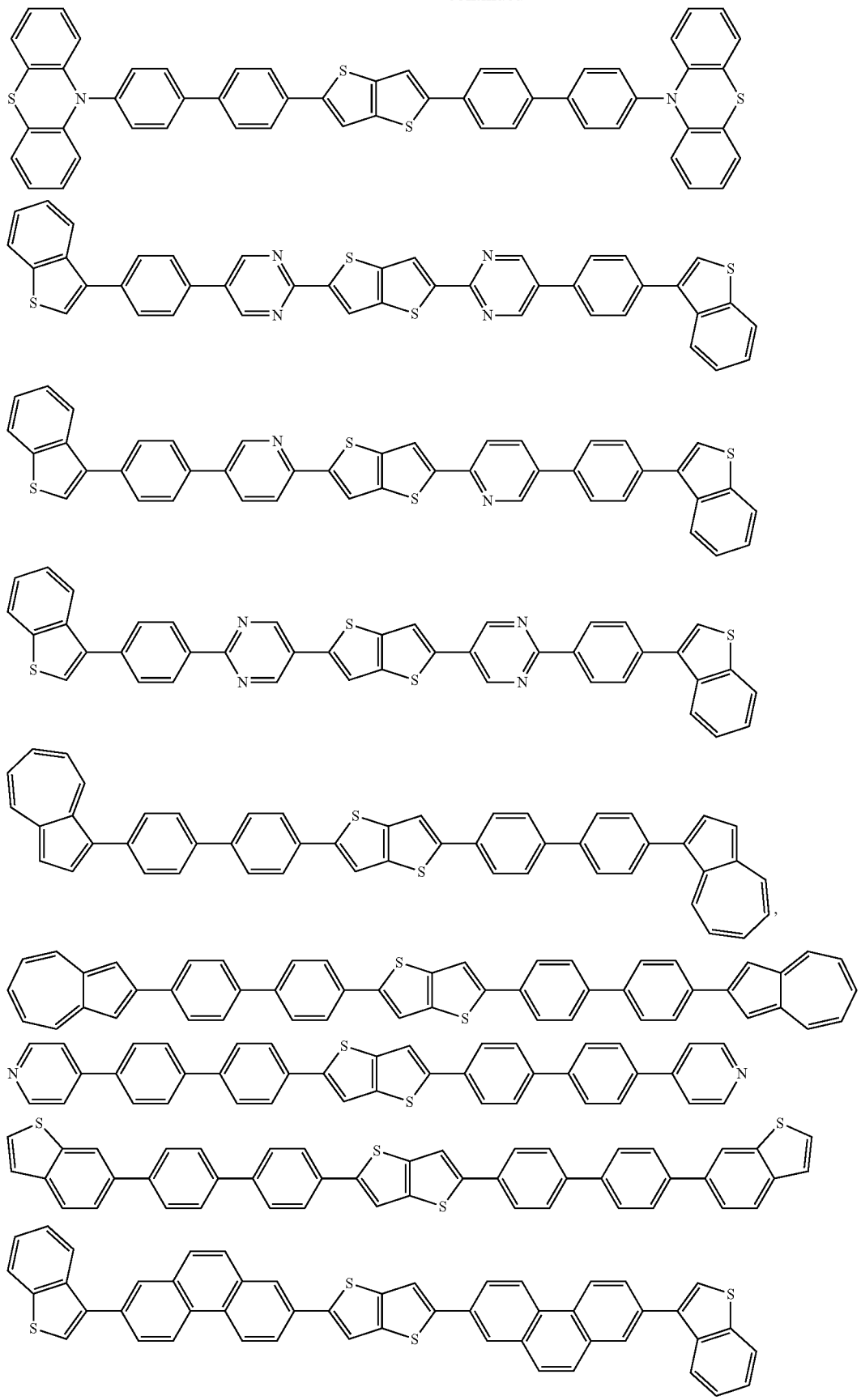

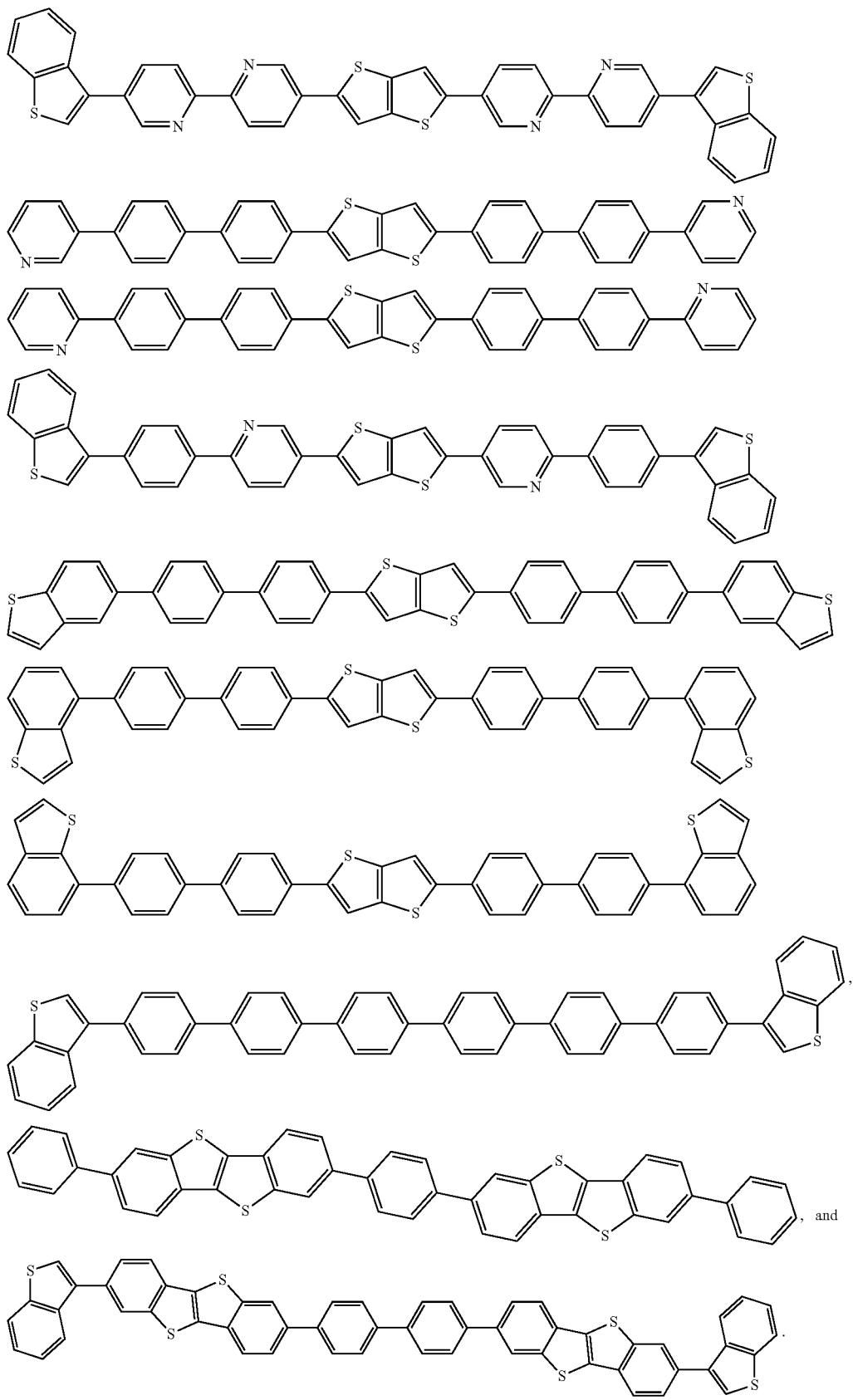

In a more preferred embodiment, the material is a thiophene-based material selected from the group of BDT3, BTBT14, BTBT2, BTBT9 and TT1:

BDT3

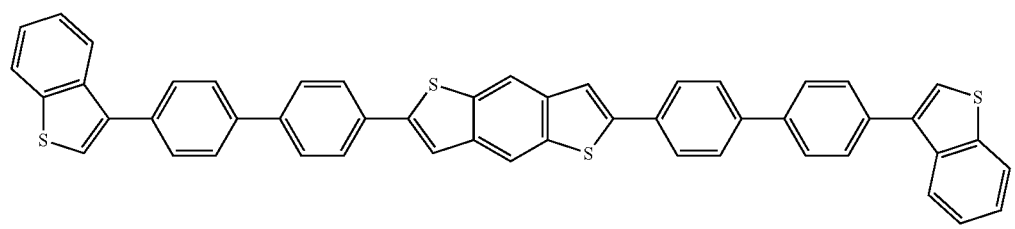 [SMILES: c1ccc2c(-c3ccc(-c4ccc(-c5cc6cc7sc(-c8ccc(-c9ccc(-c%10csc%11ccccc%10%11)cc9)cc8)cc7cc6s5)cc4)cc3)csc2c1]

BTBT14

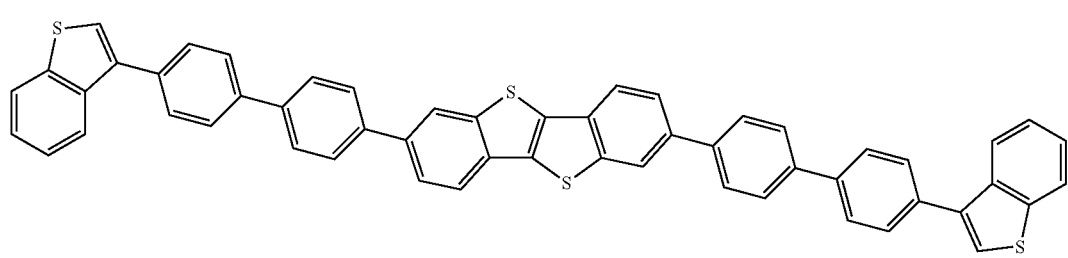

BTBT2

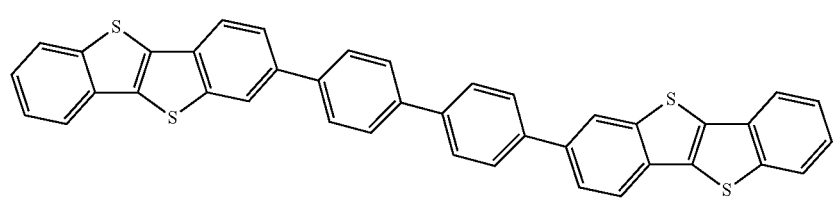

BTBT9

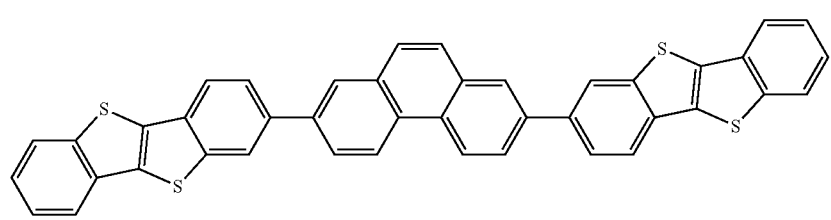

TT1

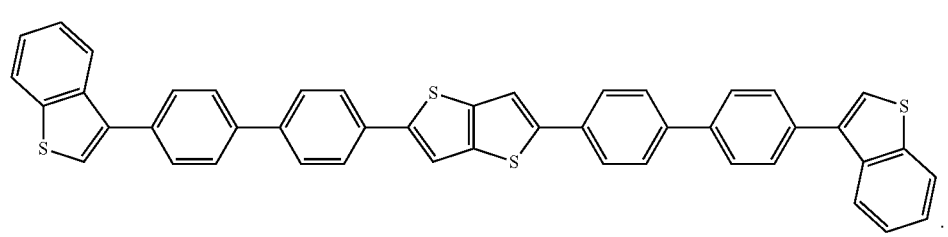

As discussed above, the present disclosure provides a P:N heterojunction, preferably a heterojunction, including a transparent P material according to the present disclosure.

In one embodiment, a transparent P material according to the present disclosure is the donor and a transparent N material is the acceptor in a P:N heterojunction. See, for example, FIG. 4.

In one embodiment of a P:N1:N2 heterojunction, one of the P materials could be a transparent P material according to the present disclosure and a donor.

In one embodiment, the P:N heterojunction, preferably the P:N1:N2 heterojunction includes a N and/or a further P material, wherein the N and/or further P material preferably exhibits absorption in the visible wavelength range (about 400 to about 700 nm).

As discussed above, the present disclosure provides the use of a transparent P material according to the present disclosure in an absorption layer.

In one embodiment, the absorption layer includes a further N and/or P material, wherein the further N and/or P material preferably exhibits absorption in the visible wavelength range (about 400 to about 700 nm).

As discussed above, the present disclosure provides the use of a transparent P material according to the present disclosure in a photoelectric conversion layer, and/or in an organic and/or hybrid module for optoelectronic application, such as image sensor, photodiode, organic photovoltaics, comprising organic photoelectric conversion layer(s), OLED and OTFT organic modules.

In one embodiment, the photoelectric conversion layer and/or the organic and/or hybrid module includes a N and/or a further P material,
wherein the N and/or further P material preferably exhibits absorption in the visible wavelength range (about 400 to about 700 nm).

As discussed above, the present disclosure provides a photoelectric conversion layer comprising a transparent P material according to the present disclosure.

In one embodiment, the photoelectric conversion layer comprises an N and/or further P material, wherein the N and/or further P material preferably exhibits absorption in the visible wavelength range (about 400 to about 700 nm).

In one embodiment, the photoelectric conversion layer comprises further molecule(s).

As discussed above, the present disclosure provides an absorption layer comprising a transparent P material according to the present disclosure.

In one embodiment, the absorption layer includes an N and/or further P material, wherein the N and/or further P material preferably exhibits absorption in the visible wavelength range (about 400 to about 700 nm).

In one embodiment, the absorption layer comprises further molecule(s).

As discussed above, the present disclosure provides a device, including transparent P material(s) according to the present disclosure or photoelectric conversion layer(s) according to the present disclosure.

Said device can be an organic image sensor, a hybrid image sensor, photodiode, organic photovoltaics, organic light-emitting diode (OLED), organic thin-film transistor (OTFT).

In one embodiment, said photoelectric conversion layer exhibits photo response in the visible absorption range.
In this embodiment, the photoelectric conversion layer of the device includes the transparent P material(s) according to the present disclosure and an N and/or further P material(s), preferably exhibiting absorption in the visible wavelength range (about 400 to about 700 nm).

According to the present disclosure, when one of the active materials is transparent offers the following possibilities:
Tuning overall absorption spectrum of the heterojunction/active layer via tuning absorption of one active material only;
Tuning of exciton diffusion efficiencies of the partner (absorbing) material only; Tuning of charge generation efficiencies through HOMO or LUMO independently;
Tuning of only electron (for transparent n) or only hole (transparent p) mobility;
Generally: decoupling of absorption properties in the visible range from electron/hole transfer and transport properties.

In one embodiment, the photoelectric conversion layer of the device includes further molecule(s).

The photoelectric conversion layer can include different components (dyes) and combinations thereof.

In one embodiment, the photoelectric conversion layer and/or the absorption layer includes further n and p type materials (molecules) and their derivatives that can be used together with the material(s) of the present disclosure, such as phthalocyanines (Pc), subphthalocyanines (SubPc), merocyanines (MC), diketopyrrolopyrroles (DPP), borondipyrromethenes (BODIPY), isoindigo (ID), perylenediimides (PDI) and perylenemonoimides (PMI), and quinacridones (QD), fused acenes, such as pentacene and tetracene and triphenylamine and its derivatives (TPAs) as donor;
and/or
fullerenes, rylenediimides and monoimides (e.g. PDI and PMIs but not limited to), phthalocyanines and subphthalocyanines, borondipyrromethenes (BODIPY) and cyanopentacenes as acceptor.

As discussed above, the present disclosure provides an organic image sensor, including photoelectric conversion layer(s) according to the present disclosure.

The organic image sensor of the present disclosure preferably includes
(a) anorganic photoelectric conversion unit comprising photoelectric conversion layer(s) according to the present disclosure,
(b) at least one electrode,
(c) a substrate,
(d) optionally, a second electrode on top of said photoelectric conversion layer(s).

The substrate can be silicon, quartz, glass, polymer, such as PMMA, PC, PS, COP, COP, PVA, PVP, PES, PET, PEN, mica, or combinations thereof.

The substrate can also be other photoelectric conversion unit(s).

This means, a device of this disclosure can include (i) two inorganic units with one organic unit, (ii) one inorganic unit with two organic units, or (iii) three organic units combined with each other in the organic image sensor. Any of the organic units can contain molecules/layers/devices according to this disclosure.

In a preferred embodiment, an organic image sensor consists of three organic conversion units containing molecules in layers as of this disclosure (in devices, each with transparent electrodes), combined with each other and operating each in one of the ranges 400 nm to 500 nm, 500 nm to 600 nm and 600 nm to 700 nm.

Combined units can be realized either by vertical and/or horizontal stacking of the organic-organic or organic-inorganic units.

The electrode material can be
transparent metal oxide, such as indium tin oxide (ITO), fluorine-doped indium oxide (IFO), tin oxide, fluorine-doped tin oxide (FTO), antimony-doped tin oxide (ATO), zinc oxide (including Al, B and Ga doped zinc Oxide), indium oxide-zinc oxide (IZO), $TiO_2$,
non transparent or semitransparent metal or alloy or conductive polymer, such as Au, Ag, Cr, N1, Pd, AlSiCu, or any metal or metal alloy or metal combination with suitable workfunction; PEDOT/PSS, PANI or PANI/PSS, graphene.

As discussed above, the present disclosure provides a hybrid Silicon-organic image sensor or organic image sensor, including
(a) anorganic photoelectric conversion unit or units comprising photoelectric conversion layer(s) according to the present disclosure,
(b) optionally, a Si based photoelectric conversion unit,
(c) metal wiring,
(d) a (CMOS) substrate,
(e) insulating layer(s), preferably oxide.

In one embodiment, said organic photoelectric conversion unit of the image sensors of the present disclosure includes different layers within the organic based photoelectrical conversion unit(s), such as
n-type material,
p-type material,
n-buffer layer,
p-buffer layer,
or combinations and/or mixtures (e.g. n material and p material co-deposited in one layer) thereof.

For example, the organic image sensor of the present disclosure can have the structure:
- substrate/first electrode/n-buffer layer/n-material/p-material/p buffer layer/second electrode;
- substrate/first electrode/n-buffer layer/n-material/mixture of n- and p- material/p-material/p buffer layer/second electrode;
- substrate/first electrode/n-buffer layer/n-material/mixture of n- and p- material/p buffer layer/second electrode;
- substrate/first electrode/p-buffer layer/p-material/n-material/n buffer layer/second electrode;
- substrate/first electrode/p-buffer layer/p-material/mixture of n- and p- material/n-material/n buffer layer/second electrode;
- substrate/first electrode/p-buffer layer/p-material/mixture of n- and p- material/n buffer layer/second electrode.

The organic image sensor of the present disclosure can include different layer structures, in particular regarding the position of the n and p material with respect to the CMOS part.

The organic photoconversion unit can be used in combination with a Si based photoelectrical conversion unit where different layers absorb different color (BGR) in a hybrid silicon-organic image sensor (see FIG. 2) or can be used without Si based photoelectrical conversion unit. In this case the organic photoconversion unit has the capability of absorbing different color (BGR).

The BGR ranges are 400-500 nm, 500-600 nm and 600-700 nm and the absorption outside of the range is preferably less than 25%, more preferably less than 20%, even more preferably less than 10 and 5%.

As discussed above, the substrate can also be other photoelectric conversion unit(s).

As discussed above, a device of this disclosure can include (i) two inorganic units with one organic unit, (ii) one inorganic unit with two organic units, or (iii) three organic units combined with each other in the organic image sensor. Any of the organic units can contain molecules/layers/devices according to this disclosure.

The deposition methods to produce the organic photoelectrical conversion layer are PVD, CVD, spin coating, dipping coating, casting process, inkjet printing, screen printing, spray coating, offset printing.

Different process temperatures for processing the layer are possible, namely from 50 to 245° Celsius. The processing (annealing) of the layers can be done before and/or after the deposition of the top electrode.

As discussed above, the present disclosure provides a method for synthesis of thiophene- or selenophene-based materials (represented by a general formula IX) comprising the steps of
a) palladium- and SPhos-system catalyzed Suzuki coupling of the specific R-boronic acid and subsequent borylation with bis(pinacolato)diboron in palladium catalyst system;
b) parallel reaction of chlorobenzaldehyde with sodium hydrogensulfide hydrate and bromination with elemental bromine;
c) palladium- and SPhos-system catalyzed Suzuki coupling of product of a) and the product of b).

The present disclosure provides also a method for synthesis of thiophene- or selenophene-based materials (represented by a general formula Xb) comprising the steps of
a) palladium- and SPhos system catalyzed Suzuki coupling of the specific R-dibromide;
b) palladium- and SPhos system catalyzed Suzuki coupling of two equivalents of the product of a) with specific Xb-diboronic ester.

The present disclosure provides also a method for synthesis of thiophene- or selenophene-based material (represented by a general formula XXXI) comprising the steps of
a) reaction of chlorobenzaldehyde with sodium hydrogensulfide hydrate and bromination with elemental bromine;
b) palladium catalyzed reaction of T-specific benzothiophene with B-specific diboronic acid.

The present disclosure provides also a method for synthesis of thiophene- or selenophene-based material (represented by a general formula XXXIX) comprising the steps of a) reaction of chlorobenzaldehyde with sodium hydrogensulfide hydrate and bromination with elemental bromine;
b) palladium catalyzed reaction of T-specific benzothiophene with B-specific diboronic acid.

Note that the present technology can also be configured as described below.

(1) A transparent P material,
which has the quality when comprised in a P:N heterojunction or P:N bilayer or multilayer junction, particularly a P:N1:N2 or a P1:P2:N heterojunction or multilayer junction, to dissociate efficiently the excitons created in colored N, or in a mixture of colored N materials (N1:N2), or in another colored P or in a mixture of colored P and N materials (P2:N) via a process of HOMO dissociation,
and/or has the quality to accept hole from the colored N or the mixture of colored N materials, from another colored P material or from a mixture of colored N and another P material, and/or has the quality to transport the holes, wherein
transparent refers to:
an extinction coefficient of less than about 60,000 $M^{-1}$ $cm^{-1}$ in the visible wavelength range in the region of about 450 to about 700 nm and to an extinction coefficient of less than about 100,000 $M^1$ $cm^1$ in the visible wavelength range in the region of about 400 to about 450 nm, or
an absorption coefficient (in single material film) of less than 70,000 $cm^{-1}$ for wavelengths longer than 450 nm, or
an absorption coefficient (in single material film) of less than 40,000 cm for wavelengths longer than 500 nm, and
colored refers to an absorption coefficient of more than about 60,000 $cm^{-1}$ in the visible wavelength range in the region from about 400 nm to about 700 nm (with maxima anywhere in this region or absorbing everywhere in this region).

(2) A transparent P material, preferably the transparent P material of claim 1, wherein the material
is an organic based compound forming high quality homogenous films when using deposition methods (such as vacuum deposition or spincoating),
has an extinction coefficient of less than about 60,000 $M^{-1}$ $cm^{-1}$ in the visible wavelength range in the region of about 450 to about 700 nm and an extinction coefficient of less than about 100,000 $M^{-1}$ $cm^{-1}$ in the visible wavelength range in the region of about 400 to about 450 nm, and
is an organic based compound forming high quality homogenous films when using deposition methods (such as vacuum deposition or spincoating),
has an absorption coefficient (in single material film) of less than 70,000 $cm^{-1}$ for wavelengths longer than 450 nm, or
an absorption coeffiecient (in single material film) of less than 40,000 $cm^{-1}$ for wavelengths longer than 500 mu.

(3) The transparent P material of (1) or (2), which is selected from the group of
   thiophene-based materials,
   selenophene-based material, and
   dimers thereof.

(4) The transparent P material of (3), wherein the material is a thiophene- or selenophene-based material represented by the general formula IX

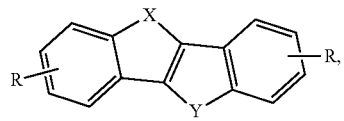

IX wherein,

X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl, and R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

(5) The transparent P material of (4), wherein the material is a thiophene- or selenophene-based material represented by the general formula IX

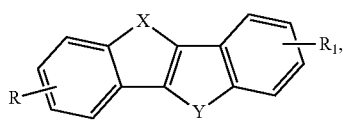

IX wherein,

X and Y are the same or different and are, at each occurrence, independently selected from S and Se, and/or R is selected from

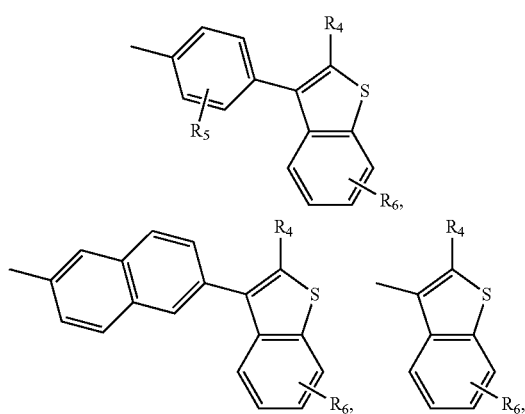

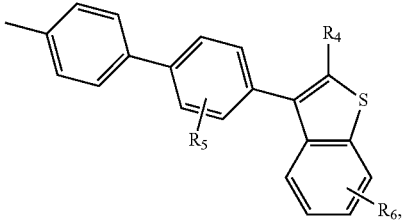

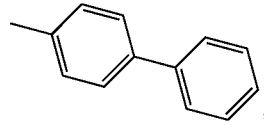

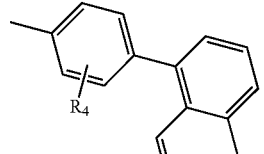

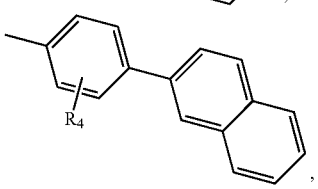

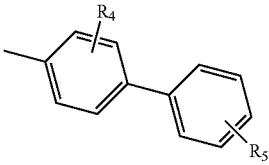

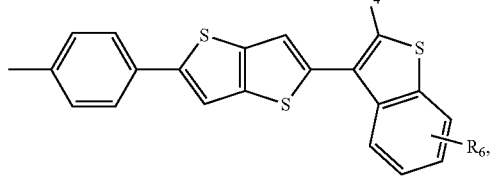

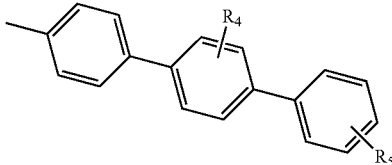

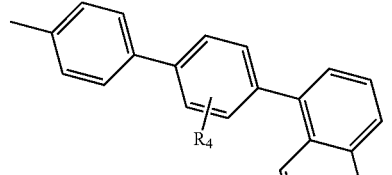

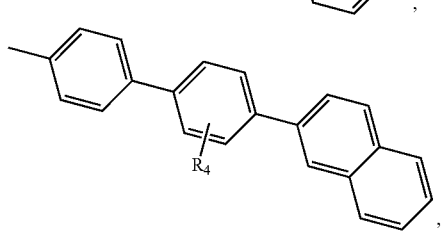

-continued
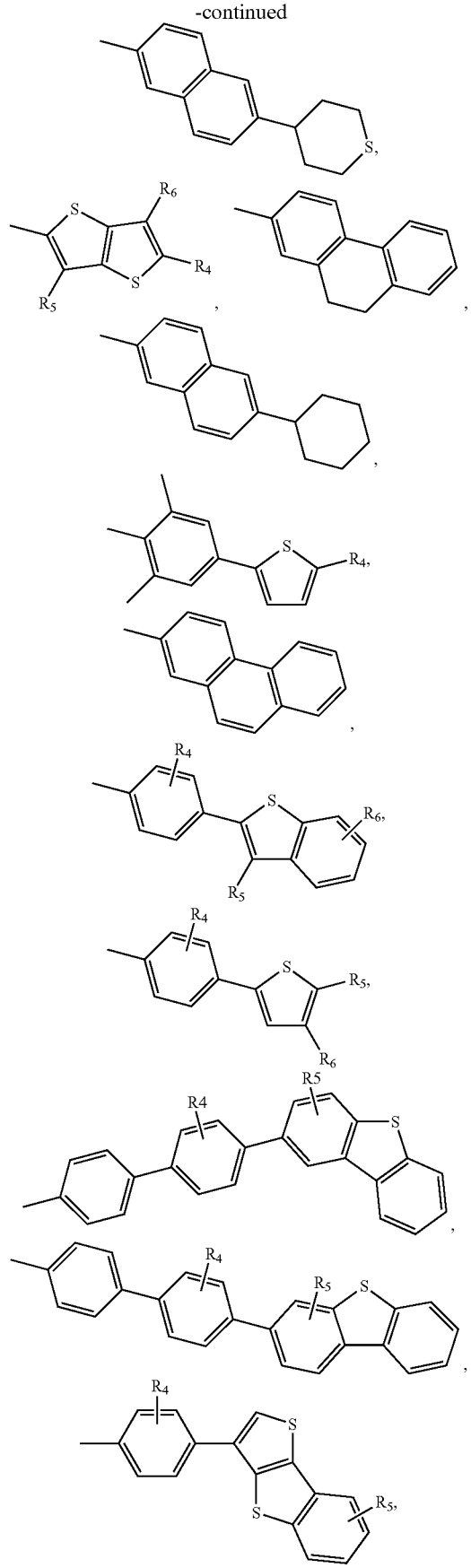
-continued
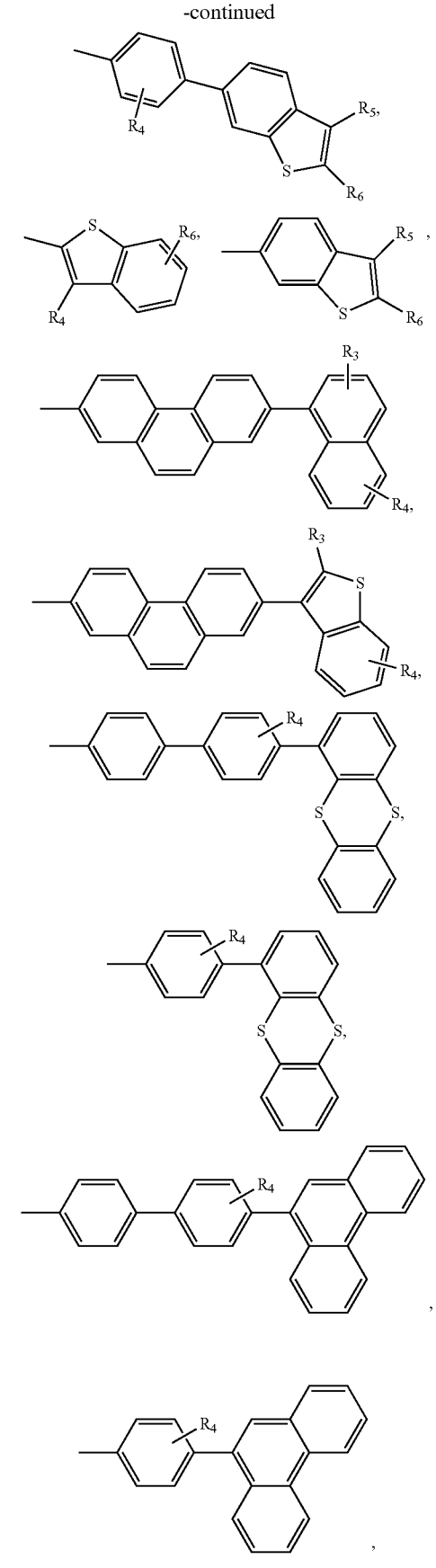

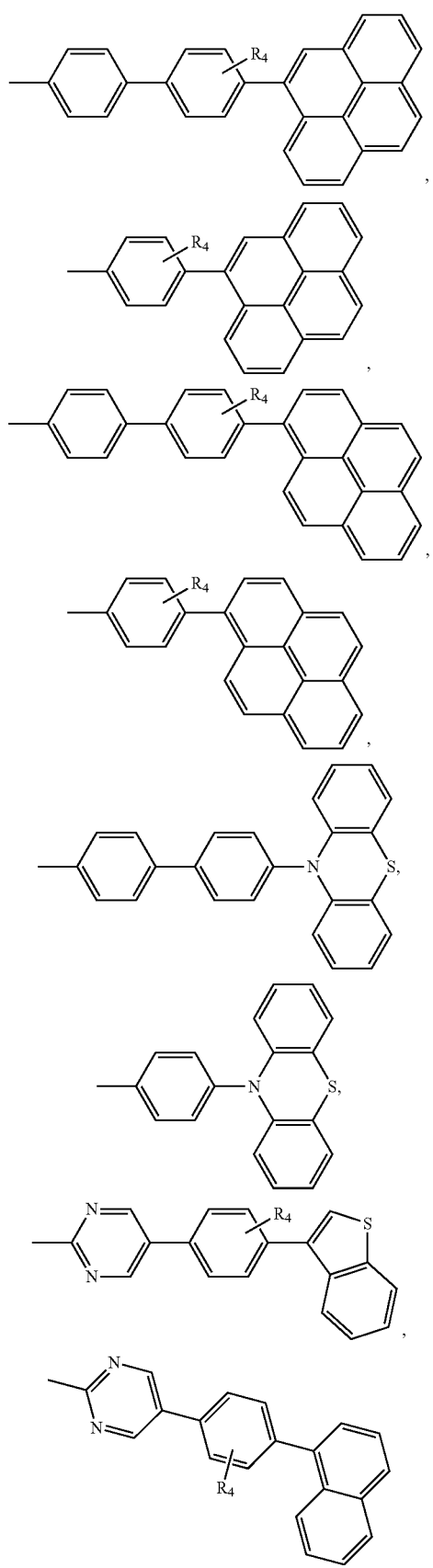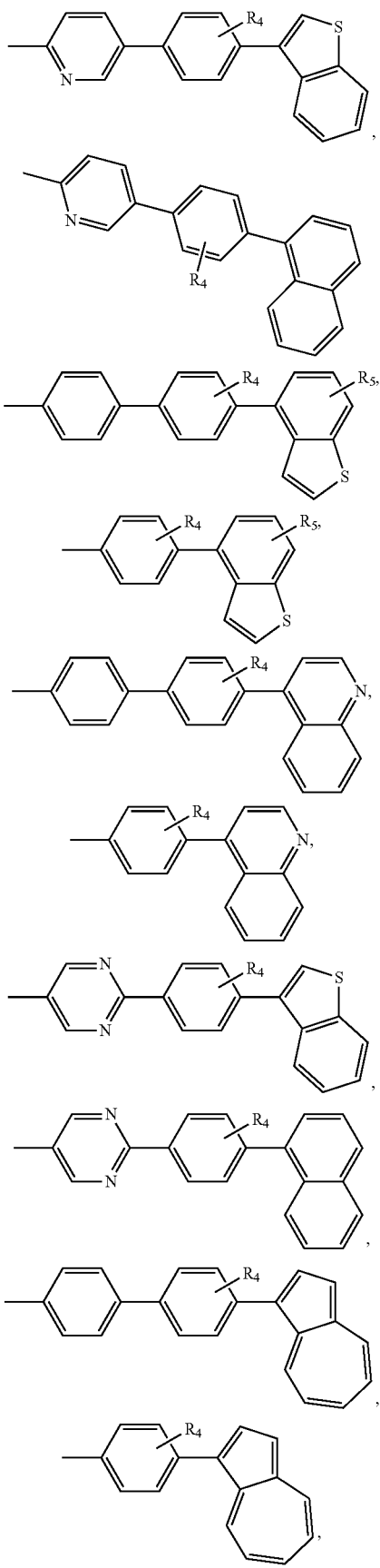

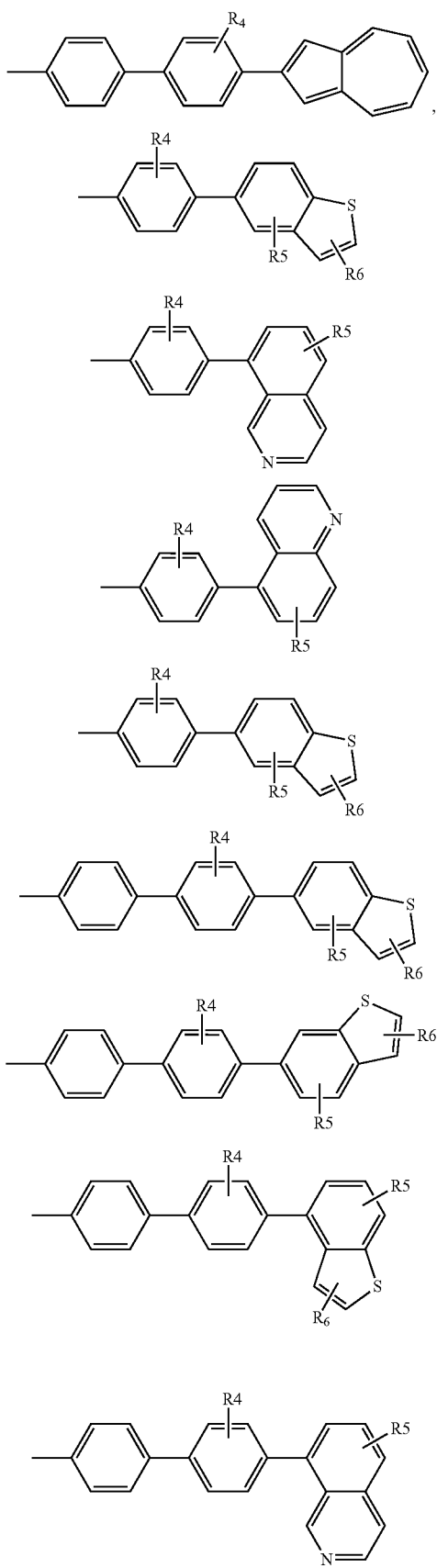
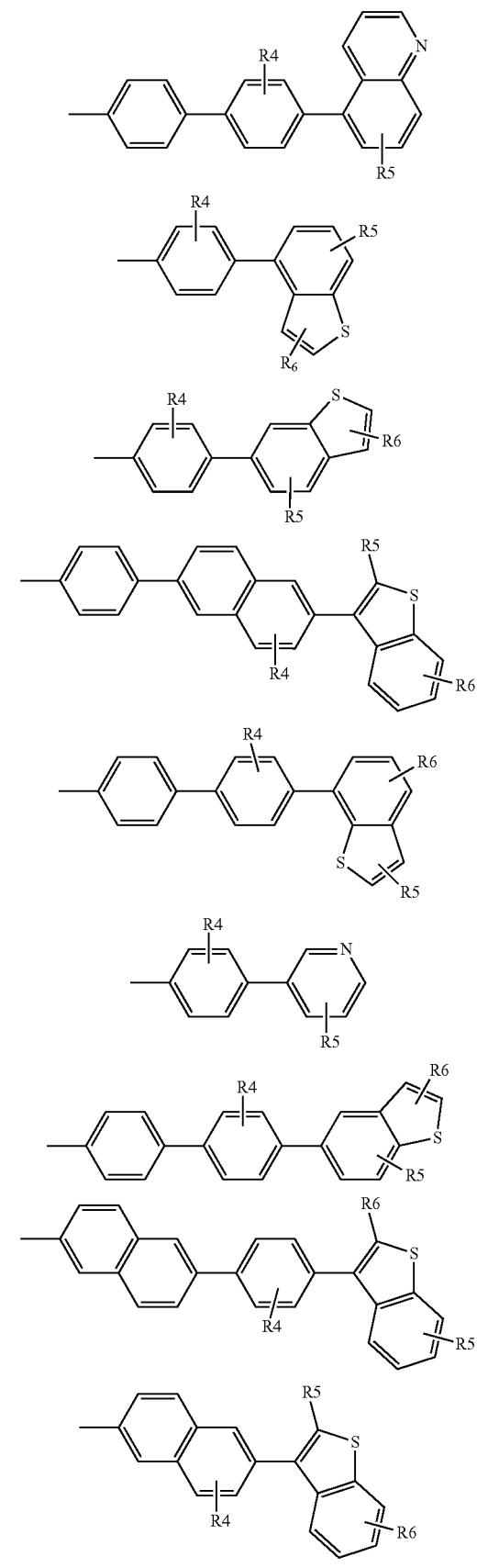

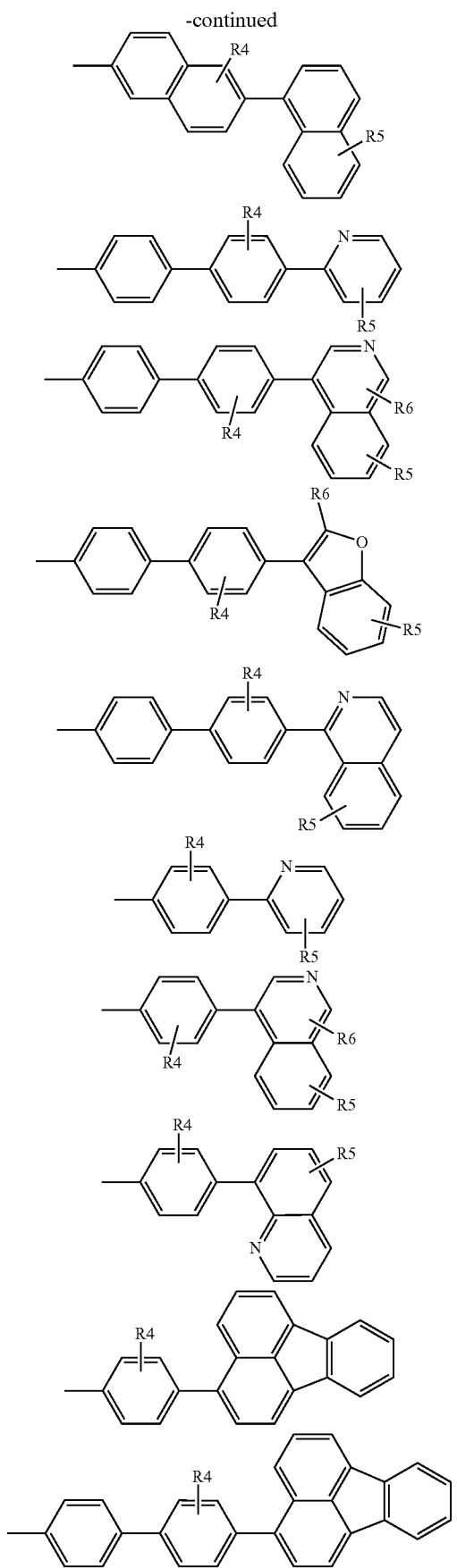
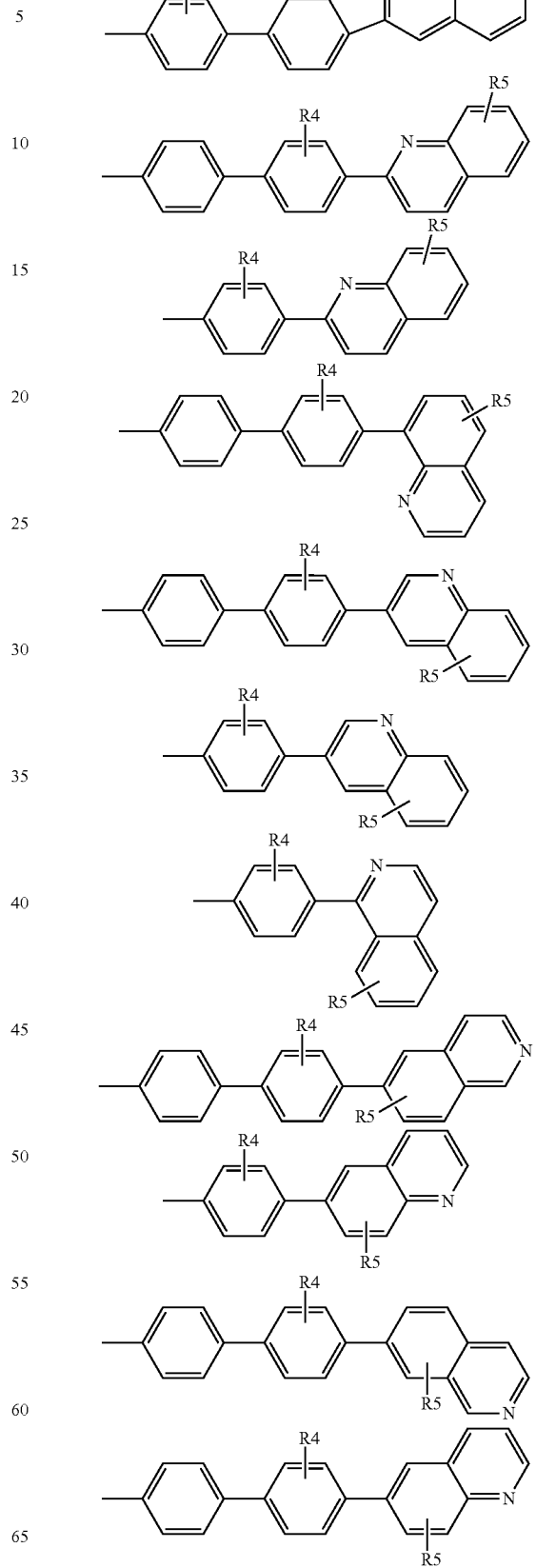

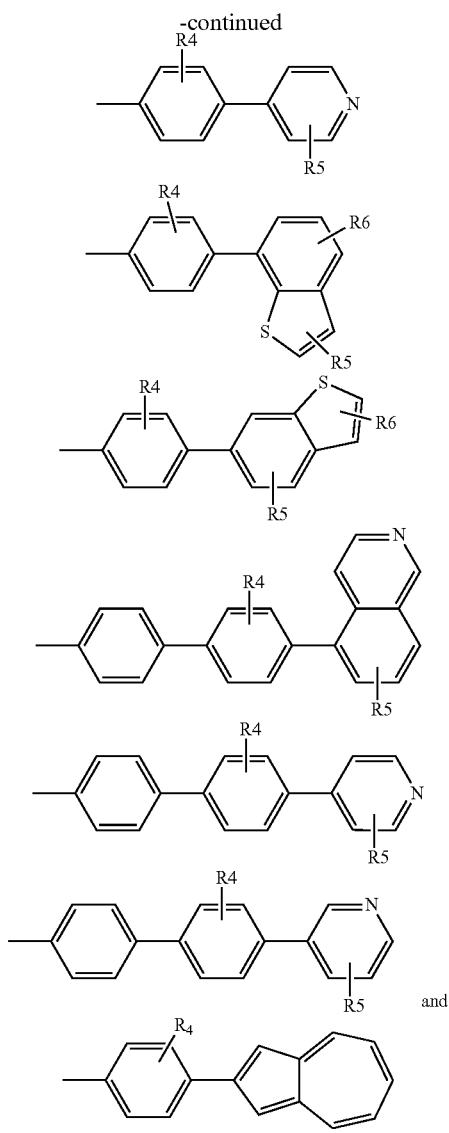

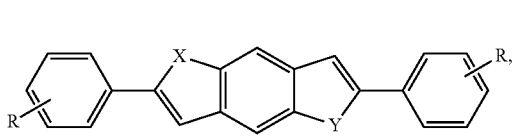

wherein R$_4$, R$_5$, R$_6$ are the same or different and are, at each occurrence, independently selected from H, F, CH$_3$, CF$_3$, aryl and alkyl.

(6) The P material of (3), wherein the material is a thiophene- or selenophene-based material represented by the general formula Xa $$\text{Xa}$$

wherein,
X and Y are the same or different and are, at each occurrence, independently selected from CR$_2$, S, O, Se, N—R and Si—R$_2$, wherein R$_2$ is selected from H, CH$_3$, CF$_3$, phenyl, alkyl and aryl; and
R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

(7) The P material of (6), wherein the material is a thiophene- or selenophene-based material represented by the general formula Xa $$\text{Xa}$$

wherein,
X and Y are the same or different and are, at each occurrence, independently selected from S and Se,
and/or
R is selected from

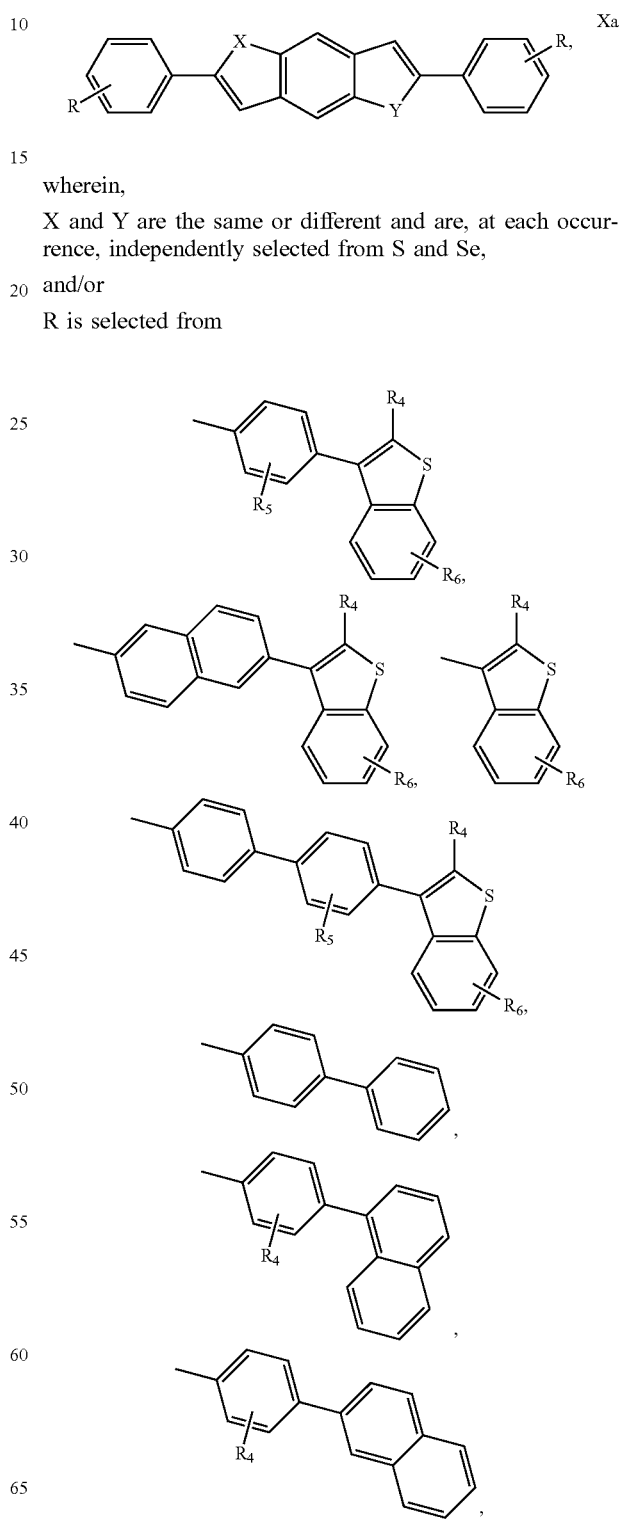

-continued
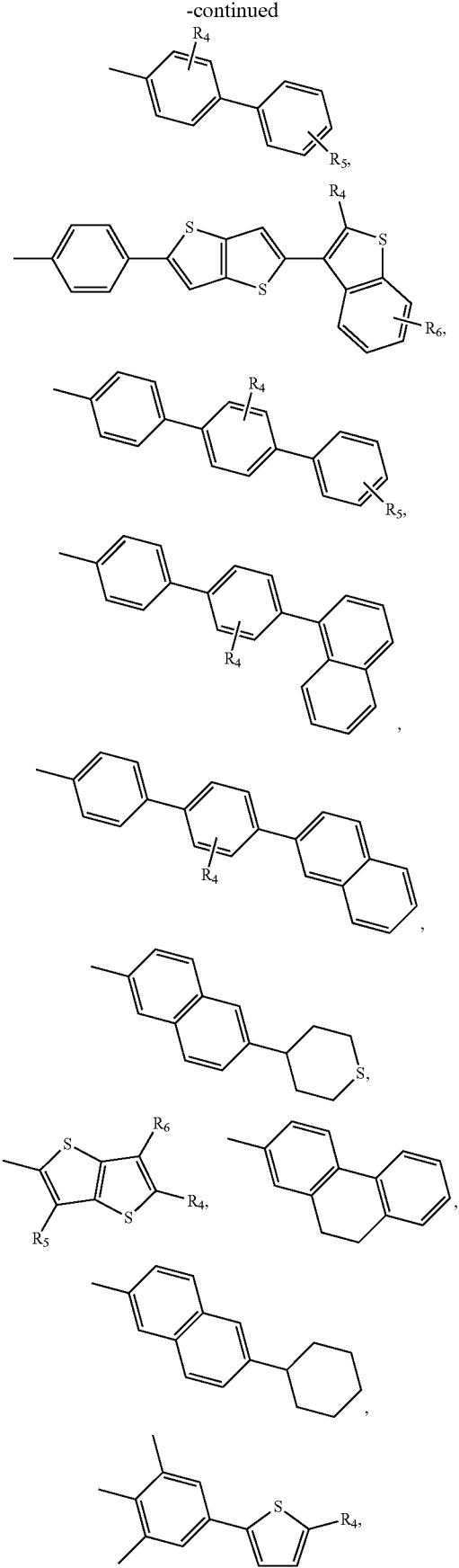
-continued
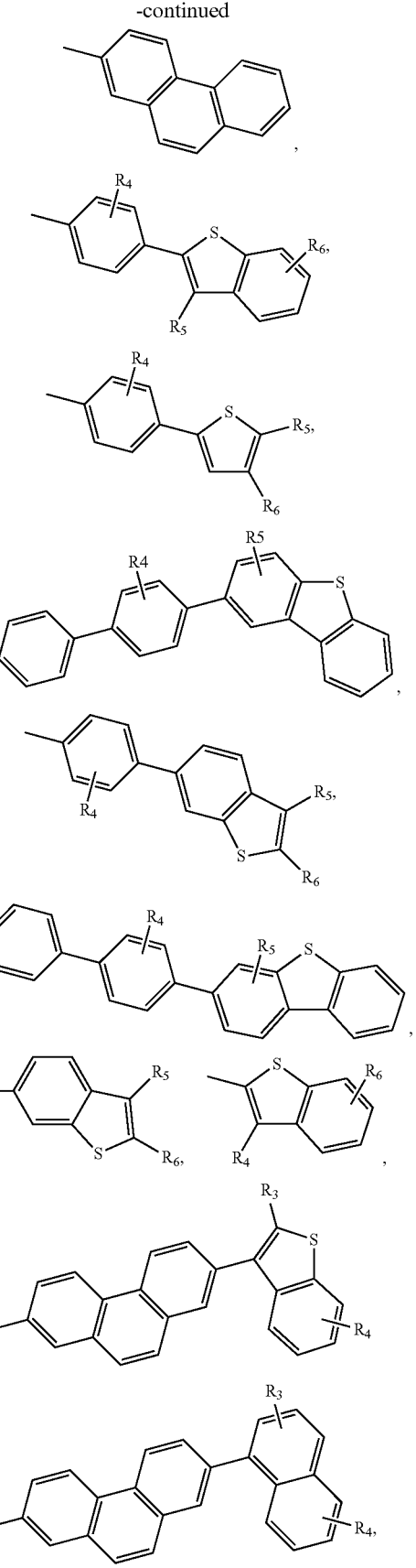

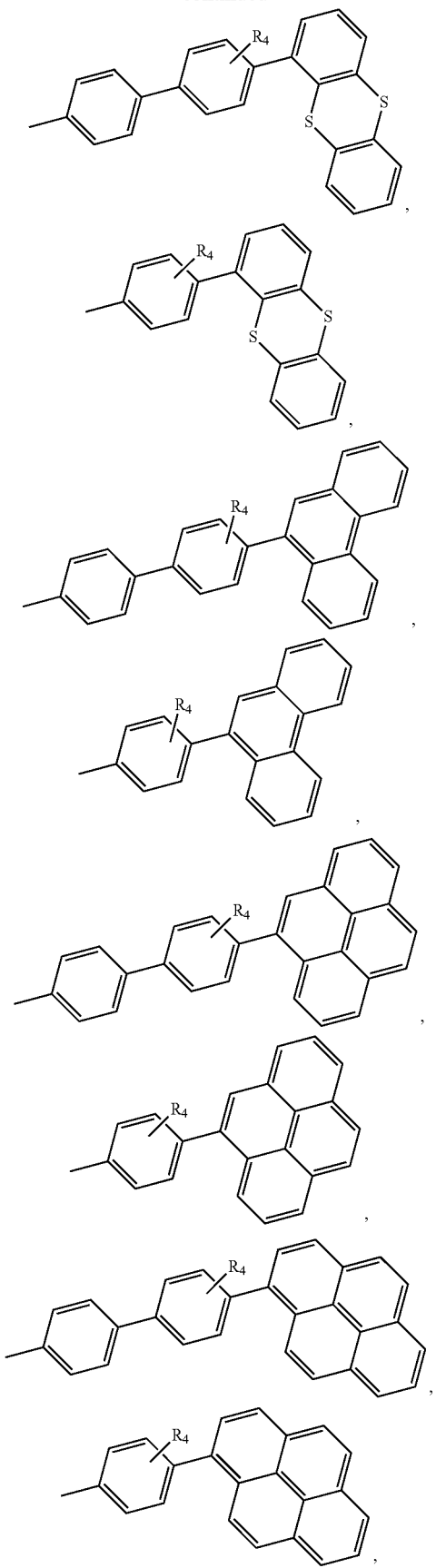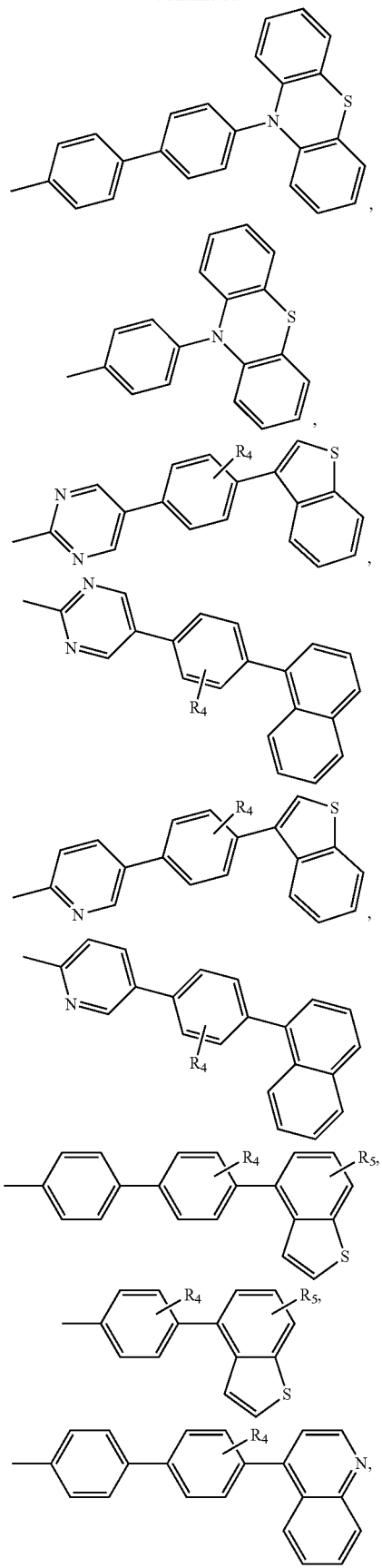

-continued
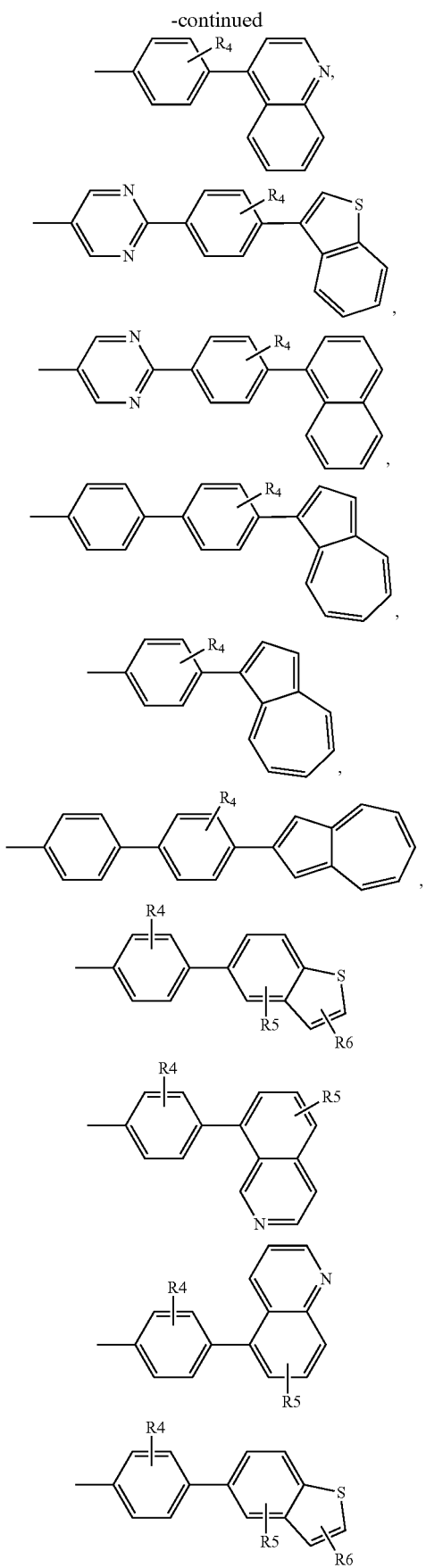
-continued
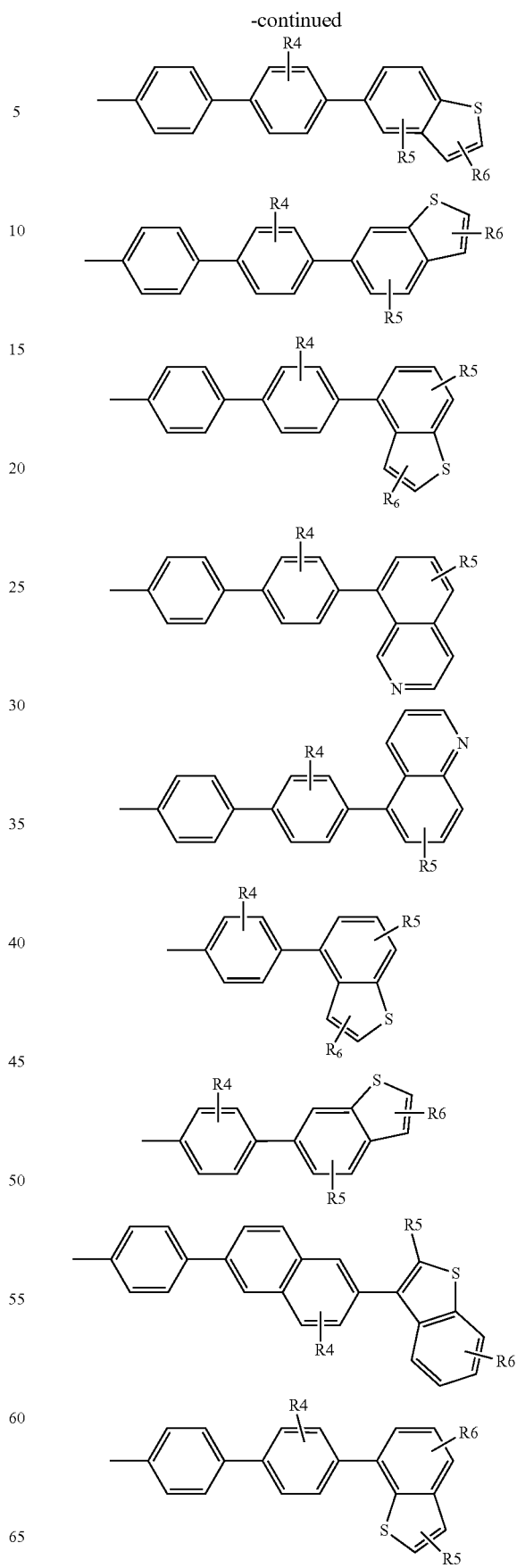

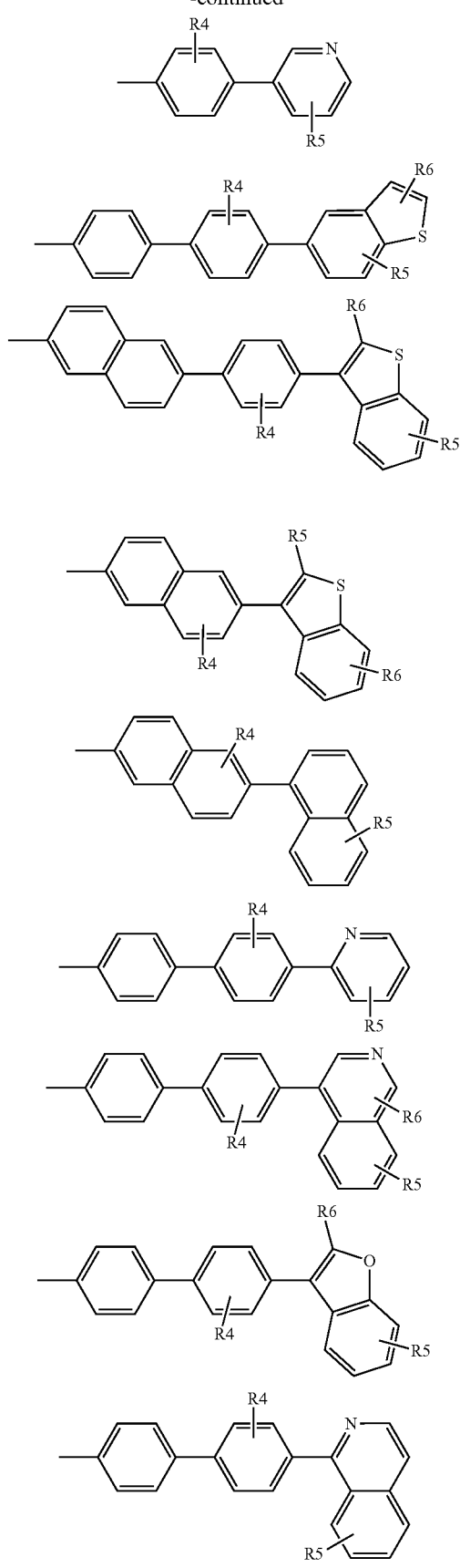
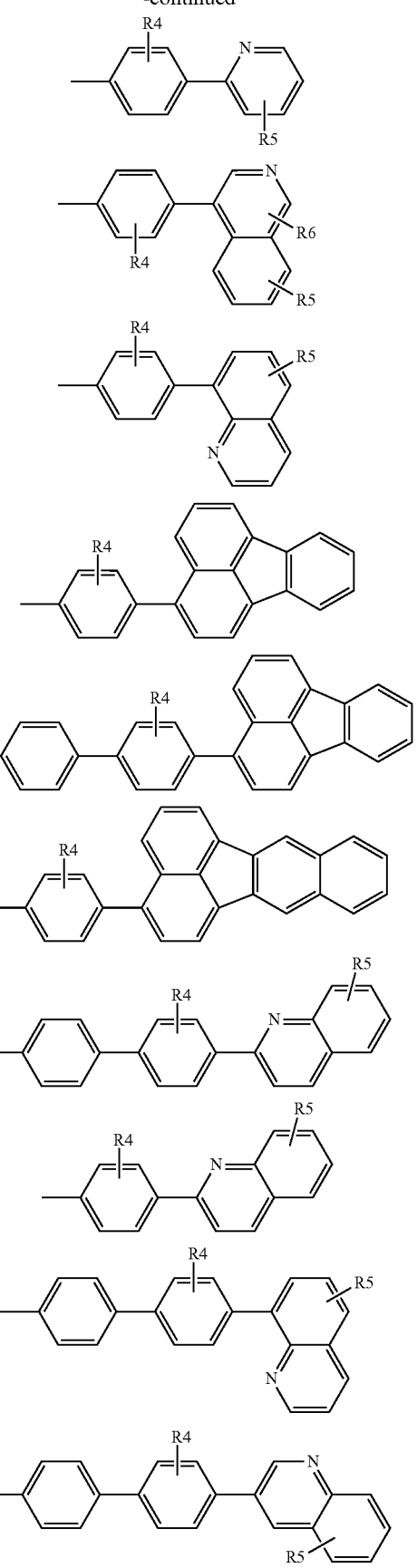

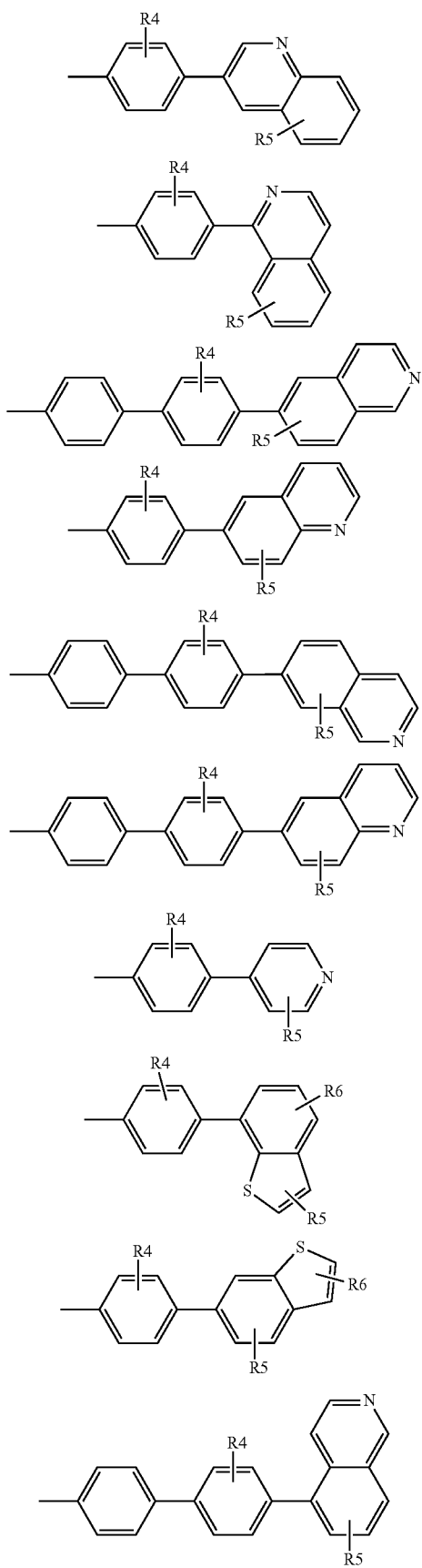

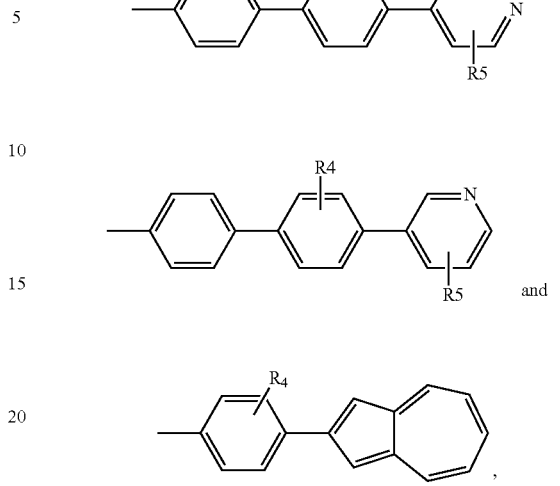

wherein $R_4$, $R_5$, $R_6$ are the same or different and are, at each occurrence, independently selected from H, F, $CH_3$, $CF_3$, aryl and alkyl.

(8) The transparent P material of (3), wherein the material is a thiophene- or selenophene-based material represented by the general formula Xb

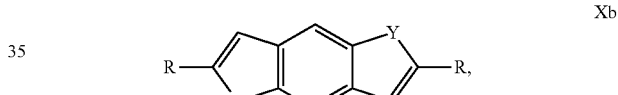

wherein,

X and Y are the same or different and are independently, at each occurrence, selected from $CR_2$, S, O, Se, N—R and Si—$R_2$, wherein $R_2$ is selected from H, $CH_3$, $CF_3$, phenyl, alkyl and aryl; and R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

(9) The transparent P material of (8), wherein the material is a thiophene- or selenophene-based material represented by the general formula Xb

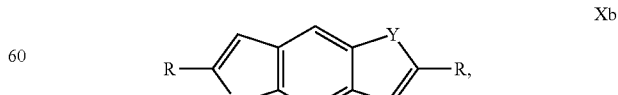

wherein,

X and Y are the same or different and are, at each occurrence, independently selected from S and Se, and/or
R is selected from
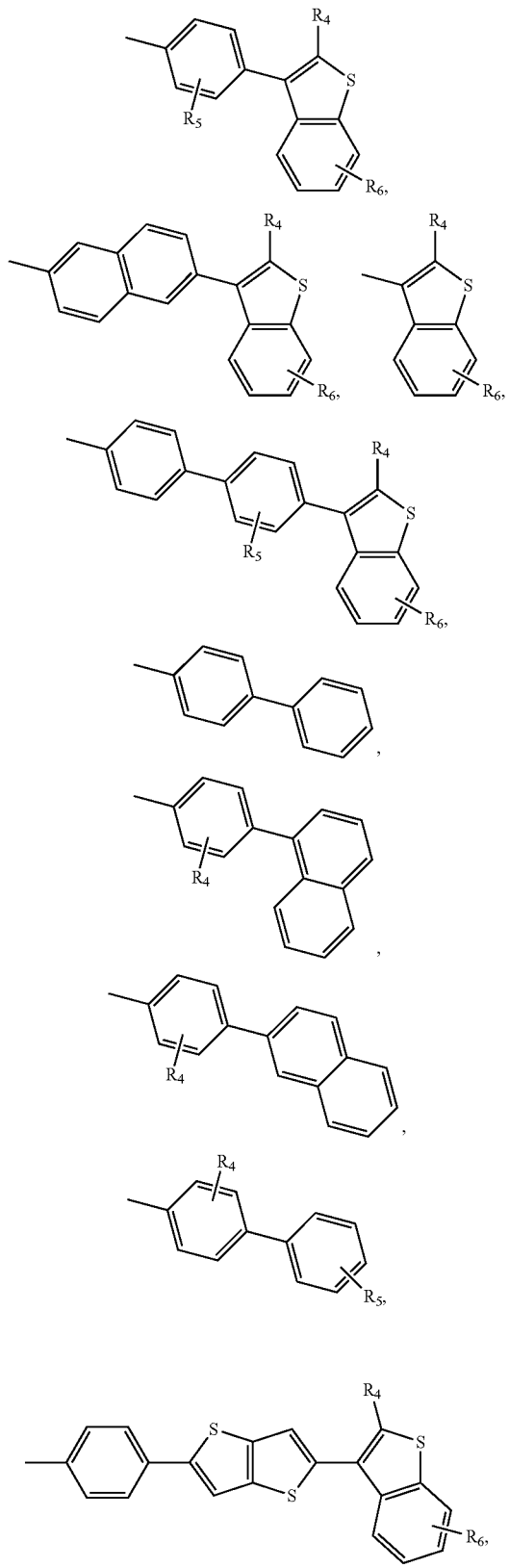
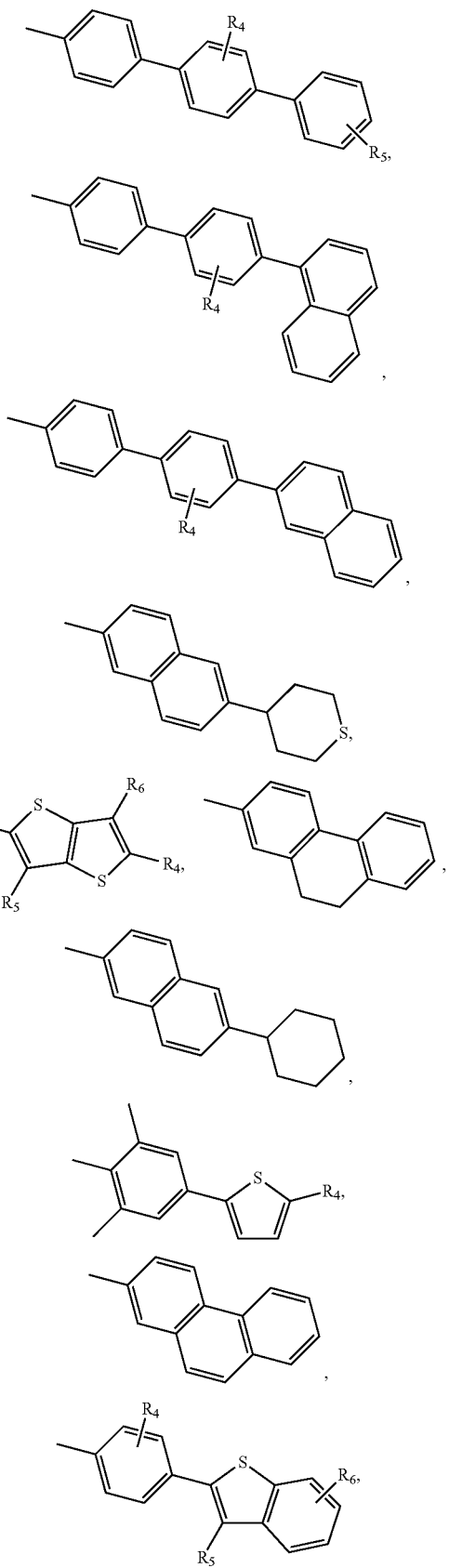

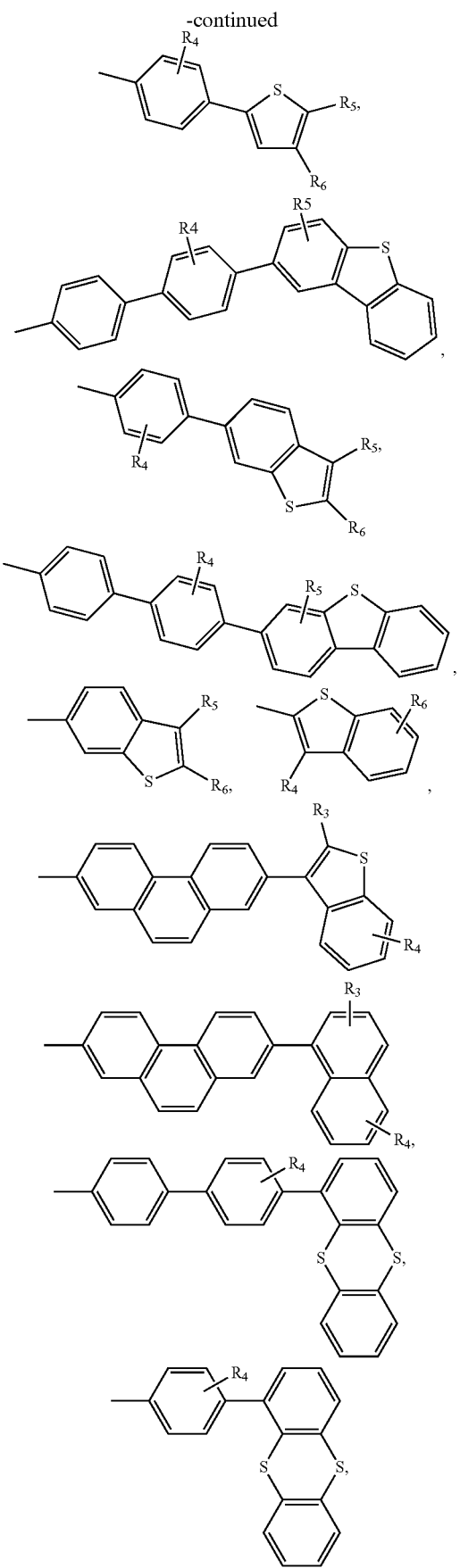
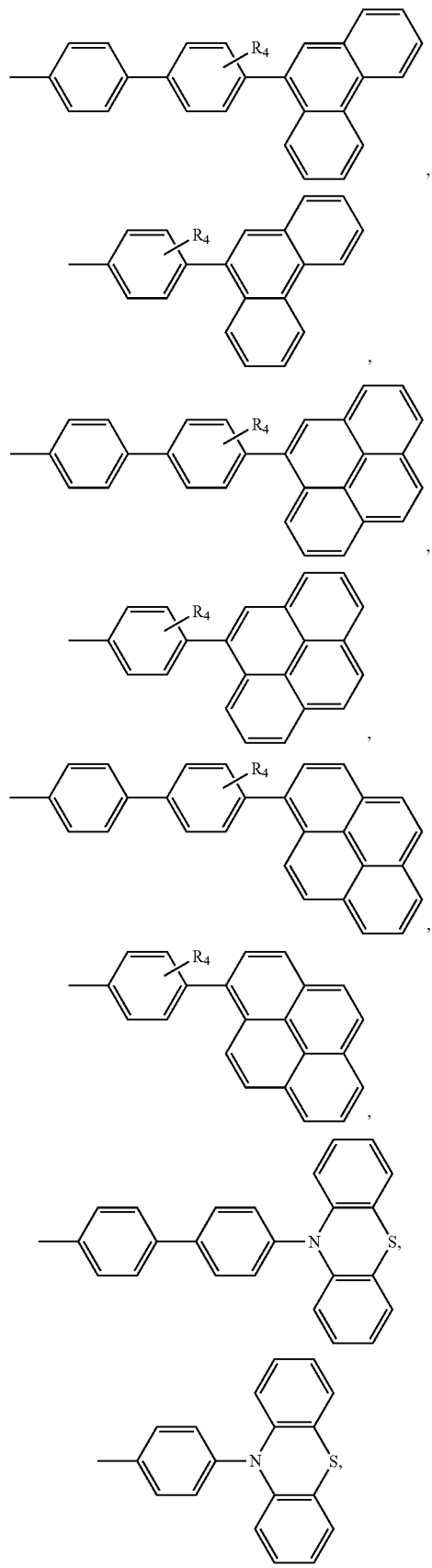

193
-continued
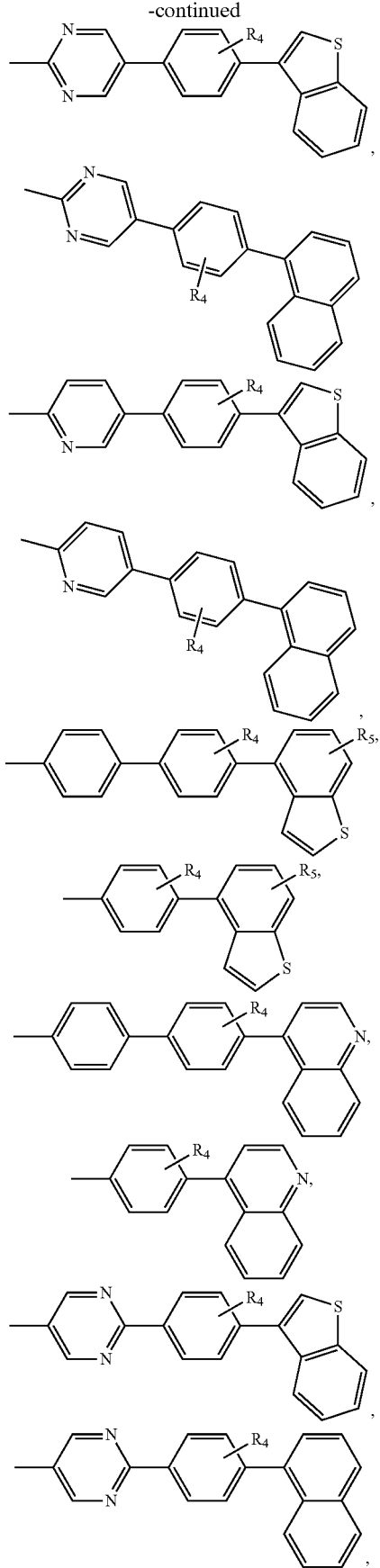
194
-continued
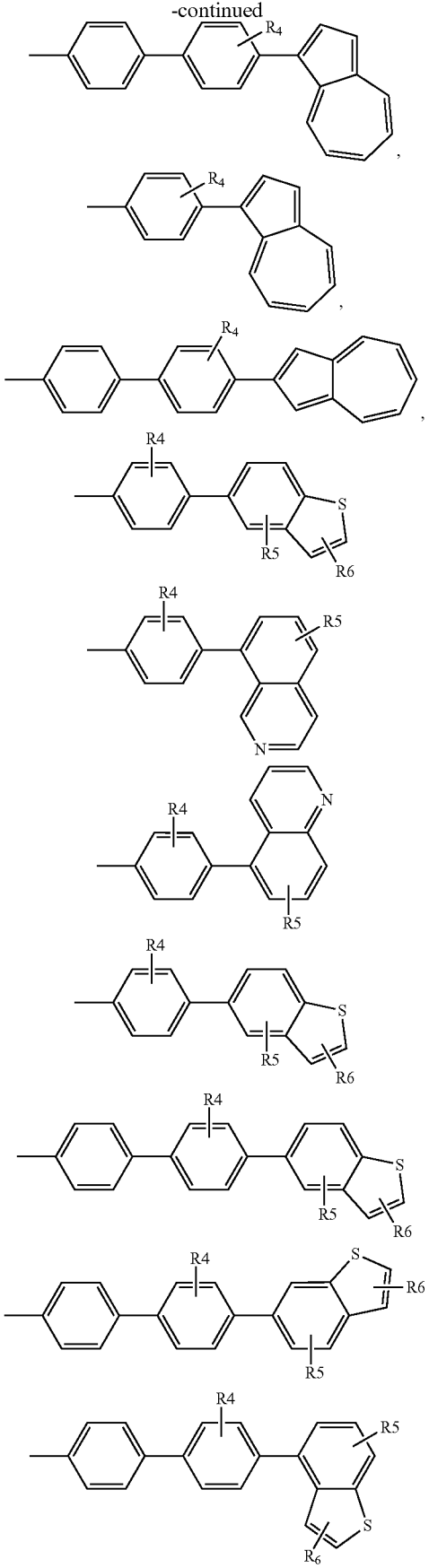

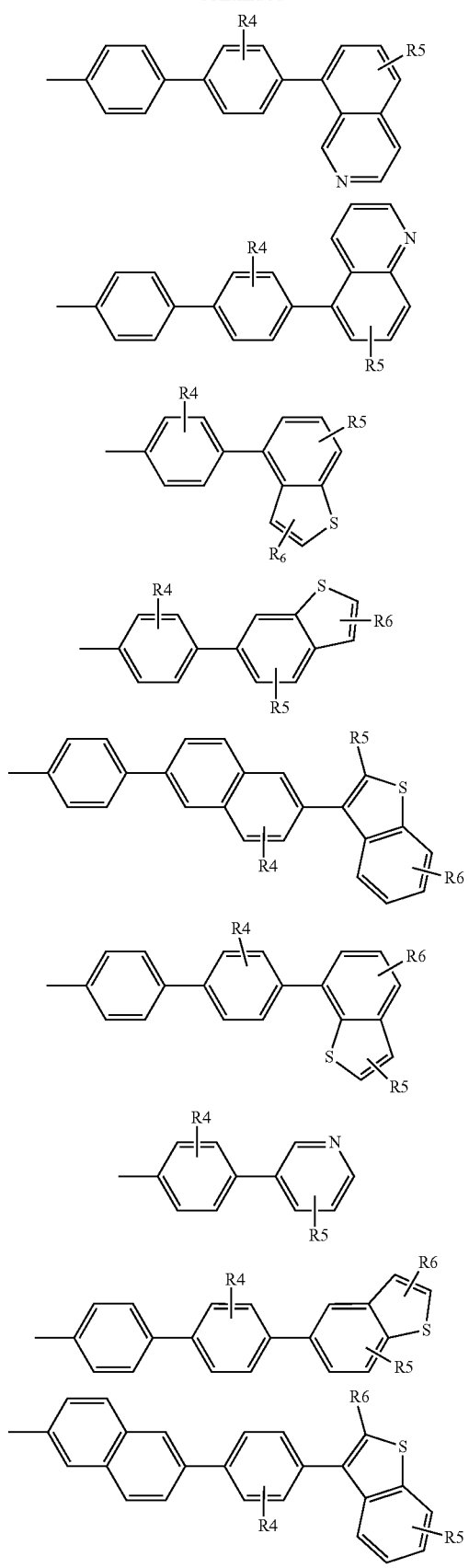
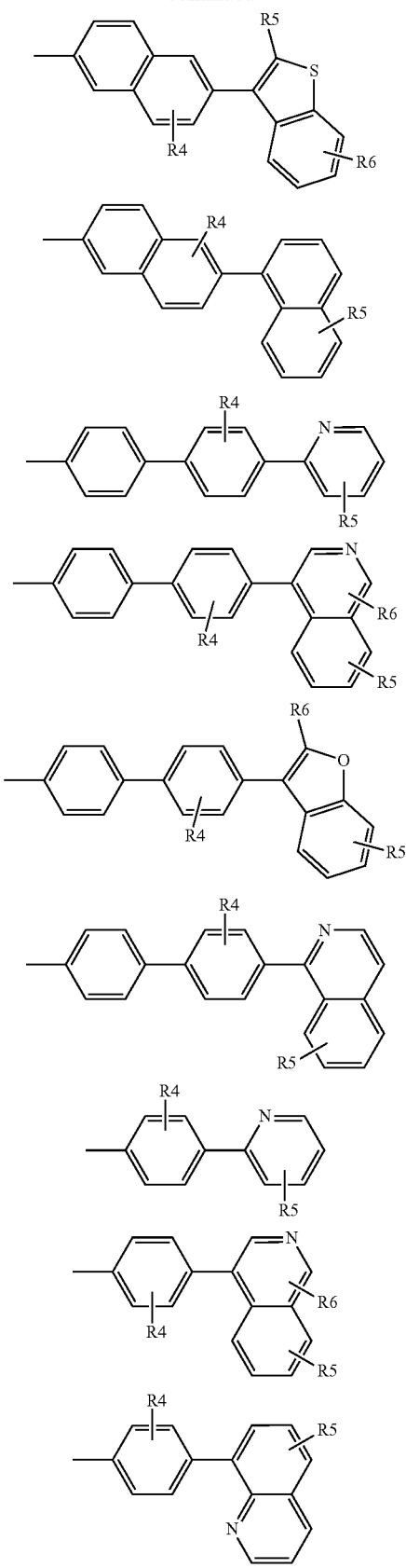

-continued
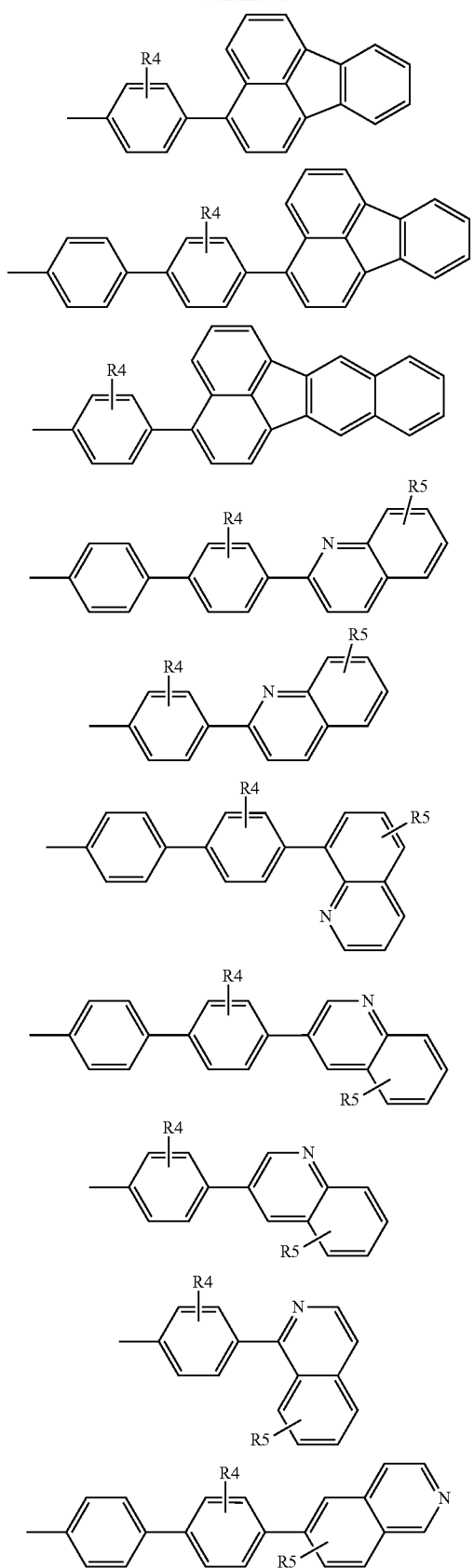
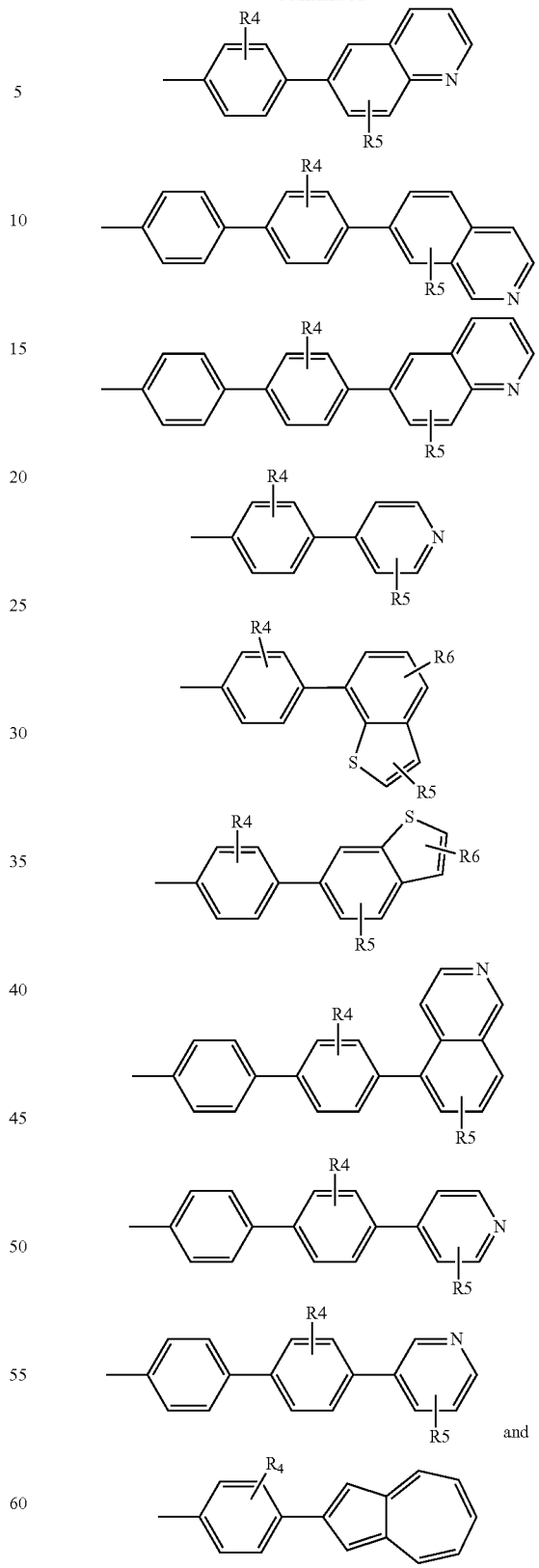
wherein $R_4$, $R_5$, $R_6$ are the same or different and are, at each occurrence, independently selected from H, F, $CH_3$, $CF_3$, aryl and alkyl.

(10) The P material of (3), wherein the material is a thiophene- or selenophene-based material represented by the general formula XXXIa and XXXIb

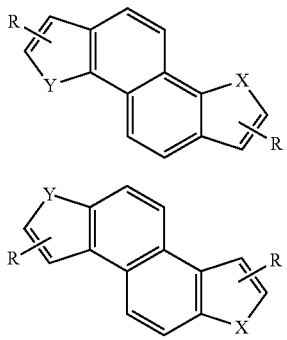

XXXIa

XXXIb wherein,
X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl; and
R is selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group.

(11) The P material of (10), wherein the material is a thiophene- or selenophene-based material represented by the general formula XXXIa and XXXIb

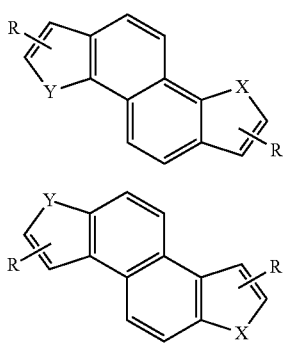

XXXIa

XXXIb wherein,
X and Y are the same or different and are, at each occurrence, independently selected from S and Se,
and/or
R is selected from

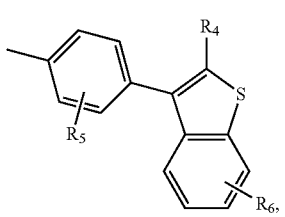

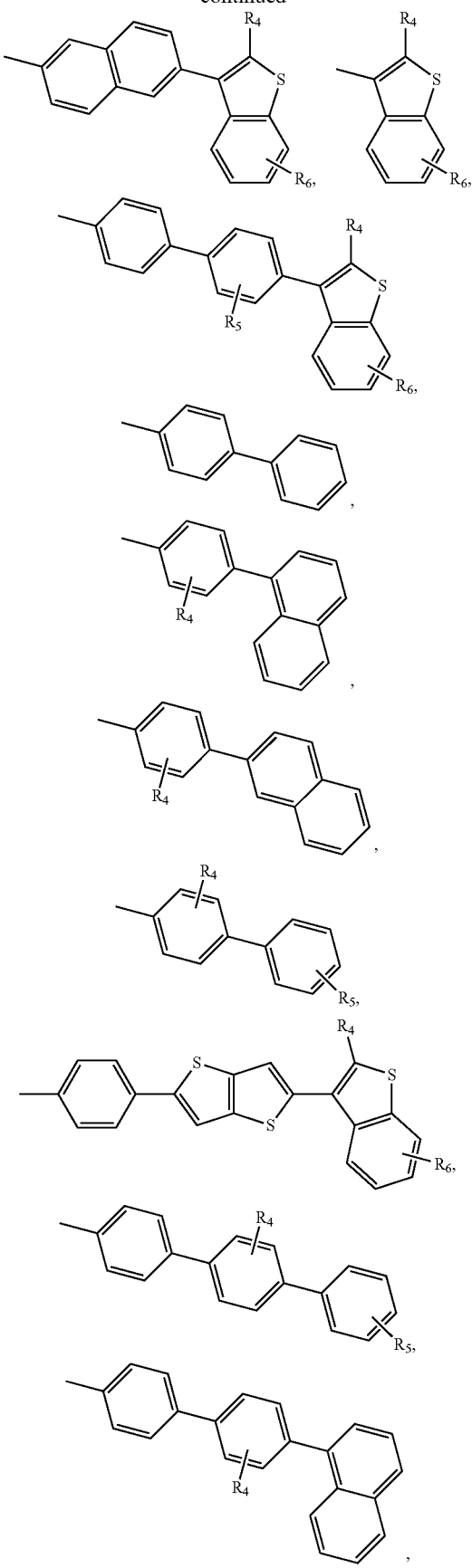

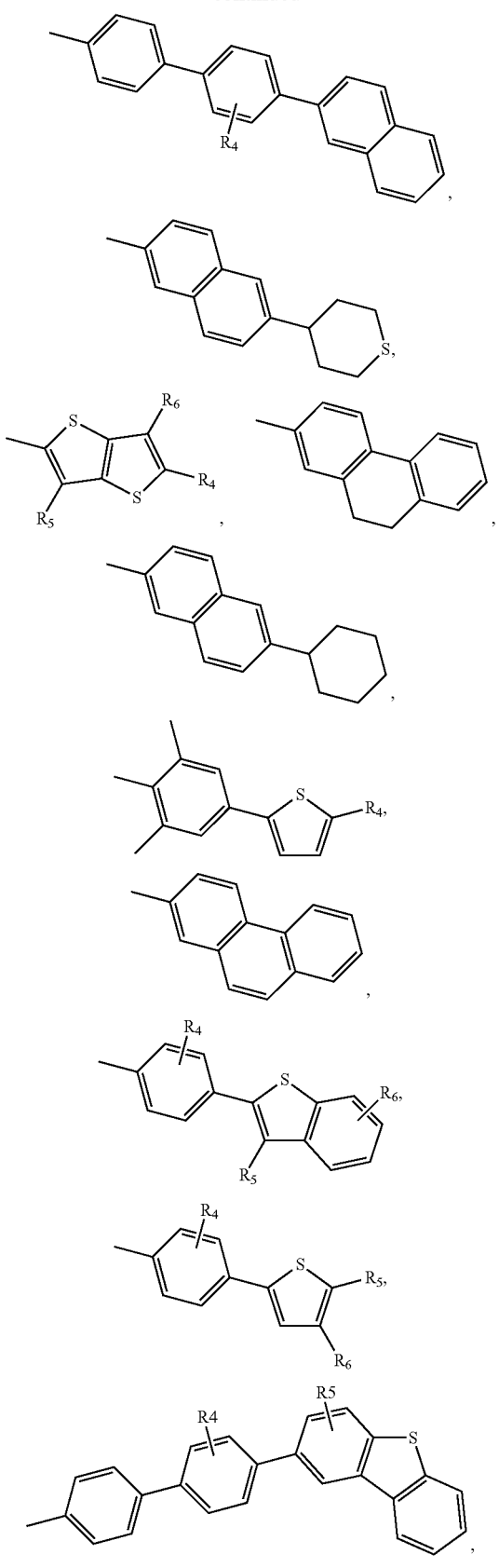
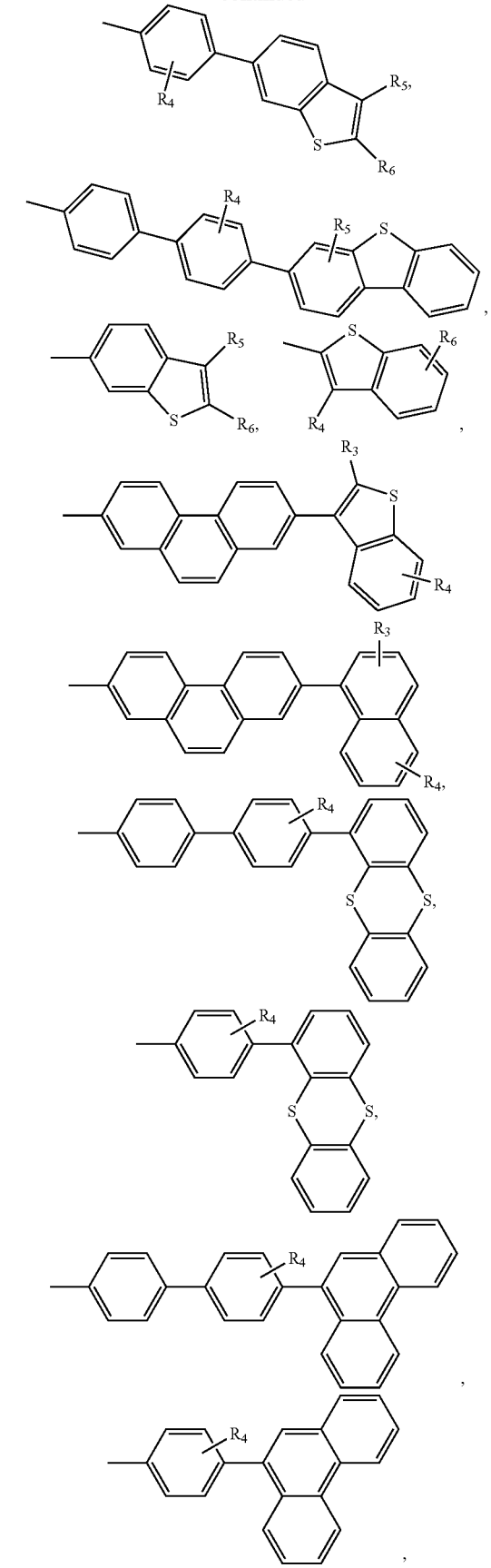

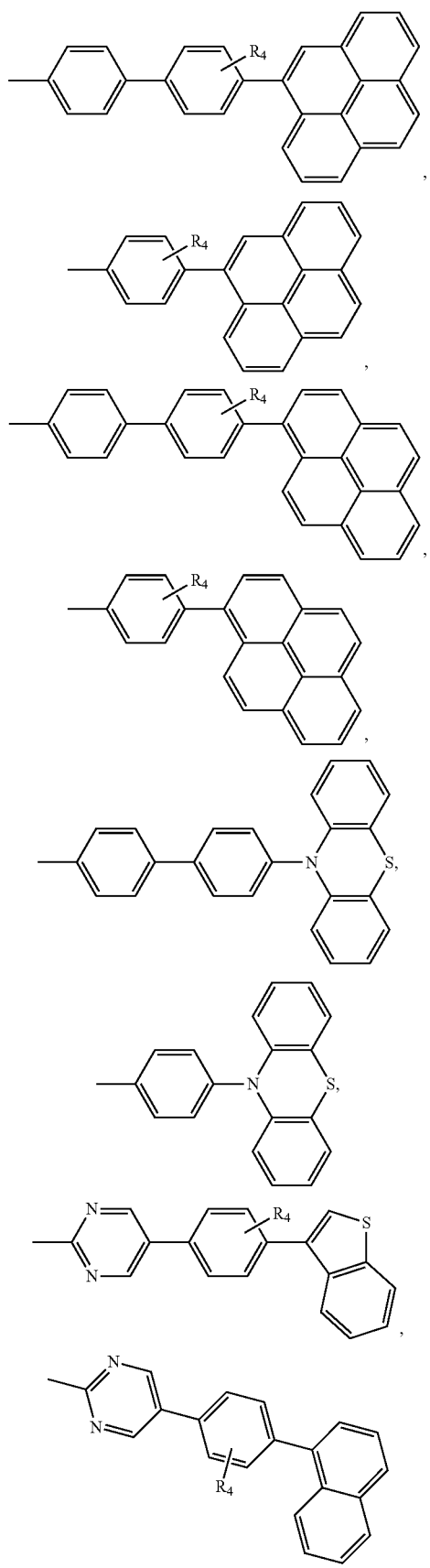
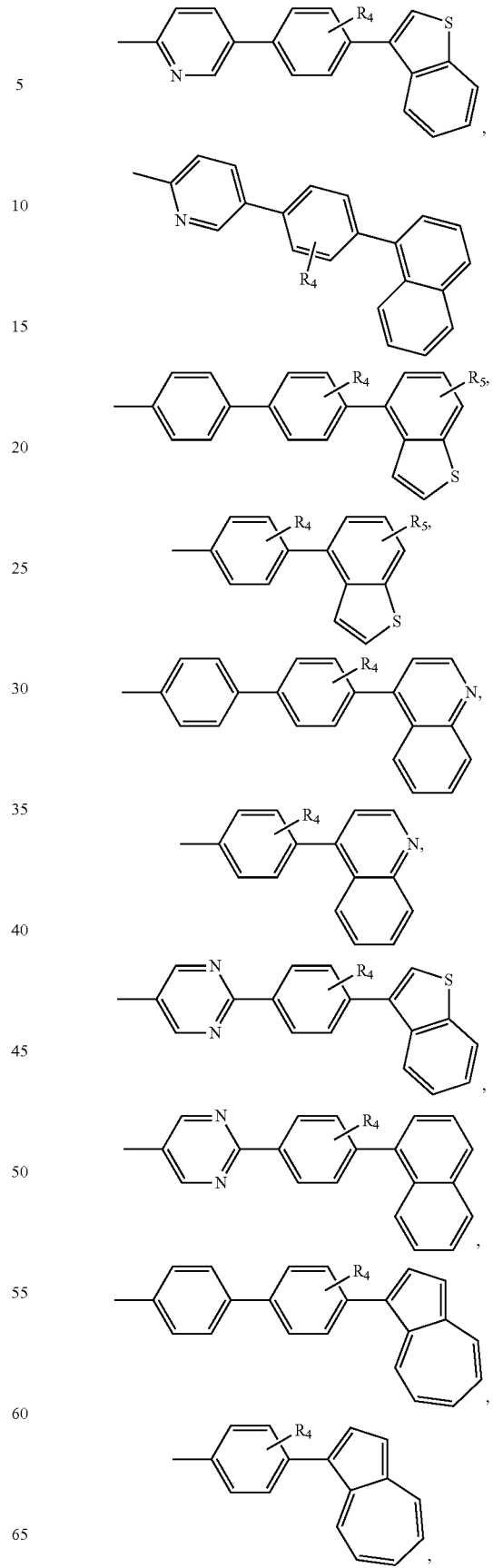

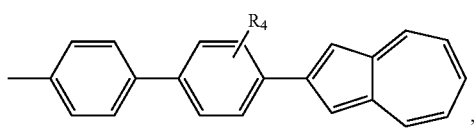
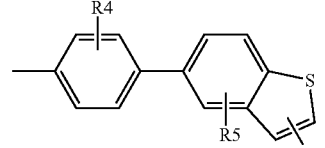
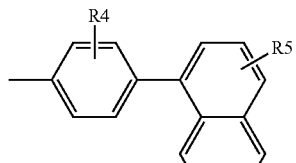
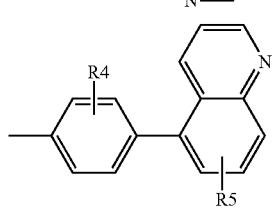
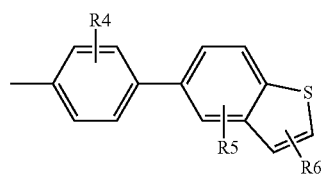
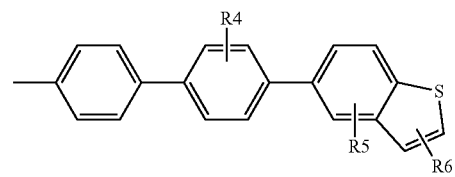
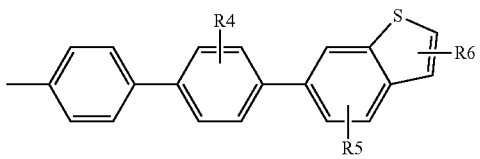
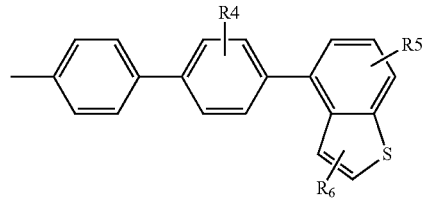
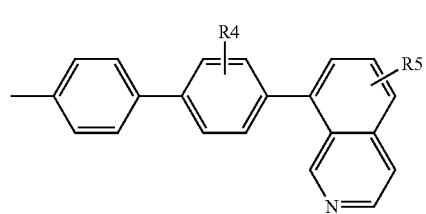
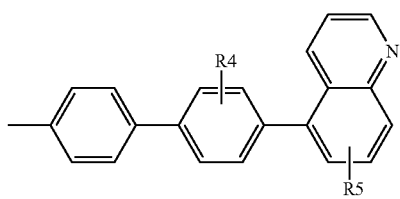
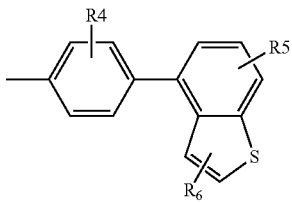
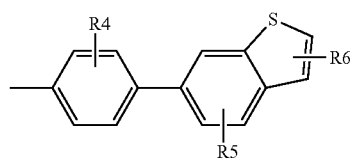
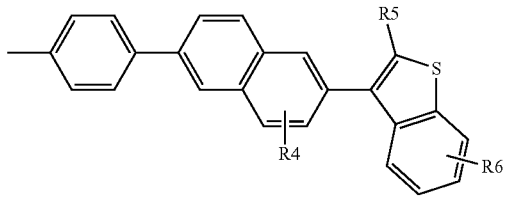
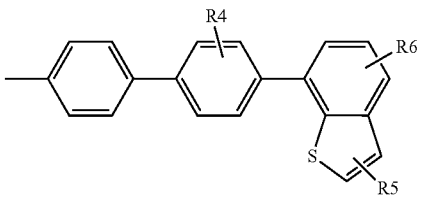
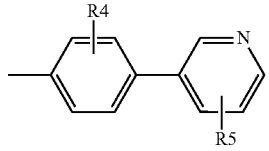
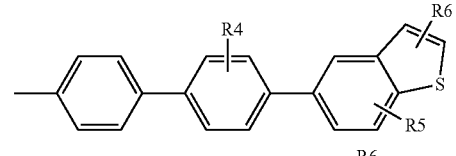
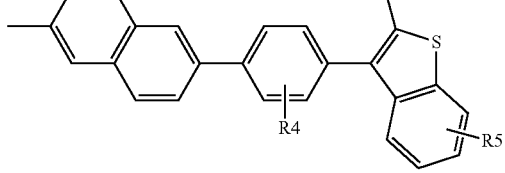
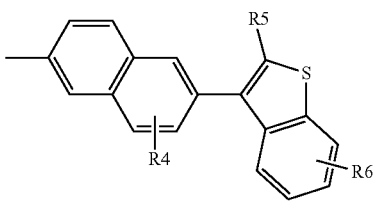

-continued
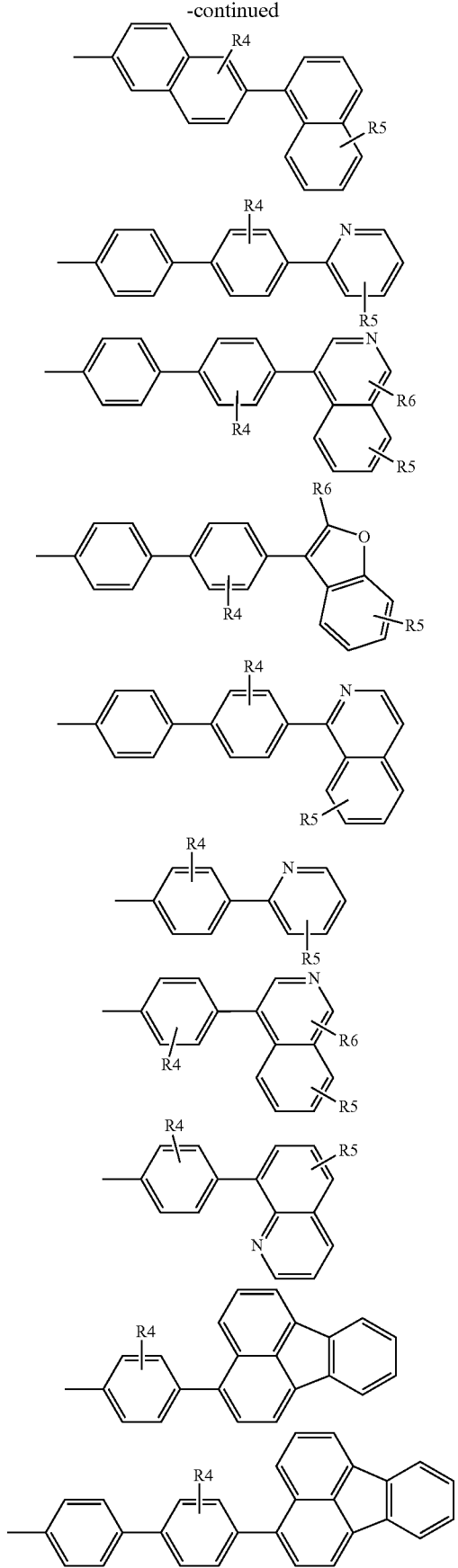
-continued
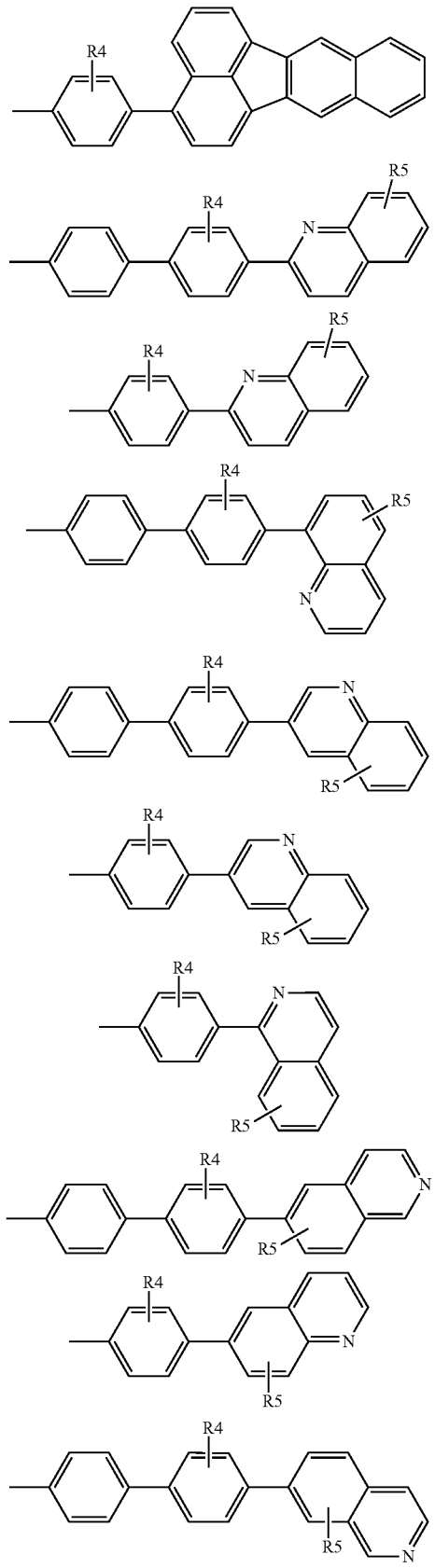

-continued

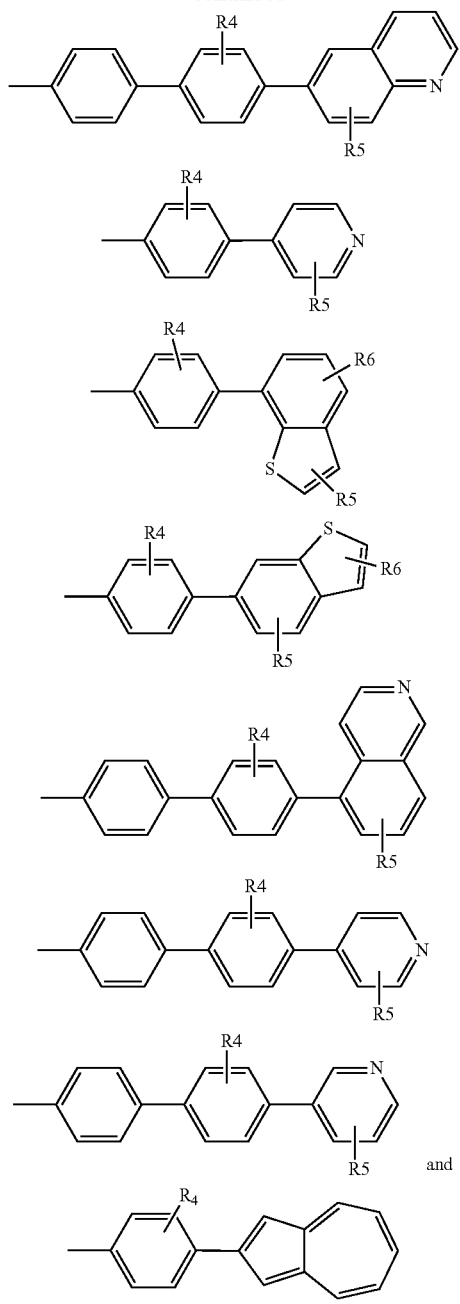

wherein $R_4$, $R_5$, $R_6$ are the same or different and are, at each occurrence, independently selected from H, F, $CH_3$, $CF_3$, aryl and alkyl.

(12) The transparent P material of (3), wherein the material is a thiophene- or selenophene-based material represented by the general formula XXXIX,

T-B-T           XXXIX, wherein,

T is selected from a structure with one of the general formulas IX, Xa, Xb, XI, XIIa, XIIb, XXII to XXXVIII:

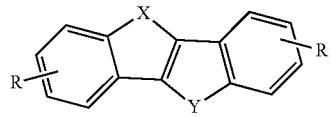
IX

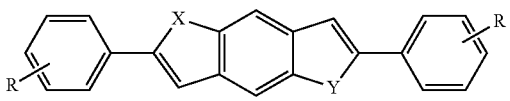
Xa

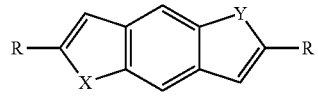
Xb

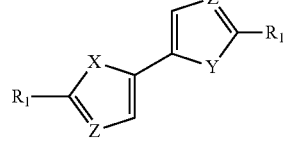
XI

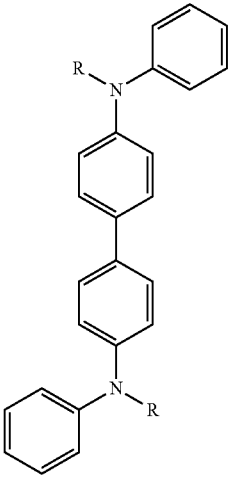
XIIa

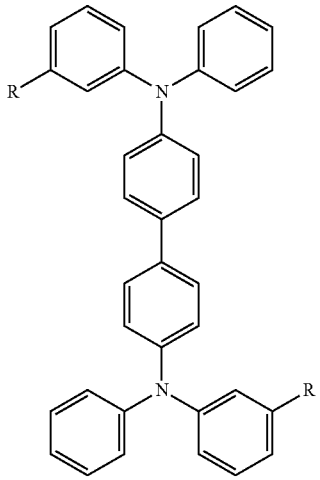
XIIb

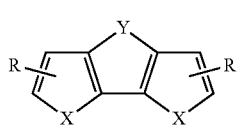
XXII

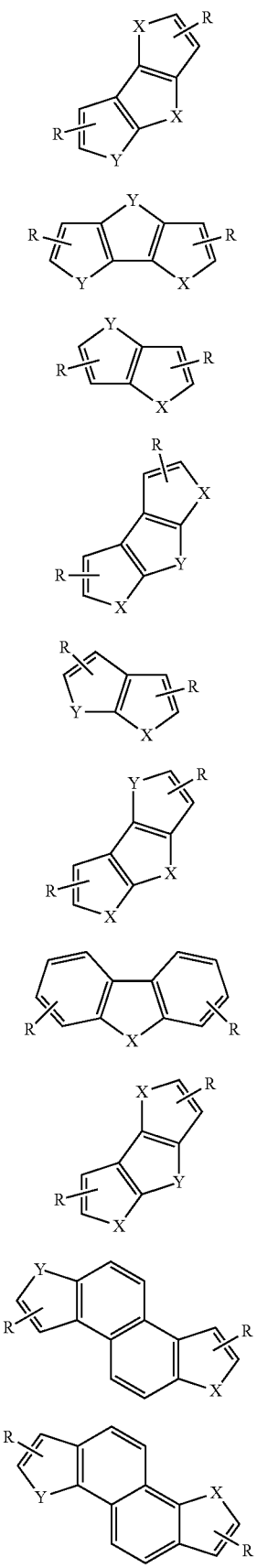
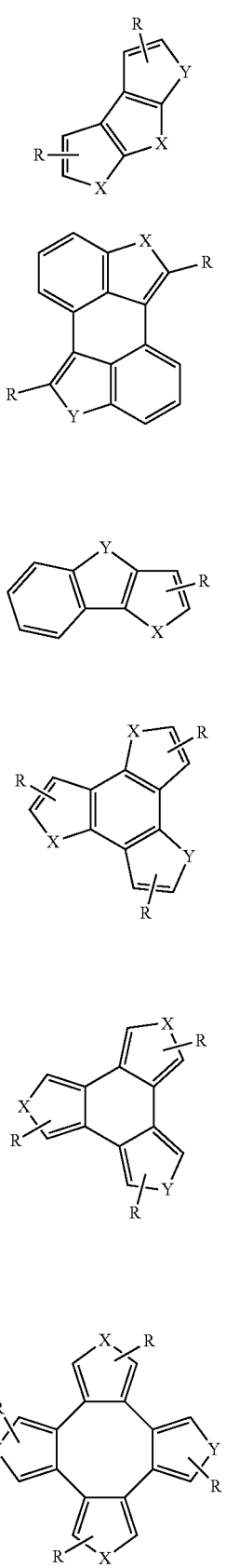

-continued

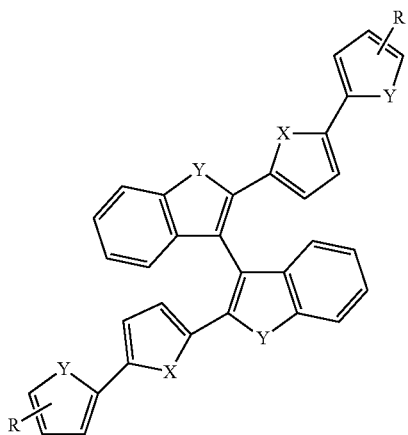

XXXVIII wherein,
- X and Y are the same or different and are, at each occurrence, independently selected from CR$_2$, S, O, Se, N—R and Si—R$_2$, wherein R$_2$ is selected from H, CH$_3$, CF$_3$, phenyl and alkyl;
- R and R$_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group, and
- B is selected from none,

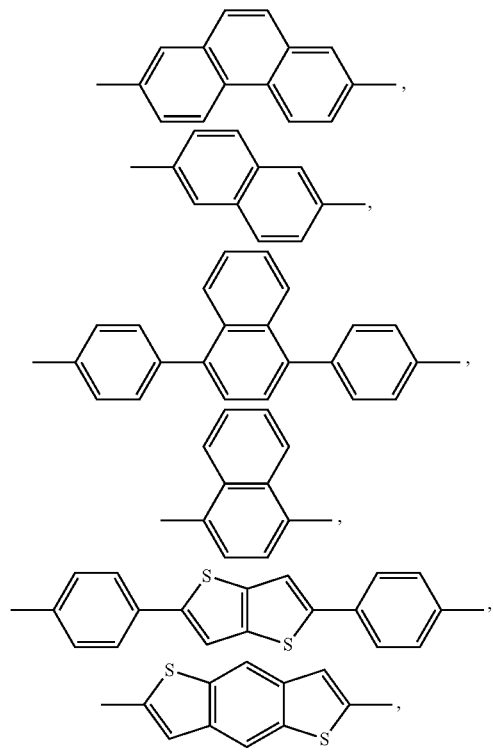

-continued

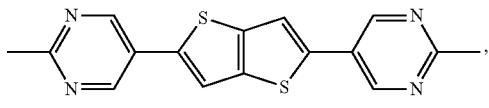

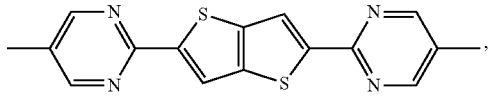

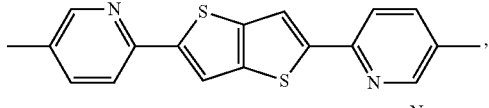

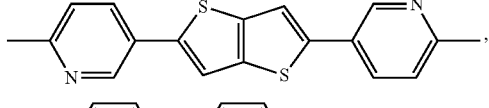

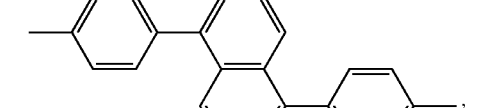

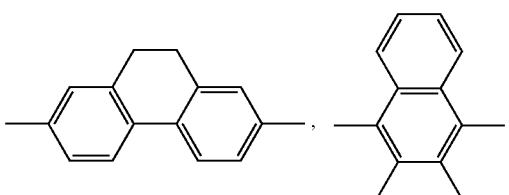

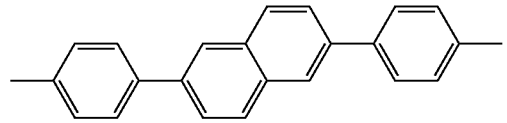

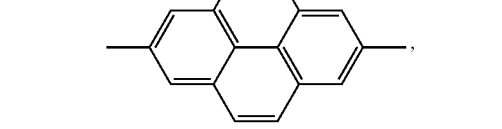

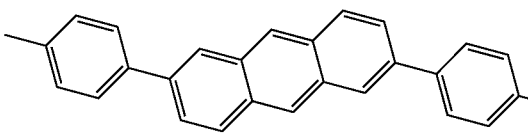

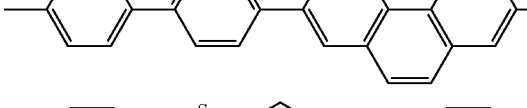

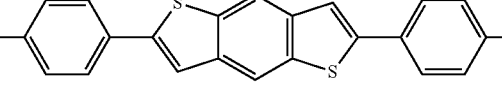

215

-continued

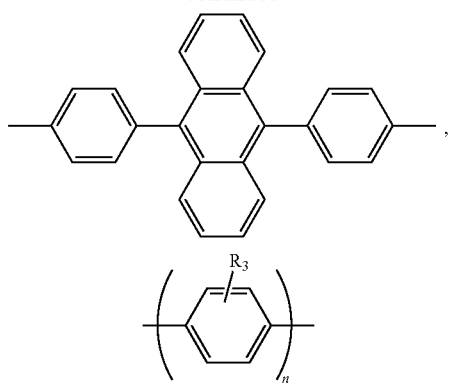

with R₃ selected from

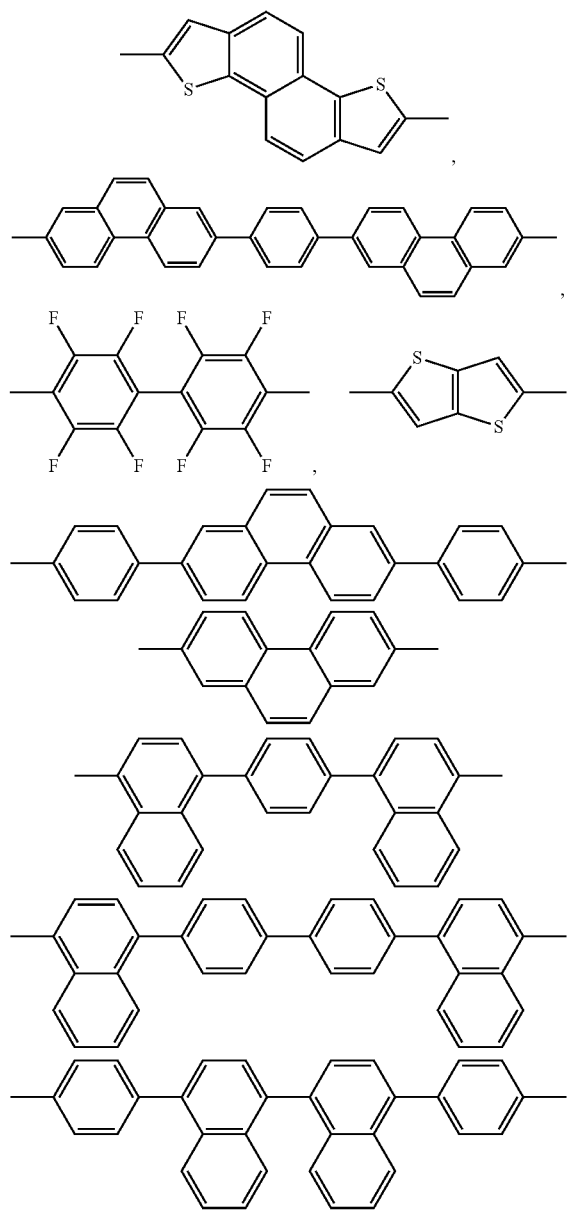

216

-continued

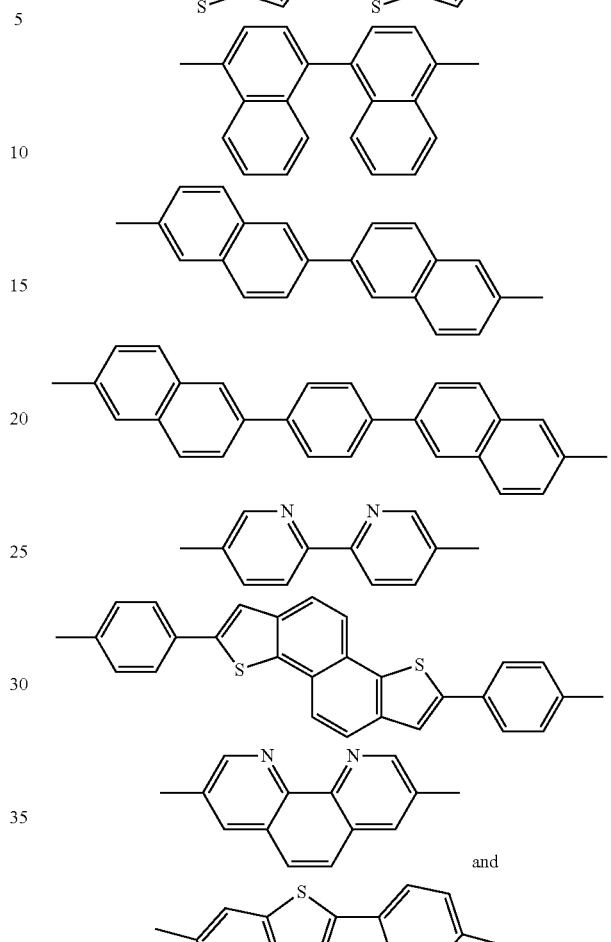

H, alkyl group, aryl group or halogen and n being 0 to 6,

(13) The transparent P material of (3), wherein the material is a thiophene- or selenophene-based material represented by the general formula XL:

$$T\text{-}H \qquad \qquad XL,$$

wherein,

T is selected from a structure with one of the general formulas IX, Xa, Xb, XI, XIIa, XIIb, XXII to XXXVIII:

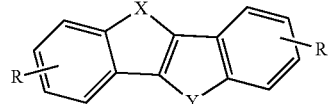

IX

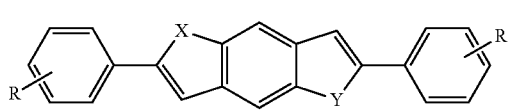

Xa

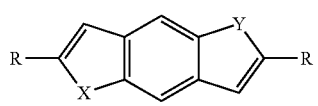
Xb
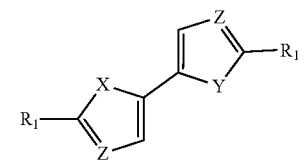
XI
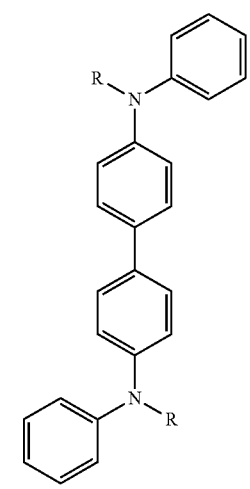
XIIa
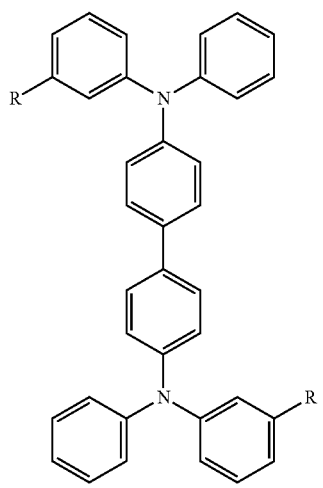
XIIb
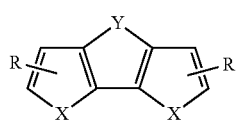
XXII
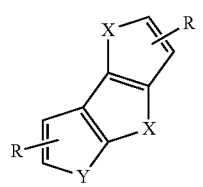
XXIII
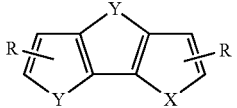
XXIV
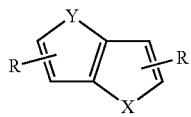
XXV
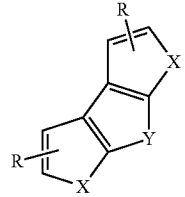
XXVI
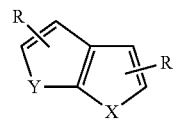
XXVII
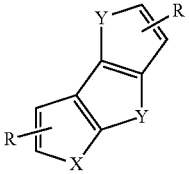
XXVIII
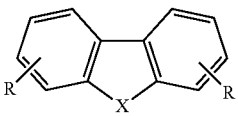
XXIX
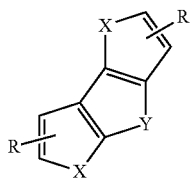
XXX
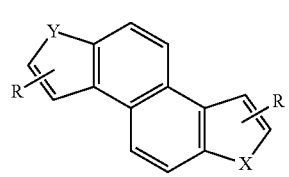
XXXIb
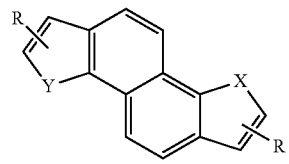
XXXIa

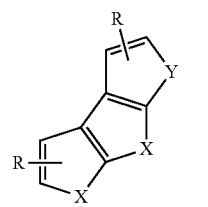

XXXII

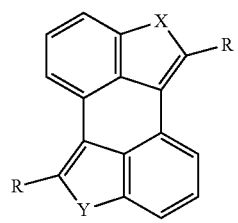

XXXIII

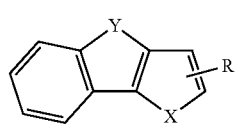

XXXIV

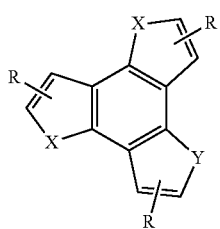

XXXV

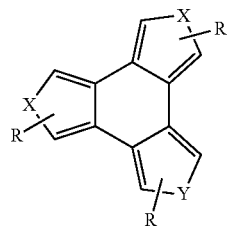

XXXVI

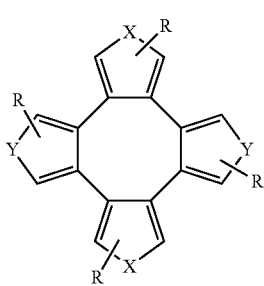

XXXVII

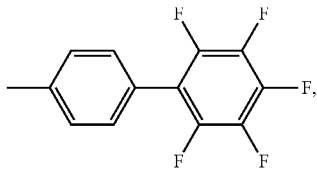

XXXVIII wherein

X and Y are the same or different and are, at each occurrence, independently selected from $CR_2$, S, O, Se, N—R and Si—$R_2$, wherein $R_2$ is selected from H, $CH_3$, $CF_3$, phenyl, alkyl and aryl;

R and $R_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group; and H is selected from any one of

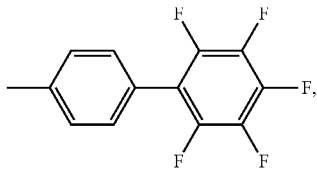

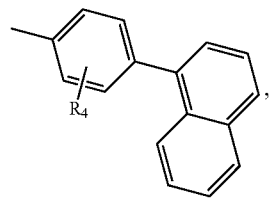

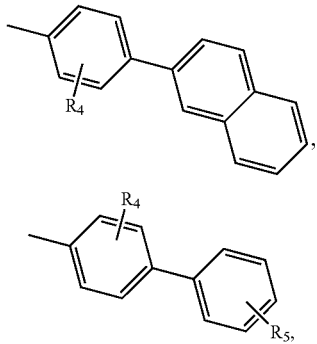

221
-continued
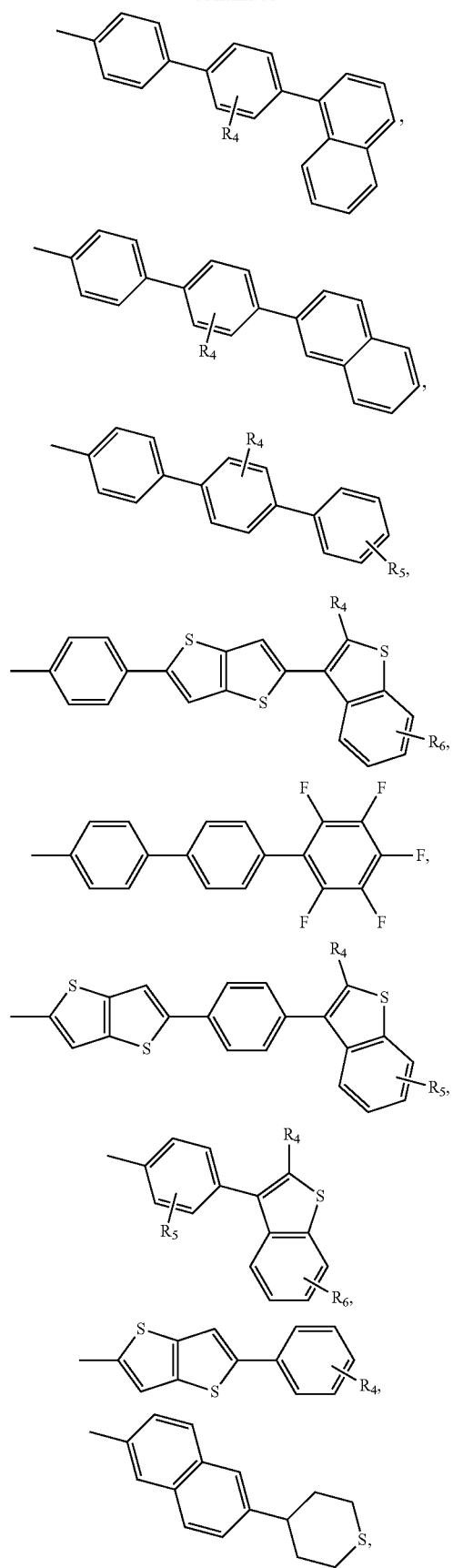
222
-continued
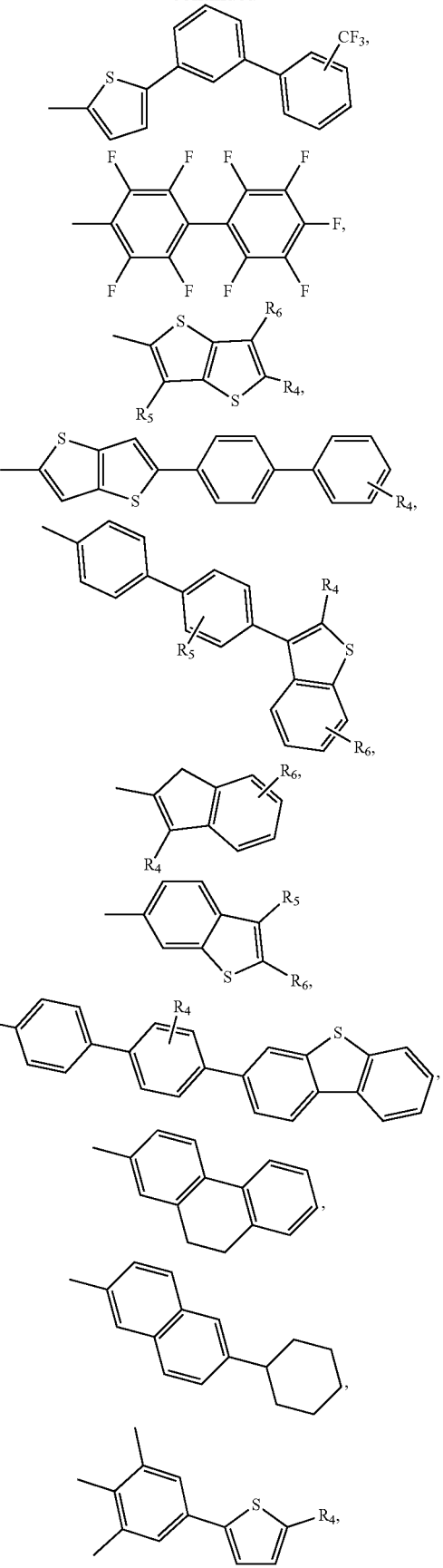

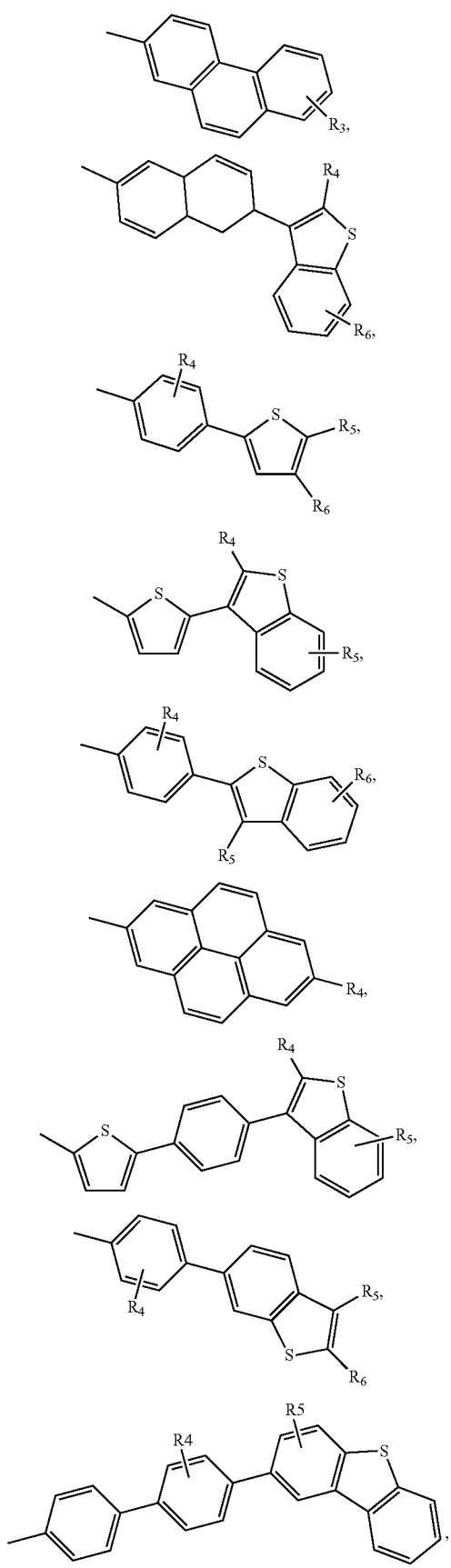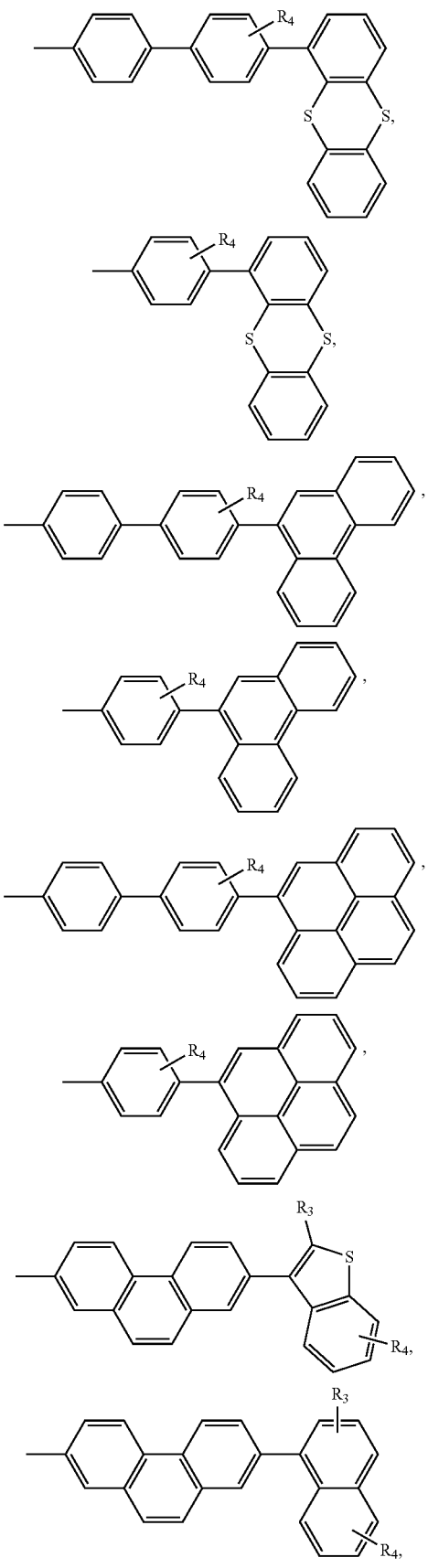

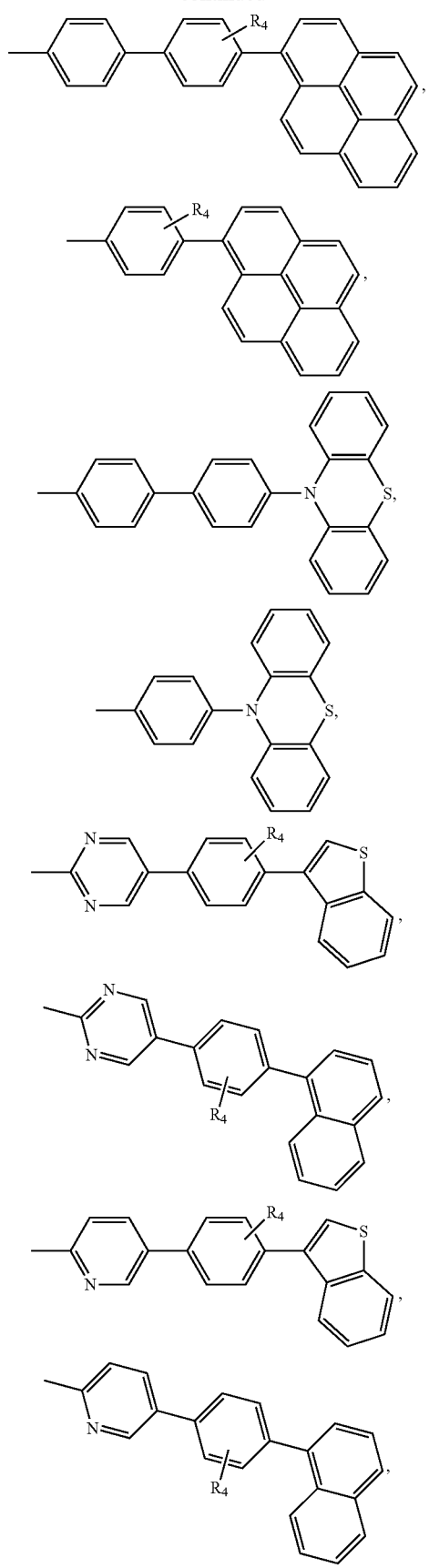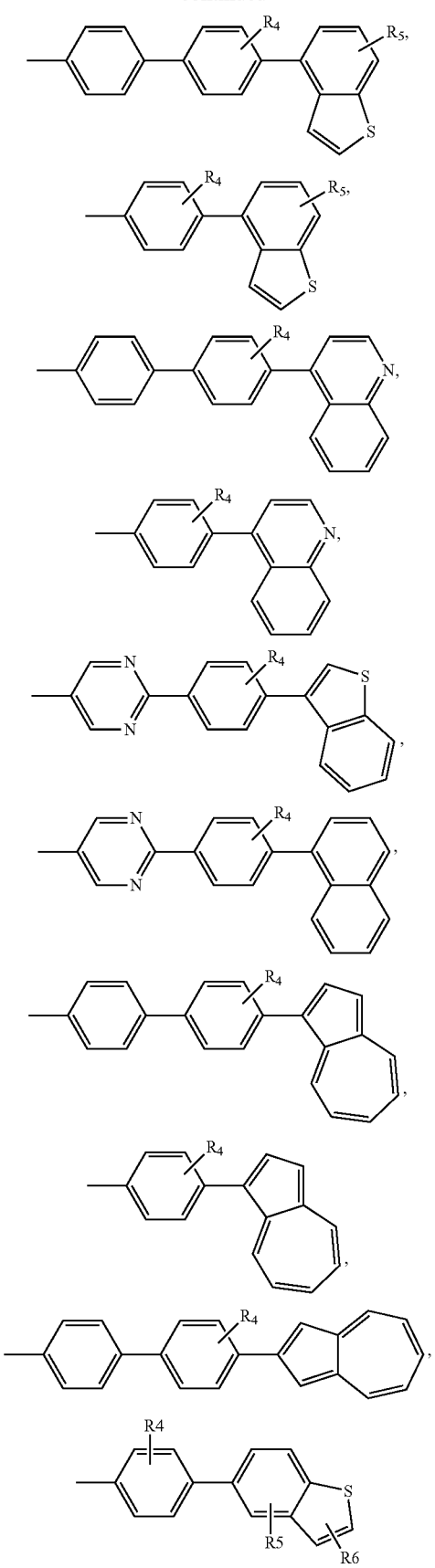

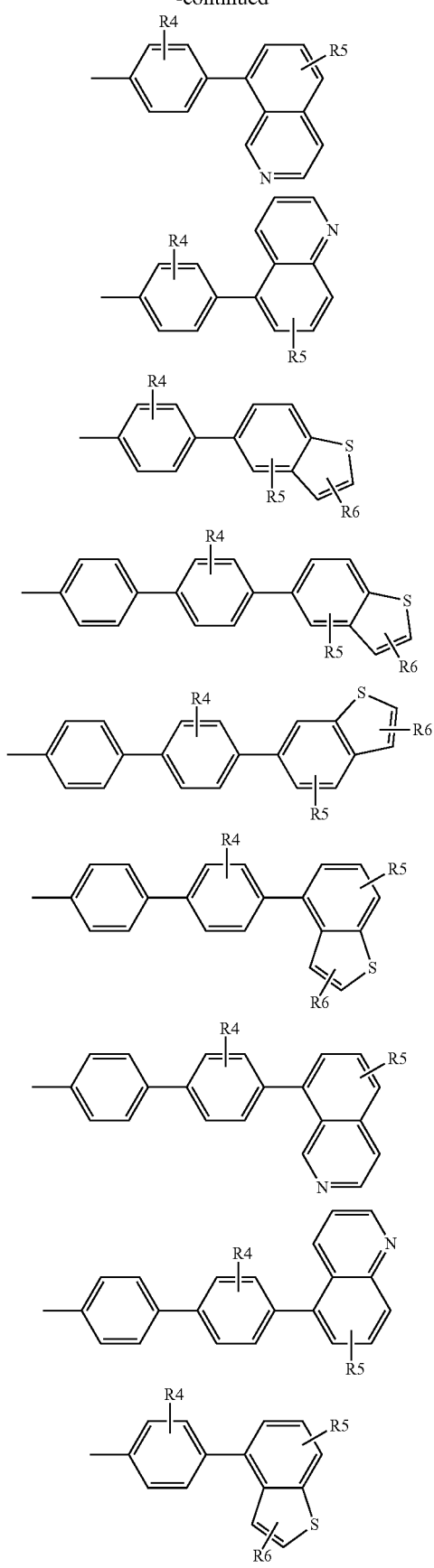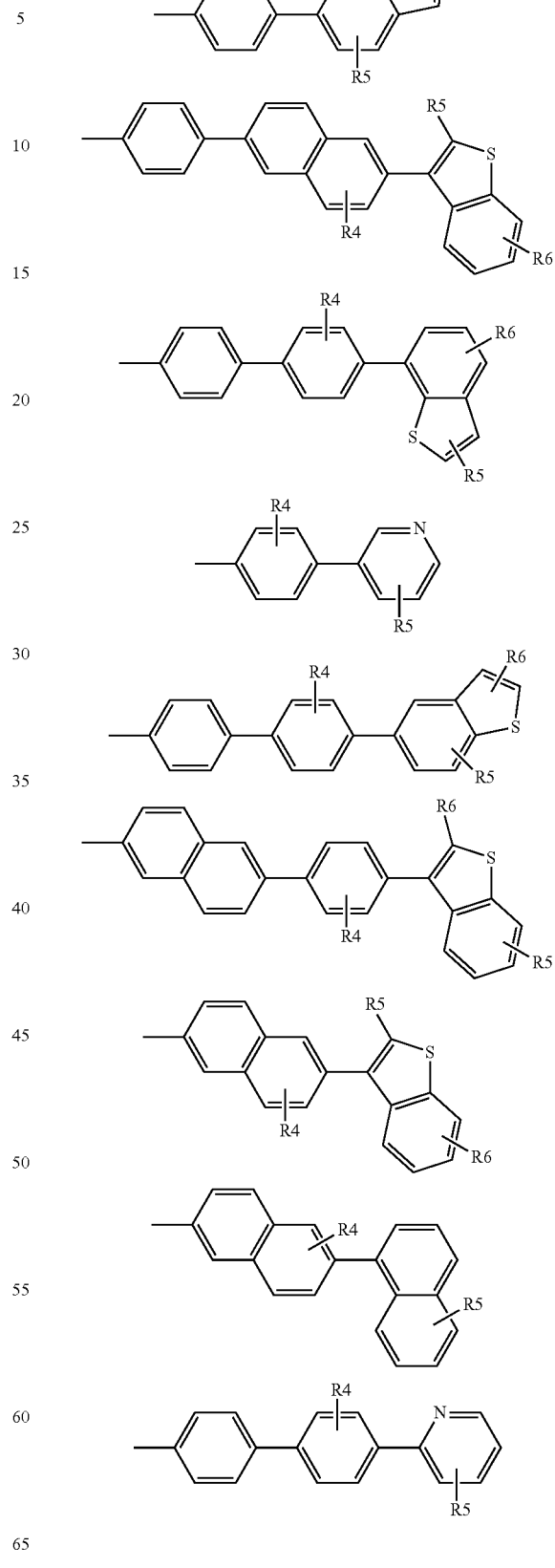

-continued
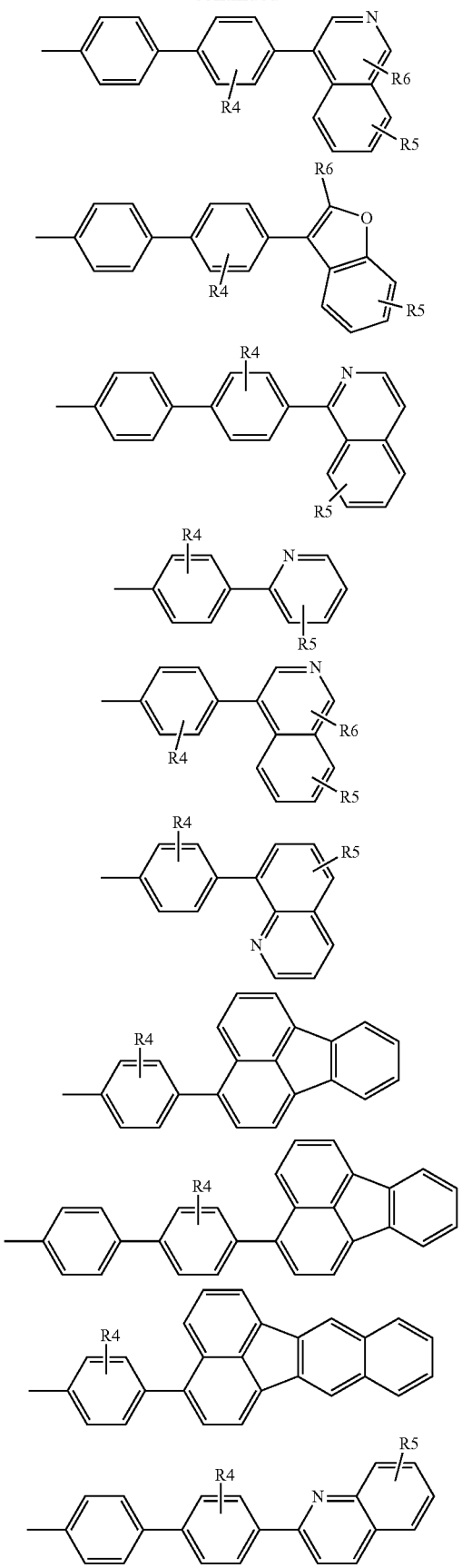
-continued
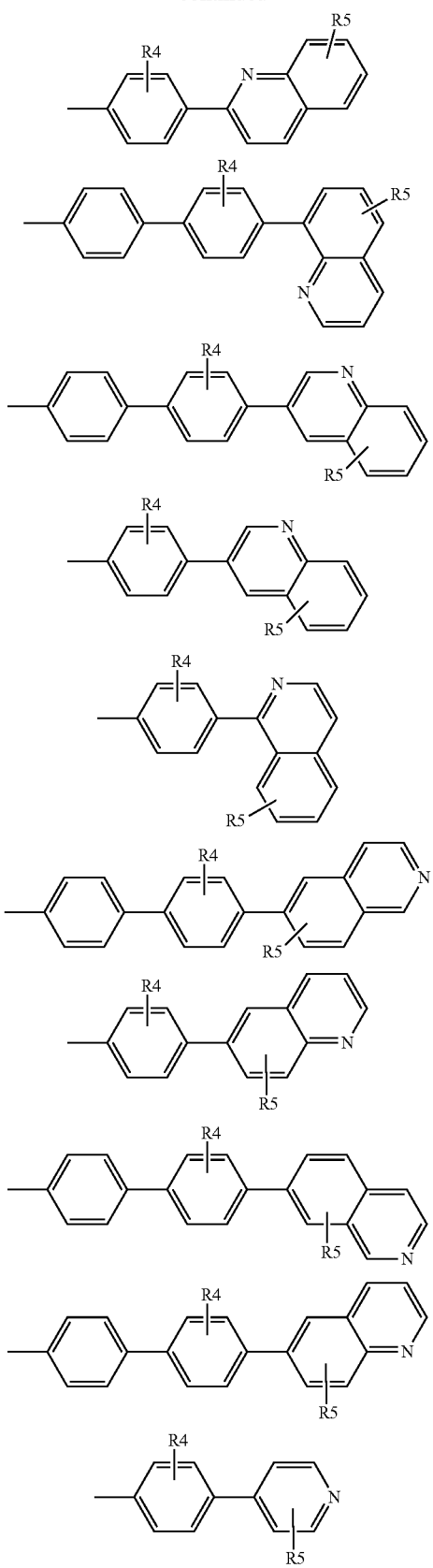

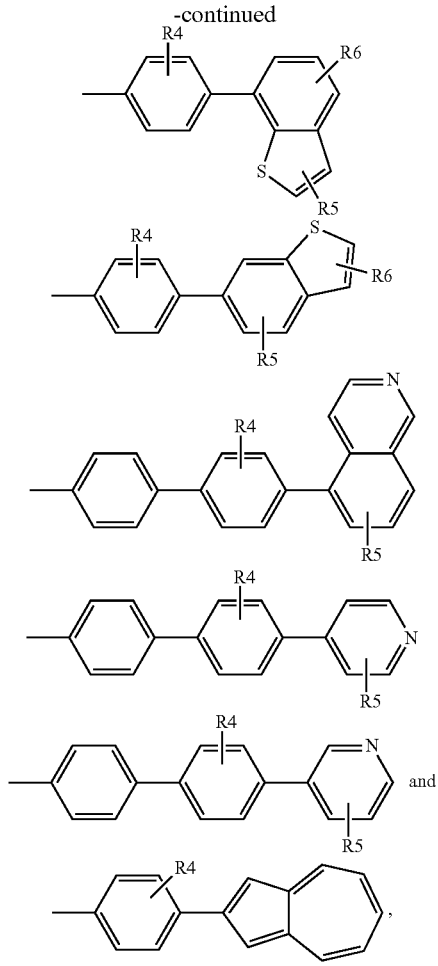

wherein $R_4$, $R_5$, $R_6$ are the same or different and are, at each occurrence, independently selected from H, F, $CH_3$, alkyl group and aryl group.

(14) The transparent P material of (3), wherein the material is a thiophene- or selenophene-based material represented by the general formula XLI:

H-T-B-T-H     XLI, wherein,
T is none or selected from a structure with one of the general formulas IX, Xa, Xb, XI, XIIa, XIIb, XXII to XXXVIII:

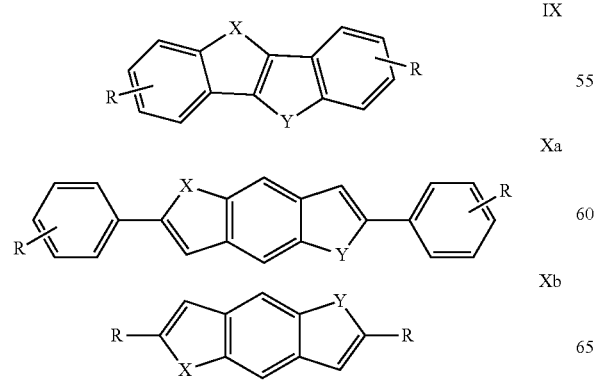

XI

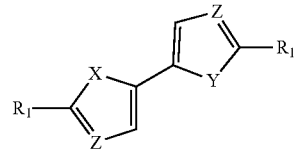

XIIa

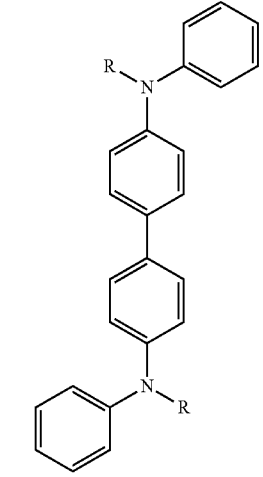

XIIb

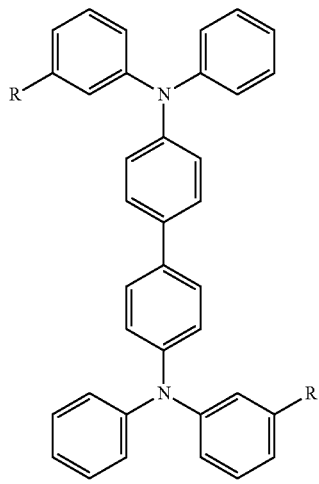

XXII

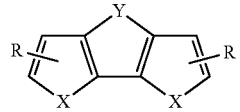

XXIII

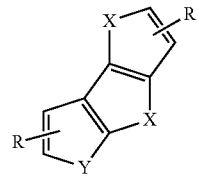

XXIV

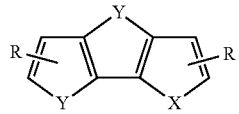

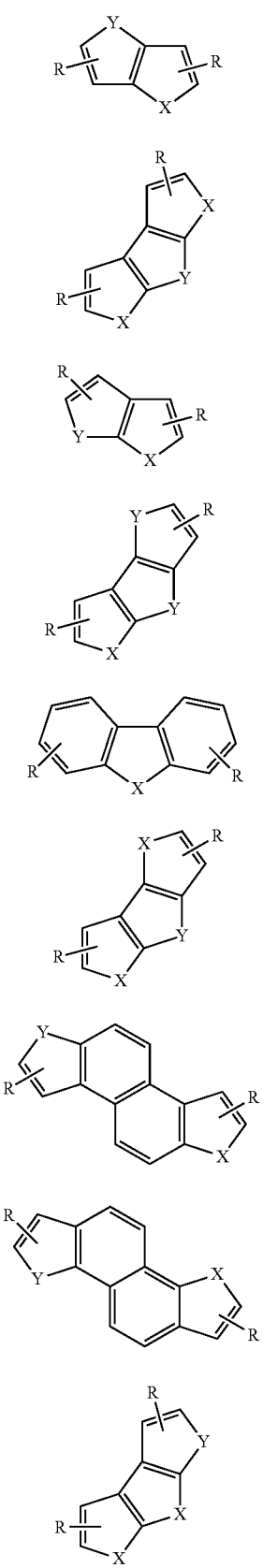
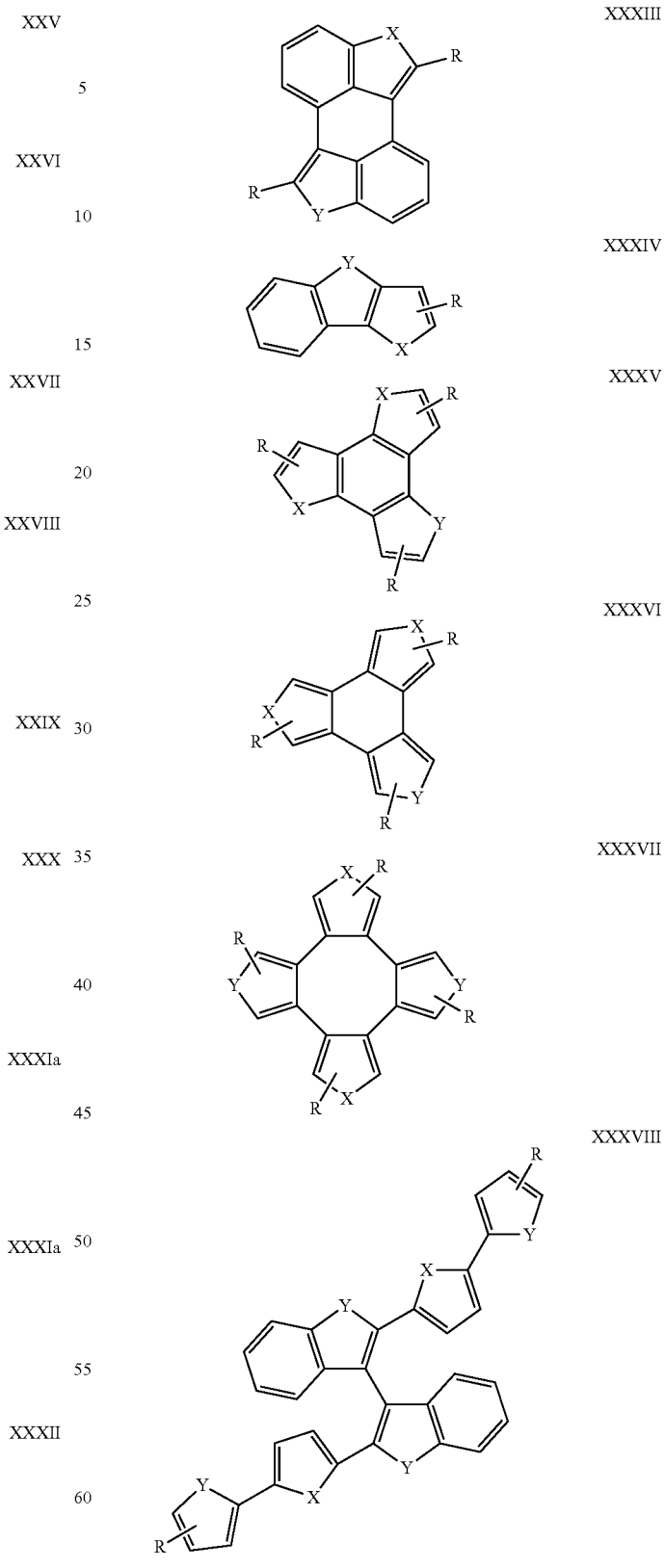
wherein,
X and Y are the same or different and are, at each occurrence, independently selected from CR$_2$, S, O, Se, N—R and Si—R$_2$, wherein R$_2$ is selected from H, CH$_3$, CF$_3$, phenyl, alkyl and aryl; and R and R$_1$ are the same or different and are, at each occurrence, independently selected from H, linear and branched alkyl group, cycloalkyl group, linear and branched alkoxy group, halogenated alkyl group, halogen atoms, alkyl or aryl sulfanyl group, alkyl or aryl amine, aryl group, halogenated aryl group, biaryl group, halogenated alkyl group, heteroaryl group and fluorenyl group;

B is selected from none,

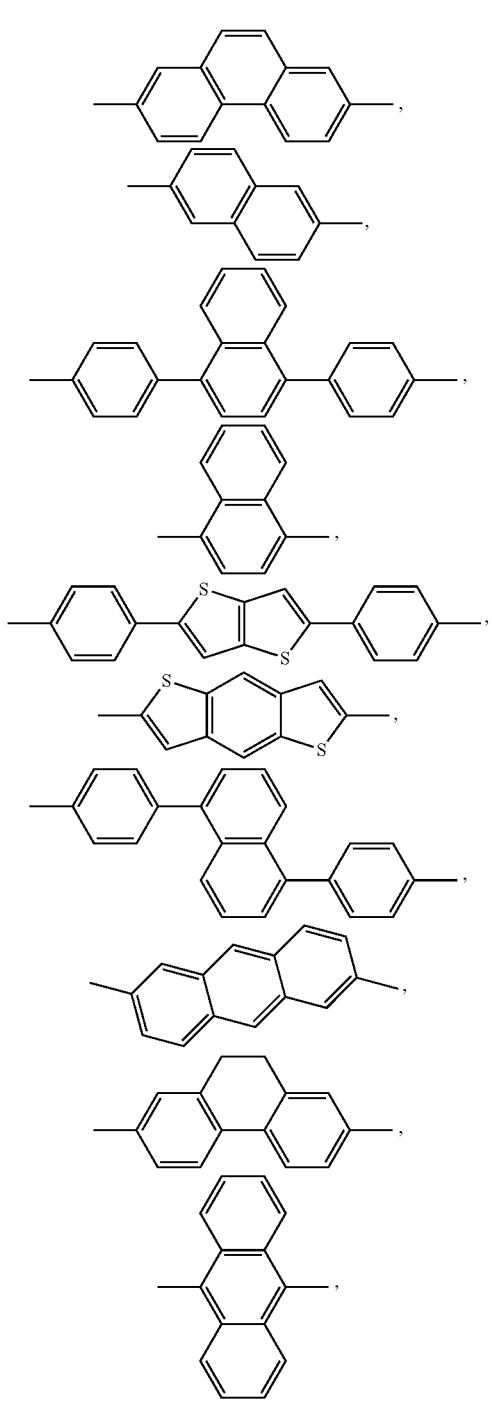

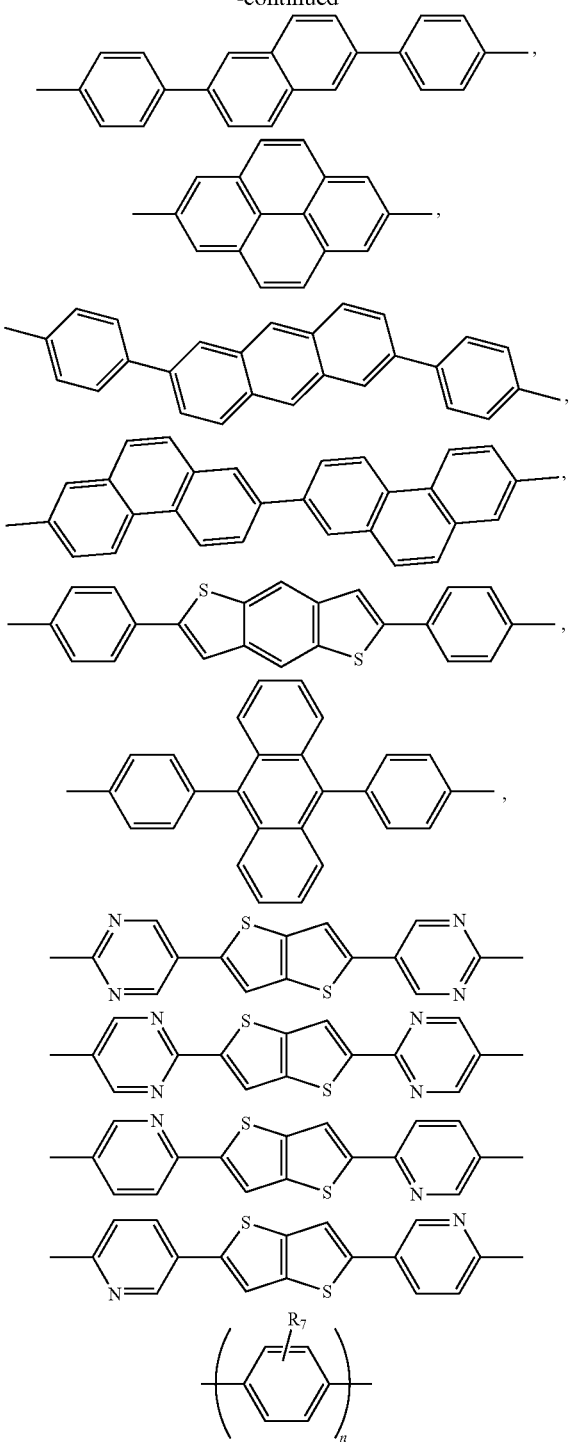

with R$_7$ selected from

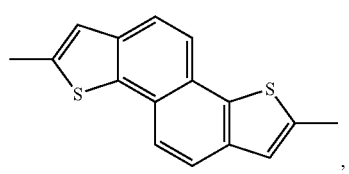

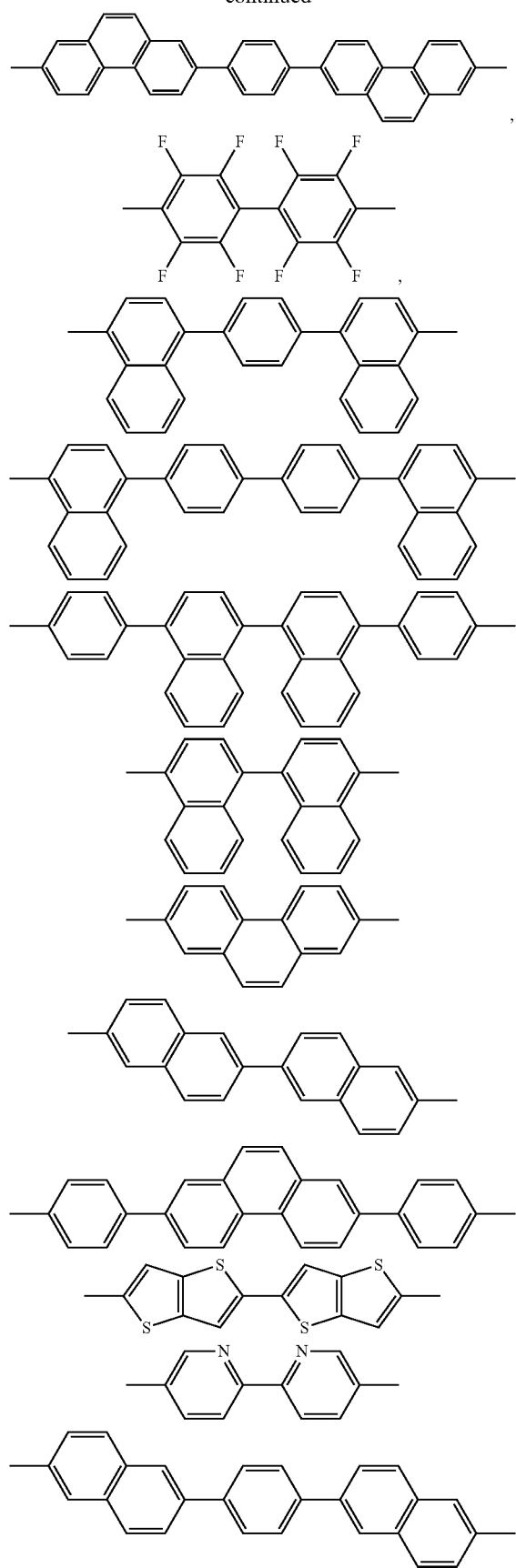
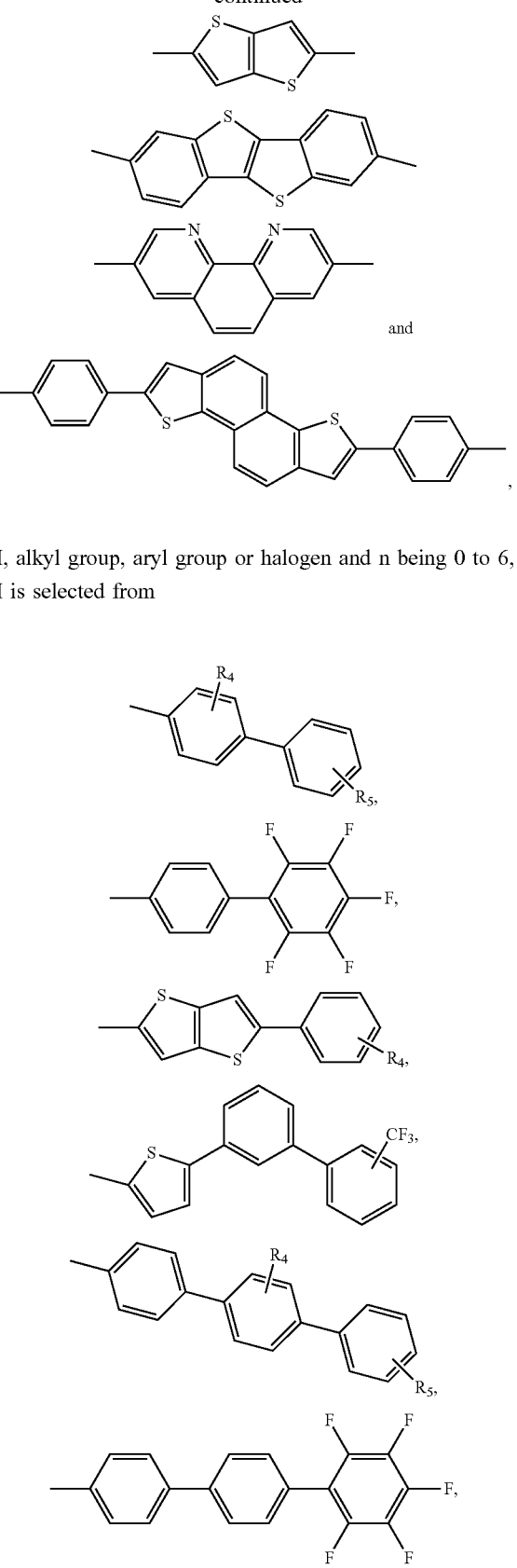
H, alkyl group, aryl group or halogen and n being 0 to 6, H is selected from

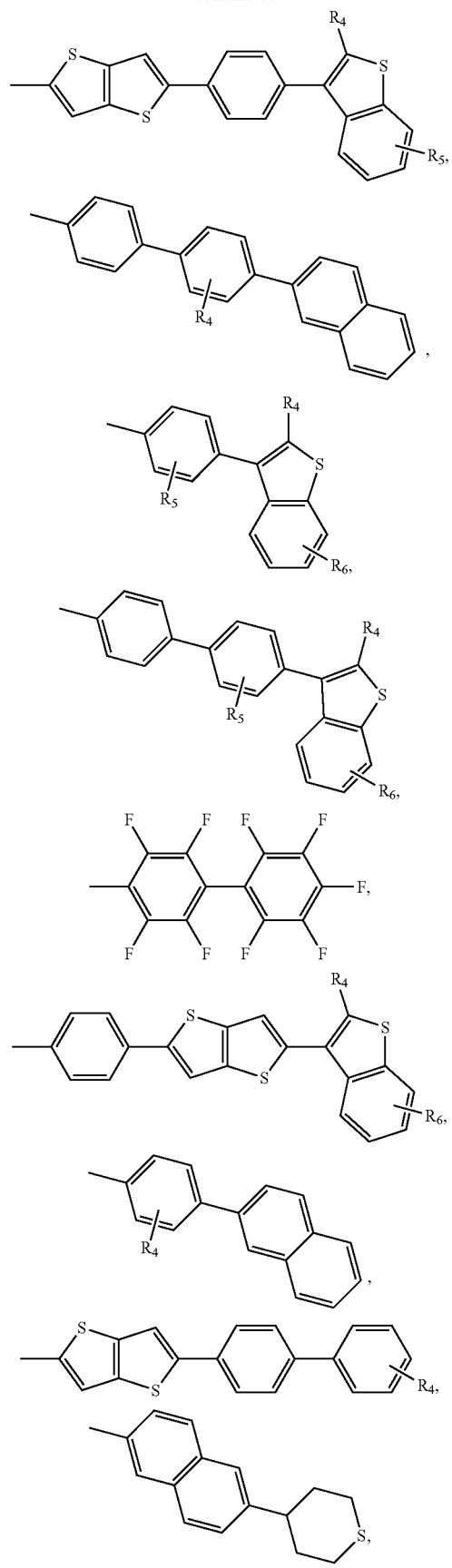
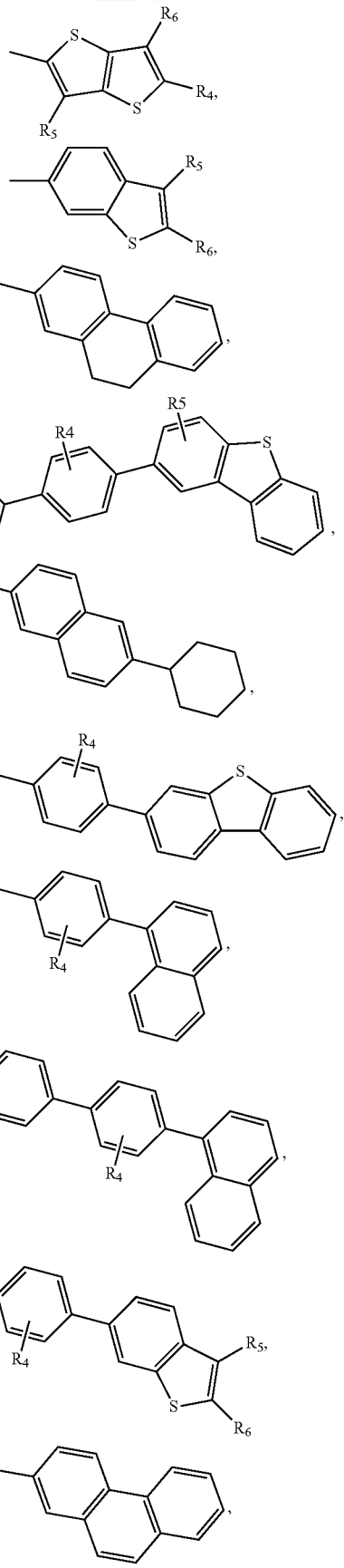

-continued
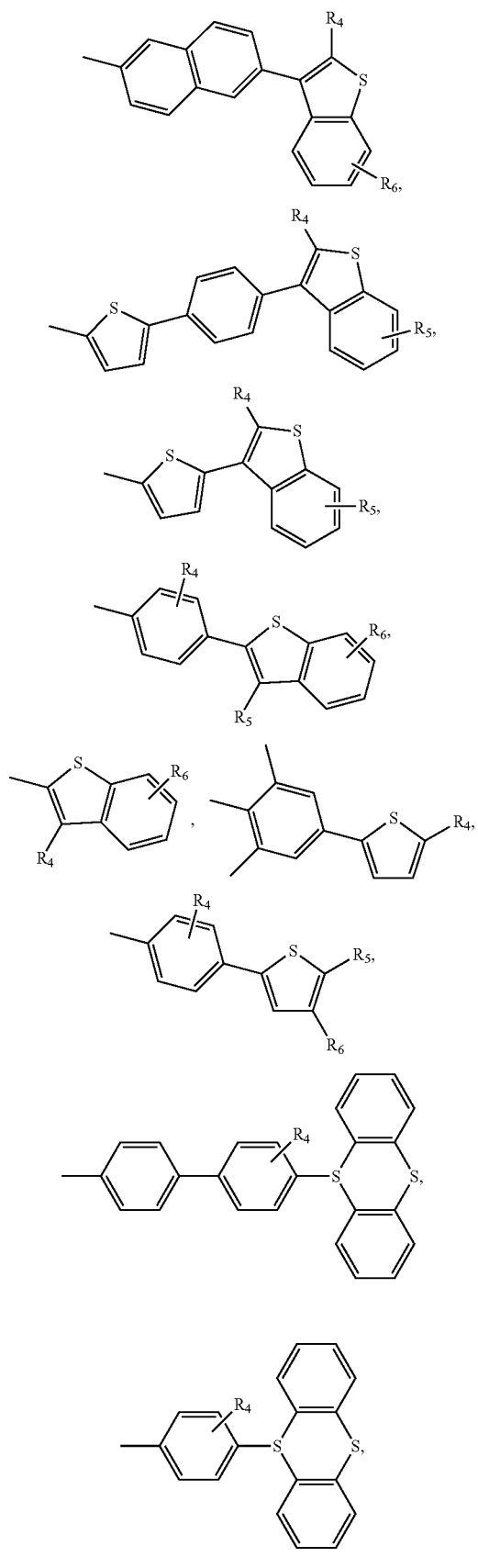
-continued
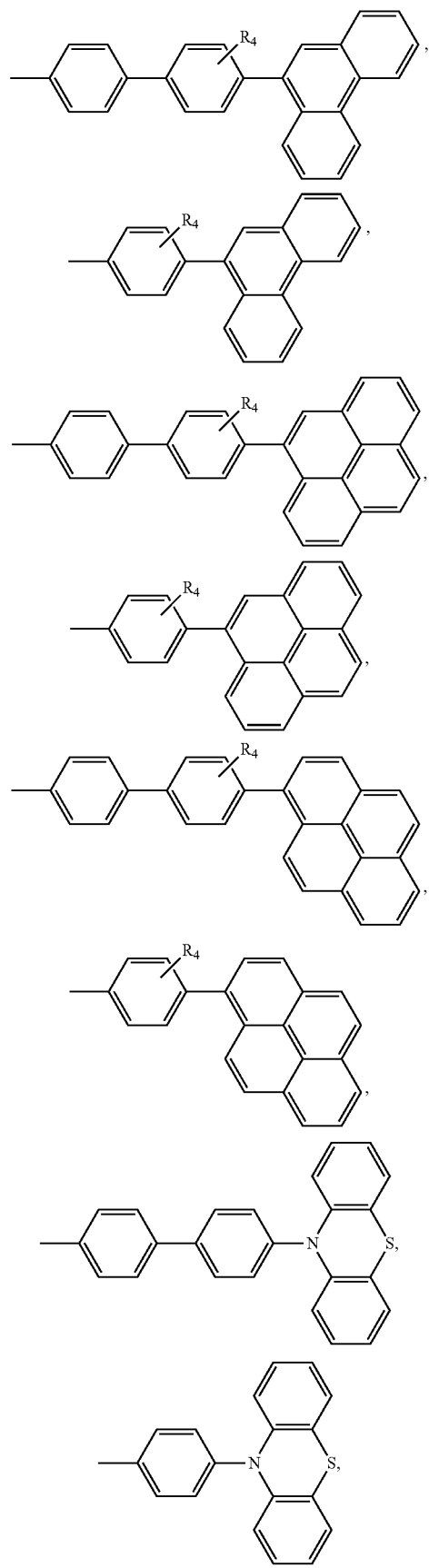

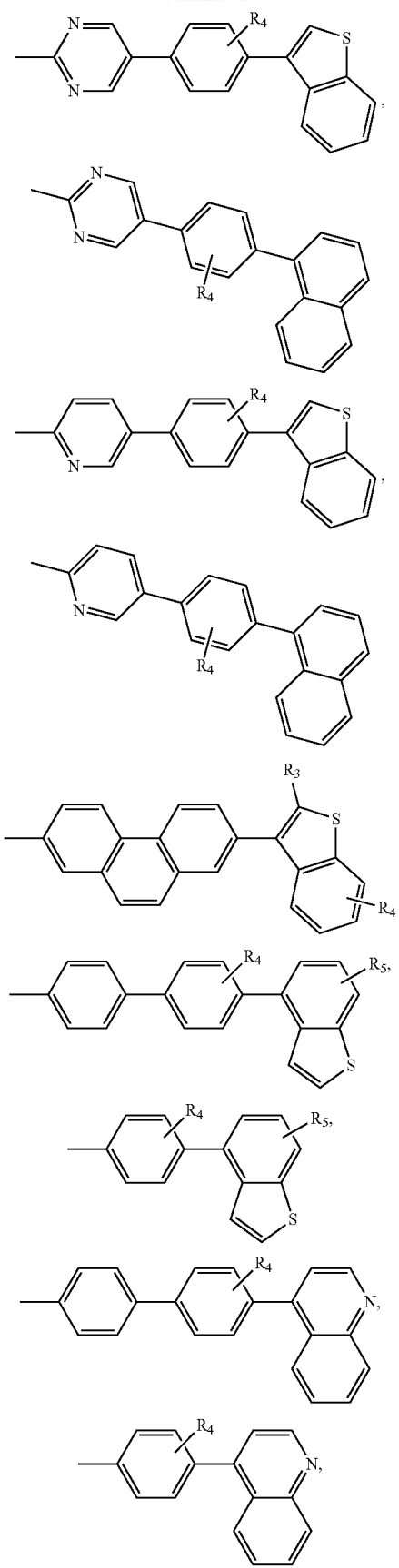
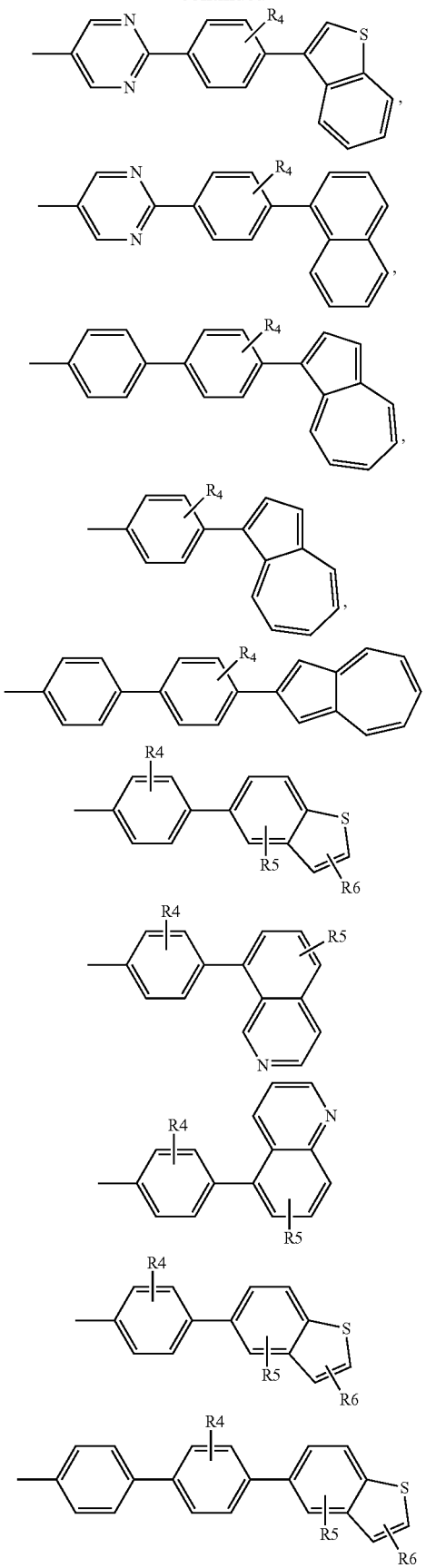

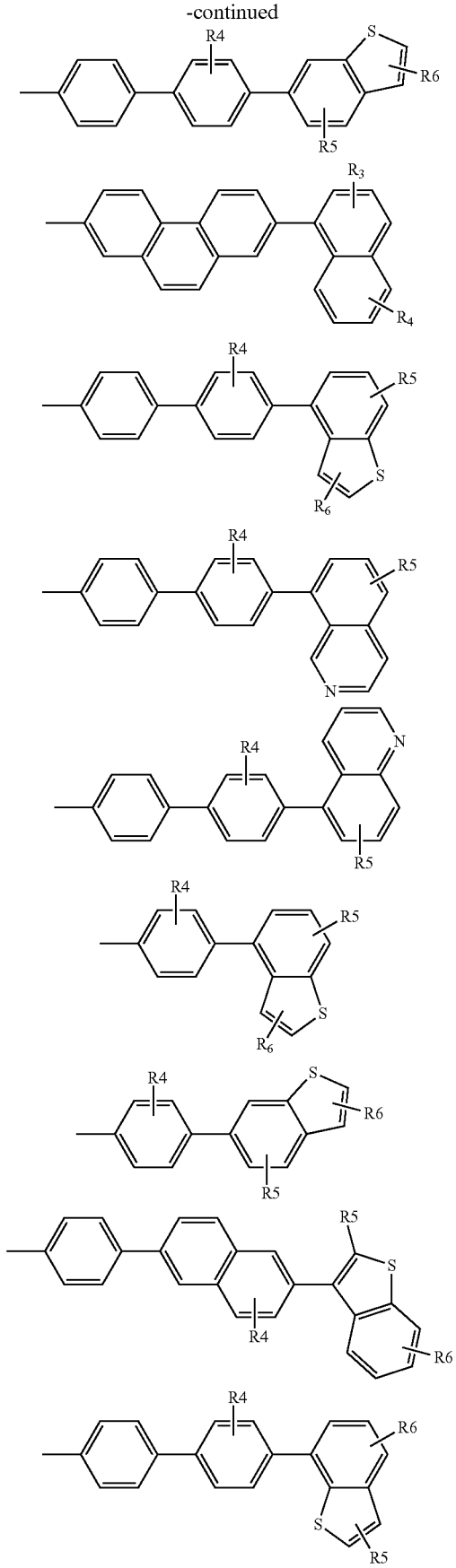
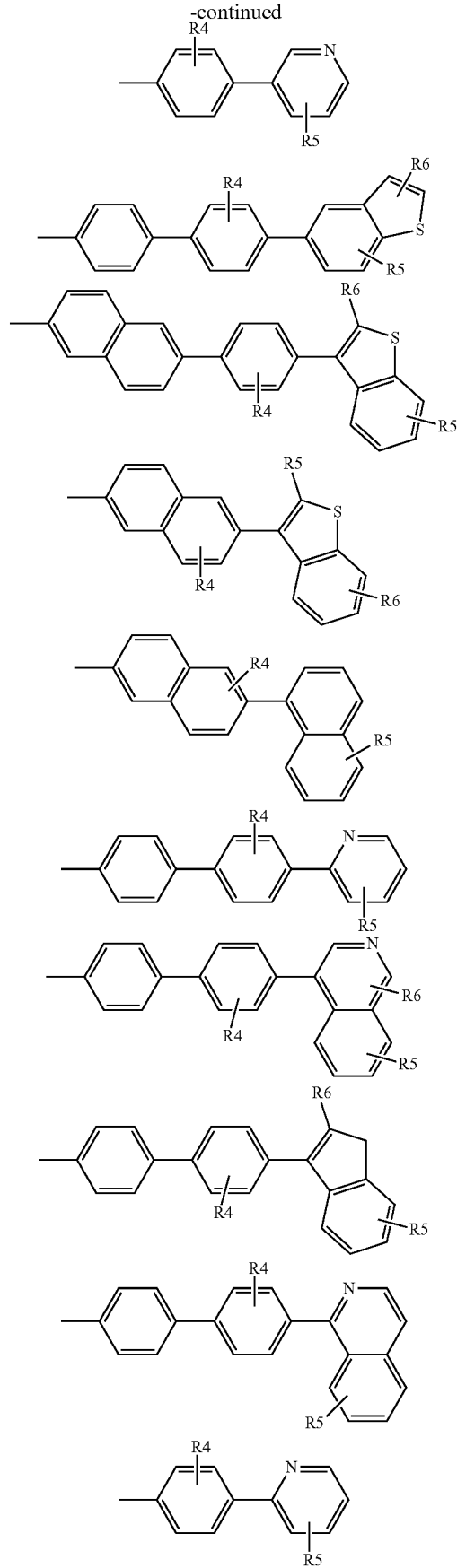

-continued
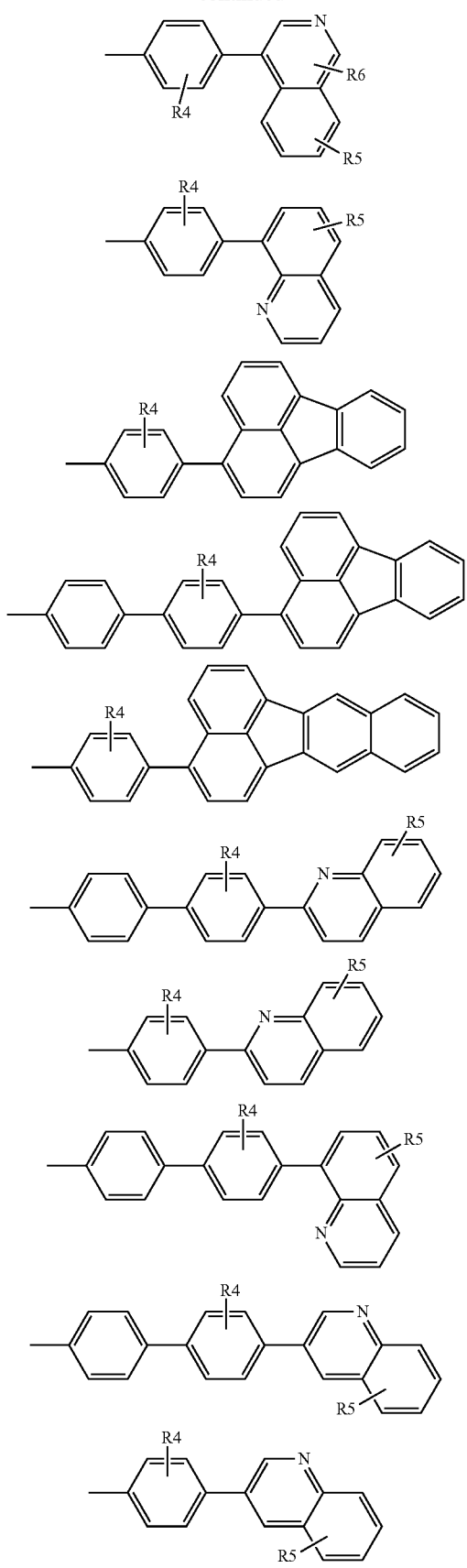
-continued
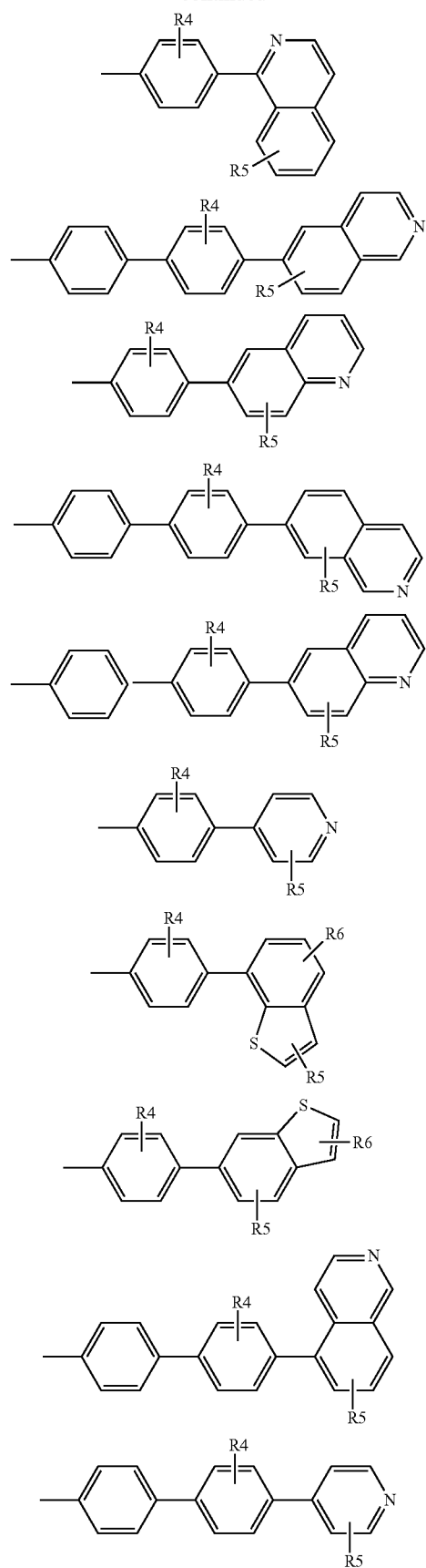

-continued

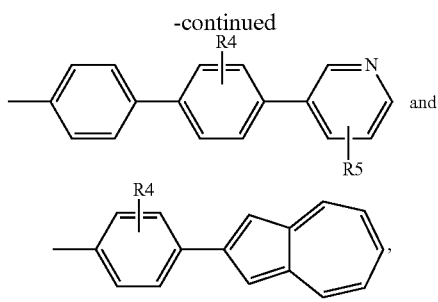
and wherein $R_4$, $R_5$, $R_6$ are the same or different and are, at each occurrence, independently selected from H, F, $CH_3$, alkyl and aryl.

(15) The transparent P material of (3), wherein the material is a thiophene-based material selected from the group of BDT3, BTBT14, BTBT2, BTBT9 and TT1:

(16) A P:N heterojunction, particularly a P:N1:N2 heterojunction, comprising a transparent P material according to any of (1) to (15),
and comprising a N and/or a further P material,
wherein the N and/or further P material particularly exhibits absorption in the visible wavelength range (about 400 to about 700 nm).

(17) Use of a transparent P material according to any of (1) to (15) in an absorption layer, and comprising a N and/or a further P material,
wherein the N and/or further P material particularly exhibits absorption in the visible wavelength range (about 400 to about 700 nm).

(18) Use of a transparent P material according to any of (1) to (15) in a photoelectric conversion layer and/or in an organic and/or hybrid module for optoelectronic application, such as image sensor, photodiode, organic photovoltaics, comprising organic photoelectric conversion layer(s), OLED and OTFT organic modules,

BDT3

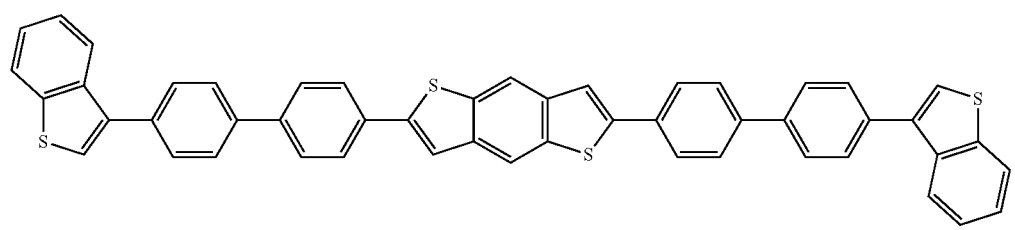

BTBT14

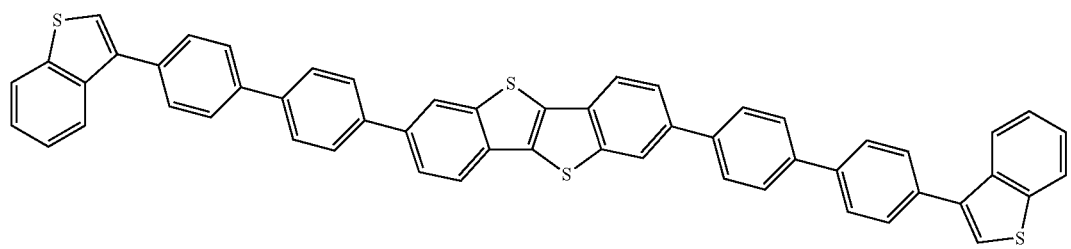

BTBT2

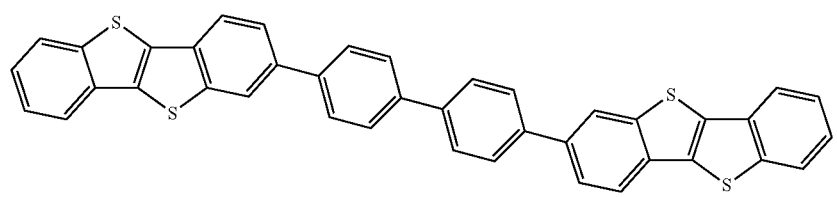

BTBT9

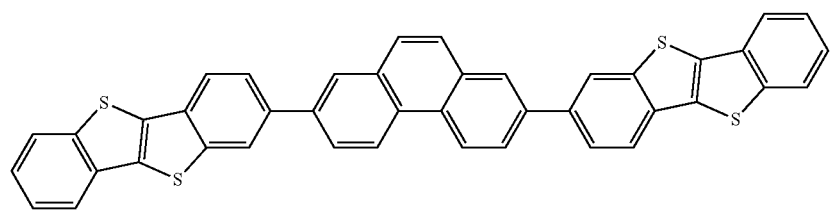

TT1

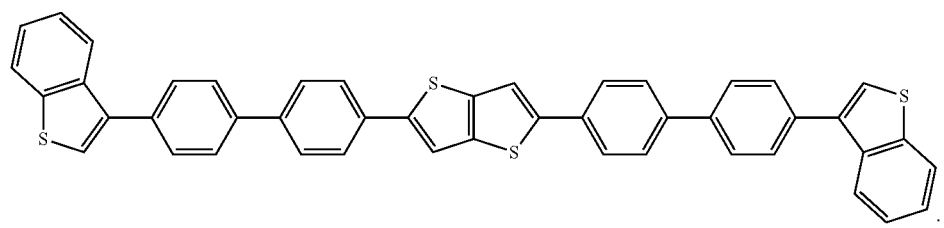

and comprising a N and/or a further P material,
wherein the N and/or further P material particularly exhibits absorption in the visible wavelength range (about 400 to about 700 nm).
(19) A photoelectric conversion layer comprising a transparent P material according to any one of (1) to (15),
and comprising a N and/or further P material,
wherein the N and/or further P material particularly exhibits absorption in the visible wavelength range (about 400 to about 700 nm).
and optionally comprising further molecule(s).
(20) An absorption layer comprising a transparent P material according to any one of (1) to (15),
and comprising a N and/or further P material, and
optionall comprising further molecule(s).
wherein the N and/or further P material particularly exhibits absorption in the visible wavelength range (about 400 to about 700 nm).
(21) A device, comprising transparent P material(s) according to any one of (1) to (15) or photoelectric conversion layer(s) according to (19),
wherein said device is particularly an organic image sensor, an hybrid image sensor, photodiode, organic photovoltaics, organic light-emitting diode (OLED), organic thin-film transistor (OTFT).
(22) The device according to (21), wherein said photoelectric conversion layer exhibits photo response in the visible absorption range.
(23) The device according to (21) or (22), comprising transparent P material(s) according to any one of (1) to (15) or photoelectric conversion layer(s) according to (19),
and/or comprising a N and/or further P material(s) particularly exhibiting absorption in the visible wavelength range (about 400 to about 700 nm),
and/or comprising further molecule(s).
(24) An organic image sensor, comprising
(a) anorganic photoelectric conversion unit comprising photoelectric conversion layer(s) according to (19),
(b) at least one electrode,
(c) a substrate,
(d) optionally, a second electrode on top of said photoelectric conversion layer(s).
(25) A hybrid Silicon-organic image sensor or organic image sensor, comprising
(a) anorganic photoelectric conversion unit or units comprising photoelectric conversion layer(s) according to (19),
(b) optionally, a Si based photoelectric conversion unit,
(c) metal wiring,
(d) a (CMOS) substrate,
(e) insulating layer(s), particularly oxide.
(26) The organic image sensor according to (24) or (25), wherein said organic photoelectric conversion unit comprises different layers,
such as n-type material, p-type material, n-buffer layer and/or p-buffer layer or combinations or mixtures thereof.
(27) A method for synthesis of thiophene- or selenophene-based materials (represented by a general formula IX) comprising the steps of
a) palladium- and SPhos-system catalyzed Suzuki coupling of the specific R-boronic acid and subsequent borylation with bis(pinacolato)diboron in palladium catalyst system;
b) parallel reaction of chlorobenzaldehyde with sodium hydrogensulfide hydrate and bromination with elemental bromine;
c) palladium- and SPhos-system catalyzed Suzuki coupling of product of a) and the product of b).

(28) A method for synthesis of thiophene- or selenophene-based materials (represented by a general formula Xb) comprising the steps of
a) palladium- and SPhos system catalyzed Suzuki coupling of the specific R-dibromide;
b) palladium- and SPhos system catalyzed Suzuki coupling of two equivalents of the product of a) with specific Xb-diboronic ester.
(29) A method for synthesis of thiophene- or selenophene-based material (represented by a general formula XXXI) comprising the steps of
a) reaction of chlorobenzaldehyde with sodium hydrogensulfide hydrate and bromination with elemental bromine;
b) palladium catalyzed reaction of T-specific benzothiophene with B-specific diboronic acid.
(30) A method for synthesis of thipheen- or selenophene-based material (represented by a general formula XXXIX) comprising the steps of
a) reaction of chlorobenzaldehyde with sodium hydrogensulfide hydrate and bromination with elemental bromine;
b) palladium catalyzed reaction of T-specific benzothiophene with B-specific diboronic acid.

The term "N material", as used herein, refers to a material accepting an electron.

The term "P material", as used herein, refers to a material donating an electron, which is the same as accepting a hole. It might also transport holes.

The term "thiophene material" or "thiophene-based material", as used herein, refers to a molecule in which at least a thiophene or a thiophene derivative is present in the molecular structure.

The term "selenophene material" or "selenophene-based material", as used herein, refers to a molecule in which at least a selenophene or a selenophene derivative is present in the molecular structure.

The term "absorption in the visible wavelength range" or "molecule exhibiting absorption in the visible wavelength range", as used herein, is meant to refer to a molecule/dye that is able to absorb light in only one or several parts of the entire range indicated or over the total range. For example, a molecule may only absorb in the range of from 500-700 nm, whereas another molecule may absorb in the range of from 400-700 nm or 500-600 nm, whereas a third molecule may absorb over the range of from 400-500 nm (or the above described sub-ranges of preferably 400 nm to 500 nm, or 500 nm to 600 nm, or 600 nm to 700 nm). All these scenarios are meant to be encompassed by such wording.

The term "narrow absorption band", as used herein, is meant to refer to/means that the width of the absorption band at 50% intensity is 200 nm, more preferably 150 nm, more preferably 100 nm.

The term "transparent" or "transparent material", as used herein, refers to a material having an extinction coefficient of less than about 60,000 $M^{-1}$ $cm^{-1}$ in the visible wavelength range in the region of about 450 to about 700 nm and to an extinction coefficient of less than about 100,000 $M^{-1}cm^{-1}$ in the visible wavelength range in the region of about 400 to about 450 nm.

It also refers to a material with an absorption coefficient (in single material film) of less than 70,000 $cm^{-1}$ for wavelengths longer than 450 nm or less than 60,000 $cm^{-1}$ for wave lengths longer than 500 nm.

The term "colored" or "colored material", as used herein, refers to a material having an absorption coefficient of more than about 60,000 $cm^{-1}$ in the visible wavelength range in the region from about 400 nm to about 700 nm (with maxima anywhere in this region or absorbing everywhere in this region).

In accordance with the present disclosure, the term "electrode" refers to an electrical lead to apply voltage. An electrode may be "interdigitated", meaning that it has a comb-like shape with two combs lying opposite each other and the respective figures of the combs engaging with each other. Alternatively, an electrode may be a non-interdigitated. An electrode may be transparent or non-transparent. A transparent electrode may, for example, be formed from indium tin oxide (ITO) or from fluorinated tin oxide (FTO). A non-transparent electrode may be reflective and may, for example, be formed from silver (Ag) or gold (Au).

The requirements of a photoelectric conversion layer to be used in image sensors are demanding and can be summarised as followed:
  (i) narrow absorption band of at least one active material;
  (ii) high extinction coefficient, $\varepsilon > 10^4$ Lmol$^{-1}$cm$^{-1}$—correspondingly high absorption coefficient of at least one active material;
  (iii) heat resistivity;
  (iv) high photoelectric conversion efficiency (EQE);
  (v) high-speed responsivity (high response speed)/high charge carrier mobility;
  (vi) low dark-current in device;
  (vii) thin film by thermal vapour deposition (Tvp<Tdec).

The present inventors have found—for the use as active materials for the organic photoconversion unit—material of specific structure which show no or very low absorption in the visible range (400 to 650 nm), belonging to the following different families:
  Thiophene-based materials;
  Selenophene-based materials; and
  dimers thereof.

Said materials are used in a bulk heterojunction (mixed p-n layer) or PN heterojunction (formed between a p layer and n layer) or PiN junction (p layer—mixed layer as p-n bulk heterojunction—n-layer) in the photoelectric conversion material layer together with a material that absorbs in the visible range.

The materials of the present disclosure can be used as active materials for the organic photoconversion unit.

The organic photoconversion unit can be used in combination with a Si based photoelectrical conversion unit where different layer absorbe different colour (BGR) in a hybrid Silicon-organic image sensor or can be used without Si based photoelectrical conversion unit. In this case, the organic photoconversion unit having the capability of absorbing different colour (BGR).

Figure 2:
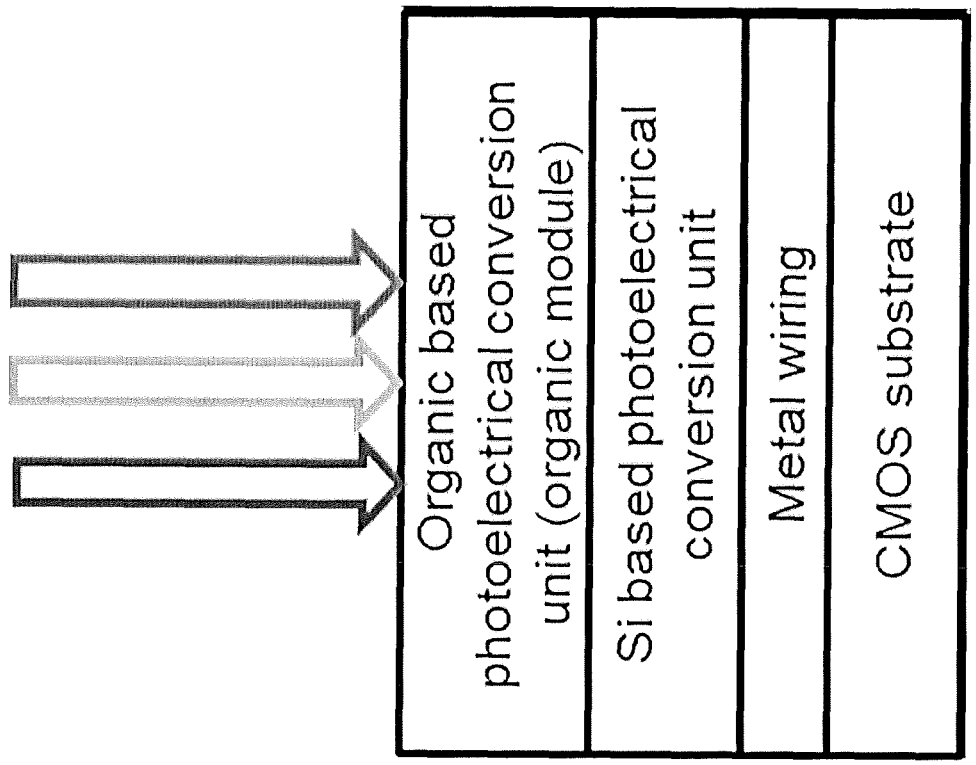
FIG. 2 shows a schematic representation of the hybrid silicon-organic image sensor.
Figure 3:
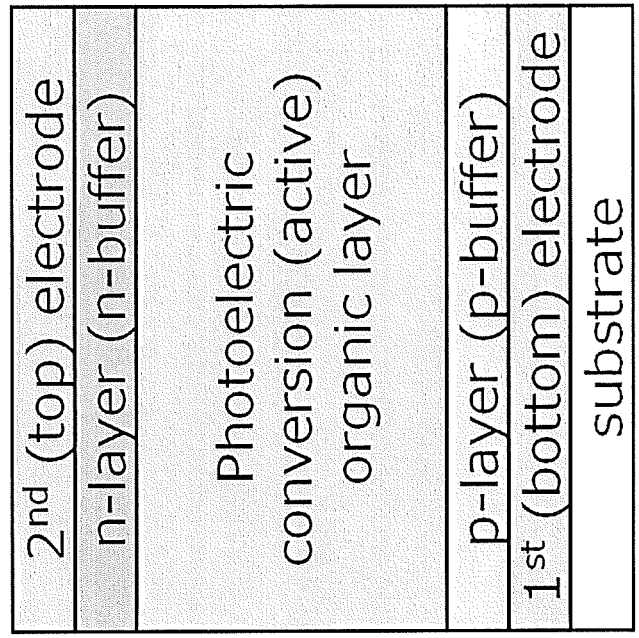
FIG. 3 shows a schematic representation of the organic based photoelectrical conversion unit with different layers.

The general structure of the resulting hybrid image sensor device as well as the details of the organic based photoelectrical conversion unit are schematic represented in the FIGS. 2 and 3.

The present inventors have found a transparent P material (transparent=absorption coefficient of less than about 70,000 M$^{-1}$ cm$^{-1}$ (in single material film) in the region of about 450 to about 700 nm and which in devices with P:N (generally P:N1:N2) heterojunctions can:
  dissociate efficiently the excitons created on the colored (colored=absorption coefficient of more than about 60,000 cm$^{-1}$ in the visible wavelength range in the region from about 400 nm to about 700 nm (with maxima anywhere in this region or absorbing everywhere in this region)) N (or the mixture of colored N materials) or of another colored P (or mixture of colored P and N materials) via the process of HOMO dissociation—donating electron into the HOMO of the excited colored material (the P material(s) or the N material(s) absorbing photons) or of accepting a hole from any of them (from the other P or from any of the N materials.

It might further be capable to transport the holes.

Figure 4:
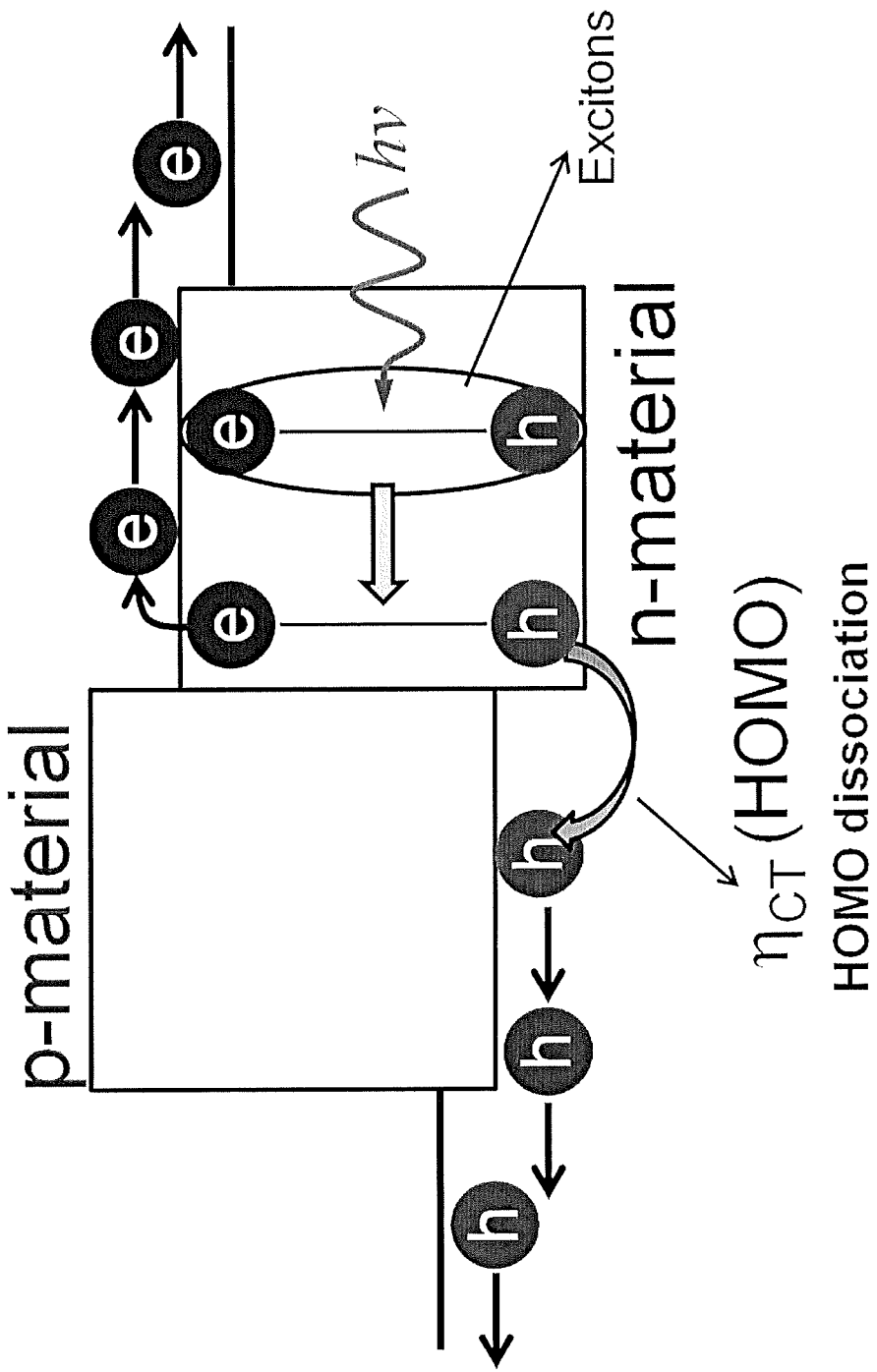
FIG. 4 describes the HOMO dissociation process in case of transparent p and colored n (P:N).

For example, in a P:N example the P material is transparent and the N material the colored one (as e.g. shown in FIG. 4). In an embodiment, where P:N1:N2 is used, one of the N materials could be colored or one (as in FIG. 5), or both of them could be colored. In one embodiment, where P1:P2:N is used, P2 can be transparent or colored, and N could be transparent or colored.

Figure 5:
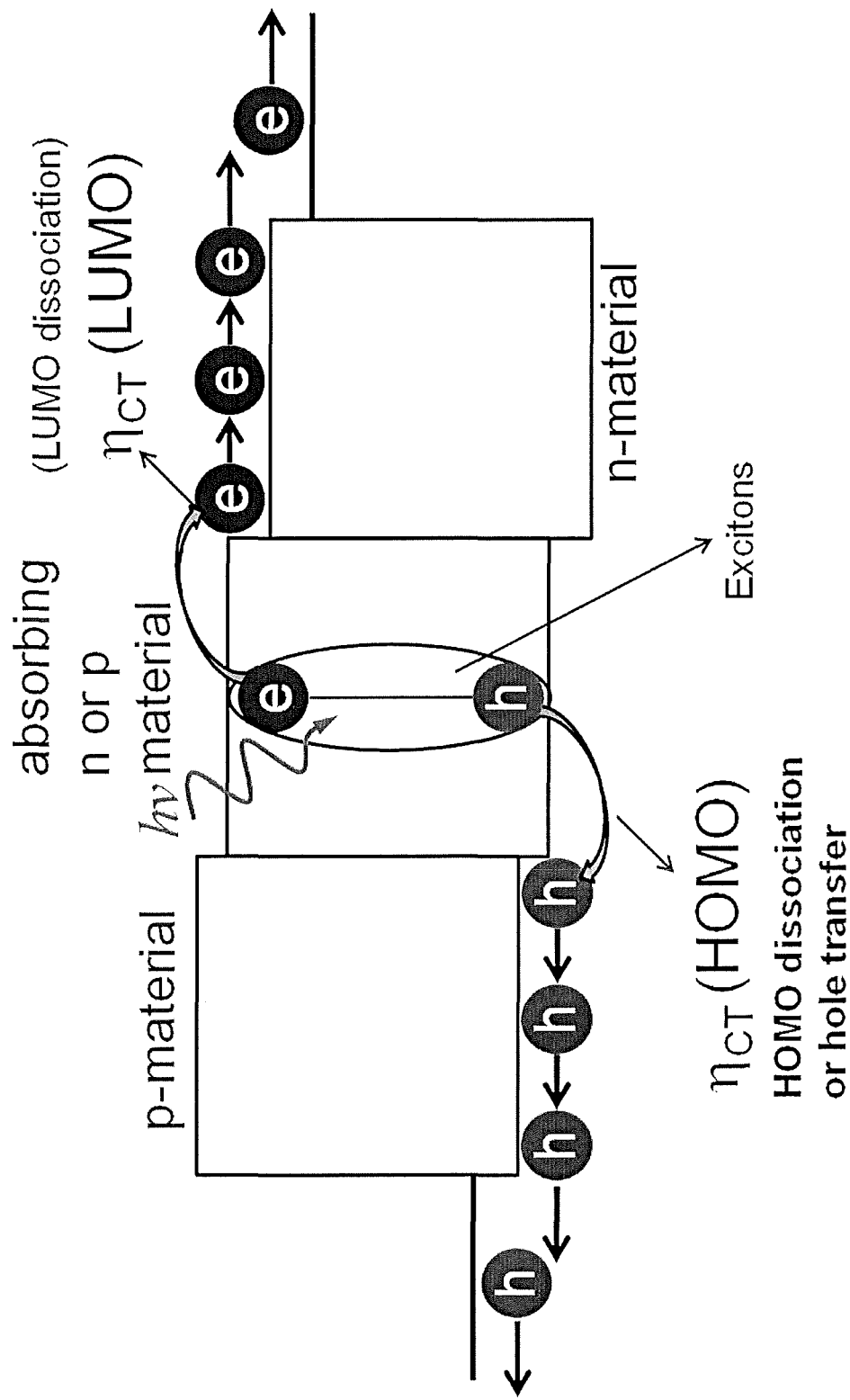
FIG. 5 shows the HOMO and LUMO dissociation process in case of transparent p and colored n or colored p together with transparent n or colored n—the embodiments P:N1:N2 or P1:P2:N.

Dissociation/charge transfer efficiency ($r_1$CT) general description:
$\eta$CT has $\eta$CT(HOMO) and $\eta$CT(LUMO) parts
In FIG. 4 (as example)
  The transparent p-material is dissociating the absorbing n-material via $\eta$CT(HOMO) and it has to be high in order to ensure efficient charge generation.
In FIG. 5 (as example)
  The transparent p-material is dissociating the absorbing n-material or the absorbing n-material via $\eta$CT (HOMO) or it is accepting a hole from it.
  In this embodiment (P1:P2:N or P:N1:N2) one or two materials can be coloured. One p-material is transparent.

The main advantages of the transparent p materials of the present disclosure, in particular for the application in photoelectrical conversion layers and devices, are as follows:
  1. The possibility to adjust the absorption spectrum of the active device via adjusting the absorption spectrum of only one active component. This will be the spectrum of the partner material—the n partner material or the p2 partner material absorption or the n1 or n2 when using ternary systems p1:p2:N or p:n1:n2.
  2. Possibility for tuning the electron mobility only in transparent n materials and the hole mobility only of transparent p materials.
  3. HOMO or LUMO level tuning (together with ensuring large band gap for high transparency in the visible range).
  4. Possibility for optimising one exciton dissociation/charge generation efficiency only—either through the LUMO (for transparent n) or through the HOMO (for transparent p materials (see FIGS. 4 and 5).

The main advantages of the new p materials without absorption or with a very low absorption in the visible wavelengths (400-700 nm) as active materials for the application in photoelectrical conversion layers are as follows:
  excellent photostability—especially due to UV absorption only;
  possibility for tuning of the absorbtion spectrum of the device via the absorption of the partner (the other) active component—i.e. the absorption spectrum of p material in case of transparent n and the absorption of n material in case of transparent p;
  easy alteration of HOMO and LUMO energy levels;
  high thermal stability (300 to 500° C. depending on substituents but at least 300° C.);
  high electrons (for n) and/or holes (for p) mobilities—especially the independent tuning of mobilities—e.g. only high electrones mobility for transparent n material is needed;
  high exciton dissociation ability—to allow for photoconversion devices with high EQE;

high charge generation efficiencies of the devices—high charge transfer efficiency and charge separation efficiency;

especially independent tuning of the charge generation efficiency—through the LUMO (for transparent n) and through the HOMO (for transparent p);

can be used as n-buffer or p-buffer layers correspondingly—allows for further device optimisation via possible tuning of morphology of the active layer and/or energy level alignment through the device.

The main advantages of the transparent thiophene based molecules for the application in photoelectrical conversion layers are as follows:

exhibit good photo- and thermal stability (until 300° C.);
easy alteration of HOMO and LUMO energies is possible;
very low extinction coefficients in the visible range;
high hole mobilities;
give possibility for highly efficient HOMO based dissociation of the excitons formed in the absorbing n partner;
in case of dimers:
  3D structure and HOMO degeneration which increases dissociation efficiency (HOMO dissociation);
  higher hole mobilities.

The energy levels and the morphology in thin film are tunable by the type of substituents R and $R_1$ as well as the heteroatoms in the core structure. This makes the thiophene based molecules very versatile molecules to be used in the organic photoelectric conversion layer in combination with a material that absorbs in the visible range.

According to the present disclosure, when one of the active materials is transparent this offers the following possibilities for respective devices and so on:

Tuning overall absorption spectrum via tuning absorption of one active material only;
Tuning of exciton diffusion efficiencies of the partner (absorbing) material only;
Tuning of charge generation efficiencies through HOMO or LUMO independently;
Tuning of only electron (for transparent n) or only hole (transparent p) mobility;
Generally: decoupling of absorption properties in the visible range from electron/hole transfer and transport properties.

EXAMPLES

Example 1: BDT3

Figure 7A:
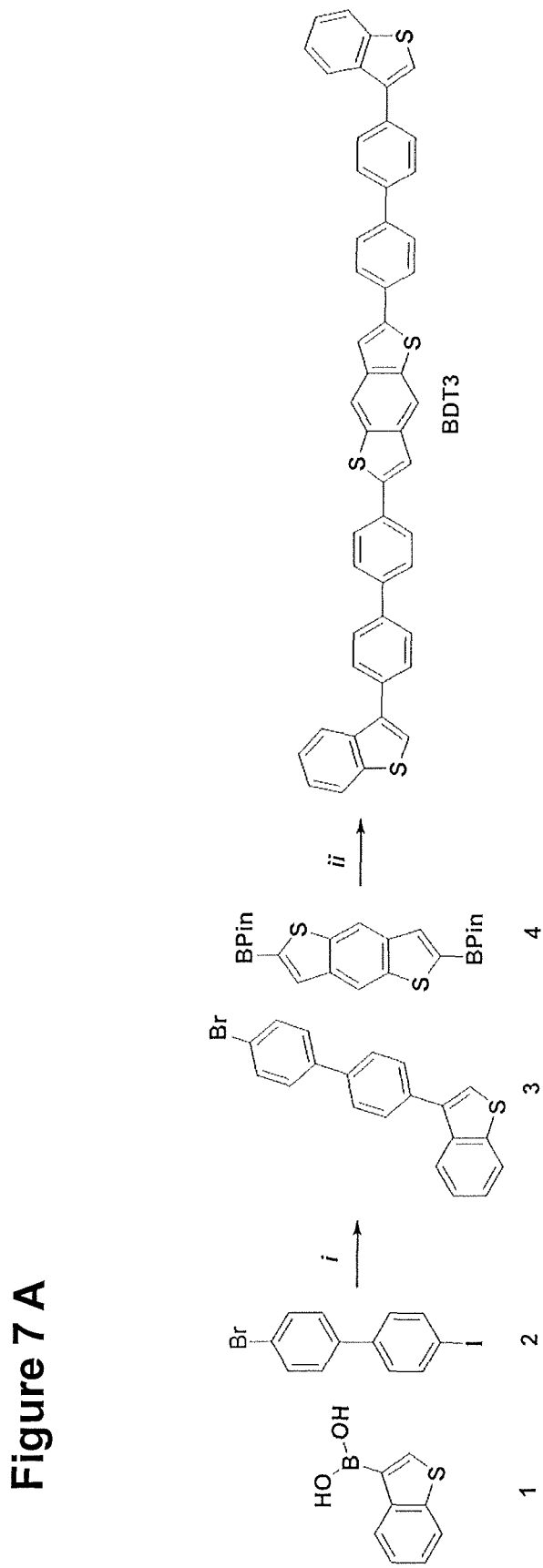
FIG. 7A shows the synthetic route for the preparation of a thiophen-based P material, called BDT3, according to Example 1.

In the scheme below, the synthetic route for a BDT3 is reported (see also FIG. 7A):

Scheme 1: Synthesis of BDT3

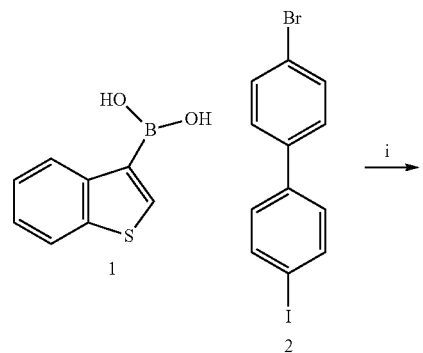

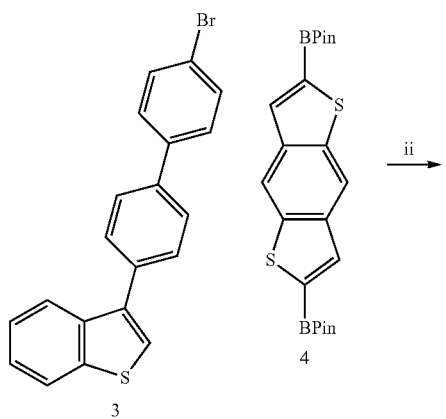

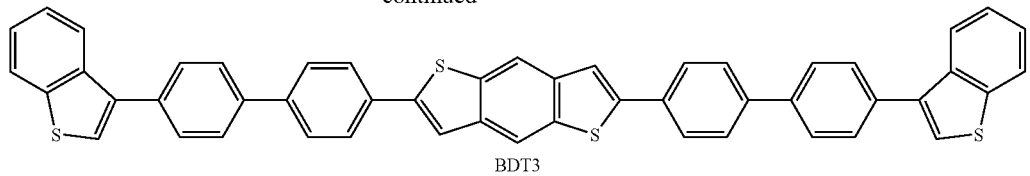

BDT3 i: Pd(OAc)₂, SPhos, K₃PO₄, Dioxane, H₂O, RT, 16 h;
ii: Pd(OAc)₂, SPhos, K₃PO₄, Dioxane, H₂O, 105° C., 20 h.

3-(4-Bromobiphenyl)-benzothiophene (3) was prepared by a chemoselective SUZUKI-type cross coupling of the benzothiophene-3-boronic acid (1) and 4-Iodo-4'-bromo-biphenyl (2).

Using the SPhos catalyst system in 1,4-Dioxane at room temperature (i) gave the target compound in moderate yields (64%). The same catalyst was used for the synthesis of BDT3 by coupling two equivalents (3) to the BDT-diboronic ester (4), the reaction was run at 105° C. for 20 h (ii).

The structure has been confirmed by MALDI-TOF Mass Spectrometry (see FIG. 7 B, i)).

The BDT3 has excellent thermal stability ($T_{decomp}$>480° C.), and according to DSC, undergoes phase transition at 451° C.

and 459° C. in the heating cycle and at 455° C. and 421° C. in the cooling cycle (see FIG. 7 B, ii)).

Figure 7:
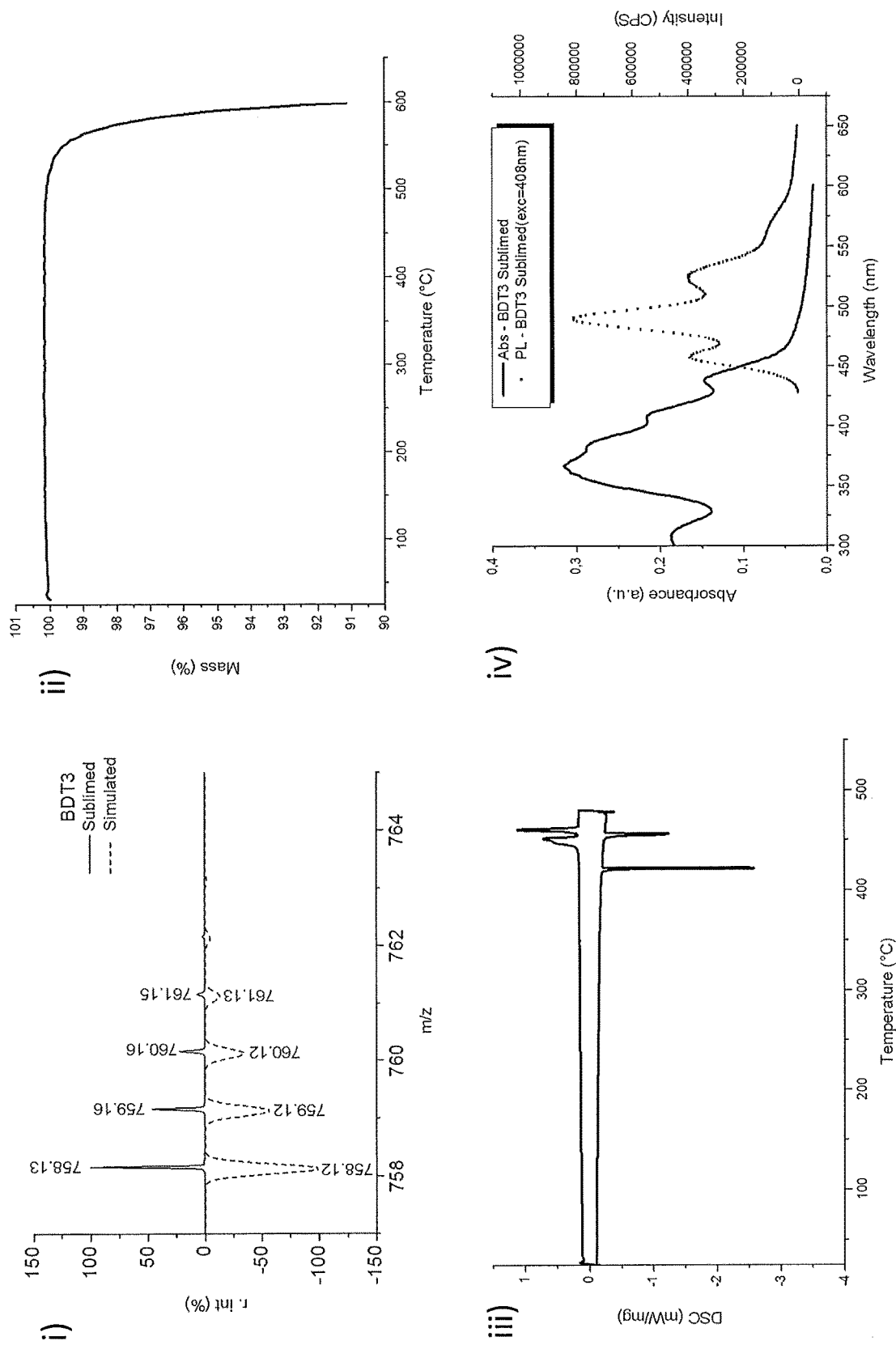
FIG. 7 B shows the MALDI-TOF Mass spectrum of BDT3 (see i), plain line: Sublimed BDT3; dotted lines, simulated mass spectrum of BDT3), TG (see ii)) and DSC (see iii)) of sublimed BDT3 and the UV-Vis absorption and PL spectra of BDT3 (see iv)).

UV-Vis absorption and PL spectra of BDT3 were recorded from thermally evaporated thin films and are given in FIG. 7 B, iii) and iv). The absorption spectrum (sublimed BDT3) has its maximum at $\lambda_{abs}$, max=367 nm as well as additional transitions at around $\lambda$=384 nm, $\lambda$=407 nm and $\lambda$=437 nm. The PL spectra shows three sharp emission maxima at $\lambda$PL, max=490 nm, 458 nm, and 525 nm Example 2: BTBT14

Figure 8:
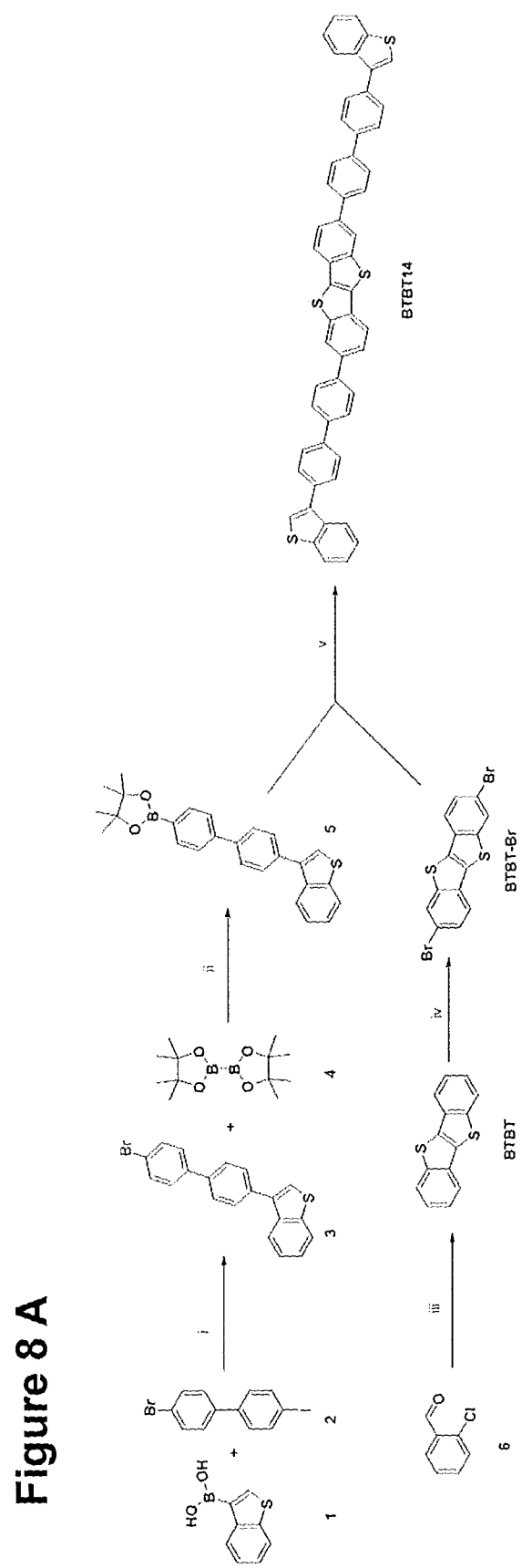
FIG. 8 B shows the MALDI-TOF mass spectrum of BTBT14 (see i), plain line: sublimed BTBT14; dotted lines, simulated mass spectrum of BTBT14), TG (see ii)) and DSC (see iii)) of sublimed BTBT14 and the UV-Vis absorption and PL spectra of BTBT14 (see iv)).
Figure 8:
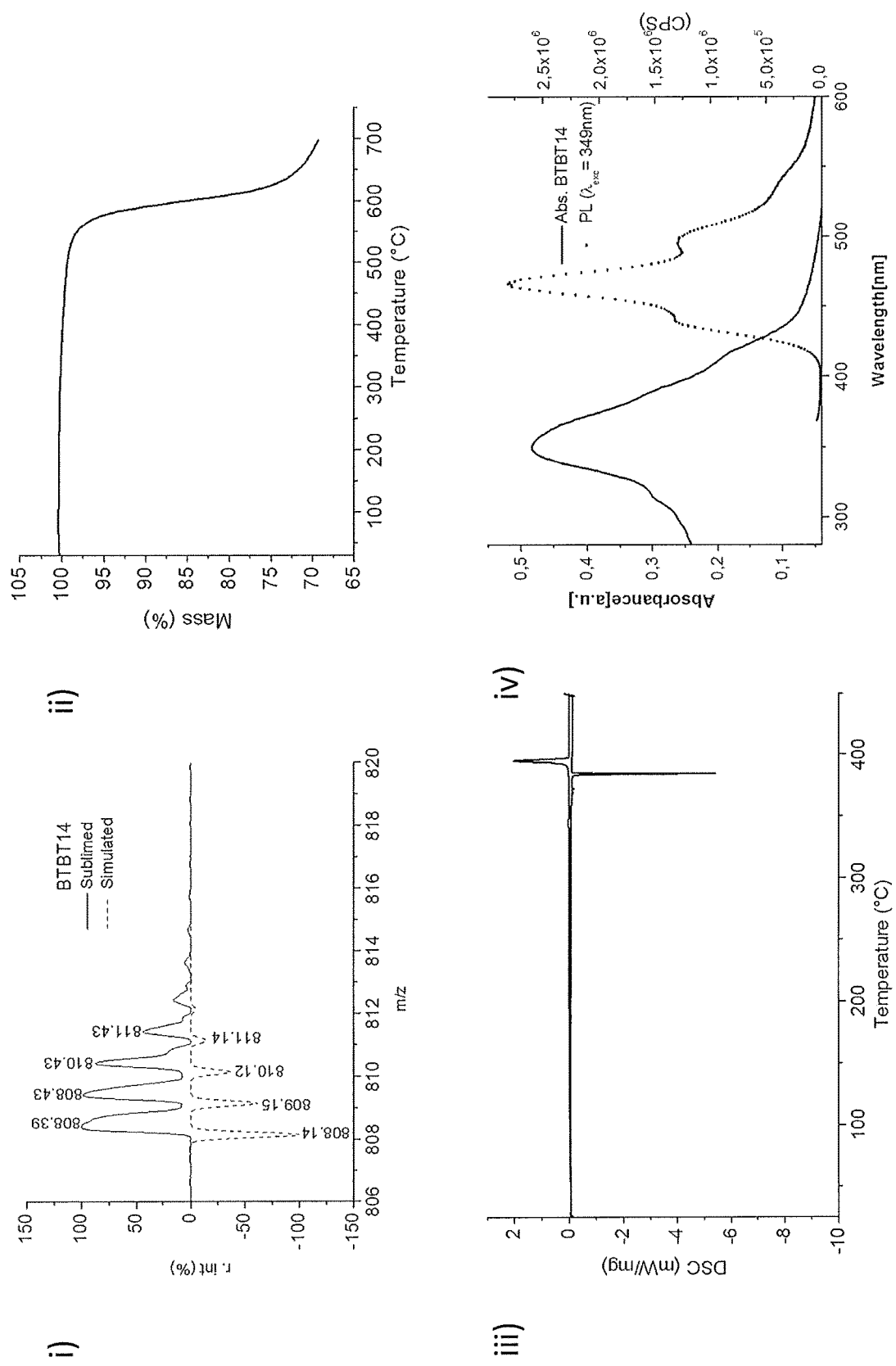

In the scheme 2 below, the synthetic route for a BTBT14 is reported (see also FIG. 8A):

Scheme 2: Synthesis of BTBT14

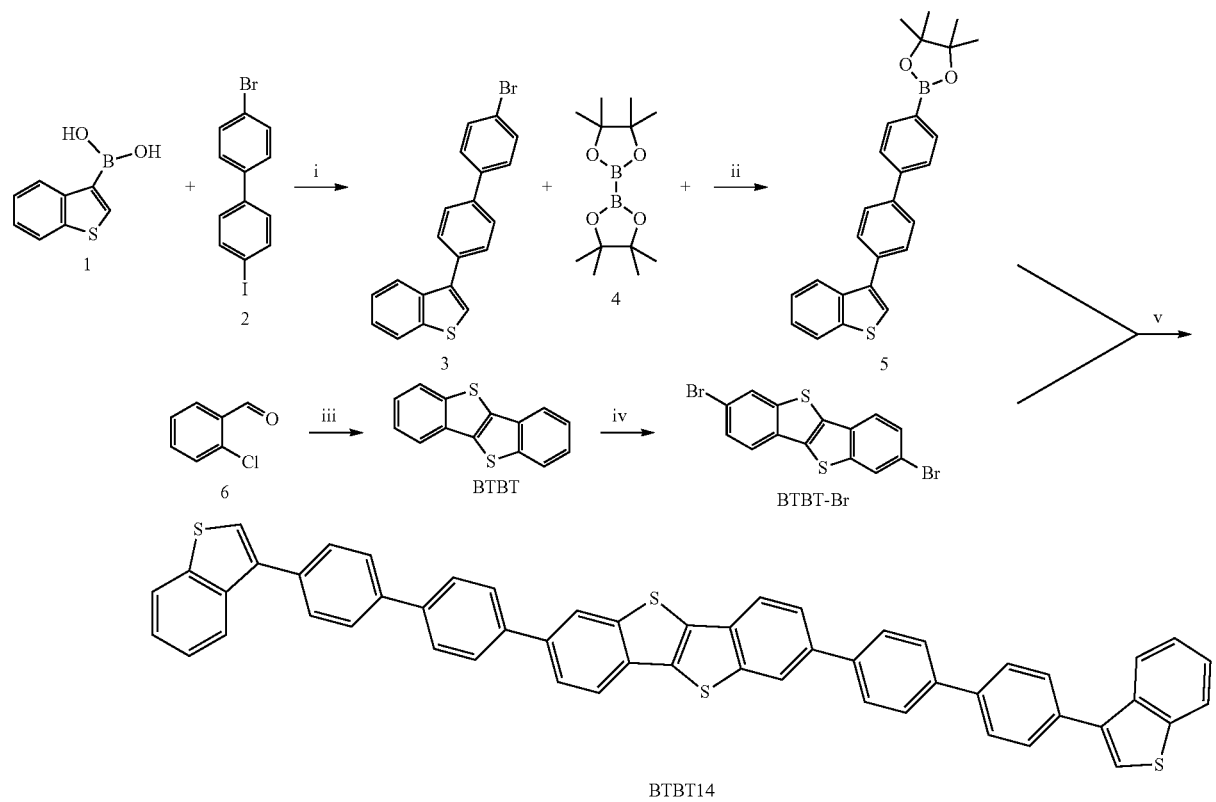

i: Pd(OAc)₂, SPhos, K₃PO₄, Dioxane, H₂O, RT, 16 h;
ii: Pd(dppf)Cl₂, KOAc, Dioxane, 100° C., 16 h;
iii: NaSH/aq. NH₄Cl, NMP, 80° C. to 180° C.;
iv: Br₂, DCM, 0° C. to RT;
v: Pd(OAc)₂, SPhos, K₃PO₄, Dioxane, H₂O, 90° C., 16 h.

3-(4-Bromobiphenyl)-benzothiophene (3) was prepared by a chemoselective SUZUKI-type cross coupling of the benzothiophene-3-boronic acid (1) and 4-iodo-4'-bromo-biphenyl (2).
Using the SPhos catalyst system in 1,4-Dioxane at room temperature (i) gave the target compound in moderate yields (64%). The borilation of (3) was done using bis(pinacolato)diboron in the 1,1'-bis(diphenylphosphino)-ferrocene dichloropalladium catalyst system in 1,4-Dioxane at 100° C. The BTBT core building block was received by reaction of chlorobenzaldehyde with sodium hydrogensulfide hydrate at high temperature in NMP (iii). Bromination of BTBT was carried out using elemental bromine in DCM (iv). The same catalyst used in (i) was used for the synthesis of BTBT14 by coupling two equivalents 5 to the BTBT-Br, the reaction was run at 90° C. for 16 h (v).
The structure has been confirmed by MALDI-TOF Mass Spectrometry (see FIG. 8 B, i)).
The BTBT14 has excellent thermal stability ($T_{decomp}$>500° C.), and according to DSC, undergoes phase transition at 395° C. in the heating cycle and at 384° C. in the cooling cycle (see FIG. 8 B, ii)).
UV-Vis absorption and PL spectra of BTBT14 were recorded from thermally evaporated thin films and are given in FIG. 8 B, iii) and iv). The absorption spectrum (sublimed BTBT14) has its maximum at $\lambda_{abs}$, max=349 nm as well as a shoulder at 414 nm and the absorption edge around 441 nm. The PL spectra shows three emission maxima at λPL, max=466 nm, 439 nm and 496 nm with an additional shoulder at 539 nm.

Example 3: BTBT2

Figure 9:
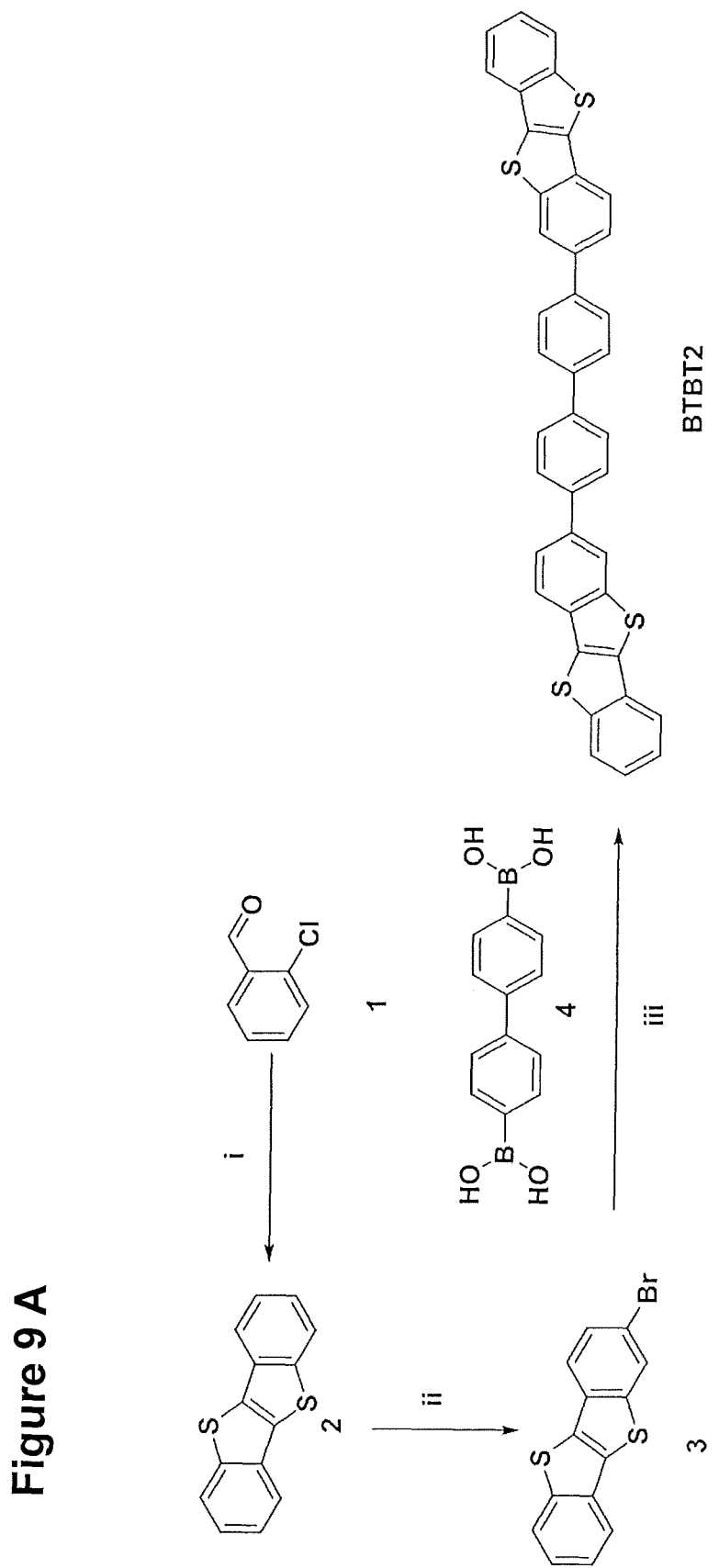
FIG. 9 A shows the synthetic route for the preparation of a thiophene-based P material, called BTBT2, according to Example 3.
Figure 9:
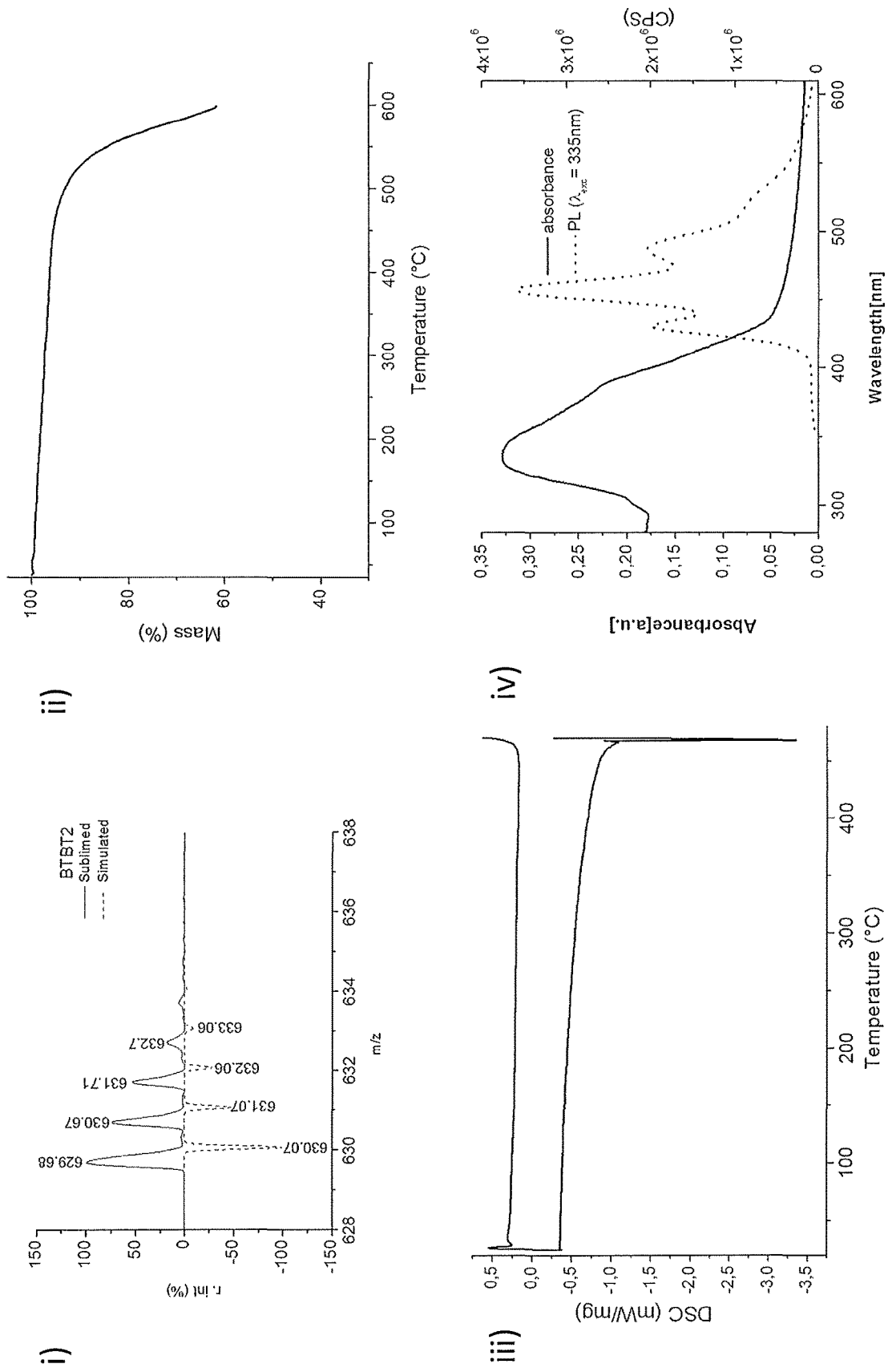

In the scheme 3 below, the synthetic route for a BTBT2 is reported (see also FIG. 9A):

Scheme 3: Synthesis of BTBT2

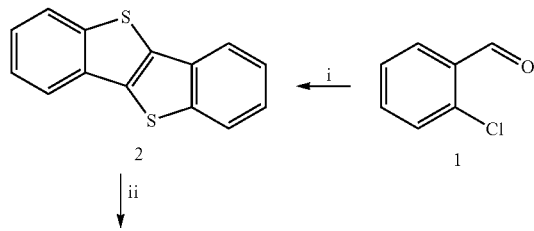

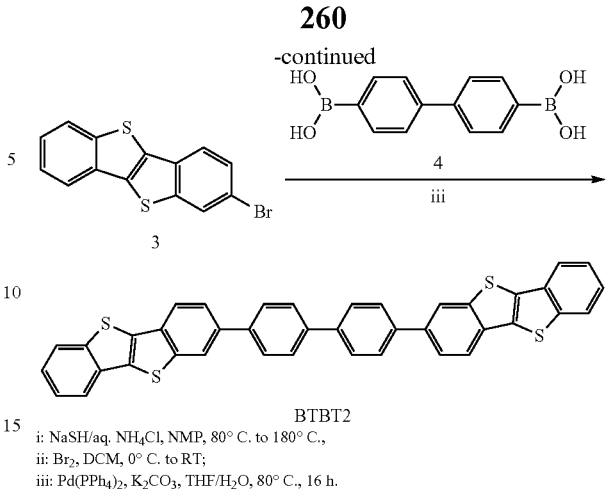

i: NaSH/aq. NH$_4$Cl, NMP, 80° C. to 180° C.,
ii: Br$_2$, DCM, 0° C. to RT;
iii: Pd(PPh$_4$)$_2$, K$_2$CO$_3$, THF/H$_2$O, 80° C., 16 h.

The BTBT core building block was received by reaction of chlorobenzaldehyde with sodium hydrogensulfide hydrate at high temperature in NMP. (i). Bromination of BTBT was carried out using elemental bromine in DCM. (ii). The final reaction to obtained BTBT2 was done using a mixture of 2-bromo-[1]benzothieno[3,2-b][1]benzothiophene (3) and 4,4'-biphenyldiboronic acid (4), potassium carbonate and Pd(PPh$_3$)$_4$ in water and at 80° C. overnight under inert atmosphere.
Structure was confirmed by MALDI-TOF Mass Spectrometry (see FIG. 9 B, i)).
The BTBT2 has excellent thermal stability ($T_{decomp}$>460° C.), and according to DSC, do not showed phase transition till at 460° C. in the heating in the cooling cycle (see FIG. 9 B, ii)).
UV-Vis absorption and PL spectra of BTBT2 were recorded from thermally evaporated thin films and are given in FIG. 9 B, iii) and iv). The absorption spectrum (sublimed BTBT2) has its maximum at a $\lambda_{abs}$, max=335 nm as well as a shoulder at 388 nm. The PL spectra shows three emission maxima at λPL,max=430 nm, 456 nm and 487 nm with an additional shoulder at 524 nm.

Example 4: BTBT9

Figure 10:
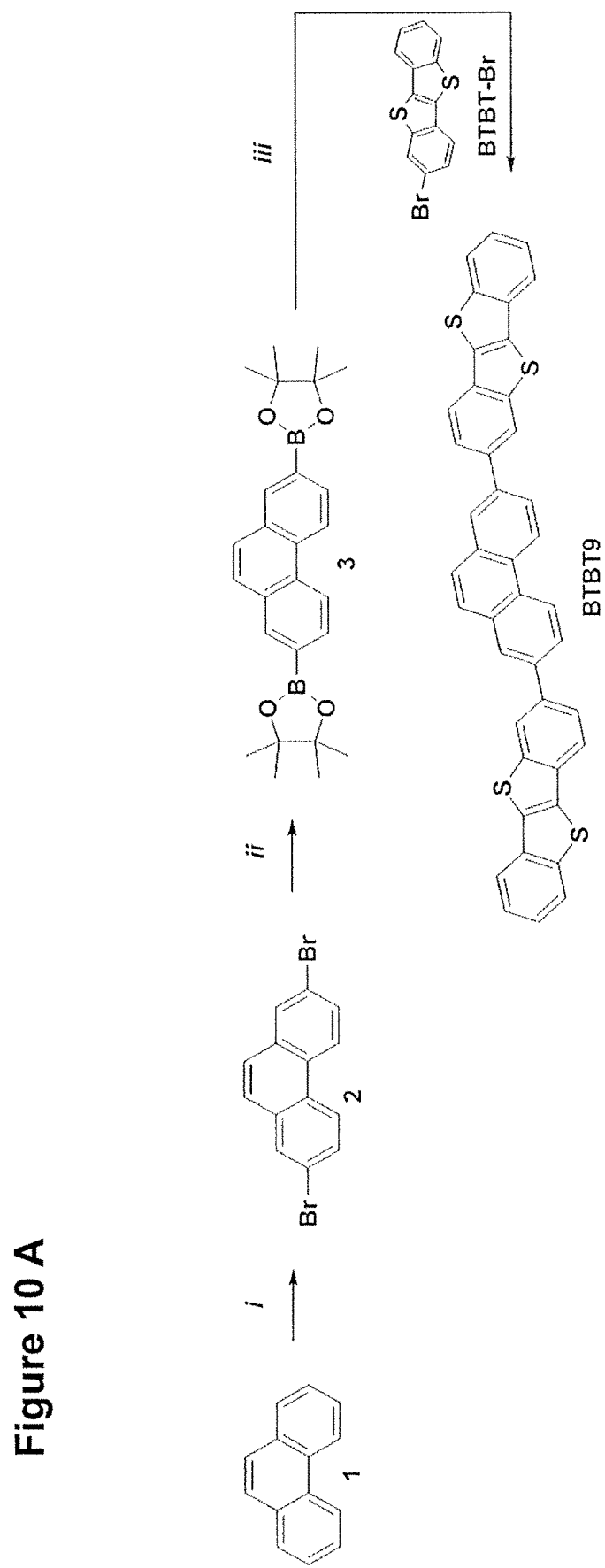
FIG. 10 A shows the synthetic route for the preparation of a thiophene-based P material, called BTBT9, according to Example 4.
Figure 10:
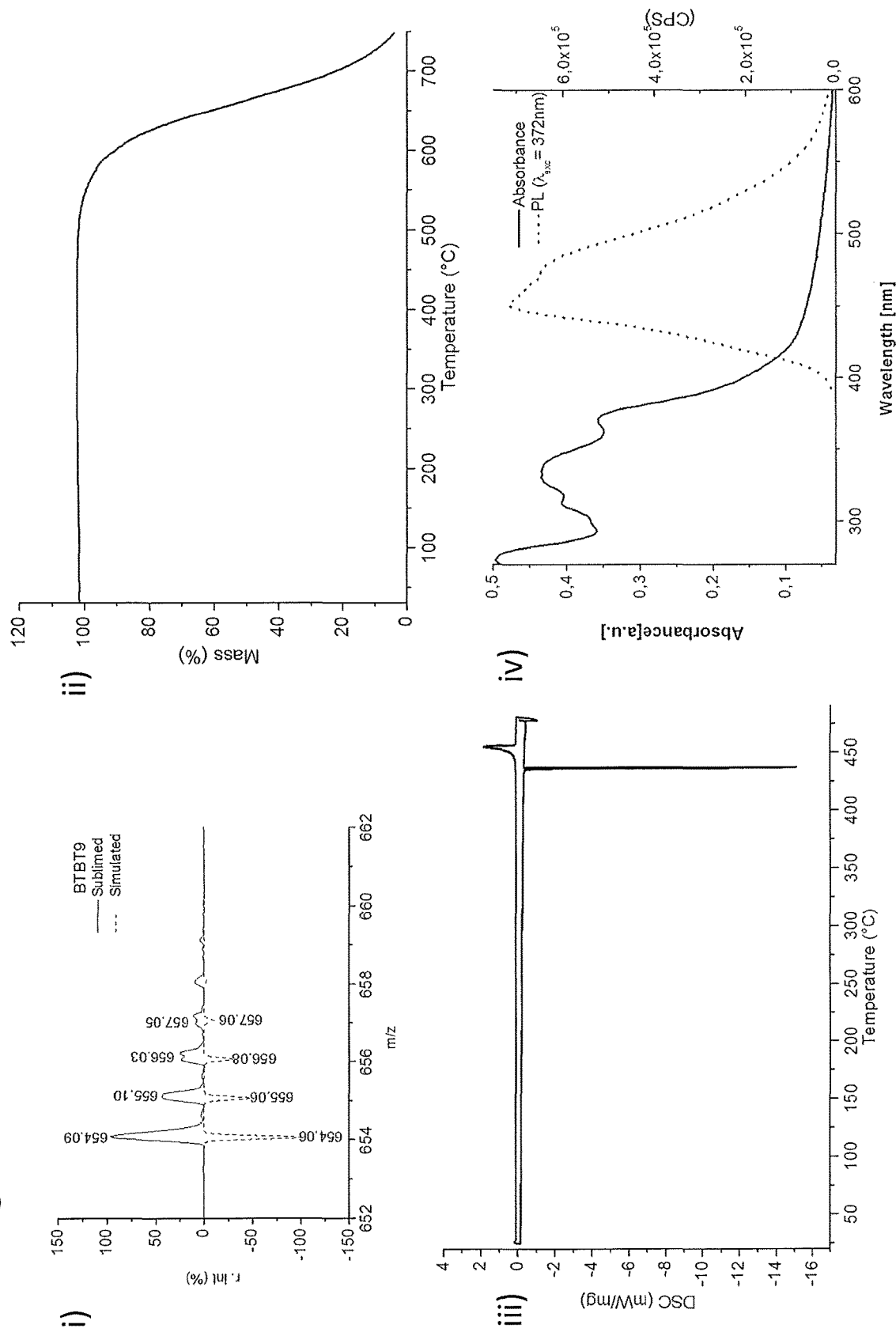

In the scheme 4 below, the synthetic route for a BTBT2 is reported (see also FIG. 10A).

Scheme 4: Synthesis of BTBT9

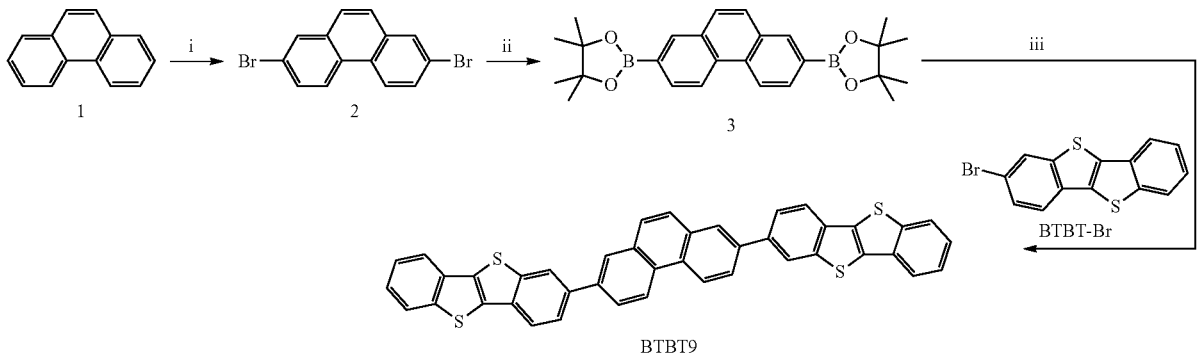

i: Br$_2$, FeCl$_3$, H$_2$O, RT, 16 h.
ii: B$_2$Pin$_2$, PdCl$_2$(DPPF), KOAc, 1,4-Dioxane, 95° C., 2 h.
iii: Pd(PPh$_3$)$_4$, 35%, Na$_2$CO$_3$, 1,4-Dioxane, H$_2$O, 95° C., 20 h.

The BTBT9 material can be obtained in convergent three step synthesis starting from phenthrene (1) that is brominated and then converted in diboronic ester (3) using MIYAURA borylation. In the last step 3 is reacted with 2.2 equivalents of BTBT-Br in a SUZUKI-type cross coupling reaction to give the desired product BTBT9.

Structure was confirmed by MALDI-TOF Mass Spectrometry (see FIG. 10 B, i)).

The BTBT9 has excellent thermal stability ($T_{decomp}$>500° C.), and according to DSC, undergoes phase transition at 454° C. in the heating cycle and at 437° C. in the cooling cycle (FIG. 10 B, ii)).

UV-Vis absorption and PL spectra of BTBT9 were recorded from thermally evaporated thin films and are given in FIG. 0 B, iii) and iv). The maximum is observed at $\lambda_{max}$=332 nm additional transitions are found at 370, 312 and 298 nm. A very intense band is seen at 273 nm. The absorption onset is detected at $\lambda_{Onset}$=409 nm. In the PL spectrum BTBT9 shows a structured emission has its maximum at $\lambda_{max}$ 451 nm with a shoulder at 479 nm.

Example 5: TT1

In the scheme 6 below, the synthetic route for a TT1 is reported (see also FIG. 11A).

using tetrakis(triphenylphosphine)palladium(0) to react two equivalents of 3 with 2,5-bis(trimethylstannyl)thieno[3,2-b]thiophene (4). The reaction was run at 105° C. for 24 h (ii). The structure has been confirmed by MALDI-TOF Mass Spectrometry (see FIG. 11 B, i)).

The TT1 has excellent thermal stability ($T_{decomp}$>490° C.), and according to DSC, undergoes phase transition at 426° C. in the heating cycle and at 407° C. in the cooling cycle (FIG. 11 B, ii) and iii)).

Figure 11:
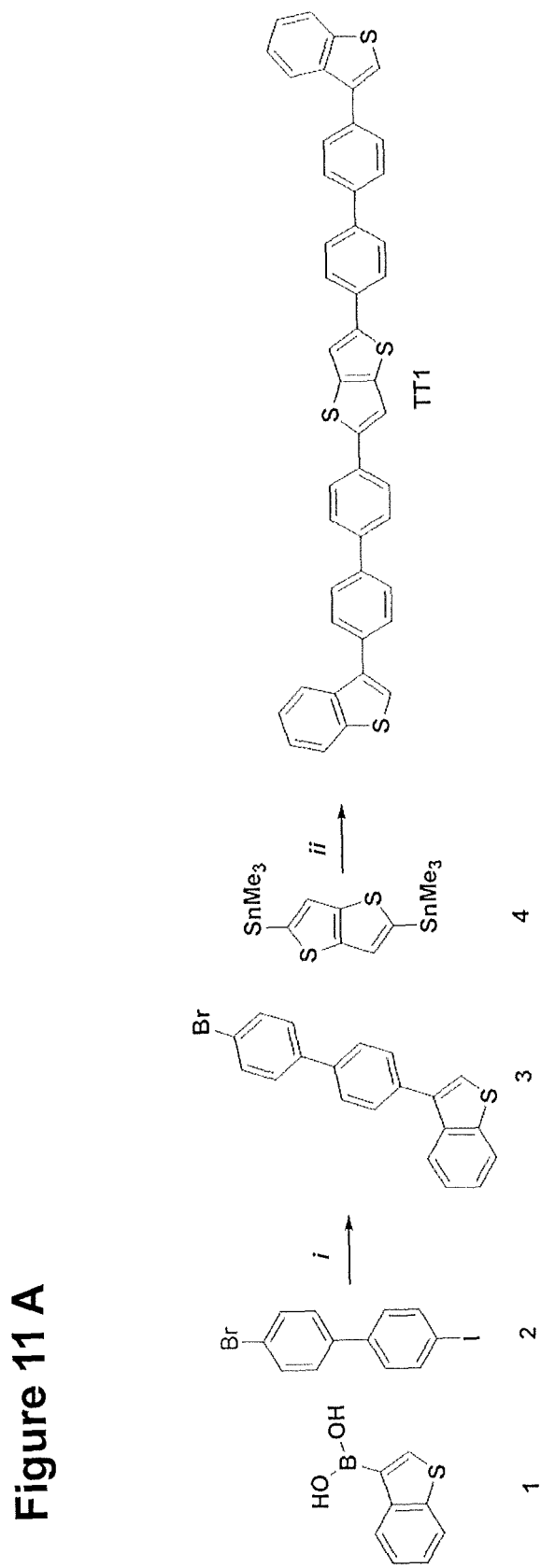
FIG. 11 A shows the synthetic route for the preparation of a thiophene-based P material, called TT1, according to Example 6.
Figure 11:
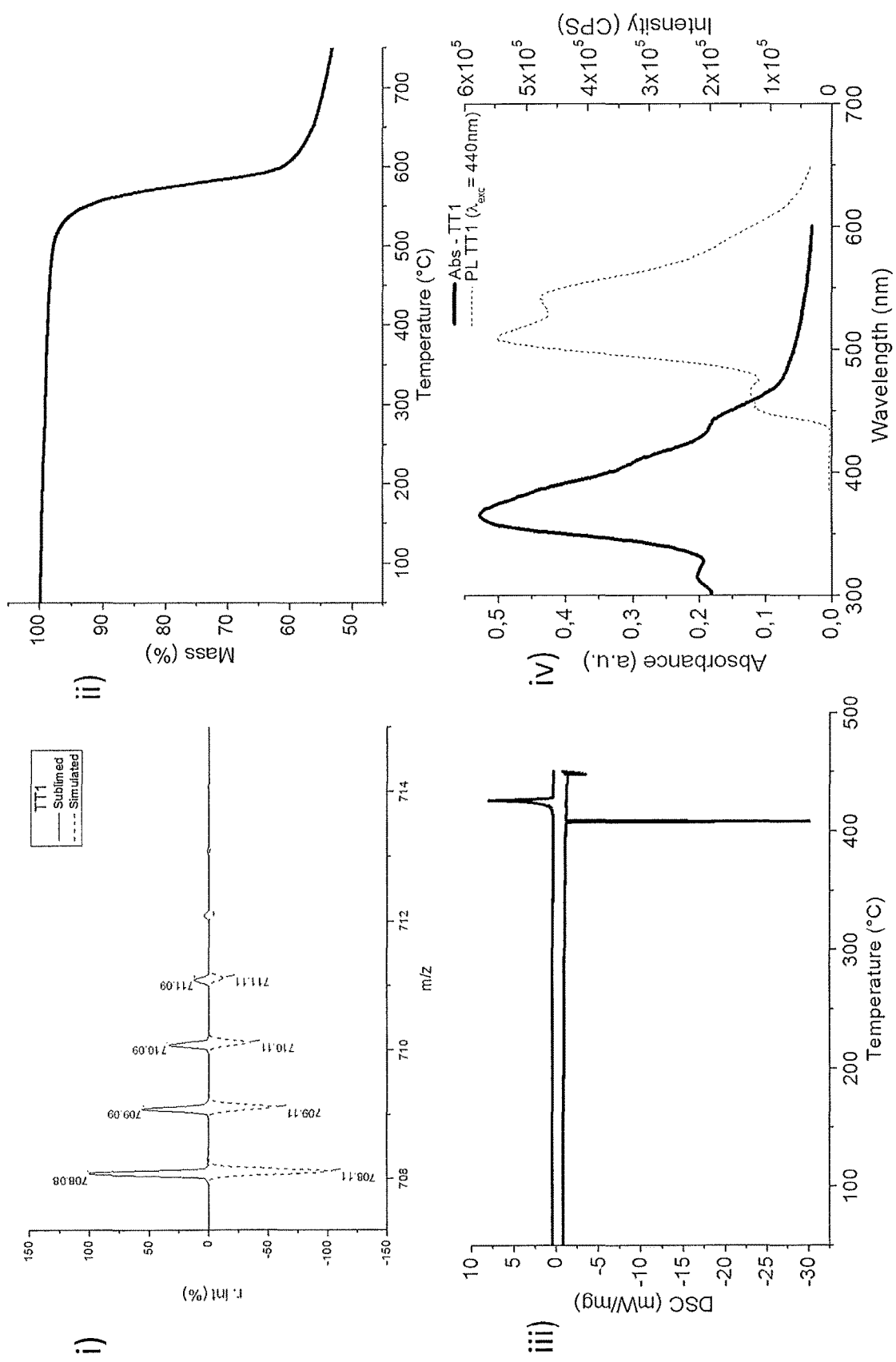
Figure 12:
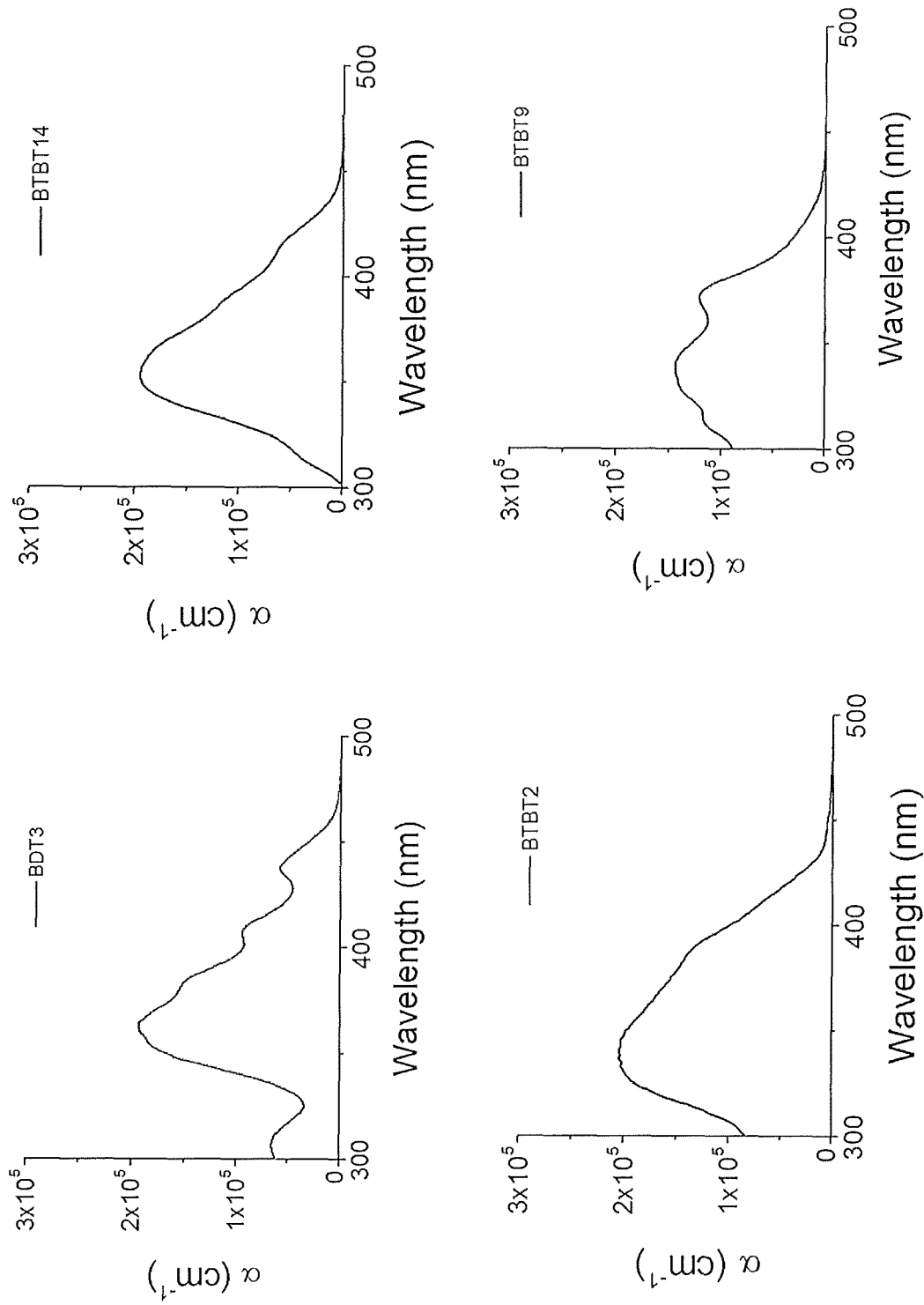
FIG. 12 shows the absorption coefficient for single material films BDT3, BTBT12, BTBT2, BTBT9 (FIG. 12A) and TT1 (FIG. 12 B) on glass.
Figure 12:
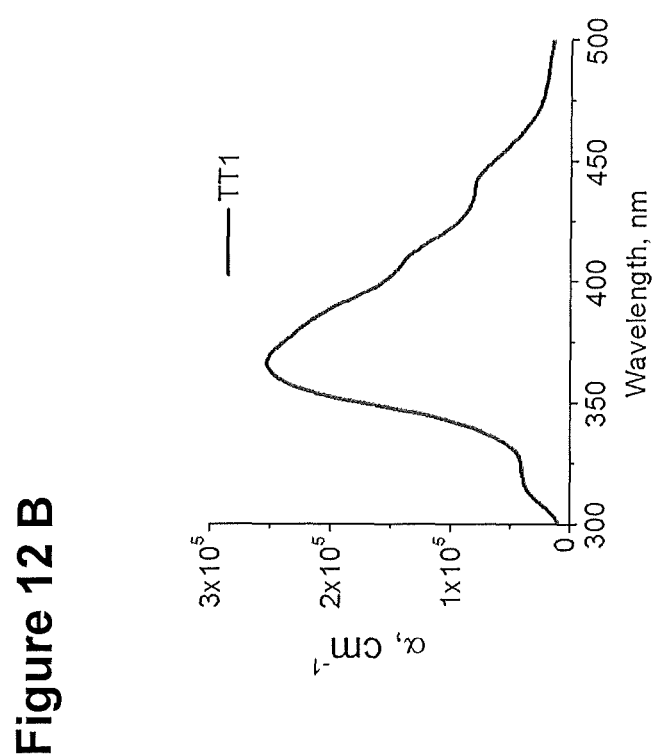

UV-Vis absorption and PL spectra of TT1 were recorded form thermally evaporated thin films and are given in FIG. 11 B iv). The absorption spectrum (sublimed TT1) has its maximum at $\lambda abs,max$=367 nm as well as additional transitions at around $\lambda$=384 nm, $\lambda$=407 nm and $\lambda$=437 nm. The PL spectra shows three sharp emission maxima at $\lambda$ PL,max=490 nm, 458 nm, and 525 nm.

Example 6

The different—material derivates (BDT3, BTBT14, BTBT2, BTBT9 and TT1) were used as transparent p-material in a ternary system containing an hexafluorinate subpthlalocyanine pentafluorinated phenoxy (F6SubPc-OC6F5=F6006F5) and C60 in the following configuration:

Scheme 6: Synthesis of TT1

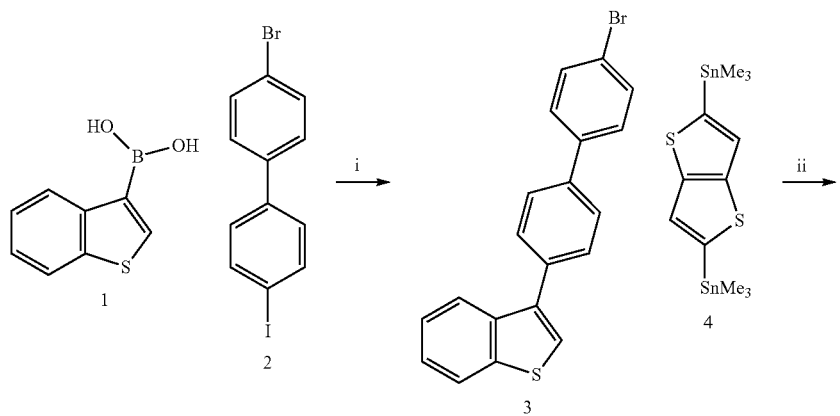

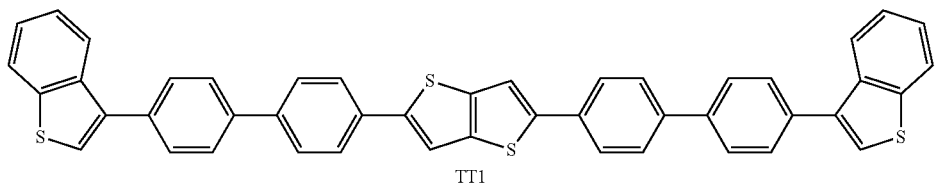
TT1 i: Pd(OAc)₂, SPhos, K₃PO₄, Dioxane, H2O, RT, 16 h;
ii: Pd(PPh3)4, Toluene, 105° C., 24 h.

3-(4-Bromobiphenyl)-benzothiophene (3) was prepared by a chemoselective SUZUKI-type cross coupling of the benzothiophene-3-boronic acid (1) and 4-Iodo-4'-bromo-biphenyl (2).

Using the SPhos catalyst system in 1,4-Dioxane at room temperature (i) gave the target compound in moderate yields (64%). TT1 was prepared by STILLE-type cross coupling ITO/10 nm p-buffer/200 nm p-material+SubPc derivative+C60 (4:4:2) (ca. 200 nm thick)/10 nm n-buffer/100 nm AlSiCuas as shown in FIG. 13.

Figure 13:
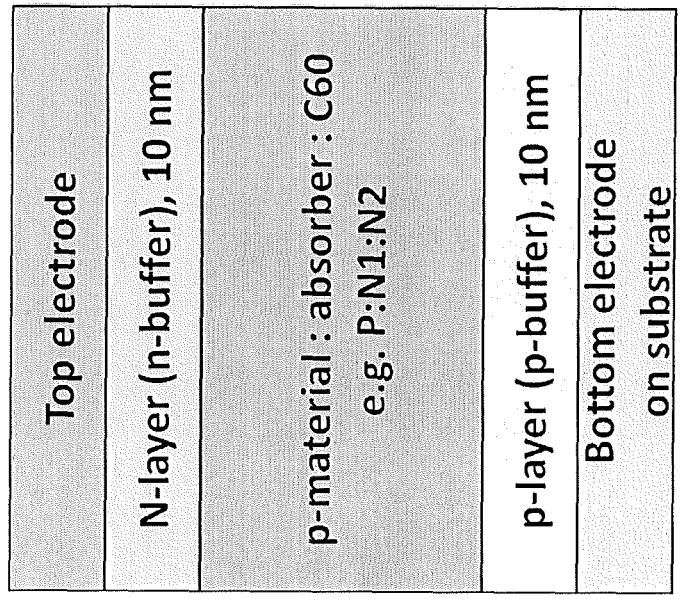
FIG. 13 shows a device structure and structure of the photoelectrical conversion layer (i-layer) according to the disclosure.
Figure 14:
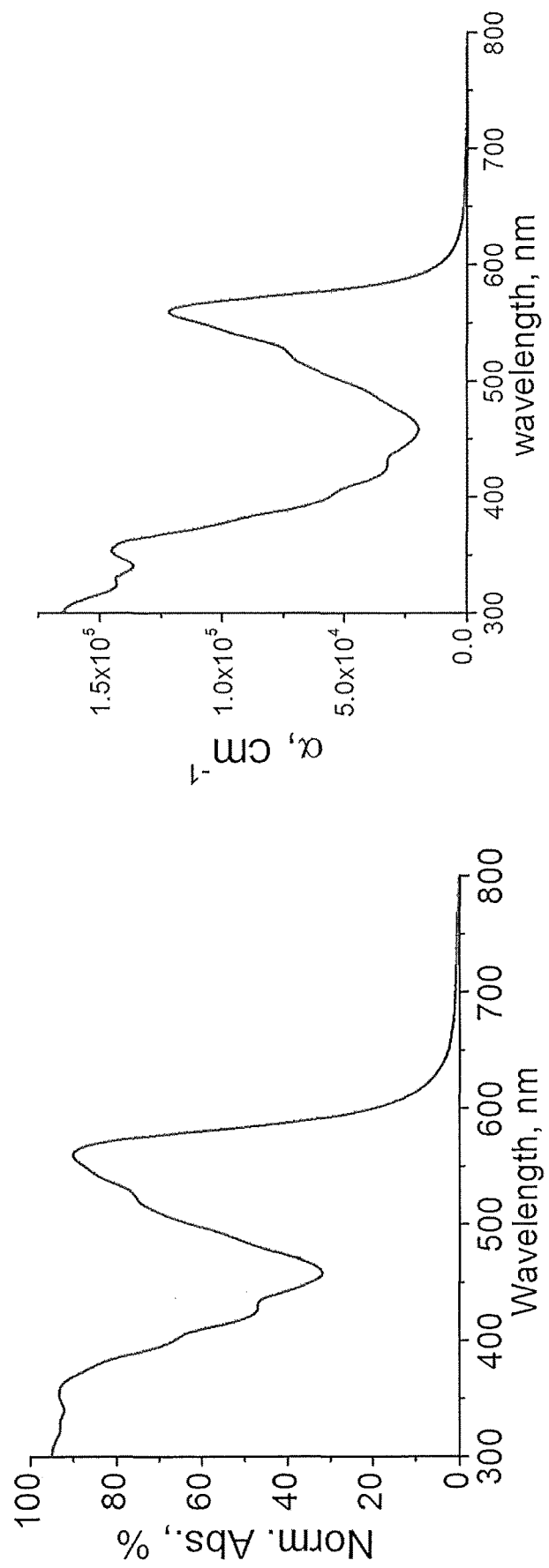
FIG. 14 shows the absorption of BDT3:F6-OC6F5:C60 5 min/160° C. annealed: Left: Normalised absorptance of the i-layer; Right: Absorption coeffiecient of the i-layer.
Figure 15:
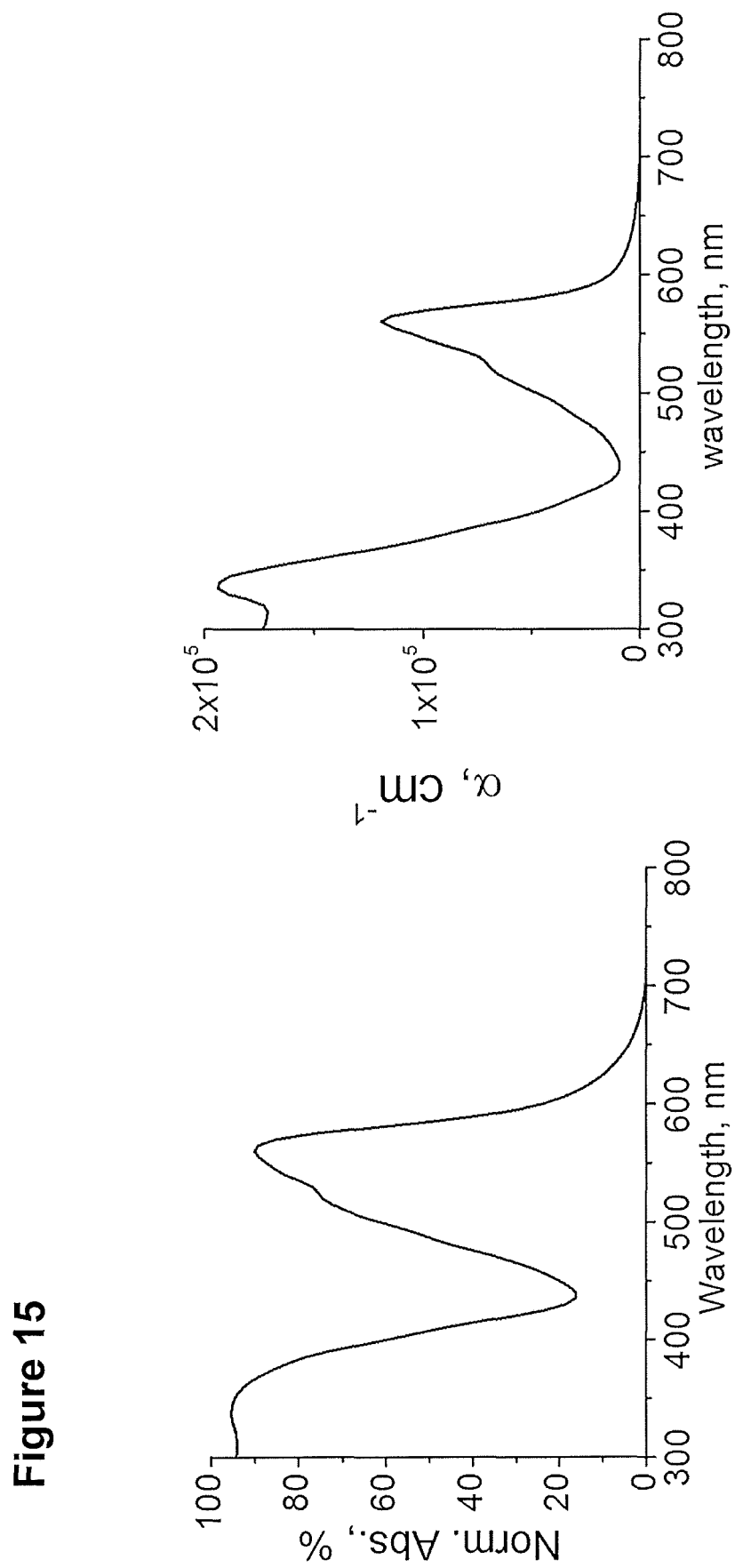
FIG. 15 shows the absorption of BTBT14:F6-OC6F5:C60 5 min/160° C. annealed: Left: Normalised absorptance of the i-layer; Right: Absorption coeffiecient of the i-layer.
Figure 16:
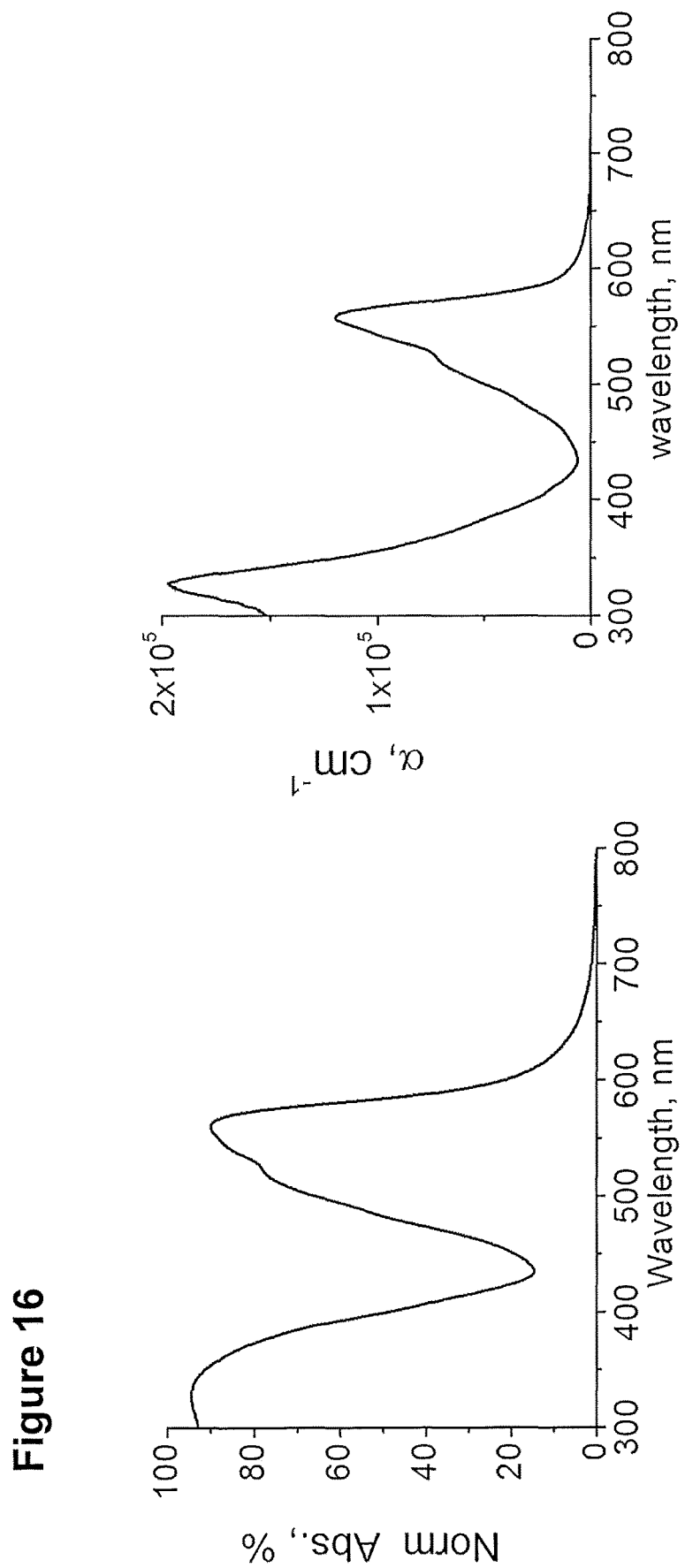
FIG. 16 shows the absorption of BTBT2:F6-OC6F5:C60 5 min/160° C. annealed: Left: Normalised absorptance of the i-layer; Right: Absorption coeffiecient of the i-layer.
Figure 17:
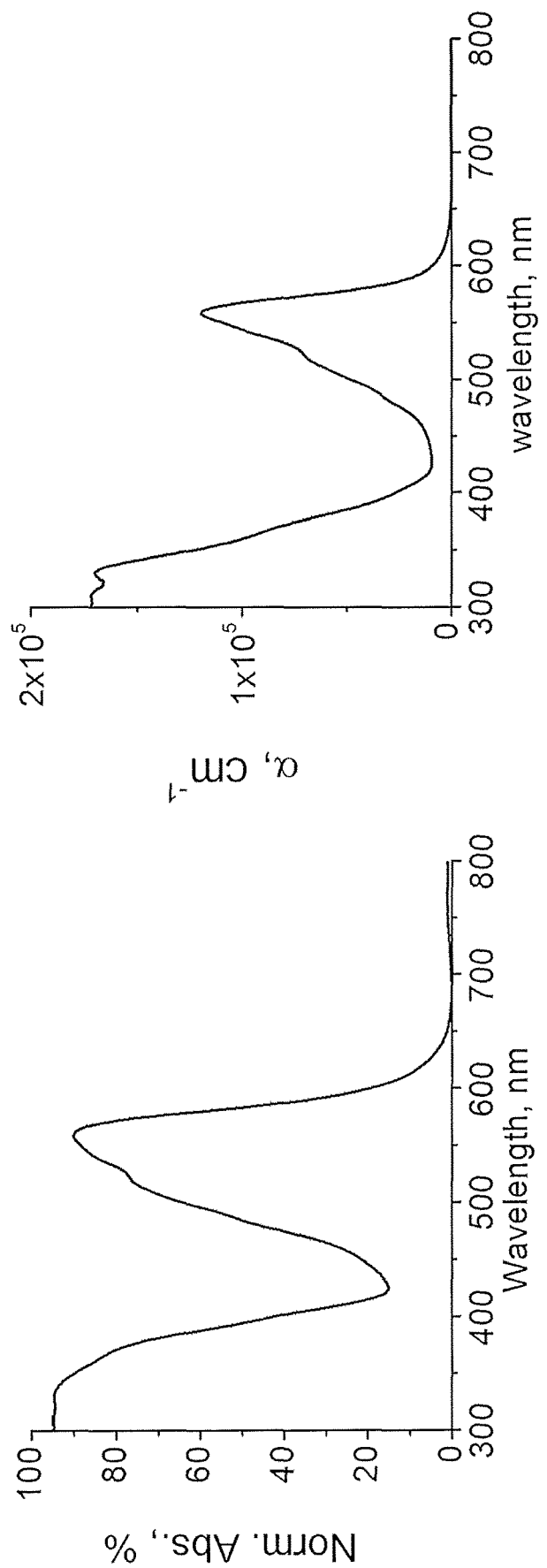
FIG. 17 shows the absorption of BTBT9:F6-OC6F5:C60 5 min/160° C. annealed: Left: Normalised absorptance of the i-layer; Right: Absorption coeffiecient of the i-layer.
Figure 18:
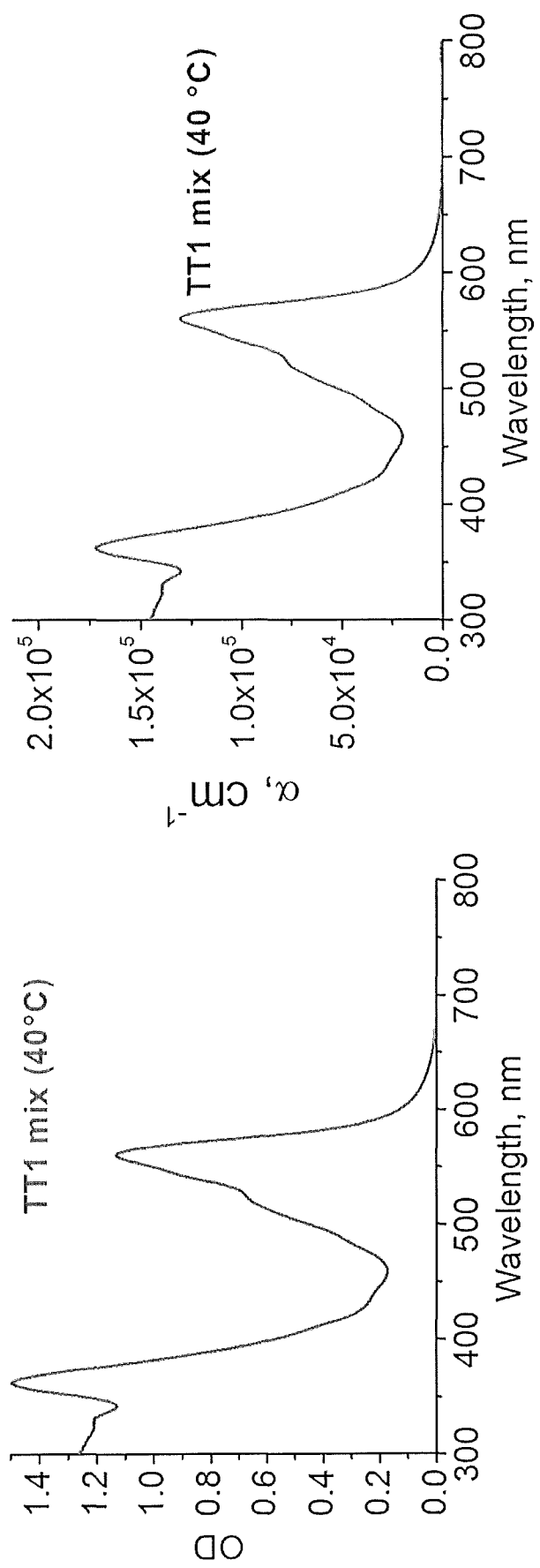
FIG. 18 shows the absorption of TT1:F6-OPh26F2:C60 5 min/160° C. annealed: Left: Normalised absorptance of the i-layer; Right: Absorption coeffiecient of the i-layer.
Figure 19:
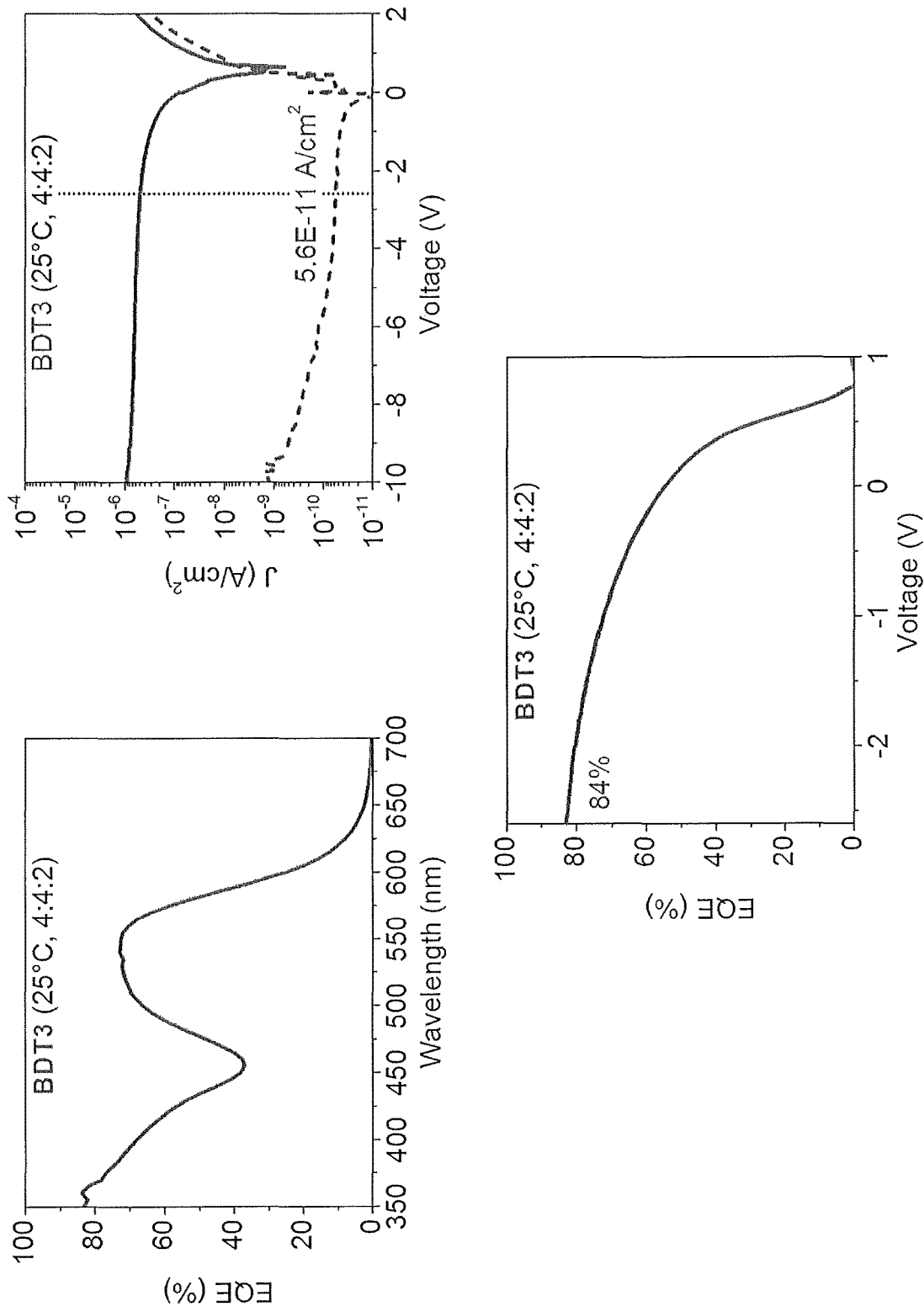
FIG. 19 shows the EQE-diagram of BDT3:F6-OC6F5:C60 5 min/160° C. annealed with EQE@-2.6V with 1.6 µW/cm$^2$ 84%.
Figure 20:
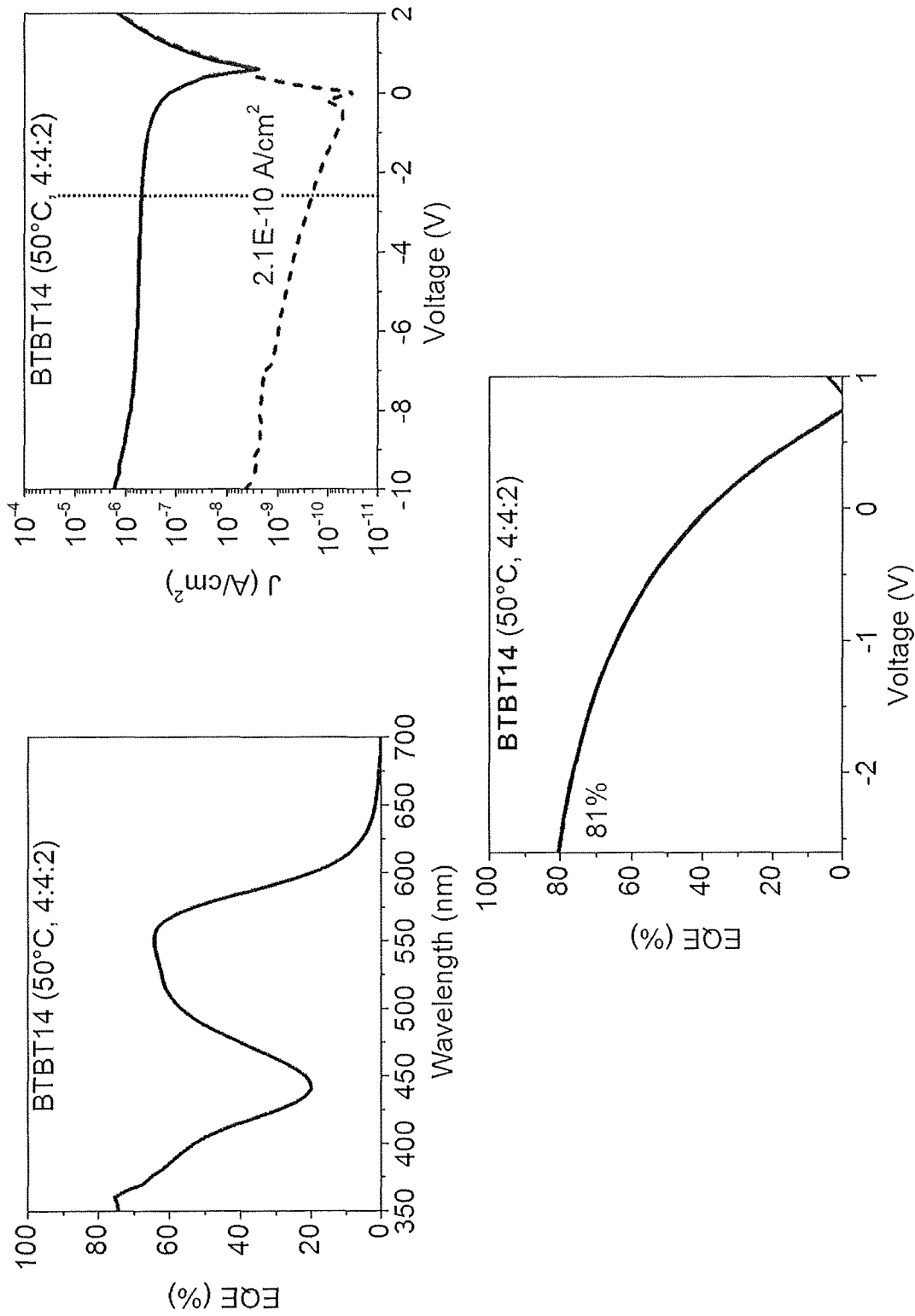
FIG. 20 shows the EQE-diagram of BTBT14:F6-OC6F5:C60 5 min/160° C. annealed with EQE@-2.6V with 1.6 µW/cm$^2$ 81%.
Figure 21:
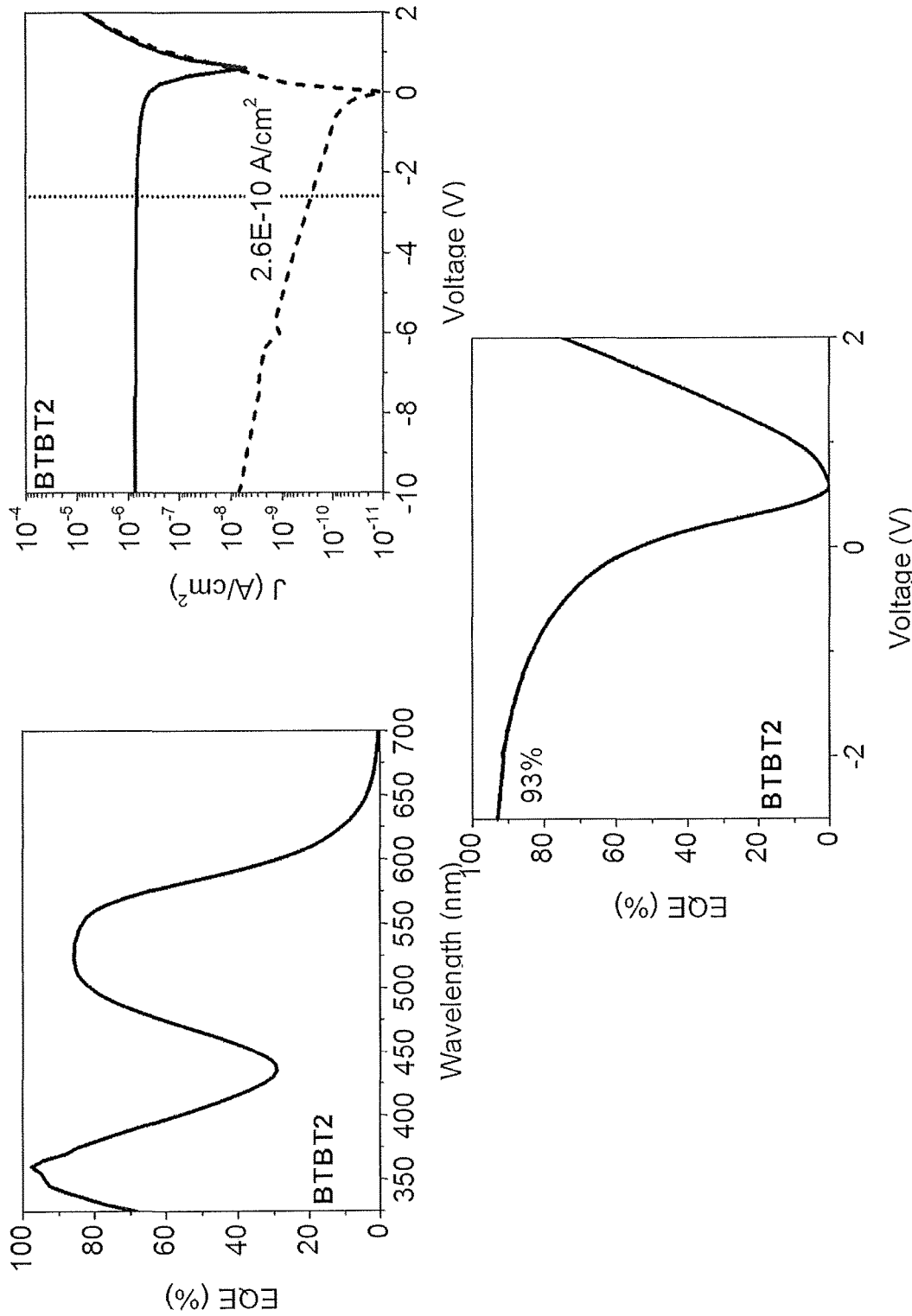
FIG. 21 shows the EQE-diagram of BTBT2:F6-OC6F5:C60 5 min/160° C. annealed with EQE@-2.6V with 1.6 µW/cm$^2$ 93%.
Figure 22:
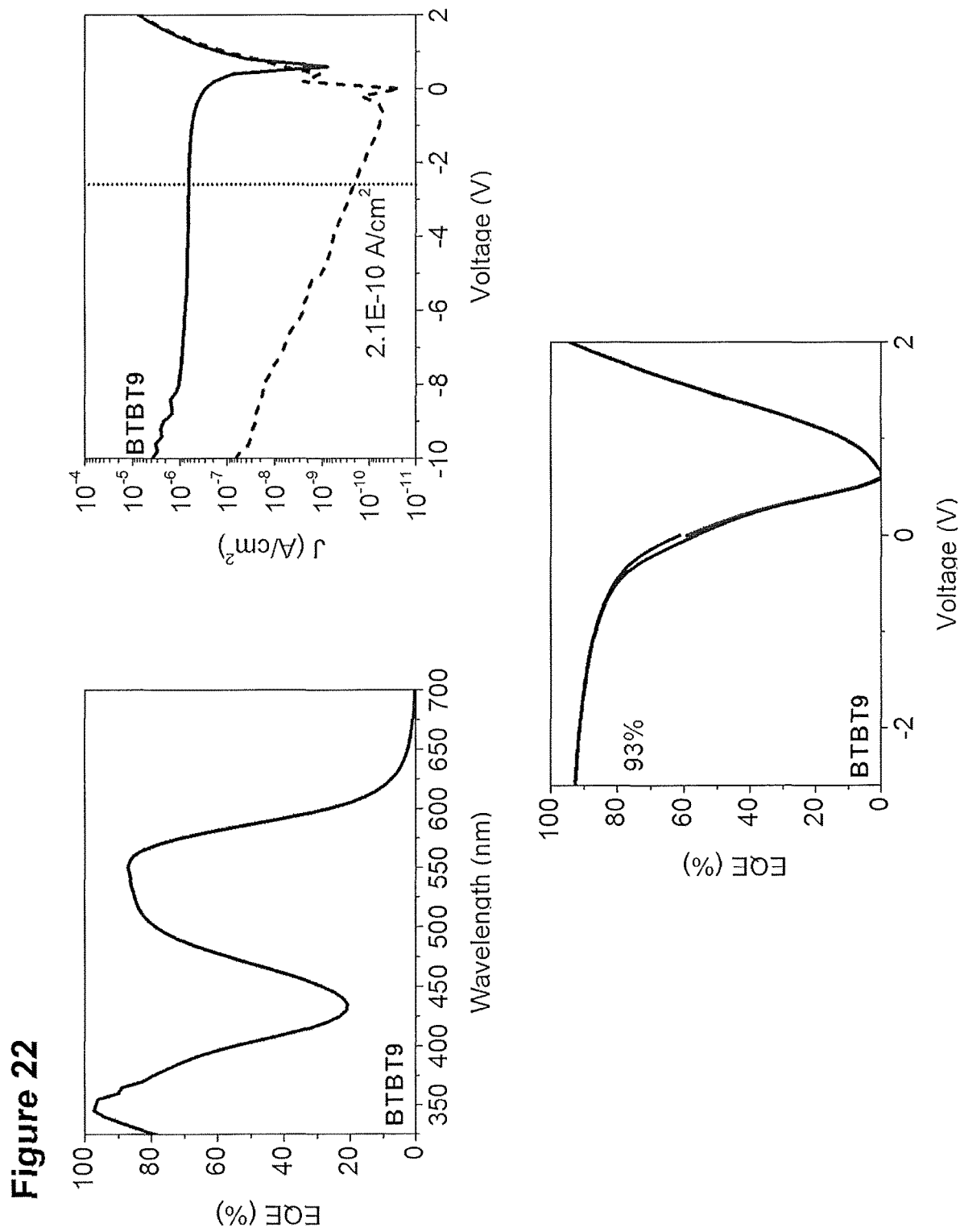
FIG. 22 shows the EQE-diagram of BTBT9:F6-OC6F5:C60 5 min/160° C. annealed with with p-buffer and EQE@-2.6V with 1.6 µW/cm$^2$ 93%.
Figure 23:
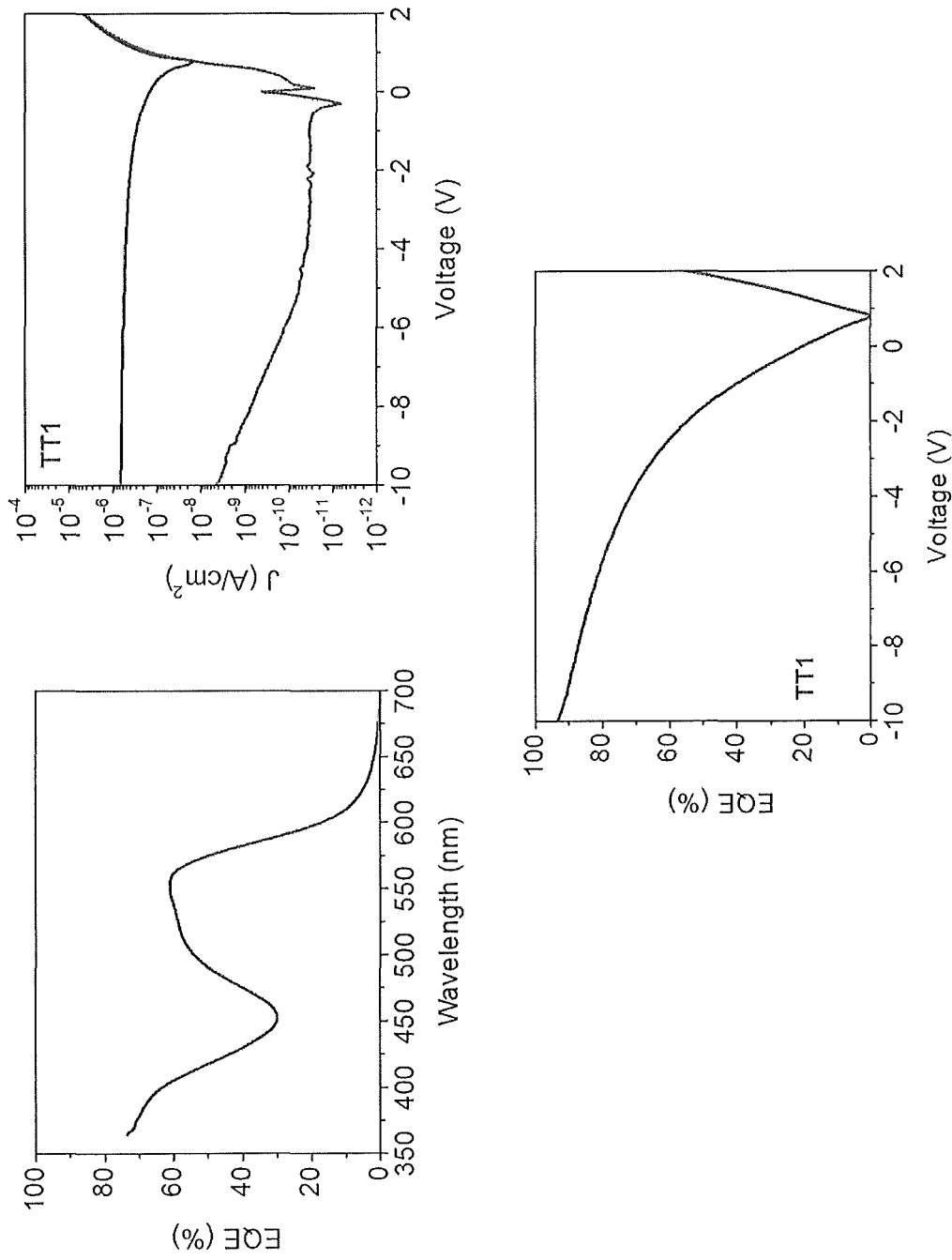
FIG. 23 shows the EQE-diagram of TT1:F6-OPh26F2:C60 5 min/160° C. annealed with EQE@-2.6V with 1.6 µW/cm$^2$ 61%.
Figure 24:
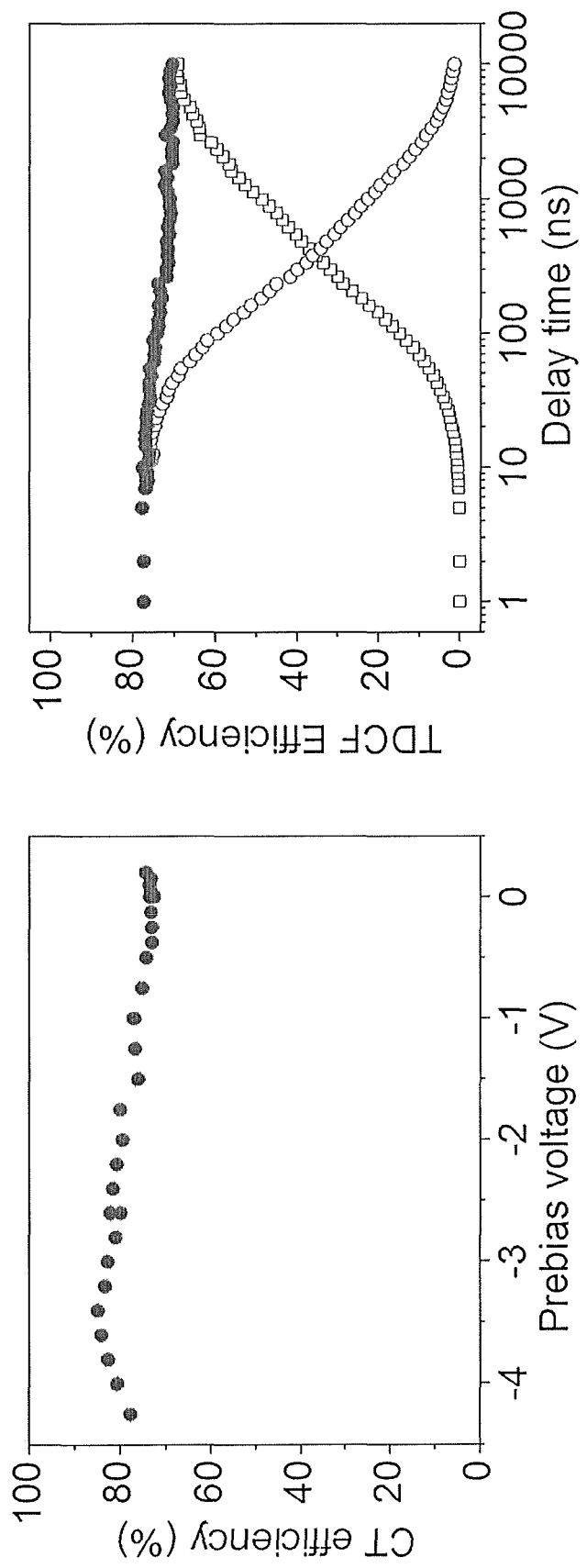
FIG. 24 shows the TDCF of BDT3:F6-OC6F5:C60 5 min/160° C. annealed; High charge generation efficiency 82% compared to deposited sample; Complete extraction of 98% at −2.6V and 10 µs delay; Low recombination of 10% at −2.6V and 10 µs delay.
Figure 25:
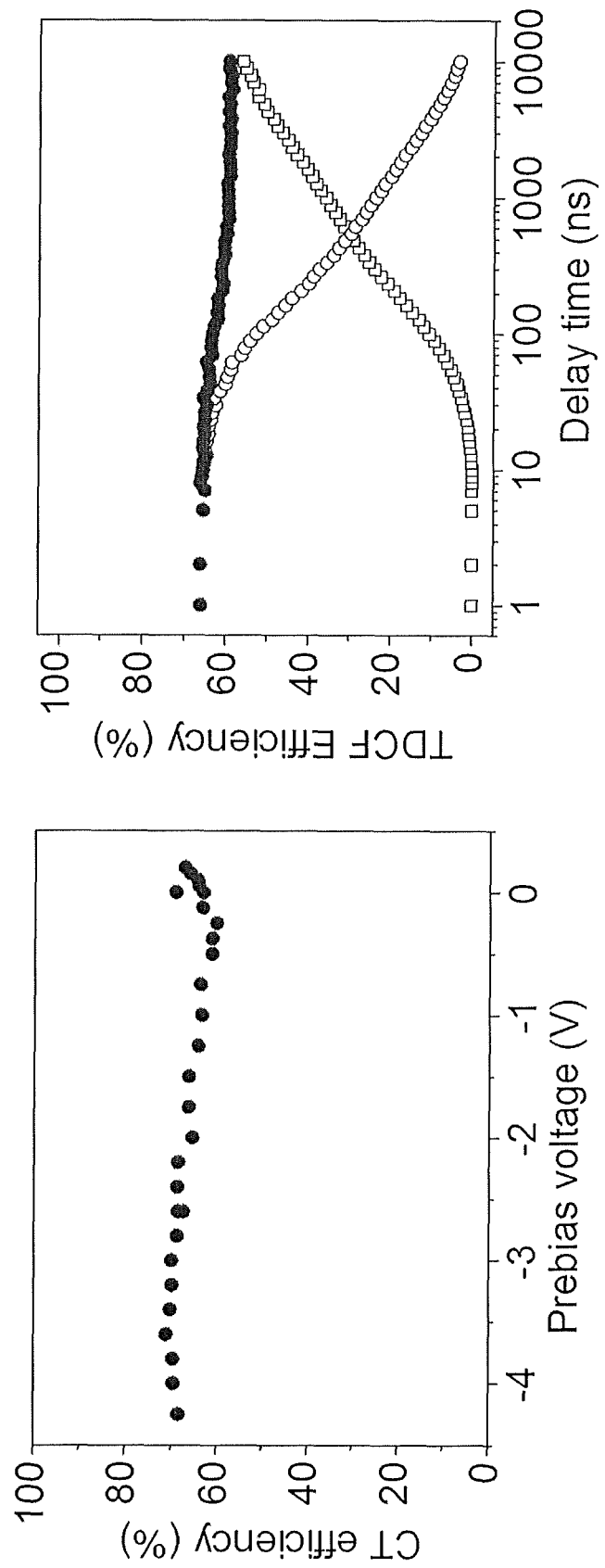
FIG. 25 shows the TDCF of BTBT14:F6-OC6F5:C60 5 min/160° C. annealed; Moderate charge generation efficiency of 68% compared to deposited sample; High extraction of 95% at −2.6V and 10 µs delay; Low recombination of 11% at −2.6V and 10 µs delay.
Figure 26:
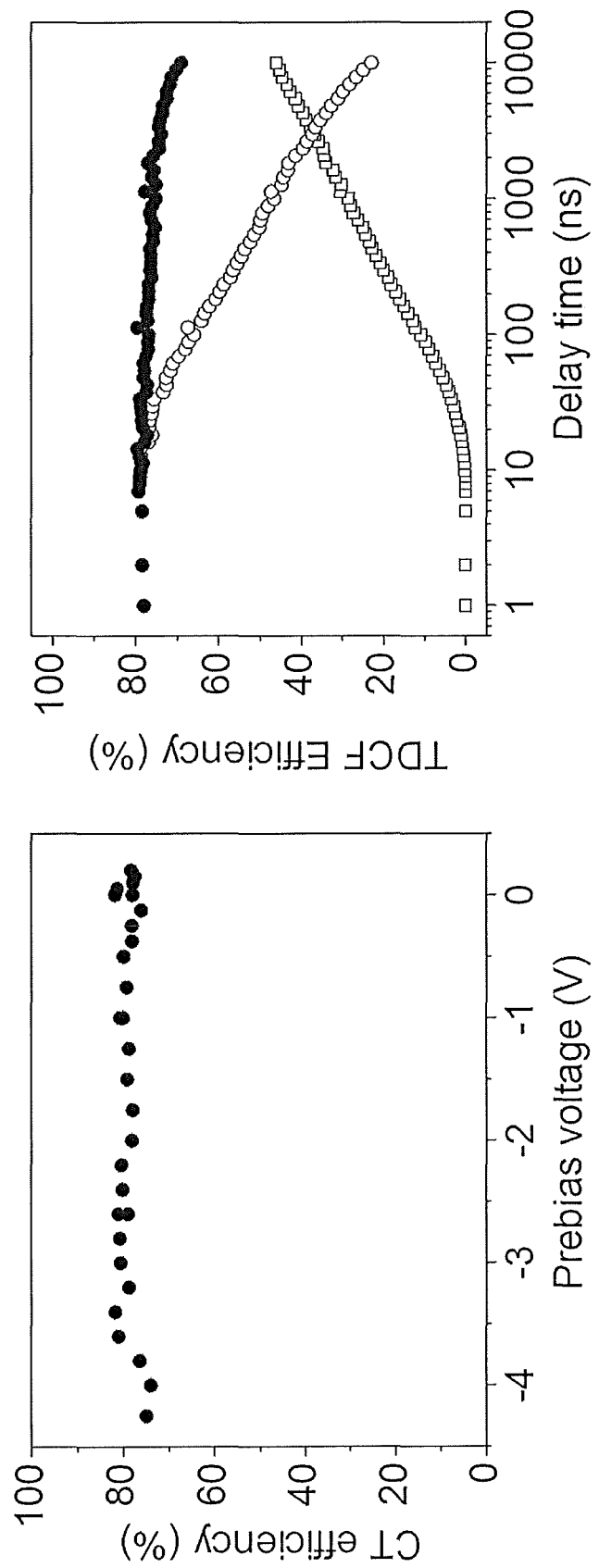
FIG. 26 shows the TDCF of BTBT2:F6-OC6F5:C60 5 min/160° C. annealed; High charge generation efficiency of 81% compared to deposited sample; Moderate extraction of 65% at −2.6V and 10 µs delay; Low recombination of 10% at −2.6V and 10 µs delay.
Figure 27:
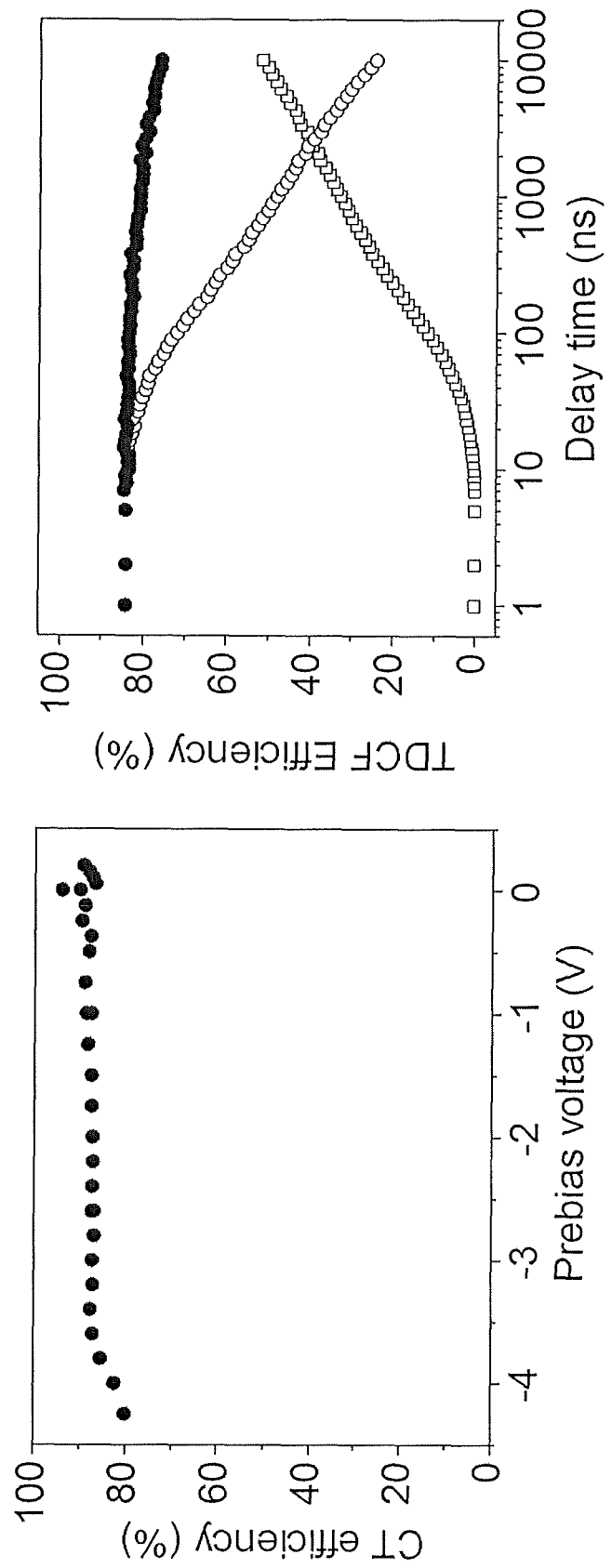
FIG. 27 shows the TDCF of BTBT9:F6-OC6F5:C60 5 min/160° C. annealed; High charge generation efficiency of 87% compared to deposited sample; Moderate extraction of 68% at −2.6V and 10 μs delay; Low recombination of 11% at −2.6V and 10 μs delay.
Figure 28:
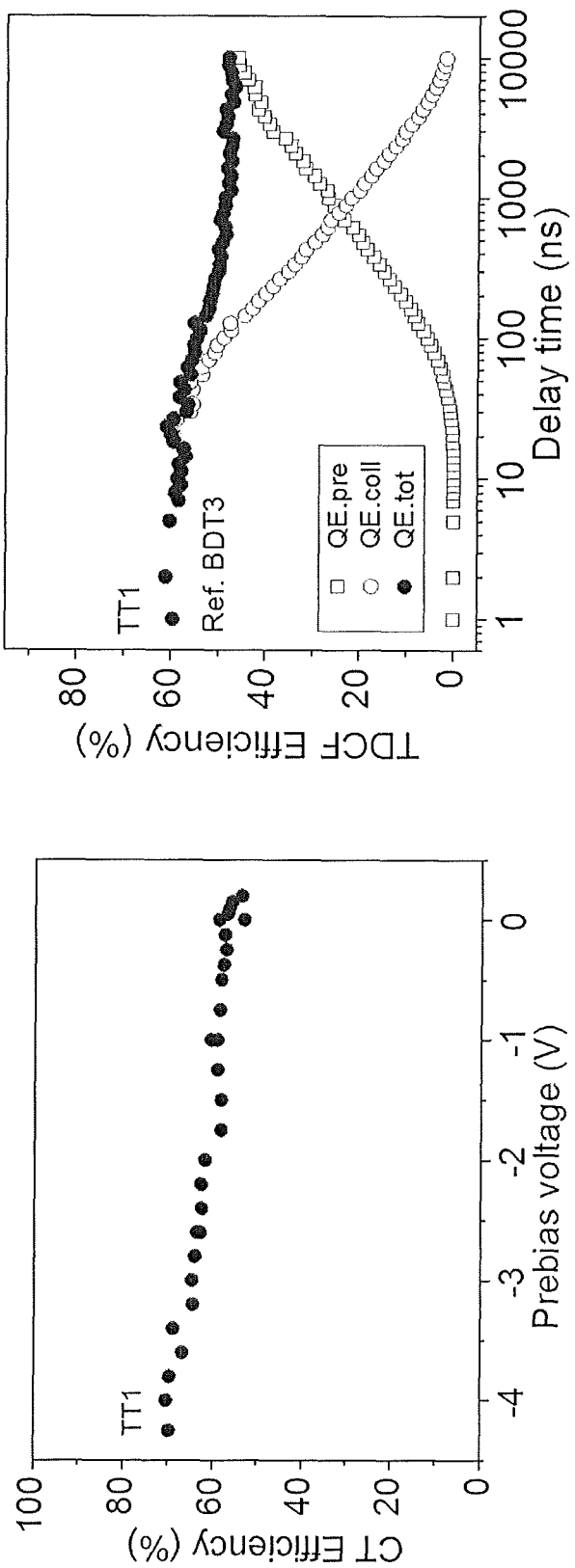
FIG. 28 shows the TDCF of TT1:F6-OPh26F2:C60 5 min/160° C. annealed; High charge generation efficiency of 64% compared to deposited sample; Moderate extraction of 96% at −2.6V and 10 μs delay; Low recombination of 21% at −2.6V and 10 μs delay.
Figure 29:
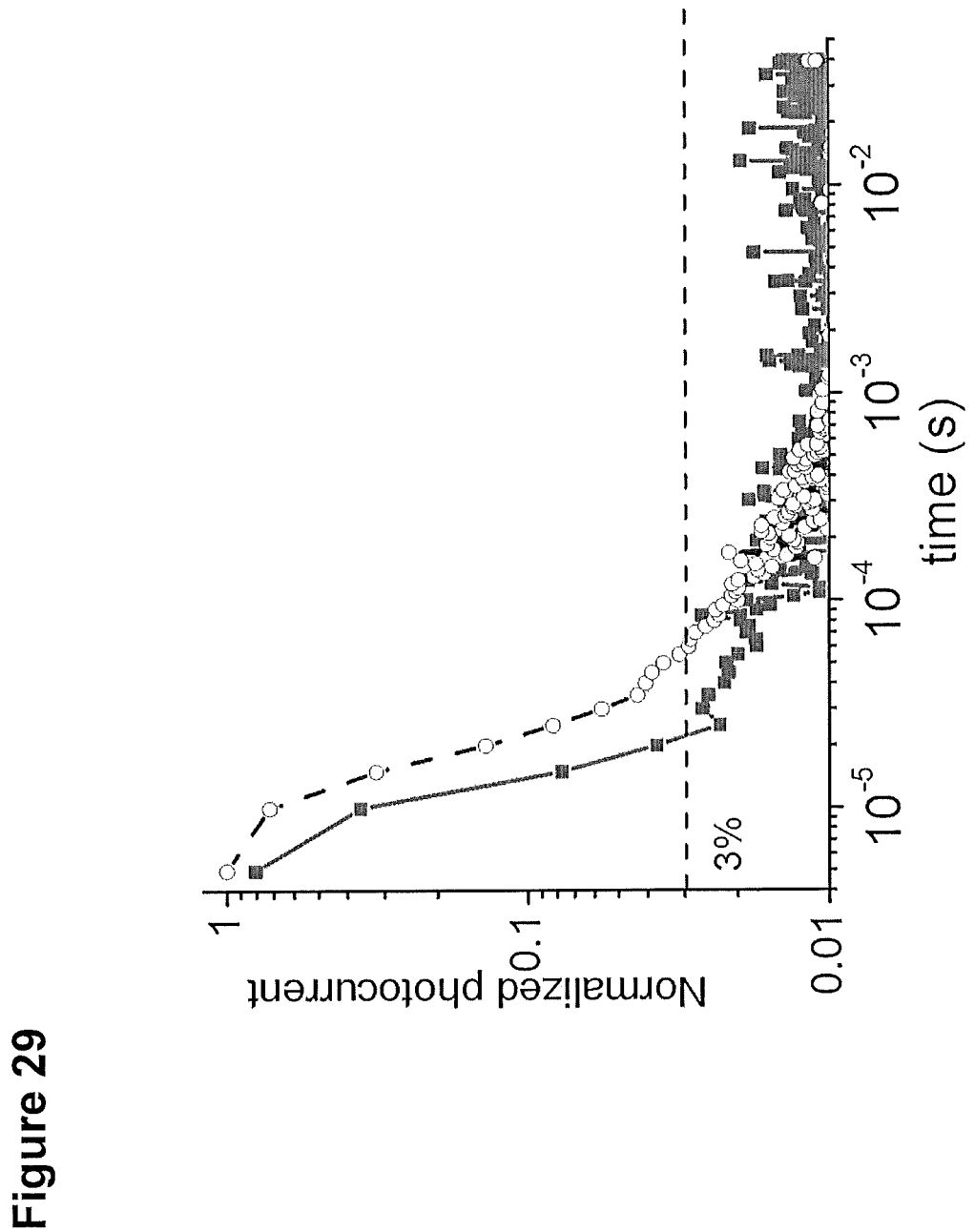
FIG. 29 shows the response/photocurrent decay: fast components of normalised current: highest for BDT3; Shortest photocurrent decay.
Figure 30:
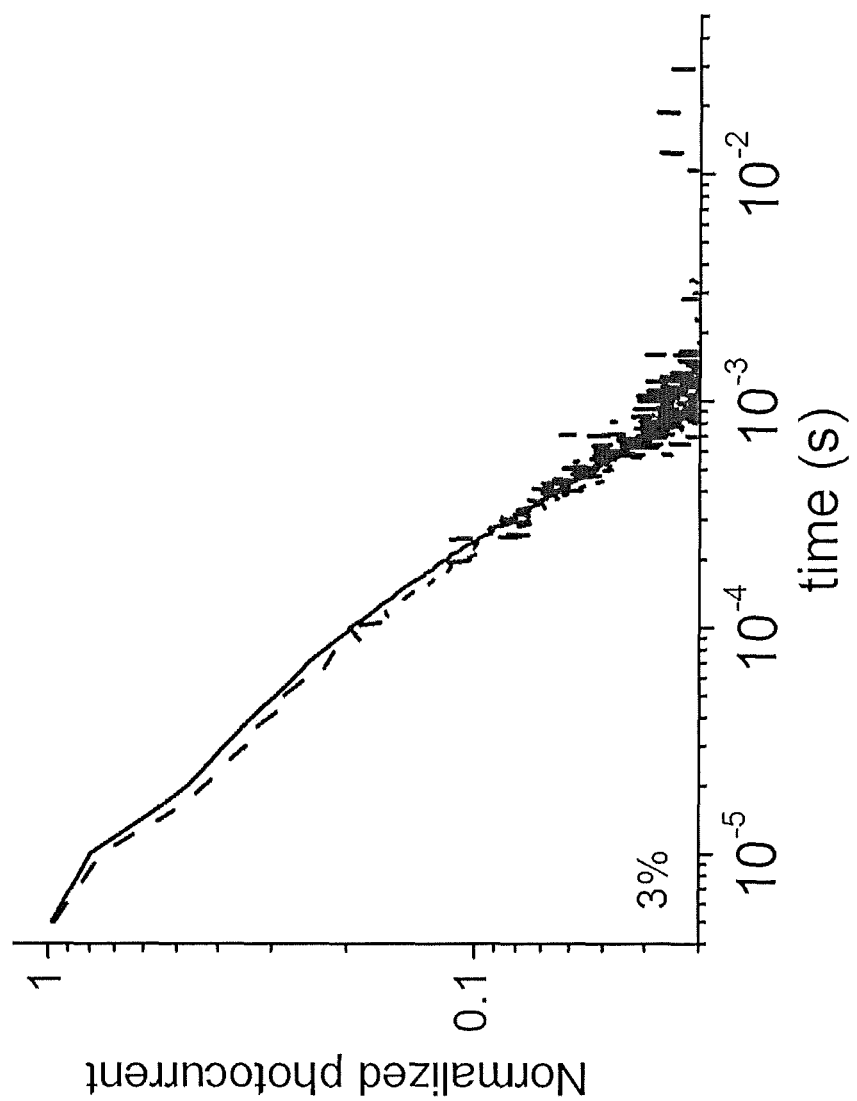
FIG. 30 shows the response/photocurrent decay: Longer photocurrent decay for dimers.
Figure 31:
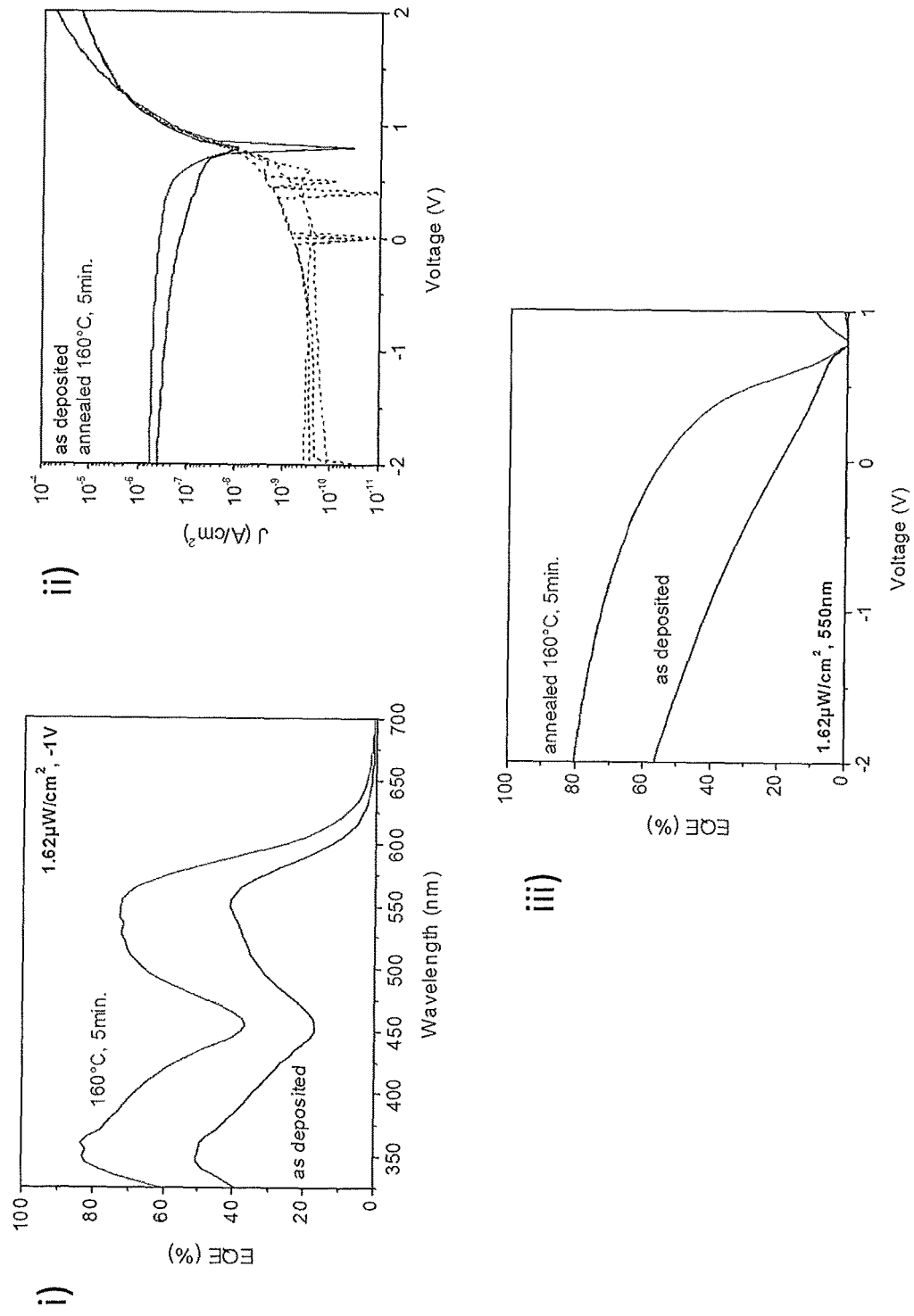
FIG. 31 shows results for BDT3 (subl):F6OC6F5:C60 (4:4:2): action spectrum (i), IV (ii) and EQE (iii). With p-buffer: EQE@-2.5V with 1.6μW/cm2 84%.
Figure 32:
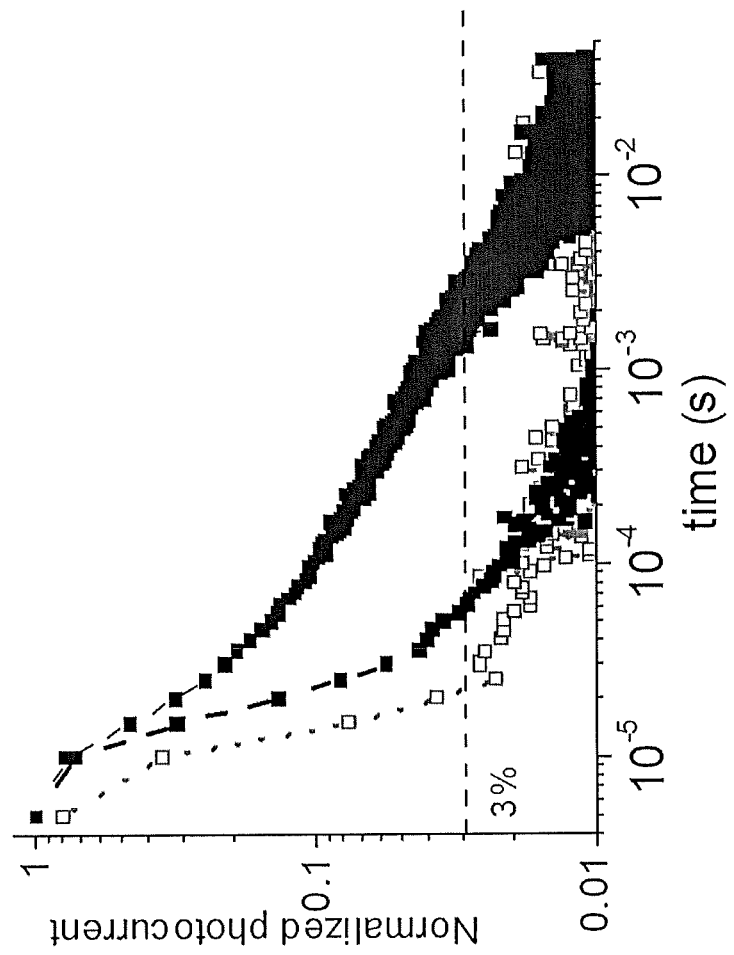
FIG. 32 shows the response/photocurrent decay: BDT3: F6OC6F5:C60 4:4:2: fast components of normalised current: highest for BDT3; Shortest photocurrent decay.

The device properties for devices with photoelectrical conversion layer as shown in FIG. 13 and the different molecules described in the Examples 1 to 5 as p-material are shown in FIGS. 14 to 32.

The invention claimed is:
1. A transparent p-type material, comprising:
a thiophene-based material comprising BDT3,

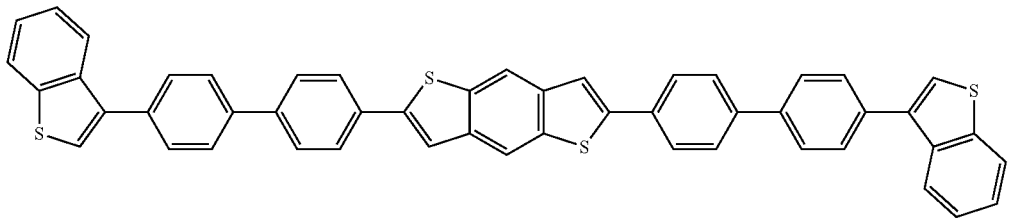

BDT3.

2. A p:n heterojunction, comprising:
the transparent p-type material of claim 1; and
an n-type material and/or a second p-type material.

3. A p:n1:n2 heterojunction, comprising:
the transparent p-type material of claim 1; and
an n-type material and/or a second p-type material.

4. The p:n heterojunction according to claim 2, wherein the n-type and/or second p-type material exhibits absorption in a visible wavelength range.

5. The p:n1:n2 heterojunction according to claim 3, wherein the n-type and/or second p-type material exhibits absorption in a visible wavelength range.

6. An absorption layer, comprising:
the transparent p-type material of claim 1; and
an n-type material and/or a second p-type material.

7. A photoelectric conversion layer, comprising:
the transparent p-type material of claim 1; and
an n-type material and/or a second p-type material.

8. An organic and/or hybrid module for optoelectronic application, comprising:
the transparent p-type material of claim 1; and
an n-type material and/or a second p-type material.

9. The absorption layer according to claim 6, wherein the n-type and/or second p-type material exhibits absorption in a visible wavelength range.

10. The photoelectric conversion layer according to claim 7, wherein the n-type and/or second p-type material exhibits absorption in a visible wavelength range.

11. The organic and/or hybrid module according to claim 8, wherein the n-type and/or second p-type material exhibits absorption in a visible wavelength range.

12. A device, comprising:
the transparent p-type material of claim 1.

13. A device, comprising:
the photoelectric conversion layer of claim 7.

14. The device according to claim 13, wherein the photoelectric conversion layer exhibits photo response in a visible absorption range, and/or the device is an organic image sensor, a hybrid image sensor, photodiode, organic photovoltaics, an organic light-emitting diode, an organic thin-film transistor.

15. The device according to claim 12, further comprising:
an n-type material and/or a second p-type material.

16. The device of claim 15, wherein the n-type and/or second p-type material exhibits absorption in a visible wavelength range.

17. An organic image sensor, comprising:
an organic photoelectric conversion unit comprising the photoelectric conversion layer of claim 7;
an electrode; and
a substrate.

18. The organic image sensor according to claim 17, further comprising:
a second electrode on the photoelectric conversion layer.

19. A hybrid silicon-organic image sensor, comprising:
an organic photoelectric conversion unit comprising the photoelectric conversion layer of claim 7;
metal wiring;
a CMOS substrate; and
an insulating layer.

20. The hybrid silicon-organic image sensor according to claim 19, further comprising:
a Si based photoelectric conversion unit.

21. The hybrid silicon-organic image sensor according to claim 19, wherein the organic photoelectric conversion unit comprises an n-type material layer, a p-type material layer, an n-buffer layer and/or a p-buffer layer.

22. The hybrid silicon-organic image sensor according to claim 20, wherein the organic photoelectric conversion unit comprises an n-type material layer, a p-type material layer, an n-buffer layer and/or a p-buffer layer.

23. An organic image sensor, comprising:
an organic photoelectric conversion unit comprising the photoelectric conversion layer of claim 7;
metal wiring;
a CMOS substrate; and
an insulating layer.

24. The organic image sensor according to claim 23, further comprising:
a Si based photoelectric conversion unit.

25. The organic image sensor according to claim 24, wherein the organic photoelectric conversion unit comprises an n-type material layer, a p-type material layer, an n-buffer layer and/or a p-buffer layer.

26. The organic image sensor according to claim 17, wherein the organic photoelectric conversion unit comprises an n-type material layer, a p-type material layer, an n-buffer layer and/or a p-buffer layer.

27. The organic image sensor according to claim 18, wherein the organic photoelectric conversion unit comprises an n-type material layer, a p-type material layer, an n-buffer layer and/or a p-buffer layer.

* * * * *